US011786323B2

(12) United States Patent
Basafa et al.

(10) Patent No.: US 11,786,323 B2
(45) Date of Patent: Oct. 17, 2023

(54) SELF-CALIBRATING CO-MANIPULATION SURGICAL SYSTEM FOR USE WITH SURGICAL INSTRUMENT FOR PERFORMING LAPAROSCOPIC SURGERY

(71) Applicant: Moon Surgical SAS, Paris (FR)

(72) Inventors: Ehsan Basafa, Redwood City, CA (US); Nicolas Linard, Montrouge (FR); David Paul Noonan, San Francisco, CA (US); Jeffery Byron Alvarez, San Carlos, CA (US); Ritwik Ummalaneni, San Francisco, CA (US); Jad Fayad, Paris (FR)

(73) Assignee: Moon Surgical SAS, Paris (FR)

( * ) Notice: Subject to any disclaimer, the term of this patent is extended or adjusted under 35 U.S.C. 154(b) by 0 days.

(21) Appl. No.: 17/816,915

(22) Filed: Aug. 2, 2022

(65) Prior Publication Data
US 2022/0378527 A1  Dec. 1, 2022

Related U.S. Application Data

(63) Continuation of application No. PCT/IB2022/052989, filed on Mar. 30, 2022.

(30) Foreign Application Priority Data

Mar. 31, 2021 (EP) .................................... 21305417
Jul. 5, 2021 (EP) .................................... 21305929
(Continued)

(51) Int. Cl.
*A61B 34/30* (2016.01)
*A61B 90/98* (2016.01)
(Continued)

(52) U.S. Cl.
CPC .......... *A61B 34/30* (2016.02); *A61B 1/00149* (2013.01); *A61B 34/20* (2016.02);
(Continued)

(58) Field of Classification Search
CPC .............. A61B 1/00149; A61B 1/3132; A61B 2017/00477; A61B 2017/00486;
(Continued)

(56) References Cited

U.S. PATENT DOCUMENTS 1,058,297 A   4/1913  Grant et al.
5,836,869 A   11/1998 Kudo et al.
(Continued)

FOREIGN PATENT DOCUMENTS

EP   2298218 A2   3/2011
EP   2413818 A1   2/2012
(Continued)

OTHER PUBLICATIONS

Andronic Devices 510(k): ENDEX Endoscopic Positioning System, K936308 (Mar. 31, 1994).
(Continued)

*Primary Examiner* — Scott Luan
(74) *Attorney, Agent, or Firm* — Eversheds Sutherland (US) LLP; Christopher C. Bolten; Albert K. Heng

(57) ABSTRACT

Co-manipulation robotic systems are described herein that may be used for assisting with laparoscopic surgical procedures. The co-manipulation robotic systems allow a surgeon to use commercially-available surgical tools while providing benefits associated with surgical robotics. Advantageously, the surgical tools may be seamlessly coupled to the robot arms using a disposable coupler while the reusable portions of the robot arm remain in a sterile drape. Further, the co-manipulation robotic system may operate in multiple modes to enhance usability and safety, while allowing the (Continued)

surgeon to position the instrument directly with the instrument handle and further maintain the desired position of the instrument using the robot arm.

30 Claims, 46 Drawing Sheets

(30) Foreign Application Priority Data

Dec. 22, 2021 (EP) .................................. 21306904
Dec. 22, 2021 (EP) .................................. 21306905

(51) Int. Cl.
  *A61B 34/00* (2016.01)
  *A61B 34/20* (2016.01)
  *A61B 34/37* (2016.01)
  *A61B 1/00* (2006.01)
  *A61B 90/96* (2016.01)
  *A61B 90/00* (2016.01)
  *A61B 1/313* (2006.01)
  *A61B 46/10* (2016.01)

(52) U.S. Cl.
  CPC .............. *A61B 34/25* (2016.02); *A61B 34/37* (2016.02); *A61B 34/70* (2016.02); *A61B 1/3132* (2013.01); *A61B 46/10* (2016.02); *A61B 90/96* (2016.02); *A61B 90/98* (2016.02); *A61B 2034/2059* (2016.02); *A61B 2034/302* (2016.02); *A61B 2034/305* (2016.02); *A61B 2034/306* (2016.02); *A61B 2090/061* (2016.02); *A61B 2090/067* (2016.02); *A61B 2560/0238* (2013.01)

(58) Field of Classification Search
  CPC .... A61B 2034/2055; A61B 2034/2059; A61B 2034/2065; A61B 2034/254; A61B 2034/256; A61B 2034/302; A61B 2034/306; A61B 2090/061; A61B 2090/064; A61B 2090/066; A61B 2090/067; A61B 2090/0804; A61B 2090/0805; A61B 2090/0807; A61B 2560/0238; A61B 34/20; A61B 34/25; A61B 34/30; A61B 34/37; A61B 34/70; A61B 34/76; A61B 46/10; A61B 90/50; A61B 90/57; A61B 90/90; A61B 90/96; A61B 90/98

See application file for complete search history.

(56) References Cited

U.S. PATENT DOCUMENTS

| | | | |
|---|---|---|---|
| 5,887,121 | A | 3/1999 | Funda et al. |
| 6,496,756 | B1 | 12/2002 | Nishizawa et al. |
| 6,714,841 | B1 | 3/2004 | Wright et al. |
| 6,786,896 | B1 | 9/2004 | Madhani et al. |
| 6,913,613 | B2 | 7/2005 | Schwarz et al. |
| 7,198,630 | B2 | 4/2007 | Lipow |
| 7,524,320 | B2 | 4/2009 | Tierney et al. |
| 7,741,802 | B2 | 6/2010 | Prisco et al. |
| 7,747,311 | B2 | 6/2010 | Quaid, III |
| 7,831,292 | B2 | 11/2010 | Quaid et al. |
| 7,833,156 | B2 | 11/2010 | Williams et al. |
| 7,907,166 | B2 | 3/2011 | Lamprecht et al. |
| 7,996,110 | B2 | 8/2011 | Lipow et al. |
| 8,004,229 | B2 | 8/2011 | Nowlin et al. |
| 8,095,237 | B2 | 1/2012 | Habibi et al. |
| 8,100,133 | B2 | 1/2012 | Mintz et al. |
| 8,246,617 | B2 | 8/2012 | Welt et al. |
| 8,273,076 | B2 | 9/2012 | Devengenzo et al. |
| 8,287,522 | B2 | 10/2012 | Moses et al. |
| 8,343,096 | B2 | 1/2013 | Kirschenman et al. |
| 8,374,677 | B2 | 2/2013 | Piferi et al. |
| 8,398,541 | B2 | 3/2013 | DiMaio et al. |
| 8,449,552 | B2 | 5/2013 | Sanders |
| 8,457,790 | B2 | 6/2013 | Blondel et al. |
| 8,489,235 | B2 | 7/2013 | Moll et al. |
| 8,498,744 | B2 | 7/2013 | Odermatt et al. |
| 8,515,576 | B2 | 8/2013 | Lipow et al. |
| 8,518,024 | B2 | 8/2013 | Williams et al. |
| 8,600,134 | B2 | 12/2013 | Vercauteren et al. |
| 8,608,773 | B2 | 12/2013 | Tierney et al. |
| 8,649,905 | B2 | 2/2014 | Ortmaier |
| 8,668,638 | B2 | 3/2014 | Donhowe et al. |
| 8,746,533 | B2 | 6/2014 | Whitman et al. |
| 8,749,190 | B2 | 6/2014 | Nowlin et al. |
| 8,808,164 | B2 | 8/2014 | Hoffman et al. |
| 8,827,135 | B2 | 9/2014 | Amid et al. |
| 8,845,622 | B2 | 9/2014 | Paik et al. |
| 8,870,049 | B2 | 10/2014 | Amid et al. |
| 8,894,634 | B2 | 11/2014 | Devengenzo et al. |
| 8,911,429 | B2 | 12/2014 | Olds et al. |
| 8,919,348 | B2 | 12/2014 | Williams et al. |
| 8,961,499 | B2 | 2/2015 | Paik et al. |
| 8,969,777 | B2 | 3/2015 | Savoire et al. |
| 8,972,057 | B1 | 3/2015 | Freeman et al. |
| 8,992,542 | B2 | 3/2015 | Hagag et al. |
| 8,996,173 | B2 | 3/2015 | Itkowitz et al. |
| 9,039,608 | B2 | 5/2015 | Donhowe et al. |
| 9,066,751 | B2 | 6/2015 | Sasso |
| 9,095,681 | B2 | 8/2015 | Wenderow et al. |
| 9,125,669 | B2 | 9/2015 | Ranawat et al. |
| 9,265,587 | B2 | 2/2016 | Vancamberg et al. |
| 9,266,239 | B2 | 2/2016 | Miller |
| 9,283,048 | B2 | 3/2016 | Kostrzewski et al. |
| 9,295,379 | B2 | 3/2016 | Sholev |
| 9,333,040 | B2 | 5/2016 | Shellenberger et al. |
| 9,339,346 | B2 | 5/2016 | Malackowski |
| 9,345,545 | B2 | 5/2016 | Shellenberger et al. |
| 9,360,934 | B2 | 6/2016 | Ruiz Morales et al. |
| 9,486,272 | B2 | 11/2016 | Bonyak et al. |
| 9,532,838 | B2 | 1/2017 | Coste-Maniere et al. |
| 9,549,781 | B2 | 1/2017 | He et al. |
| 9,566,122 | B2 | 2/2017 | Bowling et al. |
| 9,586,327 | B2 | 3/2017 | Schena |
| 9,592,096 | B2 | 3/2017 | Maillet et al. |
| 9,603,672 | B2 | 3/2017 | Shellenberger et al. |
| 9,622,831 | B2 | 4/2017 | Azizian et al. |
| 9,636,185 | B2 | 5/2017 | Quaid et al. |
| 9,652,591 | B2 | 5/2017 | Moctezuma et al. |
| 9,662,174 | B2 | 5/2017 | Taylor et al. |
| 9,681,920 | B2 | 6/2017 | Bowling et al. |
| 9,687,310 | B2 | 6/2017 | Nowlin et al. |
| 9,699,445 | B2 | 7/2017 | Hoffman et al. |
| 9,707,684 | B2 | 7/2017 | Ruiz et al. |
| 9,739,674 | B2 | 8/2017 | Malackowski et al. |
| 9,775,681 | B2 | 10/2017 | Quaid et al. |
| 9,775,682 | B2 | 10/2017 | Quaid et al. |
| 9,782,261 | B2 | 10/2017 | Collazo et al. |
| 9,788,903 | B2 | 10/2017 | Kim et al. |
| 9,795,361 | B2 | 10/2017 | Marx et al. |
| 9,795,446 | B2 | 10/2017 | DiMaio et al. |
| 9,802,323 | B2 | 10/2017 | Louveau |
| 9,814,392 | B2 | 11/2017 | Balicki et al. |
| 9,820,818 | B2 | 11/2017 | Malackowski et al. |
| 9,827,059 | B2 | 11/2017 | Robinson et al. |
| 9,895,197 | B2 | 2/2018 | Poquet et al. |
| 9,901,411 | B2 | 2/2018 | Gombert et al. |
| 9,937,058 | B2 | 4/2018 | Axelson, Jr. et al. |
| 9,943,964 | B2 | 4/2018 | Hares |
| 9,948,852 | B2 | 4/2018 | Lilagan et al. |
| 9,993,309 | B2 | 6/2018 | Bowling |
| 9,993,313 | B2 | 6/2018 | Schuh et al. |
| 10,002,427 | B2 | 6/2018 | Linard et al. |
| 10,010,377 | B2 | 7/2018 | Iorgulescu et al. |
| 10,034,719 | B2 | 7/2018 | Richmond et al. |
| 10,039,605 | B2 | 8/2018 | Kostrzewski et al. |
| 10,098,704 | B2 | 10/2018 | Bowling et al. |
| 10,118,289 | B2 | 11/2018 | Louveau |

(56) References Cited

U.S. PATENT DOCUMENTS

| | | |
|---|---|---|
| 10,123,844 B2 | 11/2018 | Nowlin et al. |
| 10,136,949 B2 | 11/2018 | Felder et al. |
| 10,159,534 B2 | 12/2018 | Maillet et al. |
| 10,178,368 B2 | 1/2019 | Zhao et al. |
| 10,201,392 B2 | 2/2019 | Frimer et al. |
| 10,247,545 B2 | 4/2019 | Elliot |
| 10,251,713 B2 | 4/2019 | Ruiz et al. |
| 10,251,714 B2 | 4/2019 | Carnes et al. |
| 10,258,416 B2 | 4/2019 | Mintz et al. |
| 10,258,419 B2 | 4/2019 | Auld et al. |
| 10,265,057 B2 | 4/2019 | Herzlinger et al. |
| 10,265,129 B2 | 4/2019 | Beira |
| 10,278,782 B2 | 5/2019 | Jarc et al. |
| 10,299,773 B2 | 5/2019 | Frimer et al. |
| 10,299,868 B2 | 5/2019 | Tsuboi et al. |
| 10,314,661 B2 | 6/2019 | Bowling et al. |
| 10,334,227 B2 | 6/2019 | Panescu et al. |
| 10,335,242 B2 | 7/2019 | Devengenzo et al. |
| 10,357,320 B2 | 7/2019 | Beira |
| 10,357,324 B2 | 7/2019 | Flatt et al. |
| 10,363,055 B2 | 7/2019 | Beira et al. |
| 10,365,554 B1 | 7/2019 | McDowall et al. |
| 10,390,737 B2 | 8/2019 | Malackowski et al. |
| 10,398,519 B2 | 9/2019 | Kim et al. |
| 10,410,746 B2 | 9/2019 | Moctezuma et al. |
| 10,413,374 B2 | 9/2019 | Chassot et al. |
| 10,420,625 B2 | 9/2019 | Suzuki et al. |
| 10,426,321 B2 | 10/2019 | Sholev |
| 10,441,372 B2 | 10/2019 | Devengenzo et al. |
| 10,464,209 B2 | 11/2019 | Ho et al. |
| 10,485,616 B2 | 11/2019 | Auld et al. |
| 10,512,509 B2 | 12/2019 | Bowling et al. |
| 10,512,512 B2 | 12/2019 | Richmond et al. |
| 10,517,681 B2 | 12/2019 | Roh et al. |
| 10,537,441 B2 | 1/2020 | Axelson, Jr. et al. |
| 10,548,680 B2 | 2/2020 | Beira |
| 10,568,709 B2 | 2/2020 | Beira |
| 10,582,977 B2 | 3/2020 | Morel et al. |
| 10,603,127 B2 | 3/2020 | Hasser et al. |
| 10,607,346 B2 | 3/2020 | Linard et al. |
| 10,609,291 B2 | 3/2020 | Festy et al. |
| 10,610,310 B2 | 4/2020 | Todd et al. |
| 10,636,147 B2 | 4/2020 | Linard et al. |
| 10,638,918 B2 | 5/2020 | Atarot et al. |
| 10,646,291 B2 | 5/2020 | Turner |
| 10,646,293 B2 | 5/2020 | Hasser et al. |
| 10,646,294 B2 | 5/2020 | Beira |
| 10,660,712 B2 | 5/2020 | Kostrzewski et al. |
| 10,660,724 B2 | 5/2020 | Hufnagel et al. |
| 10,667,868 B2 | 6/2020 | Malackowski |
| 10,667,876 B2 | 6/2020 | Maillet et al. |
| 10,674,900 B2 | 6/2020 | Hoffman et al. |
| 10,675,106 B2 | 6/2020 | Tsuboi et al. |
| 10,751,139 B2 | 8/2020 | Frimer et al. |
| 10,754,241 B2 | 8/2020 | McDowall et al. |
| 10,776,920 B2 | 9/2020 | Linard et al. |
| 10,782,501 B2 | 9/2020 | Hirose et al. |
| 10,786,272 B2 | 9/2020 | Beira |
| 10,786,317 B2 | 9/2020 | Zhou et al. |
| 10,786,323 B2 | 9/2020 | Ang et al. |
| 10,802,597 B2 | 10/2020 | Von Wendorff et al. |
| 10,813,704 B2 | 10/2020 | Kostrzewski et al. |
| 10,828,120 B2 | 11/2020 | Kostrzewski et al. |
| 10,864,049 B2 | 12/2020 | Beira |
| 10,864,052 B2 | 12/2020 | Beira |
| 10,869,659 B2 | 12/2020 | Thommen et al. |
| 10,874,464 B2 | 12/2020 | Roh et al. |
| 10,888,996 B2 | 1/2021 | Tabandeh et al. |
| 10,918,450 B2 | 2/2021 | Martin |
| 10,925,586 B2 | 2/2021 | Herzlinger et al. |
| 10,939,968 B2 | 3/2021 | Kostrzewski et al. |
| 11,007,020 B2 | 5/2021 | Ziraknejad et al. |
| 11,007,031 B2 | 5/2021 | Fuerst et al. |
| 11,019,329 B2 | 5/2021 | Hoffman et al. |
| 11,027,432 B2 | 6/2021 | Bowling et al. |
| 11,039,820 B2 | 6/2021 | Beira |
| 11,039,893 B2 | 6/2021 | Kostrzewski |
| 11,045,077 B2 | 6/2021 | Stern et al. |
| 11,045,276 B2 | 6/2021 | Nowatschin et al. |
| 11,058,503 B2 | 7/2021 | Chassot et al. |
| 11,103,315 B2 | 8/2021 | Malackowski |
| 11,109,917 B2 | 9/2021 | Abovitz et al. |
| 11,119,105 B2 | 9/2021 | Penny et al. |
| 11,141,230 B2 | 10/2021 | Zhou et al. |
| 11,148,297 B2 | 10/2021 | Maret |
| 11,172,997 B2 | 11/2021 | Kostrzewski et al. |
| 11,183,297 B2 | 11/2021 | Moctezuma et al. |
| 11,185,315 B2 | 11/2021 | Frimer et al. |
| 11,191,598 B2 | 12/2021 | Crawford et al. |
| 11,197,731 B2 | 12/2021 | Hoffman et al. |
| 11,504,197 B1 | 11/2022 | Noonan et al. |
| 11,622,826 B2 | 4/2023 | Basafa et al. |
| 2002/0128552 A1 | 9/2002 | Nowlin et al. |
| 2004/0034282 A1 | 2/2004 | Quaid |
| 2004/0236352 A1 | 11/2004 | Wang et al. |
| 2006/0142657 A1 | 6/2006 | Quaid et al. |
| 2007/0021738 A1 | 1/2007 | Hasser et al. |
| 2007/0044365 A1 | 3/2007 | Deken |
| 2007/0142823 A1 | 6/2007 | Prisco et al. |
| 2008/0033240 A1 | 2/2008 | Hoffman et al. |
| 2008/0039867 A1 | 2/2008 | Feussner et al. |
| 2009/0157076 A1 | 6/2009 | Athas et al. |
| 2010/0076310 A1 | 3/2010 | Wenderow et al. |
| 2010/0298636 A1 | 11/2010 | Castro et al. |
| 2010/0298839 A1 | 11/2010 | Castro |
| 2011/0060183 A1 | 3/2011 | Castro et al. |
| 2011/0066173 A1 | 3/2011 | Williams et al. |
| 2011/0092963 A1 | 4/2011 | Castro |
| 2011/0118545 A1 | 5/2011 | Williams et al. |
| 2011/0184231 A1 | 7/2011 | Page et al. |
| 2011/0196418 A1 | 8/2011 | Castro |
| 2011/0230723 A1 | 9/2011 | Castro et al. |
| 2011/0251599 A1 | 10/2011 | Shellenberger et al. |
| 2012/0143084 A1 | 6/2012 | Shoham |
| 2012/0265214 A1 | 10/2012 | Bender et al. |
| 2013/0041372 A1 | 2/2013 | Welt et al. |
| 2013/0253313 A1 | 9/2013 | Kang et al. |
| 2013/0281924 A1 | 10/2013 | Shellenberger |
| 2014/0052154 A1 | 2/2014 | Griffiths et al. |
| 2014/0222020 A1 | 8/2014 | Bender et al. |
| 2014/0222023 A1* | 8/2014 | Kim ............... A61B 34/30 606/130 |
| 2014/0276667 A1 | 9/2014 | Shellenberger et al. |
| 2014/0276950 A1 | 9/2014 | Smaby et al. |
| 2014/0314538 A1 | 10/2014 | Carter et al. |
| 2015/0001273 A1 | 1/2015 | Amid et al. |
| 2015/0066050 A1 | 3/2015 | Jardine et al. |
| 2015/0100066 A1 | 4/2015 | Kostrzewski et al. |
| 2015/0105629 A1 | 4/2015 | Williams et al. |
| 2015/0133960 A1* | 5/2015 | Lohmeier ............ A61B 90/40 606/130 |
| 2015/0238181 A1 | 8/2015 | Sanders et al. |
| 2016/0058513 A1 | 3/2016 | Giorgi |
| 2016/0089212 A1 | 3/2016 | Balicki et al. |
| 2016/0235496 A1 | 8/2016 | Hoffman et al. |
| 2016/0271385 A1 | 9/2016 | Sterlina et al. |
| 2016/0361125 A1 | 12/2016 | Balicki et al. |
| 2017/0014018 A1 | 1/2017 | Cash |
| 2017/0027654 A1 | 2/2017 | Frimer et al. |
| 2017/0119480 A9 | 5/2017 | Sholev et al. |
| 2017/0165019 A1 | 6/2017 | Penny et al. |
| 2017/0212723 A1 | 7/2017 | Atarot et al. |
| 2017/0304007 A1 | 10/2017 | Piron et al. |
| 2018/0042680 A1 | 2/2018 | DiMaio et al. |
| 2018/0042684 A1 | 2/2018 | Kostrzewski et al. |
| 2018/0214221 A1 | 8/2018 | Crawford et al. |
| 2018/0296284 A1 | 10/2018 | Miller et al. |
| 2018/0297206 A1 | 10/2018 | Larkin et al. |
| 2018/0325604 A1 | 11/2018 | Atarot et al. |
| 2018/0368930 A1 | 12/2018 | Esterberg et al. |
| 2019/0008598 A1 | 1/2019 | Frimer et al. |
| 2019/0022857 A1 | 1/2019 | Conus et al. |
| 2019/0060019 A1 | 2/2019 | Maret |
| 2019/0069962 A1 | 3/2019 | Tabandeh et al. |

(56) References Cited

U.S. PATENT DOCUMENTS

| | | |
|---|---|---|
| 2019/0133699 A1 | 5/2019 | Pomati |
| 2019/0159848 A1 | 5/2019 | Quaid et al. |
| 2019/0199915 A1 | 6/2019 | Coiseur |
| 2019/0231456 A1 | 8/2019 | Ruiz Morales et al. |
| 2019/0239968 A1 | 8/2019 | Beira |
| 2019/0254757 A1 | 8/2019 | Piron et al. |
| 2019/0269390 A1 | 9/2019 | Frimer et al. |
| 2019/0282323 A1 | 9/2019 | Petrucci et al. |
| 2019/0328475 A1 | 10/2019 | Arai et al. |
| 2019/0365481 A1 | 12/2019 | Otto et al. |
| 2019/0374293 A1 | 12/2019 | Larkin et al. |
| 2020/0030040 A1 | 1/2020 | Kostrzewski et al. |
| 2020/0038124 A1 | 2/2020 | Lin et al. |
| 2020/0038126 A1 | 2/2020 | Cau |
| 2020/0039085 A1 | 2/2020 | Yen et al. |
| 2020/0039086 A1 | 2/2020 | Meyer et al. |
| 2020/0046394 A1 | 2/2020 | Cau |
| 2020/0046439 A1 | 2/2020 | Tekiela et al. |
| 2020/0054401 A1 | 2/2020 | Yu et al. |
| 2020/0121404 A1 | 4/2020 | Morard et al. |
| 2020/0155244 A1 | 5/2020 | Sevimli et al. |
| 2020/0156259 A1 | 5/2020 | Ruiz Morales et al. |
| 2020/0167930 A1 | 5/2020 | Wang et al. |
| 2020/0187928 A1 | 6/2020 | Couture |
| 2020/0222138 A1 | 7/2020 | Diolaiti |
| 2020/0237448 A1 | 7/2020 | Kostrzewski et al. |
| 2020/0253678 A1 | 8/2020 | Hulford et al. |
| 2020/0254757 A1 | 8/2020 | Oya et al. |
| 2020/0268460 A1 | 8/2020 | Tse et al. |
| 2020/0268464 A1 | 8/2020 | Beira |
| 2020/0268472 A1 | 8/2020 | Wolf et al. |
| 2020/0279394 A1 | 9/2020 | Hong et al. |
| 2020/0281667 A1 | 9/2020 | Blondel et al. |
| 2020/0305984 A1 | 10/2020 | Zhao et al. |
| 2020/0322526 A1 | 10/2020 | Lilagan et al. |
| 2020/0324408 A1 | 10/2020 | Bourlion et al. |
| 2020/0383736 A1 | 12/2020 | Frimer et al. |
| 2020/0397515 A1 | 12/2020 | Frimer et al. |
| 2020/0397520 A1 | 12/2020 | Penny et al. |
| 2020/0405375 A1 | 12/2020 | Shelton, IV et al. |
| 2020/0405414 A1 | 12/2020 | Shelton, IV et al. |
| 2021/0000554 A1 | 1/2021 | Penny et al. |
| 2021/0038313 A1 | 2/2021 | Sholev et al. |
| 2021/0039262 A1 | 2/2021 | Maillet et al. |
| 2021/0106348 A1 | 4/2021 | Beira |
| 2021/0137624 A1 | 5/2021 | Maret |
| 2021/0228289 A1 | 7/2021 | Rohr Daniel et al. |
| 2021/0282862 A1 | 9/2021 | Bourlion et al. |
| 2021/0307737 A1 | 10/2021 | Beira |
| 2021/0307848 A1 | 10/2021 | Kostrzewski |
| 2021/0315645 A1 | 10/2021 | Hares et al. |
| 2021/0330408 A1 | 10/2021 | Chassot et al. |
| 2021/0369354 A1 | 12/2021 | Hares et al. |
| 2021/0405052 A1 | 12/2021 | Penny et al. |
| 2022/0000568 A1 | 1/2022 | Hufford et al. |
| 2022/0032473 A1 | 2/2022 | Maret |
| 2022/0192765 A1 | 6/2022 | Brasset et al. |
| 2023/0114137 A1 | 4/2023 | Wu et al. |

FOREIGN PATENT DOCUMENTS

| | | |
|---|---|---|
| EP | 2413819 A1 | 2/2012 |
| EP | 2760361 A1 | 8/2014 |
| EP | 2814644 A1 | 12/2014 |
| EP | 3175810 A1 | 6/2017 |
| EP | 3363401 A1 | 8/2018 |
| EP | 3366255 A1 | 8/2018 |
| EP | 3585297 B1 | 6/2020 |
| EP | 3582706 B1 | 7/2020 |
| EP | 3706656 A1 | 9/2020 |
| EP | 3538006 B1 | 4/2021 |
| FR | 3032346 A1 | 8/2016 |
| KR | 102188334 B1 | 12/2020 |
| WO | WO-02060653 A2 | 8/2002 |
| WO | WO-2006124390 A2 | 11/2006 |
| WO | WO-2016124752 A2 | 8/2016 |
| WO | WO-2019092372 A1 | 5/2019 |
| WO | WO-2021011533 A1 | 1/2021 |

OTHER PUBLICATIONS

EP Partial Search Report dated Jun. 17, 2022 in EP Patent Application Serial No. 22305572.4.

Extended EP Search Report dated Apr. 21, 2022 in EP Patent Application Serial No. 21305929.8.

Extended EP Search Report dated Sep. 29, 2021 in EP Patent Application Serial No. 21305417.4.

International Search Report & Written Opinion dated Jul. 25, 2022 in Int'l PCT Patent Appl. Serial No. PCT/IB2022/052989.

Lefkovich, Charlotte, "The Use of Predicates in FDA Regulation of Medical Devices: A Case Study of Robotic Surgical Devices," Thesis. Rochester Institute of Technology (2018).

Partial EP Search Report dated Jan. 12, 2022 in EP Patent Application Serial No. 21305929.8.

Extended EP Search Report dated Jun. 13, 2022 in EP Patent Application Serial No. 21306904.0.

Extended EP Search Report dated Jun. 14, 2022 in EP Patent Application Serial No. 21306905.7.

Extended EP Search Report dated Sep. 19, 2022 in EP Patent Application Serial No. 22305572.4.

International Search Report & Written Opinion dated Feb. 9, 2023 in Int'l PCT Patent Appl. Serial No. PCT/IB2022/056159.

International Search Report & Written Opinion dated Aug. 8, 2023 in Int'l PCT Patent Appl. Serial No. PCT/IB2023/053972.

\* cited by examiner

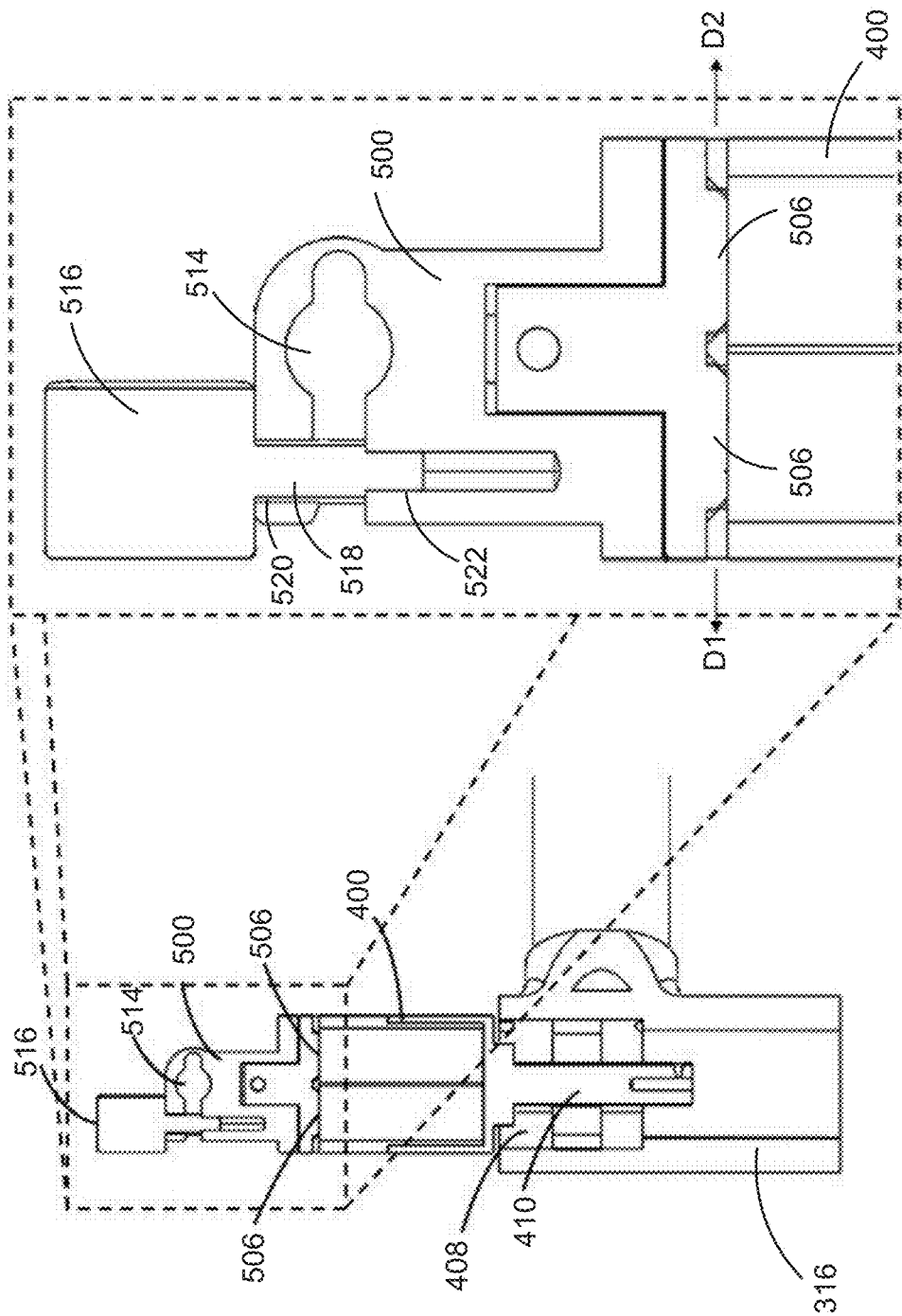

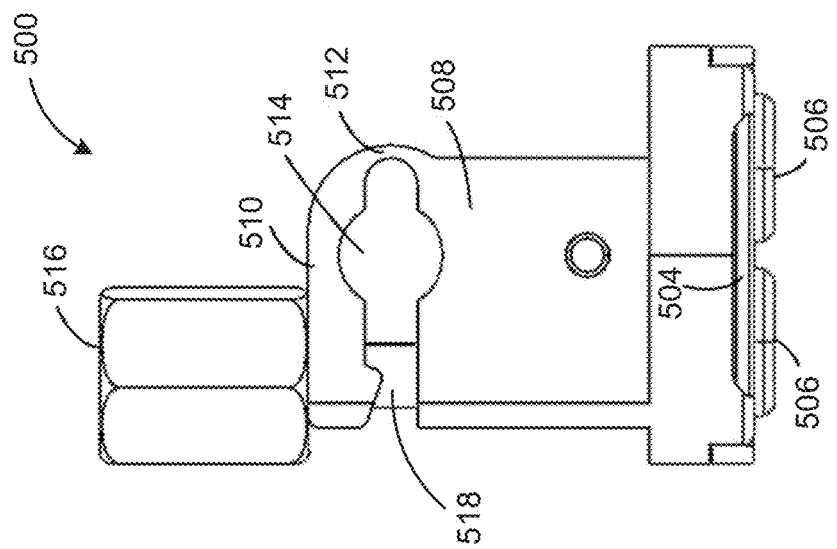
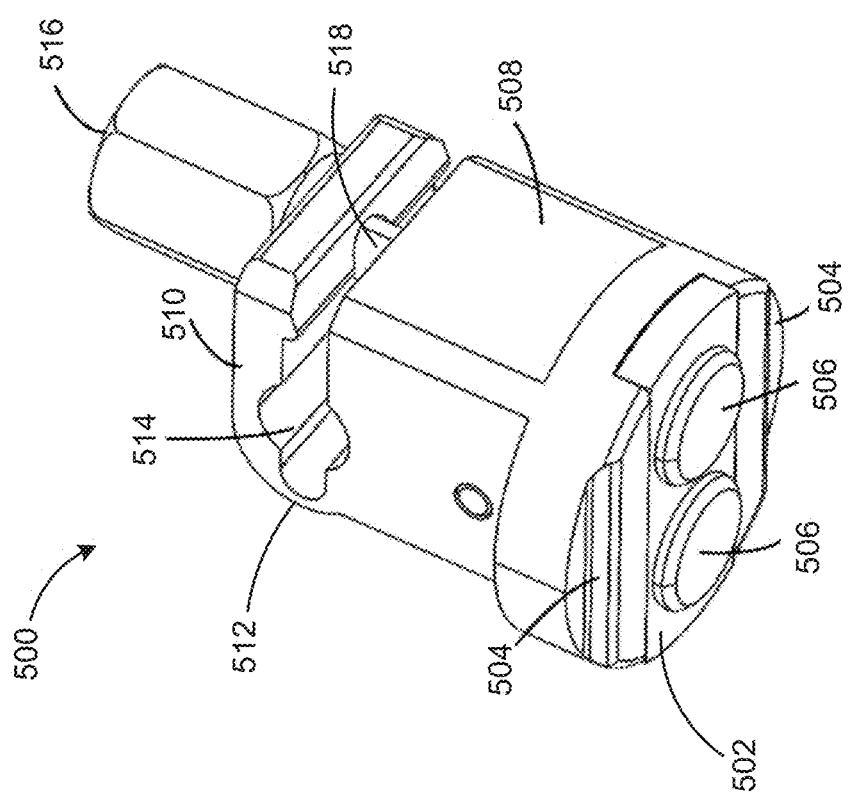
FIG. 5B
FIG. 5A

| Instrument Type | Optional Predefined Threshold Release Force | Optional Viscosity Level | Optional Threshold Dwell Time | Optional Dwell Speed |
|---|---|---|---|---|
| Scope (e.g., without limitation, 5mm or 10mm) | Medium (e.g., without limitation, 7 N, or approximately 7 N) | Variable* | Low (0.25 second) | Medium (5 mm/second or approximately 5 mm/second) |
| Tissue manipulation instruments (e.g., without limitation, grasper/retractor) | Variable due to potential for external forces on surgical instrument from tissue (e.g., without limitation, 7 N or approximately 7 N to 15 N or approximately 15 N) | Low (0 N) | Low (0.25 second) | Medium (5 mm/second or approximately 5 mm/second) |
| Suturing instruments (e.g., without limitation, needle driver) | Medium (e.g., without limitation, 7 N, or approximately 7 N) | Variable* | Low (0.25 second) | Low (1 mm/second or approximately 1 mm/second) |
| High force instruments (e.g., without limitation, stapler/clip applier) | High (e.g., without limitation, 10 N, or approximately 10 N) | Variable* | Low (0.25 second) | Low (1 mm/second or approximately 1 mm/second) |

FIG. 19

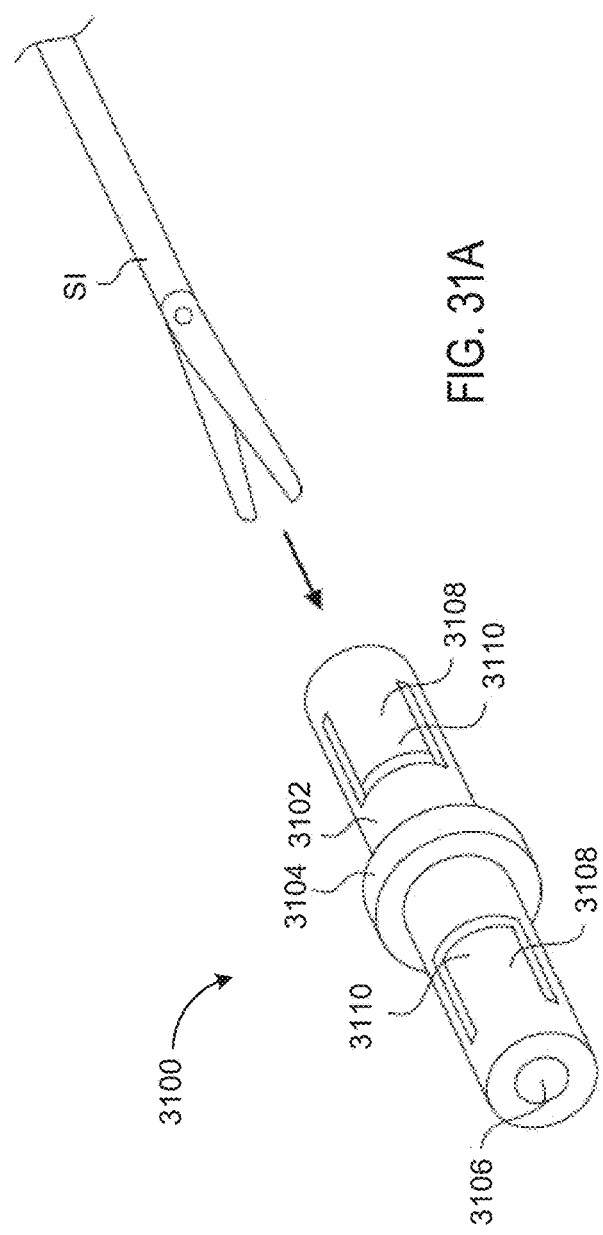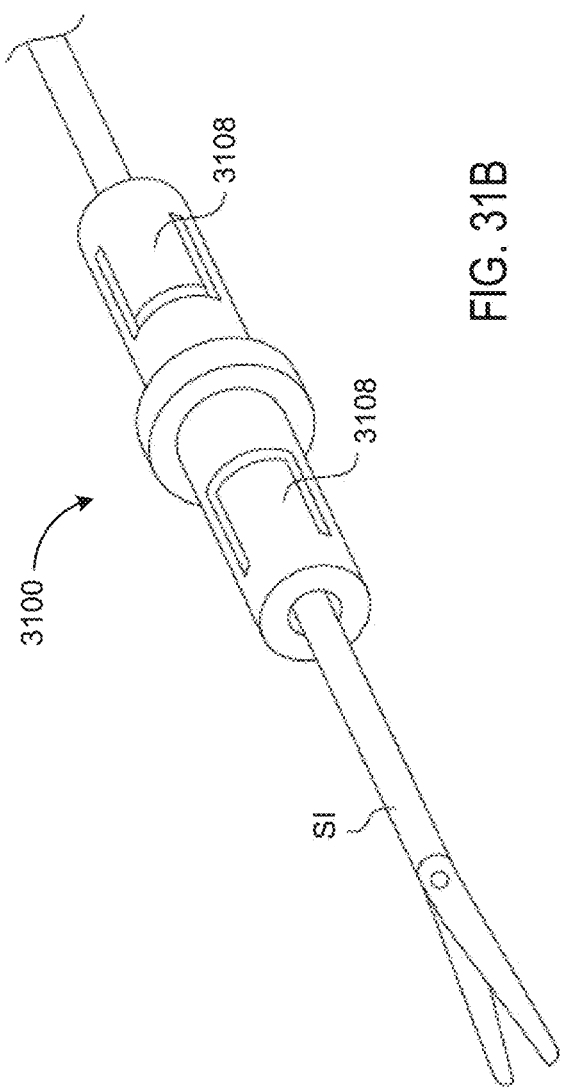
FIG. 31A
FIG. 31B

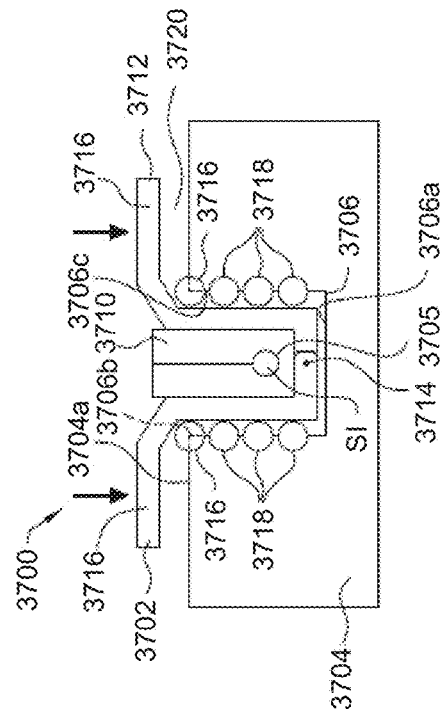
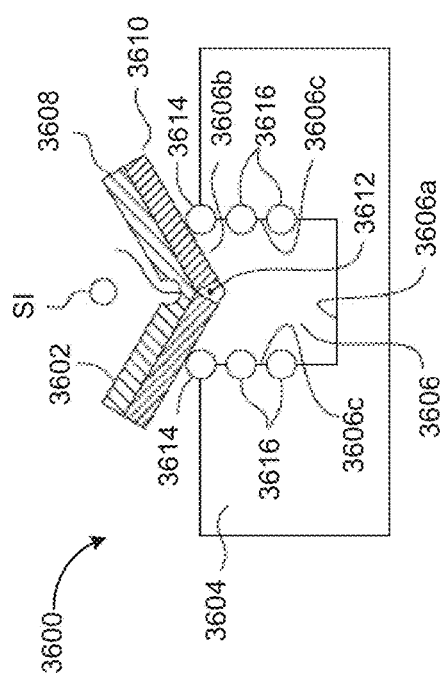
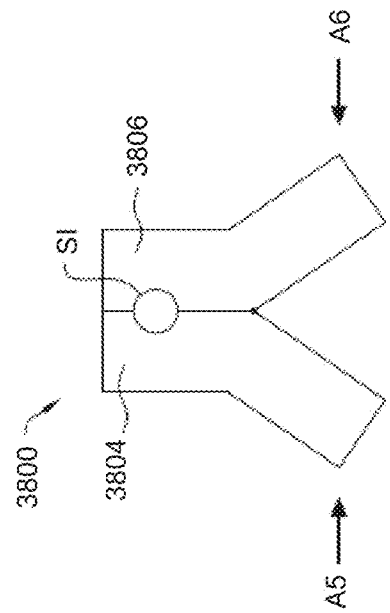
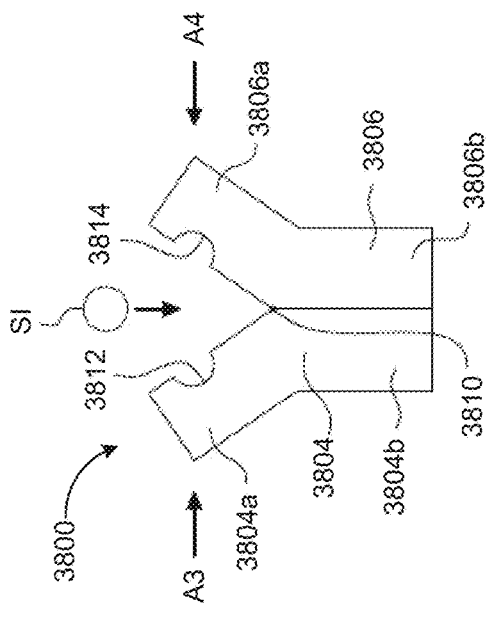

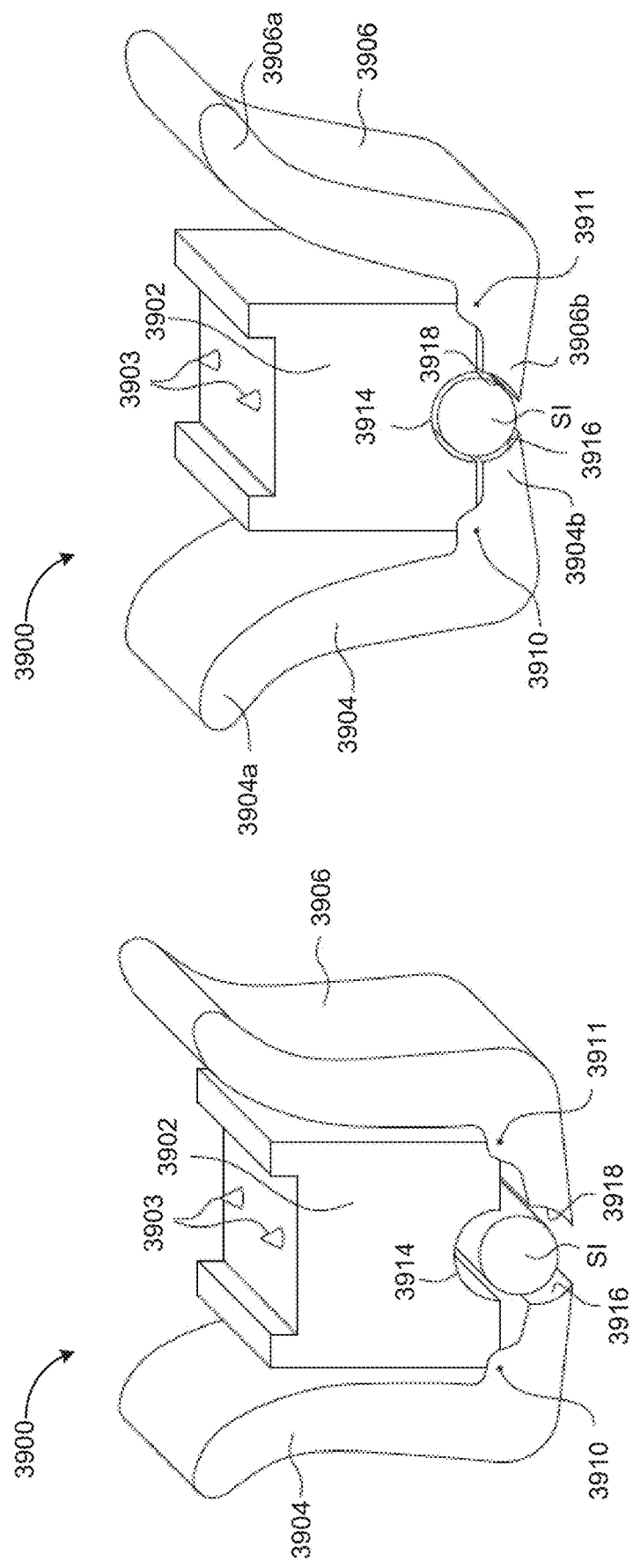

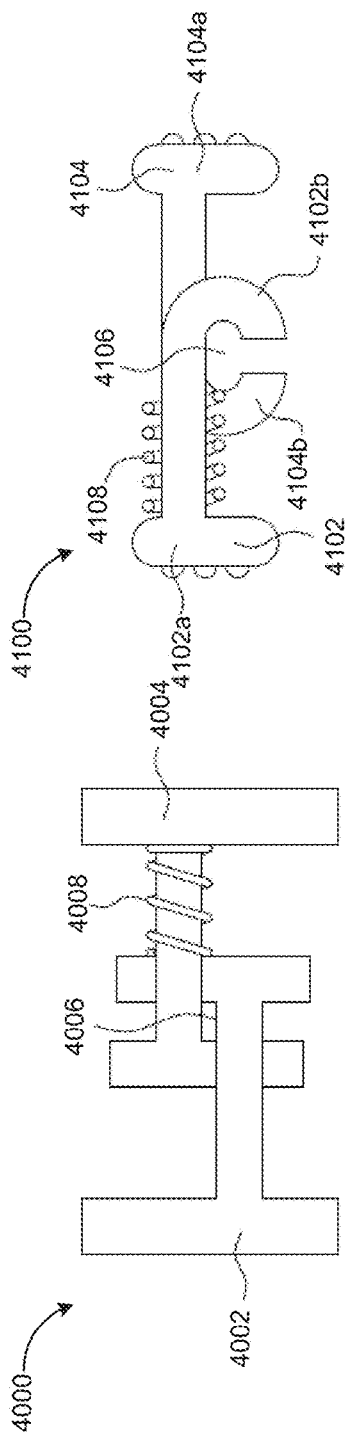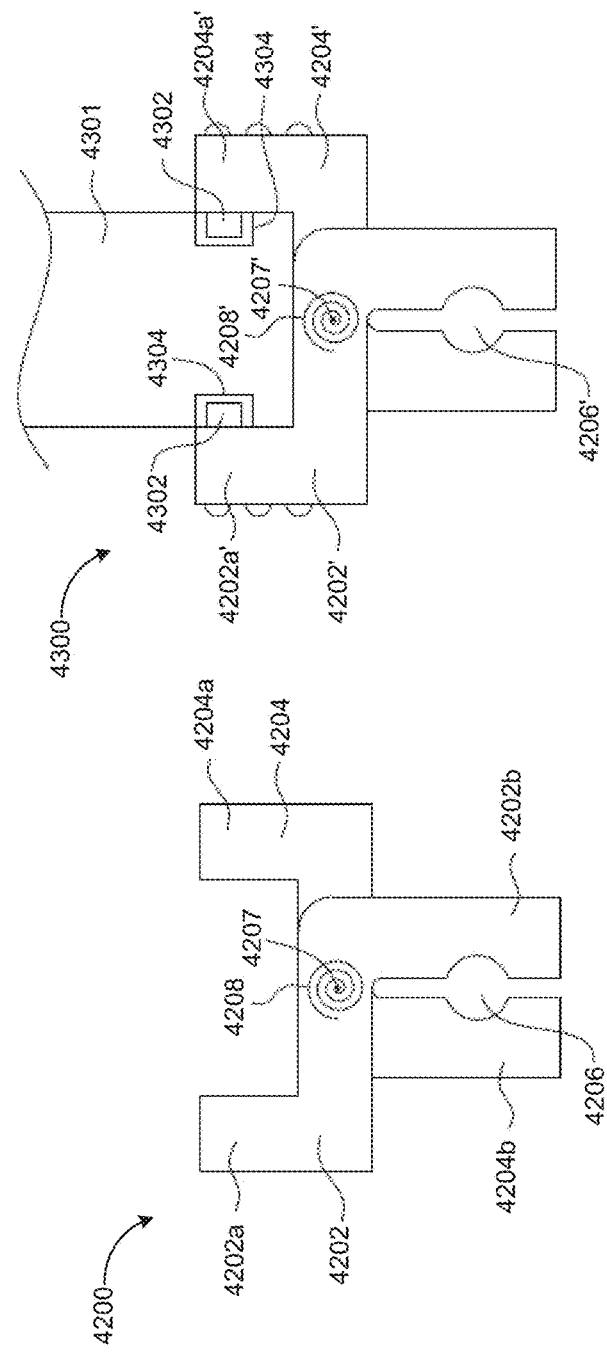

SELF-CALIBRATING CO-MANIPULATION SURGICAL SYSTEM FOR USE WITH SURGICAL INSTRUMENT FOR PERFORMING LAPAROSCOPIC SURGERY

CROSS-REFERENCE TO RELATED APPLICATION

This application is a continuation application of PCT Patent Appl. No. PCT/IB2022/052989, filed Mar. 30, 2022, which claims priority to EP Patent Appl. No. 21306904.0, filed Dec. 22, 2021, EP Patent Appl. No. 21306905.7, filed Dec. 22, 2021, EP Patent Appl. No. 21305929.8, filed Jul. 5, 2021, and EP Patent Appl. No. 21305417.4, filed Mar. 31, 2021, the entire contents of each of which are incorporated herein by reference.

FIELD OF USE

The present disclosure is directed to co-manipulation robotic systems for assisting with laparoscopic surgical procedures.

BACKGROUND

Managing vision and access during a laparoscopic procedure is a challenge. The surgical assistant paradigm is inherently imperfect, as the assistant is being asked to anticipate and see with the surgeon's eyes, without standing where the surgeon stands, and similarly to anticipate and adjust how the surgeon wants the tissue of interest exposed, throughout the procedure. For example, during a laparoscopic procedure, one assistant may be required to hold a retractor device to expose tissue for the surgeon, while another assistant may be required to hold a laparoscope device to provide a field of view of the surgical space within the patient to the surgeon during the procedure, either one of which may be required to hold the respective tools in an impractical position, e.g., from between the arms of the surgeon while the surgeon is actively operating additional surgical instruments.

Various attempts have been made at solving this issue. For example, a rail-mounted orthopedic retractor, which is a purely mechanical device that is mounted to the patient bed/table, may be used to hold a laparoscope device in position during a laparoscopic procedure, and another rail-mounted orthopedic retractor may be used to hold a retractor device in position during the laparoscopic procedure. However, the rail-mounted orthopedic retractor requires extensive manual interaction to unlock, reposition, and lock the tool in position.

Complex robot-assisted systems such as the Da Vinci Surgical System (made available by Intuitive Surgical, Sunnyvale, California) have been used by surgeons to enhance laparoscopic surgical procedures by permitting the surgeon to tele-operatively perform the procedure from a surgeon console remote from the patient console holding the surgical instruments. Such complex robot-assisted systems are very expensive, and have a very large footprint and take up a lot of space in the operating room. Moreover, such robot-assisted systems typically require unique system-specific surgical instruments that are compatible with the system, and thus surgeons may not use standard off-the-shelf surgical instruments that they are used to. As such, the surgeon is required to learn an entirely different way of performing the laparoscopic procedure.

In view of the foregoing drawbacks of previously known systems and methods, there exists a need for a system that provides the surgeon with the ability to seamlessly position and manipulate various surgical instruments as needed, thus avoiding the workflow limitations inherent to both human and mechanical solutions.

SUMMARY

The present disclosure overcomes the drawbacks of previously-known systems and methods by providing a co-manipulation surgical system to assist with laparoscopic surgery performed using a surgical instrument having a handle, an operating end, and an elongated shaft therebetween. The co-manipulation surgical system may include a robot arm having a proximal end, a distal end that may be removably coupled to the surgical instrument, a plurality of links, and a plurality of joints between the proximal end and the distal end. The co-manipulation surgical system further may include a controller operatively coupled the robot arm. The controller may be programmed to cause the robot arm to automatically switch between: a passive mode responsive to determining that movement of the robot arm due to movement at the handle of the surgical instrument is less than a predetermined amount for at least a predetermined dwell time period, wherein the controller may be programmed to cause the robot arm to maintain a static position in the passive mode; and a co-manipulation mode responsive to determining that force applied at the robot arm due to force applied at the handle of the surgical instrument exceeds a predetermined threshold, wherein the controller may be programmed to permit the robot arm to be freely moveable in the co-manipulation mode responsive to movement at the handle of the surgical instrument for performing laparoscopic surgery using the surgical instrument, and wherein the controller may be programmed to apply a first impedance to the robot arm in the co-manipulation mode to account for weight of the surgical instrument and the robot arm. The controller further may be programmed to cause the robot arm to automatically switch to a haptic mode responsive to determining that at least a portion of the robot arm is outside a predefined haptic barrier, wherein the controller may be programmed to apply a second impedance to the robot arm in the haptic mode greater than the first impedance, thereby making movement of the robot arm responsive to movement at the handle of the surgical instrument more viscous in the haptic mode than in the co-manipulation mode In addition, the co-manipulation surgical system may include a base rotatably coupled to the proximal end of the robot arm, such that the robot arm may move relative to the base. For example, the base may be rotatable about a first axis, such that rotation of the base causes rotation of the robot arm about the first axis. Accordingly, the system further may include a first motor disposed within the base and operatively coupled to the base, such that the controller is operatively coupled to the first motor and programmed to cause the first motor to apply impedance to the base. Moreover, a proximal end of a shoulder link of the plurality of links may be rotatably coupled to the base at a shoulder joint of the plurality of joints, such that rotation of the shoulder link causes rotation of links of the plurality of links distal to the shoulder link about a second axis of the shoulder joint. Accordingly, the system further may include a second motor disposed within the base and operatively coupled to the shoulder joint, such that the controller is operatively coupled to the second motor and programmed to cause the second motor to apply impedance to the shoulder joint. For example, the second axis may be perpendicular to the first axis.

Further, a proximal end of an elbow link of the plurality of links may rotatably coupled to a distal end of the shoulder link at an elbow joint of the plurality of joints, such that rotation of the elbow link causes rotation of links of the plurality of links distal to the elbow link about a third axis of the elbow joint. Accordingly, the system further may include a third motor disposed within the base and operatively coupled to the elbow joint, such that the controller is operatively coupled to the third motor and programmed to cause the third motor to apply impedance to the elbow joint. The shoulder link may include a proximal shoulder link rotatably coupled to the base and a distal shoulder link rotatably coupled to the elbow link. The distal shoulder link may be rotatable relative to the proximal shoulder link, such that rotation of the distal shoulder link relative to the proximal shoulder link causes rotation of links of the plurality of links distal to the distal shoulder link to rotate about a fourth axis parallel to a longitudinal axis of the shoulder link.

The system further may include an actuator that may be actuated to permit rotation of the distal shoulder link relative to the proximal shoulder link, wherein, in an unactuated state, the actuator prevents rotation of the distal shoulder link relative to the proximal shoulder link. In addition, a proximal end of a wrist link of the plurality of links may be rotatably coupled to a distal end of the elbow link at a proximal wrist joint of the plurality of joints, such that the wrist link may be rotated relative to the elbow link about a fifth axis of the proximal wrist joint. The system further may include an actuator that may be actuated to permit rotation of the wrist link relative to the elbow link, wherein, in an unactuated state, the actuator prevents rotation of the wrist link relative to the elbow link. The wrist link may include a proximal wrist link rotatably coupled to the distal end of the elbow link, a middle wrist link rotatably coupled to proximal wrist link about a sixth axis, and a distal wrist link rotatably coupled to the middle wrist link about a seventh axis. The distal wrist link may be removably coupled to the surgical instrument.

The system further may include a platform coupled to the base. The platform may permit vertical and horizontal movement of the base relative to the platform, to thereby cause vertical and horizontal movement of the robot arm relative to the platform. The platform may include a plurality of wheels that may permit mobility of the platform, the plurality wheels having a brake mechanism that may be actuated to prevent mobility of the platform. Moreover, the controller may be programmed to receive information associated with the surgical instrument coupled to the distal end of the robot arm, the information including at least one of instrument type, weight, center of mass, length, or instrument shaft diameter.

The system further may include a database having information associated with a plurality of surgical instruments, wherein the controller is programmed to access the database to retrieve the information associated with the surgical instrument coupled to the distal end of the robot arm. In addition, the system may include an optical scanner that may measure depth data, such that the controller is programmed to identify the surgical instrument coupled to the distal end of the robot arm based on the measured depth data. Moreover, the controller may be programmed to be calibrated to the surgical instrument when the surgical instrument is coupled to the distal end of the robot arm.

The system further may include a base housing at the proximal end of the robot arm, and motors for controlling the robot arm, such that all the motors for the robot arm are disposed within the base housing. For example, the system further may include a base rotatably coupled to the proximal end of the robot arm, such that the robot arm may move relative to the base, and a plurality of motors disposed within the base that are operatively coupled to at least some joints of the plurality of joints, such that wherein the controller is operatively coupled to the plurality of motors and programmed to measure current of the plurality of motors.

The controller further may be programmed to calculate a force applied to the distal end of the robot arm based on the measured current of the plurality of motors. Moreover, the controller may be programmed to determine a point of entry of the surgical instrument into a patient in real-time based on a longitudinal axis of the surgical instrument when the surgical instrument is coupled to the distal end of the robot arm. For example, the controller may be programmed to determine the point of entry of the surgical instrument into the patient in real-time by determining a point of intersection of a plurality of virtual lines parallel to the longitudinal axis of the surgical instrument as the surgical instrument moves relative to the point of entry. In addition, the controller may be programmed to calculate a force applied to the operating end of the surgical instrument based on the force applied to the distal end of the robot arm, the length of the surgical instrument, the center of mass of the surgical instrument, and the point of entry. Additionally, the controller may be programmed to calculate a force applied to the patient at the point of entry of the surgical instrument into the patient based on the force applied to the distal end of the robot arm, the center of mass of the surgical instrument, and the point of entry. The controller further may be programmed to detect a fault condition of the co-manipulation surgical system, and wherein, if a major fault condition is detected, the controller may cause actuation of brakes of the plurality of motors. Moreover, the controller may be programmed to apply a third impedance to the robot arm to resist movement of the robot arm if the force applied to the distal end of the robot arm exceeds a predetermined force threshold within a predetermined time period.

The system further may include a plurality of encoders disposed on at least some joints of the plurality of joints, wherein the plurality of encoders may measure angulation of corresponding links of the plurality of links at the at least some joints, such that the controller may be programmed to determine a position of the distal end of the robot arm in 3D space based on the angulation measurements by the plurality of encoders. In addition, the system may include one or more indicators disposed on at least one link of the plurality of links of the robot arm, wherein the one or more indictors may illuminate a plurality of colors, each color indicative of a state of the co-manipulation surgical system. For example, a first color of the plurality of colors may indicate that the robot arm is in the passive mode, a second color of the plurality of colors may indicate that the robot arm is in the co-manipulation mode, and a third color of the plurality of colors may indicate that the robot arm is in the haptic mode. Moreover, a fourth color of the plurality of colors may indicate a fault condition of the co-manipulation surgical system is detected by the controller. Additionally, a fifth color of the plurality of colors may indicate that no surgical instrument is coupled to the distal end of the robot arm.

The predefined haptic barrier may be used to guide the surgical instrument coupled to the distal end of the robot arm to assist with the laparoscopic surgery. For example, the predefined haptic barrier may be a haptic funnel that may guide the surgical instrument coupled to the distal end of the robot arm into a trocar. The controller may be programmed to apply a third impedance to the robot arm to account for weight of the robot arm when no surgical instrument is coupled to the distal end of the robot arm. Moreover, in the passive mode, the controller may be programmed to apply a third impedance to the robot arm to account for weight of the surgical instrument, the weight of the robot arm, and a force applied to the distal end of the robot arm due to an external form applied to the surgical instrument to cause the robot arm to maintain the static position.

The system further may include a graphical user interface that may display information associated with the surgical instrument coupled to the distal end of the robot arm. The graphical user interface may permit a user to adjust at least one of: the predetermined amount of movement at the handle of the surgical instrument or the predetermined dwell time period to cause the robot arm to automatically switch to the passive mode, the predetermined threshold of force applied at the handle of the surgical instrument to cause the robot arm to automatically switch to the co-manipulation mode, a position of the predefined haptic barrier, an identity of the surgical instrument coupled to the distal end of the robot arm, a vertical height of the robot arm, or a horizontal position of the robot arm.

The system further may include a coupler body that may be removably coupled to a coupler interface disposed at the distal end of the robot arm. The coupler body may have a lumen sized and shaped to receive the elongated shaft of the surgical instrument therethrough, may transition between an open state where the elongated shaft is slidably moveable within the lumen, and a closed state where longitudinal movement of the elongated shaft relative to the coupler body is inhibited while rotational movement of the elongated shaft relative to the coupler body is permitted responsive to movement at the handle of the surgical instrument. For example, when the coupler body is coupled to the coupler interface in the closed state, the robot arm may be permitted to be freely moveable responsive to movement at the handle of the surgical instrument for performing laparoscopic surgery if the force applied at the robot arm due to force applied at the handle of the surgical instrument exceeds the predetermined threshold. In the closed state, longitudinal movement of the elongated shaft relative to the coupler body may be inhibited while rotational movement of the elongated shaft relative to the coupler body is permitted responsive to movement at the handle of the surgical instrument due to frictional forces between the lumen of the coupler body and the elongated shaft of the surgical instrument.

In addition, the coupler body may be removably coupled to the coupler interface via a magnetic connection. The controller may be programmed to determine an orientation of the surgical instrument relative to the distal end of the robot arm when the coupler body is coupled to the coupler interface based on an alignment of the magnetic connection. The system further may include a sterile drape that may be disposed between the coupler body and the coupler interface, such that the sterile drape prevents contact between the surgical instrument and the robot arm during the laparoscopic surgery. The distal end of the robot arm may be removably coupled to at least one of a laparoscope, a retractor tool, a grasper tool, or a surgical cutting tool. For example, when the distal end of the robot arm is coupled to a laparoscope, the controller may be programmed to optically track an end-effector of one or more surgical instruments within a field of view of the laparoscope, and to cause the robot arm to automatically switch to a robotic assist mode responsive to determining that the end-effector of the one or more surgical instruments are not within a predefined boundary within the field of view of the laparoscope. Moreover, the controller may be programmed to cause the robot arm to move the laparoscope to adjust the field of view of the laparoscope such that the end-effector of the one or more surgical instruments are within the predefined boundary within the field of view of the laparoscope.

The co-manipulation surgical system may not be teleoperated via user input received at a remote surgeon console. In addition, the co-manipulation surgical system may be structured such that a surgeon performing the laparoscopic surgery does not contact any portion of the co-manipulation surgical system to move the surgical instrument while performing the laparoscopic surgery. Moreover, the system may include an optical scanner, e.g., a LiDAR device, for measuring depth data. For example, the controller may be programmed to determine whether a movement applied to the surgical instrument coupled to the distal end of the robot arm is by an intended user. Additionally, the controller may be programmed to identify the surgical instrument coupled to the distal end of the robot arm based on the depth data.

In addition, the system may include a second robot arm having a proximal end, a distal end that may be removably coupled to a second surgical instrument having a handle, an operating end, and an elongated shaft therebetween, a plurality of links, and a plurality of joints between the proximal end and the distal end. Accordingly, the controller may be operatively coupled the second robot arm, and programmed to cause the second robot arm to automatically switch between: the passive mode responsive to determining that movement of the second robot arm due to movement at the handle of the second surgical instrument is less than a predetermined amount for at least a predetermined dwell time period associated with the second robot arm, wherein the controller may be programmed to cause the second robot arm to maintain a static position in the passive mode; the co-manipulation mode responsive to determining that force applied at the second robot arm due to force applied at the handle of the second surgical instrument exceeds a predetermined threshold associated with the second robot arm, wherein the controller may be programmed to permit the second robot arm to be freely moveable in the co-manipulation mode responsive to movement at the handle of the second surgical instrument for performing laparoscopic surgery using the second surgical instrument, and wherein the controller may be programmed to apply a third impedance to the second robot arm in the co-manipulation mode to account for weight of the second surgical instrument and the robot arm; and optionally the haptic mode responsive to determining that at least a portion of the second robot arm is outside the predefined haptic barrier, the controller may be programmed to apply a fourth impedance to the second robot arm in the haptic mode greater than the third impedance, thereby making movement of the second robot arm responsive to movement at the handle of the second surgical instrument more viscous in the haptic mode than in the co-manipulation mode.

In accordance with another aspect of the present disclosure, a co-manipulation robotic surgical device for manipulating an instrument is provided. The device may include a base portion, a first arm coupled with the base portion, a motor coupled with the first arm that may rotate the first arm relative to the base portion, an instrument coupled with an end portion of the first arm, and a controller that may be programmed to control the first arm according to at least two of the following operational modes: passive assistant mode; co-manipulation assistant mode; robotic assistant mode; and haptic mode. For example, in the passive assistant mode, the first arm is static. In the co-manipulation assistant mode, the first arm may be freely movable by an operator while the motor at least partially simultaneously moves the first arm to improve a position and/or orientation of the instrument coupled with the end portion of the first arm and/or to compensate at least for a force of gravity on the first arm and the instrument that is coupled with the end portion of the first arm. In the robotic assistant mode, the motor may move the first arm to reposition the instrument coupled with the end portion of the first arm. In the haptic mode, the first arm may be movable by an operator while the motor compensates at least for a force of gravity on the first arm and/or the instrument that is coupled with the end portion of the first arm and at least guides the instrument along a predefined trajectory, prevents unwanted movements of the first arm and/or the instrument coupled with the end portion of the first arm, prevents a movement of the first arm outside of a particular space, and/or prevents a movement of the first arm into a particular space.

In one embodiment, the controller may be switchable between any one of at least three of the operational modes. Alternatively, the controller may be switchable between any one of the four operational modes. The co-manipulation robotic surgical device may be programmed to automatically identify the particular instrument that is coupled with the end portion of the first arm using an RFID transmitter chip, a barcode, a near field communication device, a Bluetooth transmitter, and/or a weight of the instrument that is coupled with the end portion of the first arm. Moreover, the co-manipulation robotic surgical device may be programmed to automatically change to a predetermined one of the operational modes when a particular instrument is coupled with the end portion of the first arm without any additional input from an operator. For example, the co-manipulation robotic surgical device may be programmed to change to the passive assistant mode when a particular instrument is coupled with the end portion of the first arm without any additional input from an operator.

In accordance with another aspect of the present invention, another co-manipulation surgical system to assist with laparoscopic surgery performed using a surgical instrument having a handle, an operating end, and an elongated shaft therebetween is provided. The co-manipulation surgical system may include a robot arm having a proximal end, a distal end that may be removably coupled to the surgical instrument, a plurality of links, and a plurality of joints between the proximal end and the distal end. The distal end of the robot arm may include a coupler interface. The system further may include a coupler body that may be removably coupled to the coupler interface. The coupler body may include a lumen sized and shaped to receive the elongated shaft of the surgical instrument therethrough, and may to transition between an open state where the elongated shaft is slidably moveable within the lumen, and a closed state where longitudinal movement of the elongated shaft relative to the coupler body is inhibited while rotational movement of the elongated shaft relative to the coupler body is permitted responsive to movement at the handle of the surgical instrument. For example, when the coupler body is coupled to the coupler interface in the closed state, the robot arm is permitted to be freely moveable responsive to movement at the handle of the surgical instrument for performing laparoscopic surgery.

The coupler body may be removably coupled to the coupler interface via a magnetic connection. Accordingly, the controller may be programmed to determine an orientation of the surgical instrument relative to the distal end of the robot arm when the coupler body is coupled to the coupler interface based on an alignment of the magnetic connection. The system further may include a sterile drape that may be disposed between the coupler body and the coupler interface, such that the sterile drape prevents contact between the surgical instrument and the robot arm during the laparoscopic surgery. The coupler body may be disposable after a single laparoscopic surgery.

In accordance with another aspect of the present invention, a device for coupling an instrument, e.g., a laparoscopic surgical instrument or an endoscope, to an arm of a surgical robot is provided. The device may include a body sized and shaped to selectively couple with an instrument for use in a surgical operation, and an interface that may selectively couple with the body and may be coupled with an end portion of a robotic arm. For example, the device may permit the instrument to rotate about a longitudinal axis of the instrument relative to the device, and further may inhibit longitudinal movement of the instrument relative to the device. The body may clamp around a portion of an outside surface of the instrument. For example, the body may include a first portion coupled with a second portion with a hinge, wherein the first portion may rotate about the hinge relative to the second portion so as to selectively clamp the instrument in a recess formed in the body.

In addition, the body may clamp around a portion of an outside surface of the instrument and prevent a rotational movement of the instrument relative to the body under normal operating conditions. For example, the interface may include a recess sized and shaped to removably receive the body therein. The recess of the interface may inhibit longitudinal movement of the body relative to the interface and permit rotational movement of the body relative to the interface. Moreover, the device may move between a first state in which the instrument is removable from the device and a second state in which the instrument is nonremovable from the device. The body may have one or more projections extending away from a surface of the body and the interface may have one or more depressions for receiving the one or more projections to align the body with the interface.

In accordance with yet another aspect of the present invention, a co-manipulation surgical robot system for performing a surgical procedure is provided. The system may include a first surgical robot having a base, an arm coupled with the base, and a motor coupled with the arm and that may move the arm relative to the base, as well as a controller programmed to control the arm, and an optical scanner that may collect depth data. For example, the optical scanner may collect depth data related to a position and an orientation of an instrument with respect to the co-manipulation surgical robot. The system may be programmed to use the depth data to determine if the instrument is coupled with the first surgical robot. Moreover, the system may be programmed to determine an identity of the instrument based at least in part on the depth data.

The optical scanner may collect depth data related to a position and a movement of an instrument, wherein the instrument may be freely held by a surgeon and not coupled with a surgical robot. Moreover, the optical scanner may collect depth data related to a trocar inserted into the patient. Accordingly, the system may be programmed to move the arm and/or the base of the first surgical robot if the position of the trocar changes more than a threshold amount. The system further may include a second surgical robot having a second base, a second arm coupled with the second base, a second motor coupled with the second arm and that may move the second arm relative to the second base. The optical scanner may have an accuracy of at least 5 mm at a range of 10 meters. The optical scanner further may collect depth data related to a surgeon's hand during a surgical procedure.

Moreover, the controller may be programmed to control the arm of the first surgical robot according to at least one of the following operational modes: passive assistant mode; co-manipulation assistant mode; robotic assistant mode; and haptic mode, as described above. The optical scanner may use the depth data to identify a potential inadvertent collision between the arm of the first surgical robot and a patient, a support platform supporting at least the first surgical robot, another surgical robot, and/or another object in an operating room and to warn a user of the potential inadvertent collision and/or inhibit a movement of the arm of the first surgical robot to avoid such a collision. In addition, the first surgical robot may be supported by a support platform and wherein the co-manipulation surgical robot system may be programmed to move the first surgical robot relative to the support platform based on the depth data collected by the optical scanner to optimize a position of the first surgical robot on the support platform. In addition, the optical scanner may collect depth data used to record a movement of a surgeon's hand during a surgical procedure.

In accordance with another aspect of the present invention, another co-manipulation surgical robot system for performing a surgical procedure is provided. The system may include a surgical robot having a base, an arm coupled with the base, and a motor coupled with the arm, as well as an optical scanner that may track a movement of one or more objects around a patient, and a controller programmed to collect data from the optical sensor regarding the movement of one or more objects and to move the arm of the surgical robot in response to the movement of one or more objects.

In accordance with another aspect of the present invention, a co-manipulation robotic surgical system for assisting in the manipulation of an instrument is provided. The system may include a base, an arm coupled with the base, the arm having a plurality of arm segments and a plurality of articulation joints, a plurality of motors coupled with the arm, wherein the plurality of motors may rotate the plurality of arm segments about the plurality of articulation joints, and a controller programmed to control at least the plurality of motors. For example, the arm may be movable by a user exerting a force directly on the arm and/or directly on an instrument coupled with the arm. Moreover, the system may be programmed to collect data related to a first operating characteristic of the arm and/or an instrument coupled with the arm. Additionally, the controller may be programmed to analyze the data related to the first operating characteristic to detect whether a first condition exists, and to modify a first operating parameter of the arm if the first condition is detected.

The system may be programmed to compare the data collected during a surgical procedure with historical data related to the same surgical procedure for a same user using the instrument to detect if the first condition exists. The system further may include an optical scanner, one or more sensors positioned on the arm, and/or an endoscope to collect data related to the first operating characteristic of the arm and/or an instrument coupled with the arm. The controller may be programmed to automatically change a position and/or an orientation of an imaging device supported by the arm to a preferred or optimal position and/or orientation if a position and/or an orientation of the imaging device is not the preferred or the optimal position of the camera for capturing an image of the instrument. In addition, the controller may be programmed to detect if an instrument coupled with the arm is replaced.

In addition, the system may be programmed to detect a magnitude and duration of one or more forces applied to the first robotic arm, and further to detect that the first condition exists if a change in a force applied to the arm meets or exceeds a first predetermined value over a threshold duration of time. The system further may be programmed to calculate an actual direction or an actual approximate direction that an end effector at a distal end of the arm is pointing to and a calculated direction or a calculated approximate direction that the end effector would be pointing to if an instrument were coupled with the end effector and to compare the actual direction or the actual approximate direction with the calculated direction or the calculated approximate direction and determine if the actual direction or the actual approximate direction and the calculated direction or the calculated approximate direction are different. The controller may be programmed such that, if a first instrument coupled with the arm is replaced by a second instrument, the controller updates a data file associated with the second instrument, wherein the data file associated with the second instrument includes at least a center of gravity of the second instrument and viscosity parameter of the second instrument.

In addition, the controller may be programmed to detect if a magnitude of force exerted at a distal end of an instrument coupled with the arm equals or exceeds a first value and/or if a magnitude of a force exerted on a trocar through which the instrument passes equals or exceeds a second value and to provide an alert to a user of the arm if the magnitude of force exerted at the distal end of the instrument coupled with the arm equals or exceeds the first value and/or if the magnitude of the force exerted on the trocar through which the instrument passes equals or exceeds the second value. Moreover, the controller may be programmed to detect if a dwell time of the arm and/or an instrument coupled with the arm equals or exceeds a threshold dwell time, and further to change an operational state of the arm to a static hold state if the dwell time of the arm and/or an instrument coupled with the arm equals or exceeds the threshold dwell time, wherein the dwell time is an amount of time that the arm and/or an instrument coupled with the arm is held in a static position.

In the static hold state, the system may be programmed to hold the arm in a static position and to inhibit a movement of the arm from the static position of the arm except when a force applied to the arm and/or an instrument held by the arm by a user of the system equals or exceeds a predefined threshold release force value. The arm and/or an instrument coupled with the arm may be considered to be held in a static position when the arm is not moved more than 5 mm in any direction during the dwell time. In some embodiments, the threshold dwell time may be less than one-half of a second. In addition, the controller may be programmed to detect whether a user is attempting to remove a first instrument from the arm, such that the controller may be programmed to reduce a coupling force applied by the arm to the first instrument if the controller detects that the user is attempting to remove the first instrument from the arm.

The system further may include a support platform for supporting at least the base. Accordingly, the controller may be programmed to detect whether a surgical procedure is being initiated, and to move the support platform supporting the base to an initial position and/or the arm to an initial position and/or orientation for the particular surgical procedure before the surgical procedure has started if the controller detects that a surgical procedure is being initiated.

In accordance with yet another aspect of the present invention, another co-manipulation robotic surgical system for assisting in the manipulation of an instrument is provided. The system may include a base, an arm coupled with the base, the arm having a plurality of arm segments and a plurality of articulation joints, a plurality of motors coupled with the arm, wherein the plurality of motors may rotate the plurality of arm segments about the plurality of articulation joints, and a controller programmed to control at least the plurality of motors. For example, the arm may be movable by a user exerting a force directly on the arm and/or directly on an instrument coupled with the arm. Upon an identification of a first user, the system may be programmed to automatically load a data file associated with the first user comprising at least a first operating parameter configured to modify an operating characteristic of the co-manipulation robotic surgical system. Accordingly, the controller may be programmed to control the plurality of motors according to at least the first operating parameter.

The first operating parameter of the data file associated with the first surgeon may be based at least in part on data collected during prior surgical procedures performed by the first user. Additionally, the first operating parameter of the data file associated with the first user may be based at least in part on manually entered preferences for the first user. The system may be programmed to automatically identify the first user using an optical scanner. In addition, the co-system may be programmed to automatically load the data file associated with the first user upon manual input of an identity of the first user. The data file associated with the first user may include a threshold dwell time value based on dwell time data collected from procedures performed by the first user and/or preferences manually input for the first user. Moreover, the data file associated with the first user may include a dwell speed value based on data collected from procedures performed by the first user and/or preferences manually input for the first user.

In addition, the data file associated with the first user may include a laparoscopic view parameter based on laparoscopic view data collected from procedures performed by the first user, such that the controller may be programmed to automatically change a position and/or an orientation of a laparoscope according to the laparoscopic view data collected from procedures performed by the first user. The data file associated with the first user may include a setup joint parameter based on setup joint position data collected from past procedures performed by the first user. In addition, the data file may include instrument calibration parameters based on instrument calibration values input by the first user. The first operating parameter may be based on at least one of a pose of the first user, a height of the first user, or a hand preference of the first user.

Moreover, the controller may be programmed to automatically detect when the instrument coupled with the arm is not in an optimal or preferred location based on data collected from procedures performed by the first user and to move the arm so that the instrument is in the optimal or preferred location. In addition, the system may be programmed to detect when the first user desires to change an operating mode of the system to a static hold mode even when a dwell time of the arm and/or an instrument coupled with the arm is less than a threshold dwell time. The data file may be communicable from a network database in communication with the co-manipulation surgical robot system. Additionally, the first operating parameter of the data file associated with the first user may be based at least in part on data collected during prior surgical procedures performed by a plurality of users.

BRIEF DESCRIPTION OF THE DRAWINGS

FIG. 4C is a close-up view of an exemplary surgical instrument coupling mechanism of the wrist portion of FIGS. 4A and 4B.

FIGS. 5A and 5B illustrate an exemplary surgical instrument coupler body of the surgical instrument coupling mechanism of FIG. 4C constructed in accordance with the principles of the present disclosure.

FIG. 19 is a table of example values related to some arrangements of a passive mode of the robot arm in accordance with the principles of the present disclosure.

FIGS. 30A-43 illustrate various alternative surgical instrument coupling mechanisms constructed in accordance with the principles of the present disclosure.

DETAILED DESCRIPTION

Figure 1A:
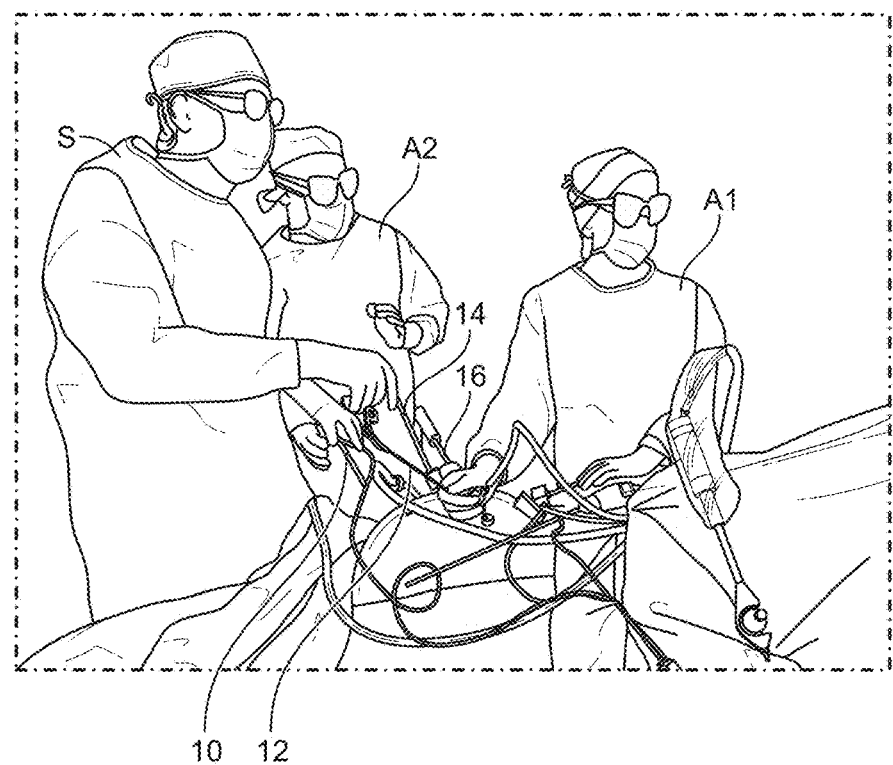
FIGS. 1A and 1B illustrate a traditional laparoscopic procedure performed by a surgeon and one or more assistants.

Disclosed herein are co-manipulation surgical robot systems for assisting an operator, e.g., a surgeon, in performing a surgical procedure, e.g., a laparoscopic procedure, and methods of use thereof. Currently, laparoscopic procedures typically require a surgeon and one or more assistants. For example, as shown in FIG. 1A, during a laparoscopic procedure assistant A1 may be required to hold retractor device 12 to expose tissue for surgeon S, while another assistant A2 may be required to hold laparoscope device 10 to provide a field of view of the surgical space within the patient to surgeon S via a display (not shown) during the procedure. As shown in FIG. 1A, assistant A2 may be required to hold laparoscope device 10 in an impractical position, e.g., from between the arms of surgeon S while the surgeon actively operates additional surgical instruments, e.g., surgical instruments 14 and 16. As further shown in FIG. 1A, surgeon S may need to let go of surgical instrument 16 in order to guide/reposition laparoscope device 10 held by assistant A2 in order to achieve the field of view desired by the surgeon.

Figure 1B:
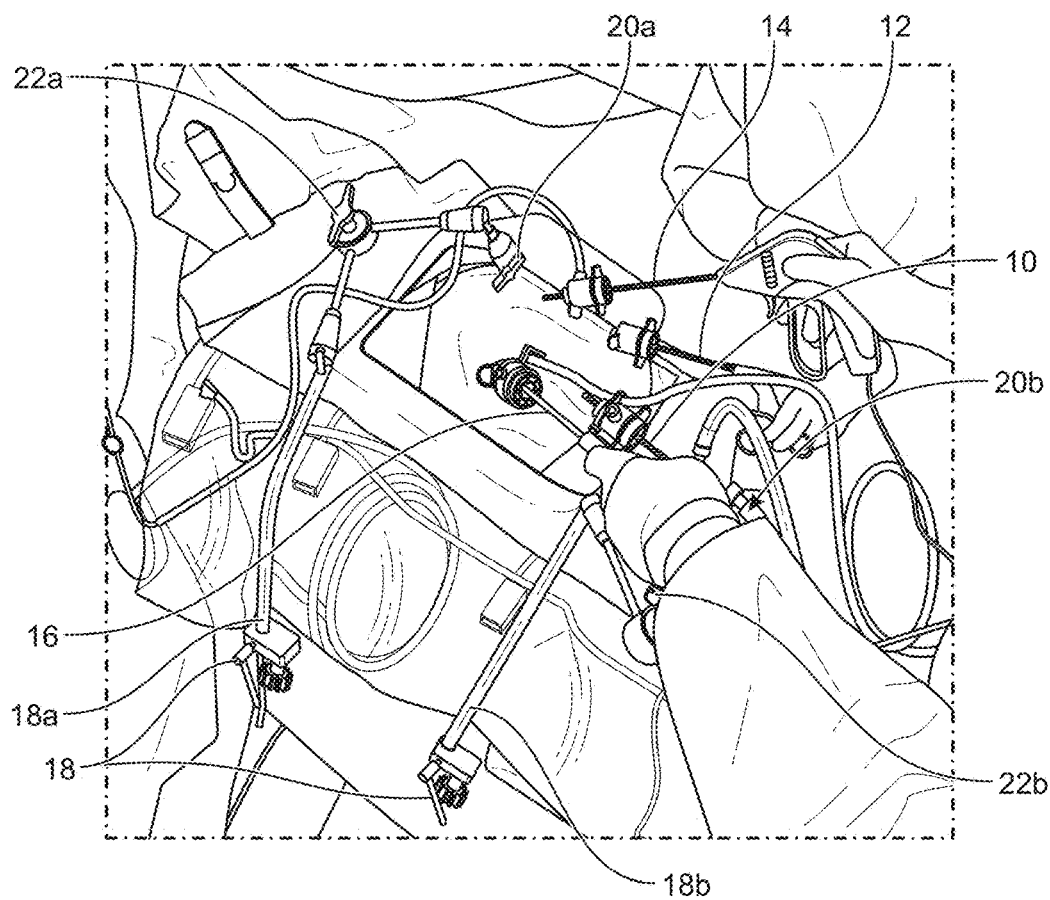

As shown in FIG. 1B, rail-mounted orthopedic retractors 18 may be used to hold one or more surgical instruments in position during the laparoscopic procedure, in attempt to free hands of the surgeon and/or assistant for other tasks, as well as for stability. As shown in FIG. 1B, first rail-mounted orthopedic retractor 18a may include retractor end 20a for engaging with and holding laparoscope device 10 in position upon actuation of lock 22a. For example, lock 22a may be disengaged such that retractor 18a may be manually positioned at a desired location relative to the patient, and re-engaged to lock retractor 18a, and accordingly laparoscopic device 10 coupled thereto, in the desired position. As shown in FIG. 1B, second rail-mounted orthopedic retractor 18b having retractor end 20b may be used during the procedure to engage with and hold another surgical instrument in position upon actuation of lock 22b. Thus, retractors 18a and 18b require extensive manual interaction with locks 22a and 22b, and with retractors 18a and 18b themselves, to reposition and lock the respective tools in position.

The co-manipulation surgical robot systems described herein provide superior control and stability such that the surgeon and/or assistant may seamlessly position various off-the-shelf surgical instruments as needed, thus avoiding the workflow limitations inherent to both human and mechanical solutions. For example, the robot arms of the co-manipulation surgical robot system may provide surgical assistance by holding a first surgical instrument, e.g., a laparoscope, via a first robot arm, and a second surgical instrument, e.g., a retractor, via a second robot arm, stable throughout the procedure to provide an optimum view of the surgical site and reduce the variability of force applied by the surgical instruments to the body wall at the trocar point. As will be understood by a person having ordinary skill in the art, the robots arms of the co-manipulation surgical robot systems described herein may hold any surgical instrument, preferably having a long and thin instrument shaft, used for surgical procedures such as laparoscopic procedures including, e.g., endoscopes/laparoscopes, retractors, graspers, surgical scissors, needle holders, needle drivers, clamps, suturing instruments, cautery tools, staplers, clip appliers, etc.

The co-manipulation surgical robot system further allows the surgeon to easily maneuver both tools when necessary, providing superior control and stability over the procedure and overall safety. Any implementations of the systems described herein enable a surgeon to directly co-manipulate instruments while remaining sterile at the patient bedside. For example, the system may include two robot arms that may be used by the surgeon to hold both a laparoscope and a retractor. During a surgical procedure, the system may seamlessly reposition either instrument to provide optimal visualization and exposure of the surgical field. Both instruments may be directly coupled to the robot arms of the system and the system may constantly monitor and record the position of the two instruments and/or the two robot arms throughout the procedure. Moreover, the system may record information such as the position and orientation of surgical instruments attached to the robot arm, sensor readings related to force(s) applied at proximal and distal ends of the surgical instruments attached to robot arms, force required to hold each instrument in position, endoscopic video streams, algorithm parameters, operating room 3D stream captured with an optical scanning device, including, e.g., position(s) of surgical entry port(s), position and movements of the surgeon's hands, surgical instrument(s) position and orientation, whether or not attached to robot arms, patient position, and patient table orientation and height.

Such data may be used to develop a database of historical data that may be used to develop the algorithms used in some implementations to control one or more aspects of an operation of the system. In addition, such data may be used during a procedure to control of one or more aspects of an operation of the system per one or more algorithms of the system. For example, the data may be used to assess a level of fatigue of a user of the system.

As the operator manipulates a robot arm of the co-manipulation surgical robot system by applying movement to the surgical instrument coupled to the robot arm, the system may automatically transition the robot arm between various operational modes upon determination of predefined conditions. For example, the system may transition the robot arm to a passive mode responsive to determining that movement of the robot arm due to movement at the handle of the surgical instrument is less than a predetermined amount for at least a predetermined dwell time period, such that in the passive mode, the robot arm maintains a static position, e.g., to prevent damage to the equipment and/or injury to the patient. Additionally, the system may transition the robot arm to a co-manipulation mode responsive to determining that force applied at the robot arm due to force applied at the handle of the surgical instrument exceeds a predetermined threshold, such that in the co-manipulation mode, the robot arm is permitted to be freely moveable responsive to movement at the handle of the surgical instrument for performing laparoscopic surgery using the surgical instrument, while a first impedance is applied to the robot arm in the co-manipulation mode to account for weight of the surgical instrument and the robot arm. Moreover, the system may transition the robot arm to a haptic mode responsive to determining that at least a portion of the robot arm is outside a predefined haptic barrier, such that in the haptic mode, a second impedance greater than the first impedance is applied to the robot arm, thereby making movement of the robot arm responsive to movement at the handle of the surgical instrument more viscous in the haptic mode than in the co-manipulation mode. The system further may transition the robot arm to a robotic assist mode responsive to detecting various conditions that warrant automated movement of the robot arm to guide the surgical instrument attached thereto, e.g., along a planned trajectory or to avoid a collision with another object or person in the surgical space.

Figure 2:
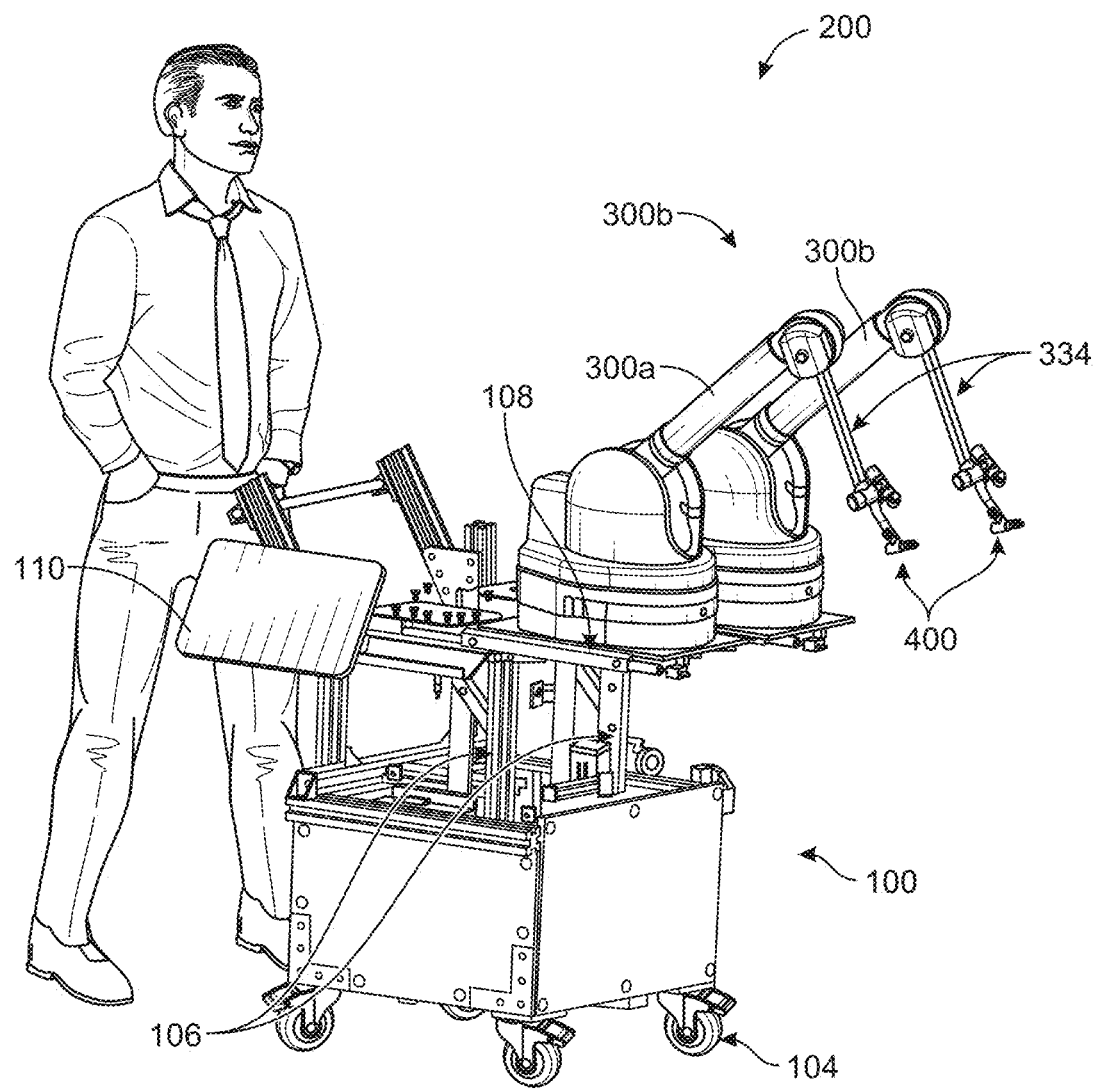
FIG. 2 illustrates an exemplary co-manipulation surgical system constructed in accordance with the principles of the present disclosure.

Referring now to FIG. 2, co-manipulation surgical robot system 200 is provided. As shown in FIG. 2, system 200 may include platform 100, e.g., a surgical cart, sized and shaped to support or more robot arms 300, e.g., robot arm 300a and robot arm 300b, each of robot arms 300 having surgical instrument coupler interface 400 for removably coupling to a surgical instrument, and a computing system operatively coupled to platform 100 and robot arms 300. As shown in FIG. 2, system 200 further may include graphical user interface display 110 for displaying operational information as well as receiving user input.

In addition, each of robot arms 300 further may include indicators 334 for visually indicating the operational mode associated with the respective robot arm in real-time. For example, indicators 334 may be positioned on at least the elbow joint of the robot arm. Additionally or alternatively, indicators 334 may be placed elsewhere on system 200, e.g., on platform 100, on display 110, etc. Moreover, indicators 334 may include lights, e.g., LED lights, that may illuminate in a variety of distinct colors and in distinct patterns, e.g., solid on or blinking. For example, each operational mode of system 200 may be associated with a uniquely colored light, such as red, yellow, blue, green, purple, white, orange, etc. Accordingly, indicators 334 may indicate a transition from one operational mode to another operational mode.

As shown in FIG. 2, platform 100 may include vertical extenders 106 for independently moving robot arm 300a and robot arm 300b vertically relative to platform 100, and horizontal extenders 108 for independently moving robot arm 300a and robot arm 300b horizontally relative to platform 100, to thereby permit the operator flexibility in positioning robot arms 300 relative to the patient. Moreover, platform 100 may include a plurality of wheels 104, e.g., castor wheels, to provide mobility of platform 100, and accordingly, robot arms 300, within the operating room. Wheels 104 may each include a braking mechanism which may be actuated to prevent movement of platform 100 via wheels 104. Accordingly, platform 100 may independently move each of robot arm 300a and robot arm 300b in any direction, including a first or vertical direction toward and away from the floor, a second or horizontal direction toward and away from the patient, and/or a third direction or horizontal direction along a length of the patient. In some embodiments, platform 100 may move robot arm 300a and robot arm 300b in the same direction simultaneously. When ready for operation, platform 100 may be moved to a desired position at the side of the patient bed and locked in place via wheels 104, and the vertical and horizontal positions of robot arms 300a and 300b may be adjusted to an optimum position relative to the patient for the procedure via vertical extenders 106 and horizontal extenders 108, responsive to user input received by graphical user interface display 110.

Surgical robot system 200 is configured for co-manipulation, such that system 200 may assist the user or operator, e.g., a surgeon and/or surgical assistant, by permitting the user to freely move robot arm 300a and/or robot arm 300b due to manipulation of one or more surgical instruments coupled with the robot arms in response to force inputs provided by the user to the surgical instruments. Accordingly, system 200 may be configured so that it is not controlled remotely, such that robot arms 300 move directly responsive to movement of the surgical instrument coupled thereto by the operator, while compensating for the mass of the surgical instrument and of the respective robot arm and providing localized impedance along the robot arm, thereby increasing the accuracy of the movements or actions of the operator as the operator manipulates the surgical instrument.

System 200 may be particularly useful in laparoscopic surgical procedures and/or other surgical procedures that utilize long and thin instruments that may be inserted, e.g., via cannulas, into the body of a patient to allow surgical intervention. As will be understood by a person having ordinary skill in the art, system 200 may be used for any desired or suitable surgical operation. Moreover, system 200 may be used in conjunction or cooperation with video monitoring provided by one or more cameras and/or one or more endoscopes so that an operator of system 200 may view and monitor the use of the instrument coupled with robot arms 300 via coupler interface 400. For example, robot arm 300a may be removeably coupled with and manipulate an endoscope, while robot arm 300b may be may be removeably coupled with and manipulate a surgical instrument.

Figure 3A:
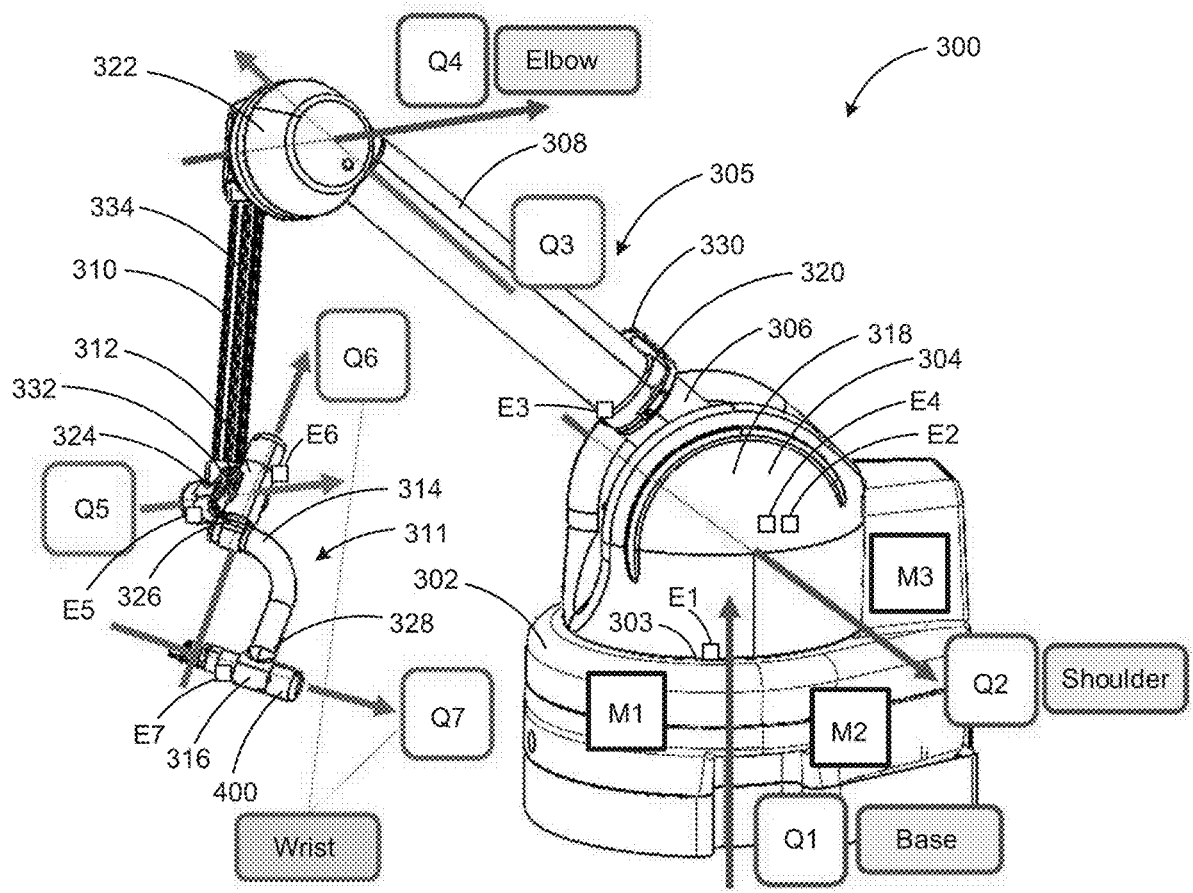
FIGS. 3A-3D illustrate an exemplary robot arm of the system of FIG. 2 constructed in accordance with the principles of the present disclosure.
Figure 3B:
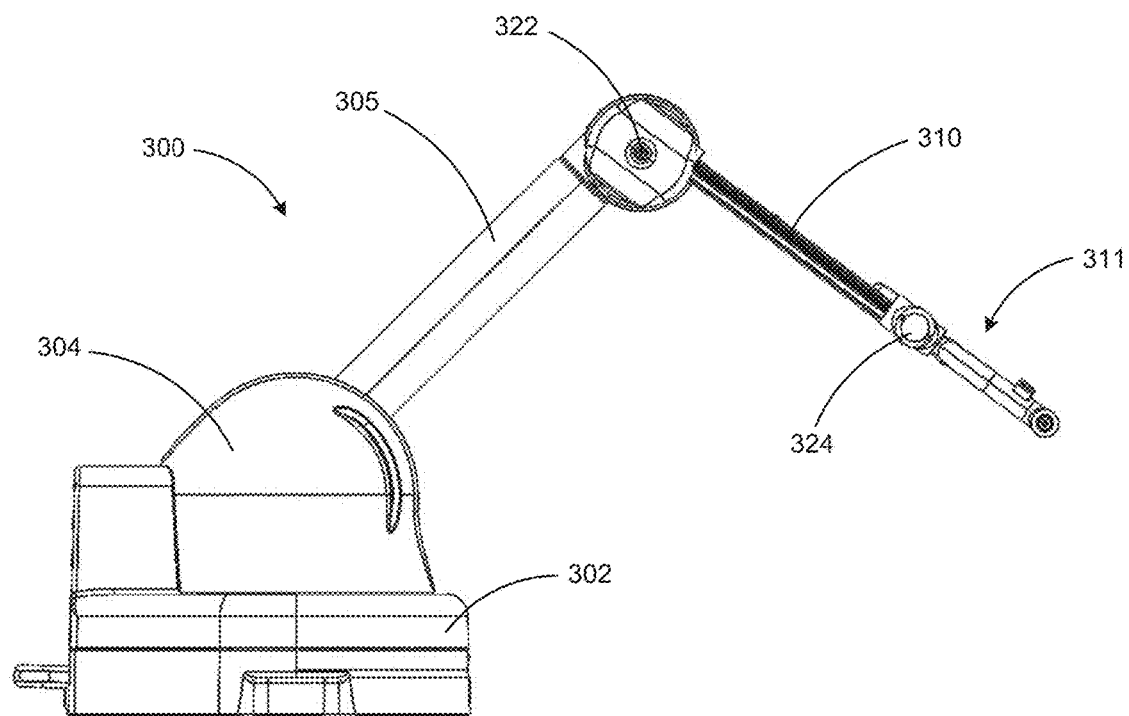
Figure 3C:
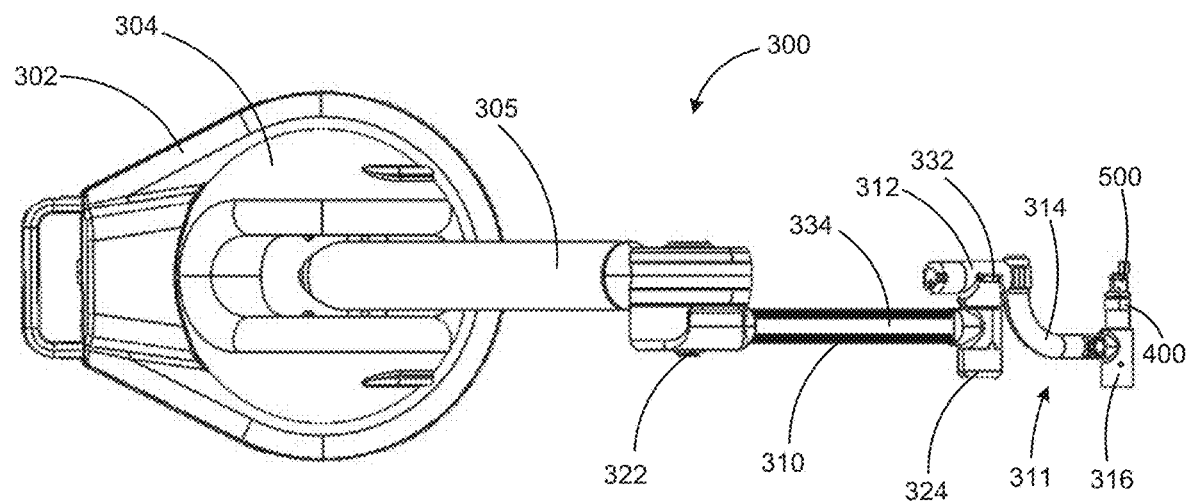
Figure 3D:
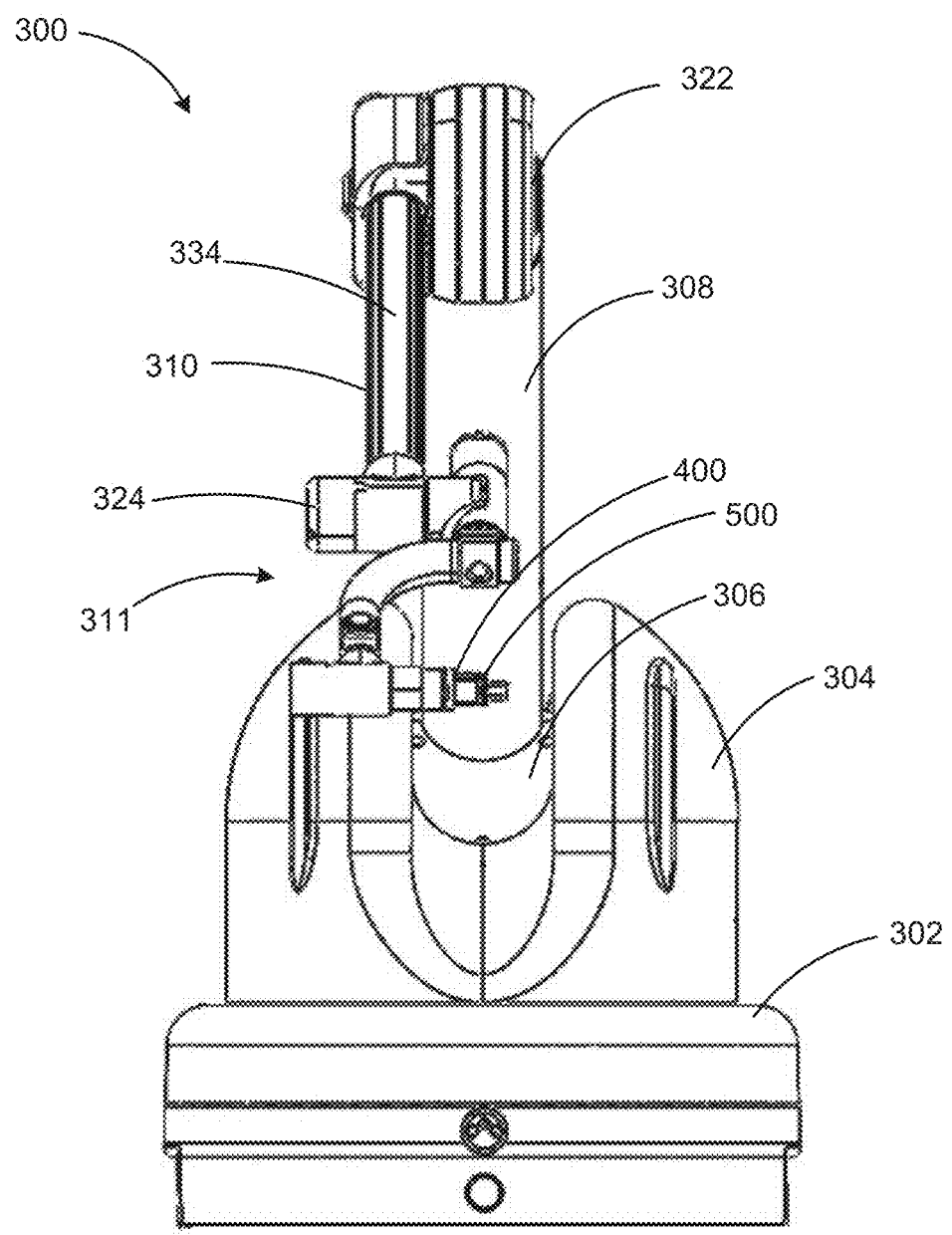

Referring now to FIGS. 3A to 3D, a surgical support arm, e.g., robot arm 300, is provided. As described above, system 200 may include a plurality of robot arms, e.g., robot arm 300a and robot arm 300b. however, as each robot arm may be constructed identically, only a single robot arm is described with regard to FIGS. 3A to 3D for brevity, collectively as robot arm 300. Aspects of the robot arms described herein may utilize structures from U.S. Pat. No. 10,118,289 to Louveau, the entire contents of which are incorporated herein by reference. Robot arm 300 may include a plurality of arm segments/links and a plurality of articulation joints 106 extending from a base portion. For example, robot arm 300 may include a base portion, a shoulder portion, an elbow portion, and a wrist portion, thereby mimicking the kinematics of a human arm. As shown in FIG. 3A, robot arm 300 may include a base, which includes base portion 302 rotatably coupled to shoulder portion 304 at base joint 303. For example, shoulder portion 304 may sit on top of base portion 302, and may be rotated relative to base portion 302 about axis Q1 at base joint 303. In some embodiments, robot arms 300 may be interchanged, swapped, or coupled with the base in any desired arrangement.

Robot arm 300 further may include shoulder link 305, which includes proximal shoulder link 306 rotatably coupled to distal shoulder link 308. A proximal end of proximal shoulder link 306 may be rotatably coupled to shoulder portion 304 of the base at shoulder joint 318, such that proximal shoulder link 306 may be rotated relative to shoulder portion 304 about axis Q2 at shoulder joint 318. As shown in FIG. 3A, axis Q2 may be perpendicular to axis Q1. The distal end of proximal shoulder link 306 may be rotatably coupled to the proximal end of distal shoulder link 308 at joint 320, such that distal shoulder link 308 may be rotated relative to proximal shoulder link 306 about axis Q3 at joint 320. As shown in FIG. 3A, axis Q3 may be parallel to the longitudinal axis of shoulder link 305. In addition, robot arm 300 may include actuator 330, e.g., a lever, button, or switch, operatively coupled to distal shoulder link 308 and/or proximal shoulder link 306, such that distal shoulder link 308 may only be rotated relative to proximal should link 306 upon actuation of actuator 330. Accordingly, axis Q3 may be a "setup" axis, such distal shoulder link 308 may be rotated and fixed relative to proximal shoulder link 306 during a setup stage prior to operating stage where robot arm 300 is used in a surgical procedure, as described in further detail with regard to FIGS. 10A to 10D.

In some embodiments, upon actuation of actuator 330, distal shoulder link 308 may be manually rotated in predefined increments relative to proximal shoulder link 306. Alternatively, upon actuation of actuator 330, distal shoulder link 308 may be automatically rotated relative to proximal shoulder link 306 until actuator 330 is released. For example, actuator 330 may be a button or switch operatively coupled to a motor operatively coupled to distal shoulder link 308 and/or proximal shoulder link 306, such that upon actuation of actuator 330, the associated motor causes distal shoulder link 308 to rotate relative to proximal shoulder link 306. Preferably, the motor is disposed within the base of robot arm 300, or alternatively, the motor may be disposed on shoulder link 305. Accordingly, actuator 330 may be a button or switch that permits dual actuation, e.g., a first actuation to cause distal shoulder link 308 to rotate in a first direction relative to shoulder link 306, and a second actuation to cause distal shoulder link 308 to rotate in a second direction opposite to the first direction. In some embodiments, the button or switch may be located on a graphical user interface such as display 110.

Figure 4B:
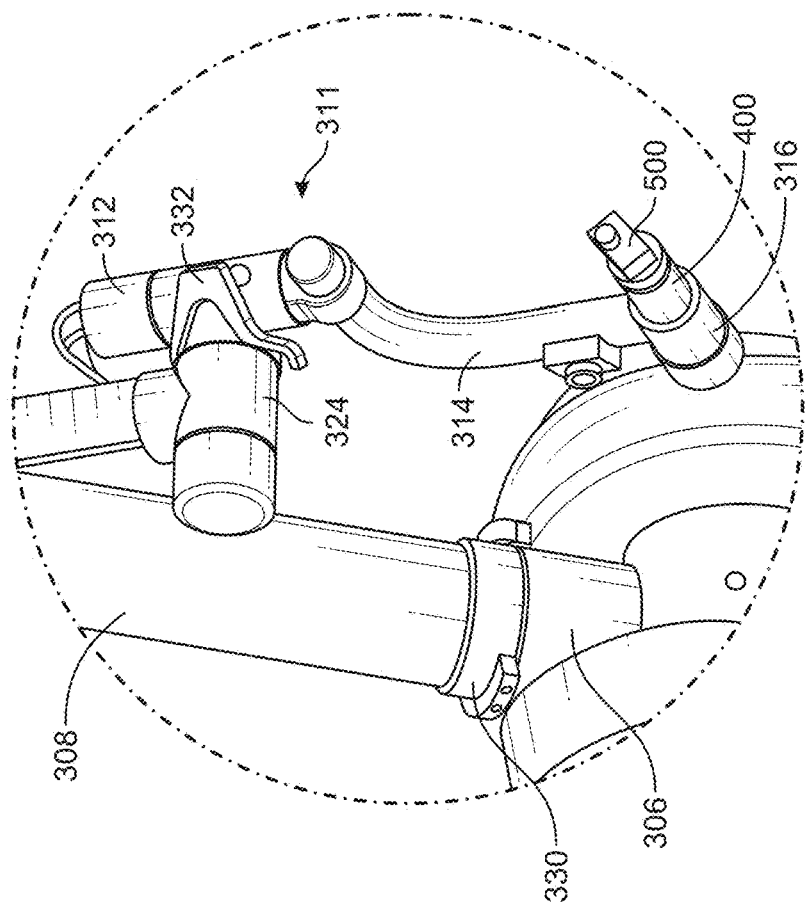
FIGS. 4A and 4B illustrate an exemplary wrist portion of the robot arm of FIGS. 3A-3D constructed in accordance with the principles of the present disclosure.

Robot arm 300 further may include elbow link 310. A proximal end of elbow link 310 may be rotatably coupled to a distal end of distal shoulder link 308 at elbow joint 322, such that elbow link 310 may be rotated relative to distal shoulder link 308 about axis Q4 at elbow joint 322. Robot arm 300 further may include wrist portion 311, which may include proximal wrist link 312 rotatably coupled to the distal end of elbow link 310 at wrist joint 324, middle wrist link 314 rotatably coupled to proximal wrist link 312 at joint 326, and distal wrist link 316 rotatably coupled to middle wrist link 314 at joint 328, as further shown in FIGS. 4A and 4B. Accordingly, wrist portion 311 may be rotated relative to elbow link 310 about axis Q5 at wrist joint 324, middle wrist portion 314 may be rotated relative to proximal wrist link 312 about axis Q6 at joint 326, and distal wrist link 316 may be rotated relative to middle wrist link 314 about axis Q7 at joint 328. In addition, as shown in FIG. 4B, robot arm 300 may include actuator 332, e.g., a lever, button, or switch, operatively coupled to elbow link 310 and/or proximal wrist link 312, such that proximal wrist link 312 may only be rotated relative to elbow link 310 upon actuation of actuator 332. Accordingly, axis Q5 may be a "setup" axis, such proximal wrist link 312 may be rotated and fixed relative to elbow link 310 during a setup stage prior to operating stage where robot arm 300 is used in a surgical procedure. In some preferred embodiments, upon actuation of actuator 332, proximal wrist link 312 may be manually rotated in predefined increments relative to elbow link 310, thereby removing the necessity of having additional motors and/or electronics at the distal region of robot arm 300. Alternatively, upon actuation of actuator 330, proximal wrist link 312 may be automatically rotated relative to elbow link 310 until actuator 332 is released.

Referring again to FIG. 3A, robot arm 300 may include a plurality of motors, e.g., motors M1, M2, M3, which may all be disposed within the base of robot arm 300. Each of motors M1, M2, M3 may be operatively coupled to a respective joint of robot arm 300, e.g., base joint 303, shoulder joint 318, and elbow joint 322, to thereby apply a localized impedance at the respective joint. For example, motors M1, M2, M3 may produce an impedance at any of base joint 303, shoulder joint 318, and elbow joint 322, respectively, to thereby effectively apply an impedance at the distal end of robot arm, e.g., at the attachment point with the surgical instrument, to improve the sensations experienced by the operator during manipulation of the surgical instrument as well as the actions of the operator during surgical procedures. For example, impedance may be applied to the distal end of robot arm 300, and accordingly the surgical instrument coupled thereto, to provide a sensation of a viscosity, a stiffness, and/or an inertia to the operator manipulating the surgical instrument. Moreover, applied impedances may simulate a tissue density or stiffness, communicate surgical boundaries to the operator, and may be used to direct a surgical instrument along a desired path, or otherwise. In some embodiments, the motors may actuate the respective joints to thereby cause movement of robot arm 300 about the respective joints. Accordingly, axis Q1, axis Q2, and axis Q4 may each be a "motorized" axis, such that motors M1, M2, M3 may apply an impedance/torque to base joint 303, shoulder joint 318, and elbow joint 322, respectively, to inhibit or actuate rotation about the respective axis. As described in further detail below, motors M1, M2, M3 may be controlled by a processor of the co-manipulation robot platform. With three motorized axes, some implementations of robot arm 300 may apply force/torque at the distal end of robot arm 300 in three directions to thereby move the surgical instrument coupled to the distal end of robot arm 300 in three degrees of freedom.

Figure 4A:
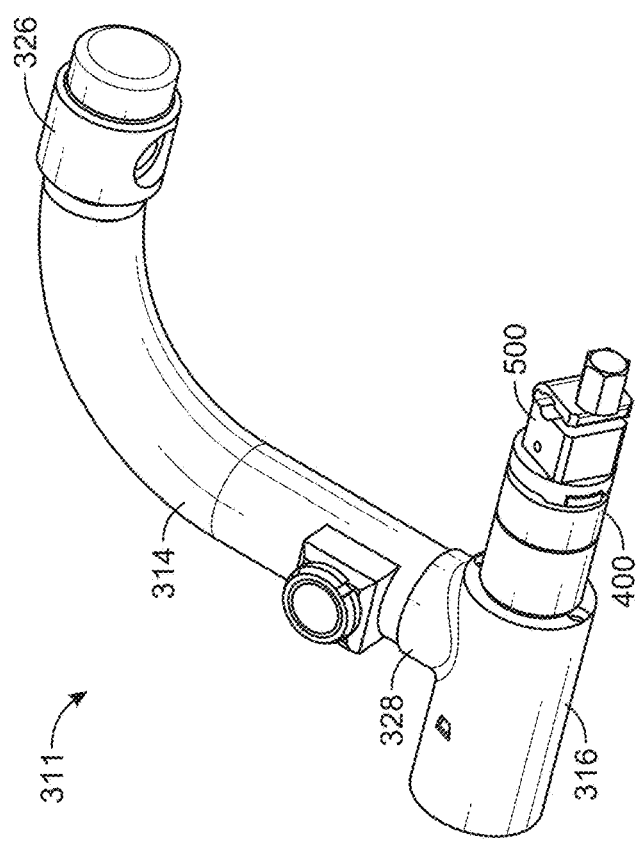

Axis Q6 and axis Q7 may be a "passive" axis, such that middle wrist link 314 may be rotated relative to proximal wrist link 312 without any applied impedance from system 200, and distal wrist link 316 may be rotated relative to middle wrist link 314 without any applied impedance from system 200. The distal end of distal wrist link 316 may include surgical instrument coupler interface 400 for removably coupling with a surgical instrument, e.g., via coupler body 500 as shown in FIGS. 4A and 4B, which may be removeably coupled to the surgical instrument and to coupler interface 400, as described in further detail below. Alternatively, wrist portion 11 may include a passive ball joint at the attachment point with the surgical instrument, as described in U.S. Pat. No. 10,582,977, the entire disclosure of which is incorporated herein by reference.

Referring again to FIG. 3A, robot arm 300 further may include a plurality of encoders, e.g., encoders E1-E7, disposed on at least some of the plurality of joints of robot arm 300. For example, encoder E1 for measuring angulation of between base portion 302 and shoulder portion 304 may be disposed on or adjacent to base joint 303 within the base, encoder E2 for measuring angulation of between shoulder portion 304 and proximal shoulder link 306 may be disposed on or adjacent to shoulder joint 318 within the base, encoder E3 for measuring angulation of between proximal shoulder link 306 and distal shoulder link 308 may be disposed on or adjacent to joint 320, encoder E4 for measuring angulation of between distal shoulder link 308 and elbow link 310 may be disposed adjacent to motor M3 operatively coupled to elbow joint 322 within the base as transmission of rotational motion at elbow joint 322 is achieved via a connection rod extending from the base to elbow joint 32, encoder E5 for measuring angulation of between elbow link 310 and proximal wrist link 312 may be disposed on or adjacent to wrist joint 324, encoder E6 for measuring angulation of between proximal wrist link 312 and middle wrist link 314 may be disposed on or adjacent to joint 326, and encoder E7 for measuring angulation of between middle wrist link 314 and distal wrist link 316 may be disposed on or adjacent to joint 328. Alternatively, encoder E4 may be disposed on or adjacent to elbow joint 322. The encoders may be absolute encoders or other position/angulation sensors configured to generate data for accurately determining the position and/or angulation of corresponding links at the respective joint and/or the exact position of the surgical instrument coupled to the distal end of robot arm 300. Accordingly, the exact position of each link, joint, and the distal end of robot 300 may be determined based on measurements obtained from the plurality of encoders. Preferably, a redundant encoder is disposed at each location along robot arm 300 where an encoder is placed, to provide more accurate position data, as well as, to detect a fault condition, as described in further detail below.

Prior to attachment with a surgical instrument, robot arm 300 may be manually manipulated by a user, e.g., to position robot arm 300 is a desired position for coupling with the surgical instrument. For example, the user may manually manipulate robot arm 300 via wrist portion 11, actuator 330, and/or actuator 332. Upon actuation of actuator 330, the user may manually rotate distal shoulder link 308, and upon actuation of actuator 332, the user may manually manipulate proximal wrist portion 312. Upon attachment to the surgical instrument, robot arm 300 may still be manipulated manually by the user exerting force, e.g., one or more linear forces and/or one or more torques, directly to robot arm 300; however, during the laparoscopic procedure, the operator preferably manipulates robot arm 300 only via the handle of the surgical instrument, which applies force/torque to the distal end of the robot arm 300, and accordingly the links and joints of robot arm 300. As the operator applies a force to the surgical instrument attached to robot arm 300, thereby causing movement of the surgical instrument, robot arm 300 will move responsive to the movement of the surgical instrument to provide the operator the ability to freely move surgical instrument relative to the patient. As described in further detail below, robot arm 300 may apply an impedance to account for weight of the surgical instrument and of robot arm 300 itself, e.g., gravity compensation, as the operator moves the surgical instrument, thereby making it easier for the operator to move the instrument despite gravitational forces and/or inertial forces being exerted on the robot arm and/or the surgical instrument. As will be understood by a person having ordinary skill in the art, robot arm 300 may include less or more articulation joints than is shown in FIG. 3A, as well as a corresponding number of motors and encoders/sensors.

Referring now to FIG. 4C, a close-up view of the coupling mechanism of coupler interface 400 and coupler body 500 is provided. Coupler interface 400 may be coupled to the distal end of distal wrist link 316 using any suitable fasteners or connectors, e.g., magnets, screws, pins, clamps, welds, adhesive, rivets, and/or any other suitable faster or any combination of the foregoing. As shown in FIG. 4C, coupler interface 400 may be coupled with the distal end of distal wrist portion 316 using fastener 410 which may be threaded or have other features that enable fastener 410, and accordingly coupler interface 400 to be selectively attached to distal wrist portion 316. Fastener 410 may be coupled with insert element 408 having an opening therein to receive fastener 410, positioned at or in the distal end of distal wrist portion 316. In some embodiments, fastener 410 may be a pin or may have other features such as a ball, a latch, or otherwise to permit fastener 410 to selectively couple with distal wrist portion 316.

Coupler body 500, which may have opening 514 sized and shaped to slidably and releasably receive the elongated shaft of a surgical instrument therethrough, may be removably coupled with coupler interface 400. For example, coupler body 500 may be removeably coupled to coupler body 500 via a magnetic connection, to thereby facilitate efficient attachment and detachment between coupler body 500 and coupler interface 400, e.g., by overcoming the magnetic coupling force between coupler body 500 and coupler interface 400. Accordingly, as shown in FIG. 4C, coupler body 500 may have one or more magnets 506 extending away from a surface of coupler body 500 that, in an assembled state, contacts a surface of coupler interface 400. Alternatively, in embodiments that do not have a coupler interface, magnets 506 may directly contact the distal end of distal wrist portion 316.

Figure 4D:
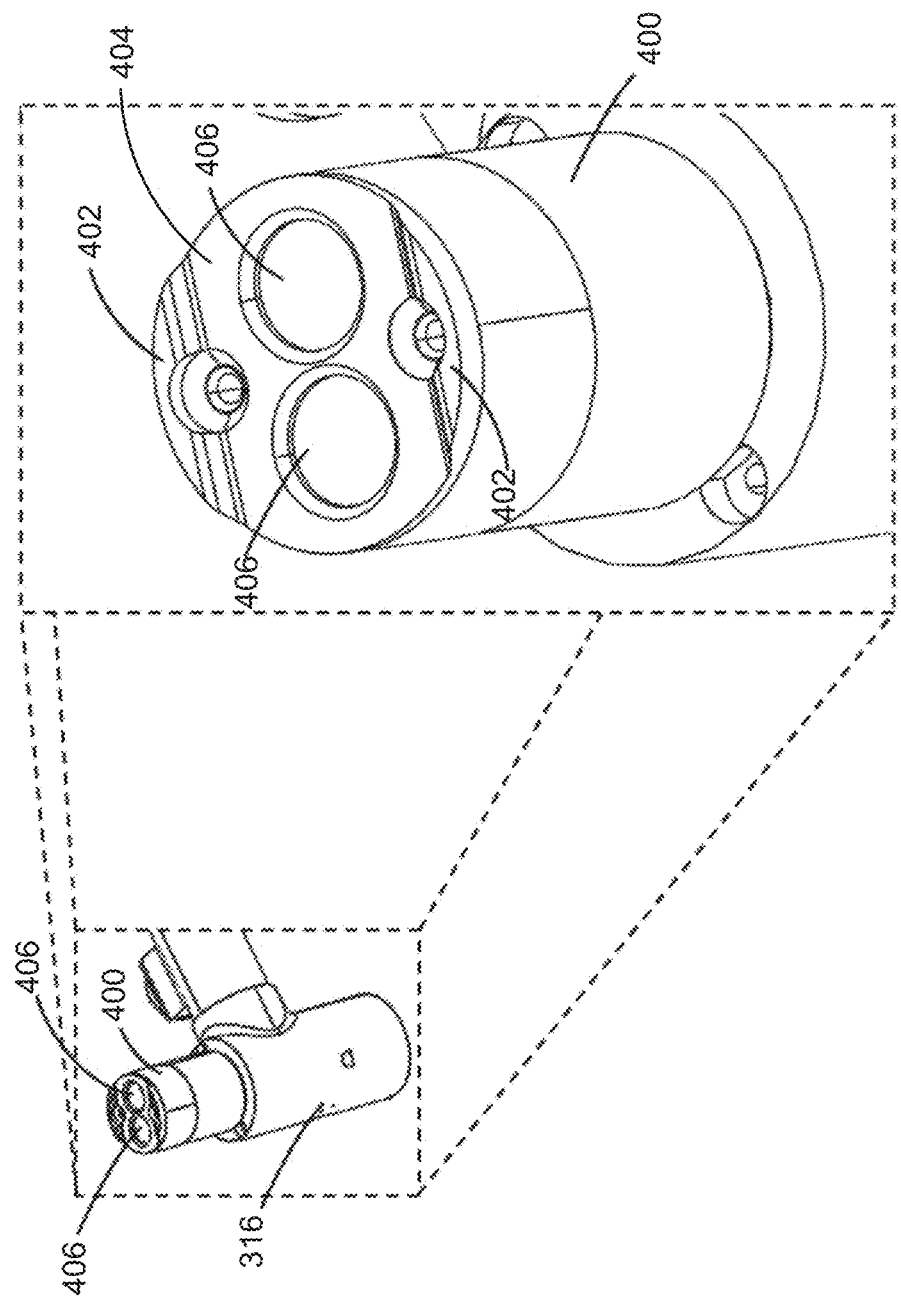
FIG. 4D is a close-up view of an exemplary robot arm coupler interface of the surgical instrument coupling mechanism of FIG. 4C constructed in accordance with the principles of the present disclosure.

Accordingly, coupler interface 400 or the distal end of distal wrist portion 316 may have a ferrous base component configured to receive and magnetically couple with magnets 506 of coupler body 500 so that coupler body 500 may be removably coupled with coupler interface 500 and/or the distal end of distal wrist portion 316. FIG. 4D illustrates surgical instrument coupler interface 400. As shown in FIG. 4D, coupler interface 400 may have recessed portion 404 sized and shaped to receive the complementary geometry of coupler body 500, defined by ridges 402. Accordingly, when the complementary geometry of coupler body 500 is received in recessed portion 404 in an assembled state, rotational movement of coupler body 500 relative to coupler interface 400 may be limited or otherwise prevented.

In addition, coupler interface 400 may have one or more recesses or depressions 406 sized and shaped to receive one or more magnets 506 therein. Coupler interface 400 may have a ferrous base component or magnets within recesses 406 to magnetically couple with magnets 506. For example, the magnets within recesses 406 may have a south magnetic pole and magnets 506 may have a north magnetic pole, or vice versa. Moreover, the polarity of the magnets can ensure appropriate coupling orientation. Recesses 406 may be sized and shaped to limit or otherwise prevent movement between coupler body 500 and coupler interface 400 in any direction that is radial or normal to an axial (e.g., longitudinal) centerline of magnets 506 when coupler body 500 is in an assembled state with coupler interface 400. As will be understood by a person having ordinary skill in the art, coupler interface 400 may have less or more than two recesses 406, such that coupler body 500 will have a corresponding amount of magnets.

Referring now to FIGS. 5A and 5B, coupler body 500 is provided. As shown in FIG. 5A, coupler body 500 may have one or more magnets 506 disposed on portion 502 having a geometry complementary to recessed portion 404 of coupler interface 400, as described above, to facilitate alignment between coupler body 500 and coupler interface 400. In addition, coupler body 500 may have one or more grooves 504 sized and shaped to engage with complementary ridges 402 of coupler interface 400. Grooves 504 and ridges 402 may interact to assist with the alignment of coupler body 500 with coupler interface 400 by limiting or otherwise preventing movement between coupler body 500 and coupler interface 400 in at least two directions D1 and D2, as shown in FIG. 4C. Accordingly, in an assembled state, coupler body 500 may be prevented from moving in any axial direction relative to coupler interface 400.

As shown in FIGS. 5A and 5B, coupler body 500 may have first portion 508 and second portion 510. First portion 508 may be coupled with, or integrally formed with, second portion 510, e.g., via hinge 512, which may be a living hinge formed from the same material as first and second portions 508, 510 and/or integrally formed with first and second portions 508, 510 so that second portion 510 may be moved or rotated relative to first portion 508 to cause opening 514 defined by first portion 508 and second portion 510 to expand (increase in size) or contract (decrease in size). First portion 508 and second portion 510 may form a clamp that may constrict about the elongated shaft of a surgical instrument that is positioned in opening 514 as screw 516, e.g., a thumb screw, is tightened, to couple the instrument 112 with the coupler body 141. Accordingly, coupler body 500 may transition between a first, unsecured/open state or position and a second, secured/closed state or position.

The diameter of opening 514 may be selected based on the surgical instrument to be coupled to coupler body 500. For example, a coupler body may be selected from a plurality of coupler bodies, each coupler body having an opening sized and shaped to receive the elongate shaft of a specific surgical instrument having a predefined elongated shaft diameter such as a laparoscopic or other surgical instrument including surgical instruments used for orthopedic and trauma surgery (OTS), a needle holder, clamp, scissors, etc. Coupler body 500 may be coupled with the surgical instrument at any desired axial position on the surgical instrument.

As shown in FIG. 5C, coupler body 500 may include recess 520 extending through second portion 510 and recess 522 extending through at least a portion of first portion 508. Recess 520 is aligned with recess 522 for receiving locking portion 518 of screw 516. For example, locking portion 518 may have a male threaded surface, and recesses 520, 522 may have a female threaded surface to engage with locking portion 518. Screw 516 may be loosened by hand to open or expand opening 514 so that the surgical instrument may be removed, repositioned, rotated, and/or slid, etc. Once coupler body 500 is coupled with the surgical instrument, e.g., via screw 516, coupler body 500 and the surgical instrument that is coupled with the coupler body 500 may be removeably coupled with coupler interface 400, via magnets 506.

Opening 514 may be defined by a first semi-circular cutout in first portion 508 and a second semi-circular cutout in the second portion 510 of coupler body 500, to thereby engage with the circular outer surface of the elongate shaft of a surgical instrument. Opening 514 may include, e.g., rubber pads, sheets, bumps, O-rings, projections, or other components or features configured to contact and grip the outer surface of the elongated shaft of the surgical instrument. For example, the rubber material may be a silicone rubber or any other suitable type of rubber. Accordingly, once coupler body 500 is coupled with the surgical instrument, e.g., by securing screw 516, the surgical instrument may be at least inhibited or otherwise prevented from moving axially, e.g., the direction along the longitudinal axis of the surgical instrument, or, in some embodiments, moving axially and rotationally, relative to coupler body 500 in the secured state. Preferably, the surgical instrument coupled with coupler body 500 may be freely rotated by an operator relative to coupler body 500, while axial movement of the surgical instrument relative to coupler body 500 is inhibited or otherwise prevented in the secured state. For example, the frictional force between the outer surface of the elongated shaft of the surgical instrument and the inner surface of coupler body 500 defining opening 514 may be selected such that rotation of the surgical instrument relative to coupler body 500 requires less force that axial movement of the surgical instrument relative to coupler body 500 in the secured state. Accordingly, coupler 500 may be configured to account for diametric variations and surface variations (including variations in a coefficient of friction of the surface) of the surgical instruments.

In some embodiments, the surgical instrument may be moved in an axial direction relative to coupler body 500 upon the application of at least a threshold force on the surgical instrument relative to coupler body 500, or upon actuation of a release or a state change of coupler body 500. For example, such actuation may be achieved by, e.g., pressing a button, loosening a locking screw such as locking screw 516 or other connector, moving a dial, or otherwise changing coupler body 500 and/or coupler interface 400 from a second, secured state to a first, unsecured state. Accordingly, the surgical instrument may be axially repositioned relative to coupler body 500 by loosening screw 516 or other hand-operated fastener or fastening mechanism such as a clamp in coupler body 500, repositioning the surgical instrument in the desired axial position, and re-tightening screw 516 or other hand-operated fastener or fastening mechanism. Coupler body 500 may be disposable, or alternatively, may be sterilizeable such that it may sterilized between surgical procedures.

Figure 6B:
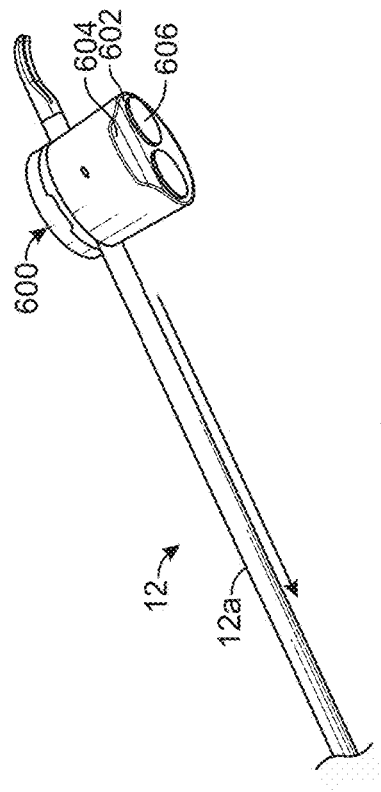
FIGS. 6B-6D illustrate attachment of the coupler body of FIG. 6A to a surgical retractor device in accordance with the principles of the present disclosure.
Figure 6D:
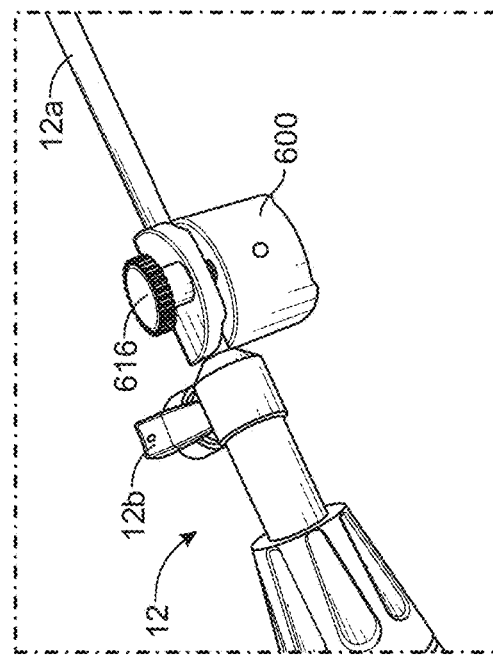
Figure 6A:
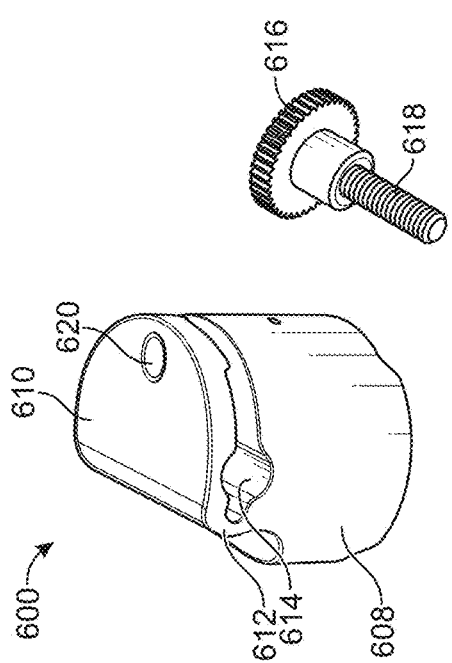
FIG. 6A illustrates an alternative exemplary surgical instrument coupler body constructed in accordance with the principles of the present disclosure.
Figure 6C:
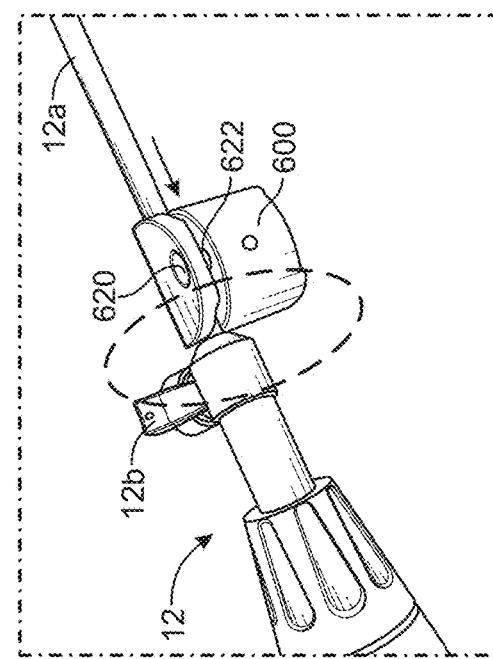

As described above, the diameter of the opening of the coupler body may be selected based on the surgical instrument to be coupled to the coupler body. Most commonly used laparoscopic surgical instruments have a predefined, known elongated shaft diameter, and thus the numerous coupler bodies may be provided, each having an opening sized and shaped to receive and engage with a specific surgical instrument. For example, FIG. 6A illustrates coupler body 600 having opening 614 sized and shaped to receive a 5 mm diameter surgical instrument, e.g., retractor device 12. Coupler body 600 may be constructed similar to coupler body 500. For example, coupler body 600 may include first portion 608 coupled to second portion 610 via hinge portion 612, and recesses 620, 622 for securely receiving locking portion 618 of screw 616. As shown in FIG. 6B, coupler body 600 may receive elongated shaft 12*a* of retractor 12 through opening 614, e.g., from the operating end of retractor 12, such that coupler body 600 may be slid over elongated shaft 12*a* until coupler body 600 engages with proximal portion 12*b* of retractor 12, as shown in FIG. 6C. Preferably, coupler body 600 is coupled to retractor 12 when coupler body 600 contacts proximal portion 12*b* as this point along retractor 12 is fixed, thereby providing a consistent point of reference for calculating force measurements, as described in further detail below. Accordingly, when coupler body 600 is in the desired location along the elongated shaft of retractor 12, e.g., adjacent to proximal portion 12*b*, screw 616 may be coupled to coupler body 600 to secure coupler body 600 to retractor 12. As described above, coupler body 600 is secured to retractor 12 such that rotational movement of retractor 12 relative to coupler body 600 is permitted, while axial movement of retractor 12 relative to coupler body 600 is constrained, e.g., the force required to move retractor 12 relative to coupler body 600 is much higher than the force required to rotate retractor 12 relative to coupler body 600.

Figure 7B:
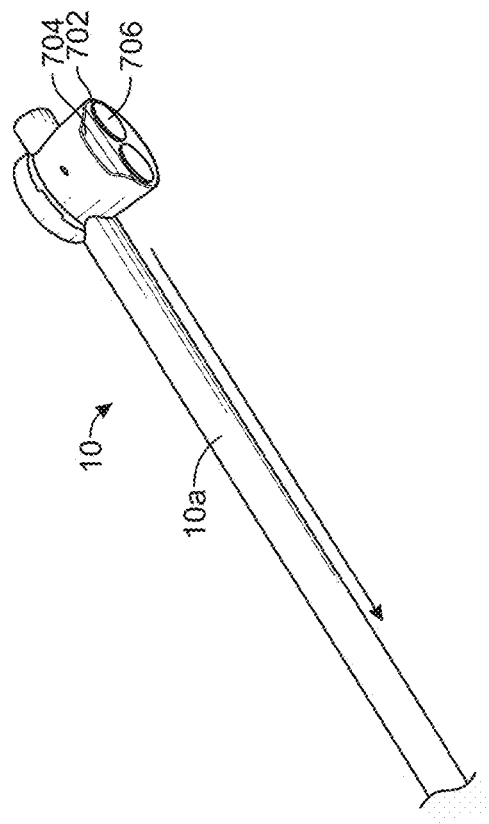
FIGS. 7B-7D illustrate attachment of the coupler body of FIG. 7A to a surgical laparoscope device in accordance with the principles of the present disclosure.
Figure 7A:
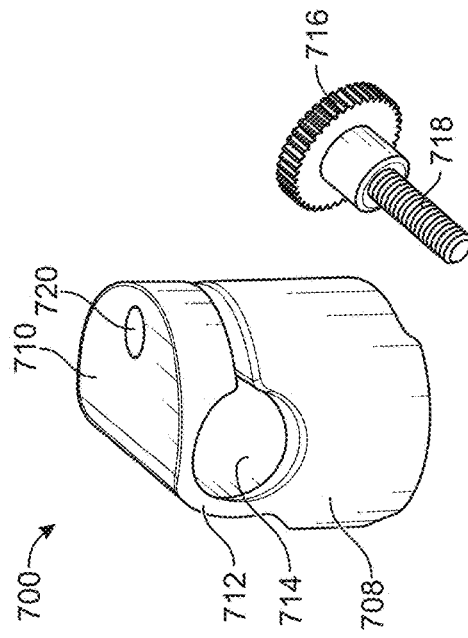
FIG. 7A illustrates another alternative exemplary surgical instrument coupler body constructed in accordance with the principles of the present disclosure.
Figure 7D:
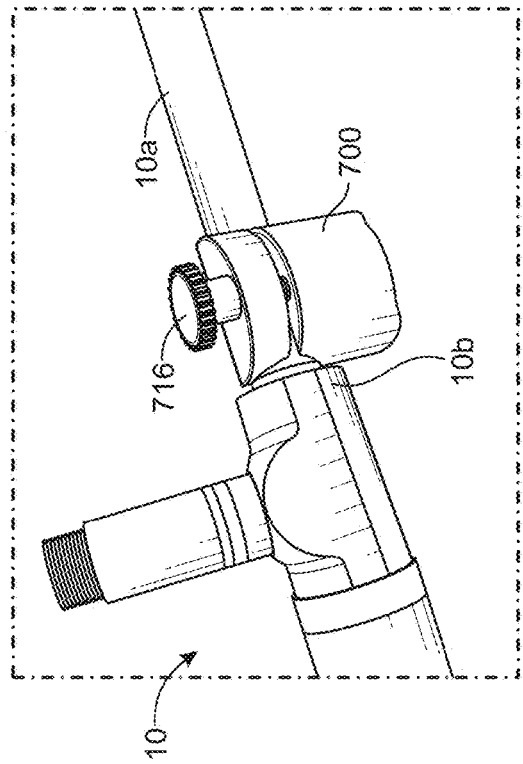
Figure 7C:
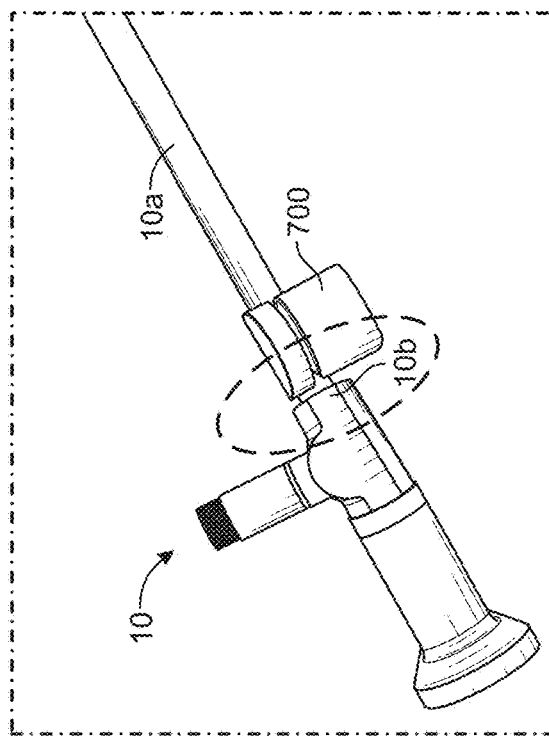

FIG. 7A illustrates coupler body 700 having opening 714 sized and shaped to receive a 10 mm diameter surgical instrument, e.g., laparoscope device 10. Coupler body 700 may be constructed similar to coupler body 600. For example, coupler body 700 may include first portion 708 coupled to second portion 710 via hinge portion 712, and recesses 720, 722 for securely receiving locking portion 718 of screw 716. As shown in FIG. 7B, coupler body 700 may receive elongated shaft 10*a* of laparoscope device 10 through opening 714, e.g., from the operating end of laparoscope 10, such that coupler body 700 may be slid over elongated shaft 10*a* until coupler body 700 engages with proximal portion 10*b* of laparoscope 10, as shown in FIG. 7C. Preferably, coupler body 700 is coupled to laparoscope 10 when coupler body 700 contacts proximal portion 10*b* as this point along laparoscope 10 is fixed, thereby providing a consistent point of reference for calculating force measurements, as described in further detail below. Accordingly, when coupler body 700 is in the desired location along the elongated shaft of laparoscope 10, e.g., adjacent to proximal portion 10*b*, screw 716 may be coupled to coupler body 700 to secure coupler body 700 to laparoscope 10. As described above, coupler body 700 is secured to laparoscope 10 such that rotational movement of laparoscope 10 relative to coupler body 700 is permitted, while axial movement of laparoscope 10 relative to coupler body 700 is constrained, e.g., the force required to move laparoscope 10 relative to coupler body 700 is much higher than the force required to rotate laparoscope 10 relative to coupler body 700.

With the appropriate sized coupler body coupled to the selected surgical instrument, the coupler body may be removeably coupled to coupler interface 400 of robot arm 300. Coupler body 500 and coupler interface 400 may be configured for single-handed coupling, such that an operator may couple coupler body 500, and accordingly the surgical instrument coupled thereto, to coupler interface 400 of robot arm 300 using a single hand. Preferably, a surgical drape may be pinched or clamped between the coupler body and coupler interface 400, and draped over robot arm 300 to maintain sterility of the surgical space and prevent contact with non-sterile components of robot arm 300. Accordingly, the sterile drape may pass continuously (e.g., without a hole, a slit, or any other type of opening) between the coupler body and the coupler interface such that the coupler body is on a first side of the sterile drape and the coupler interface, robot arm 300, and/or other components of system 200 are on the other side of the sterile drape. In some embodiments, the coupler body may be integrated with the surgical drape. Additionally or alternatively, the surgical drape may include an adapter integrated therewith, such that coupler body 500 may be coupled to coupler interface 400 via the adapter, e.g., the adapter may be positioned between coupler body 500 and coupler interface 400.

Figure 8B:
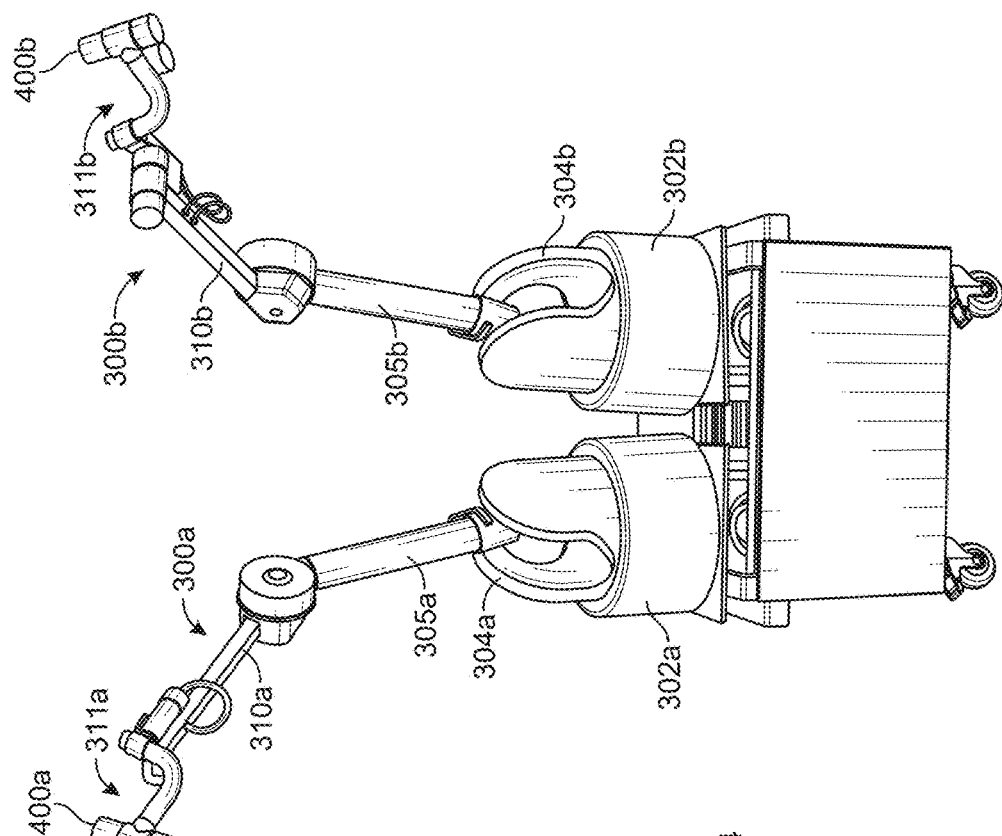
FIGS. 8A and 8B illustrate the robot arms in a sterile-drape ready configuration.
Figure 8A:
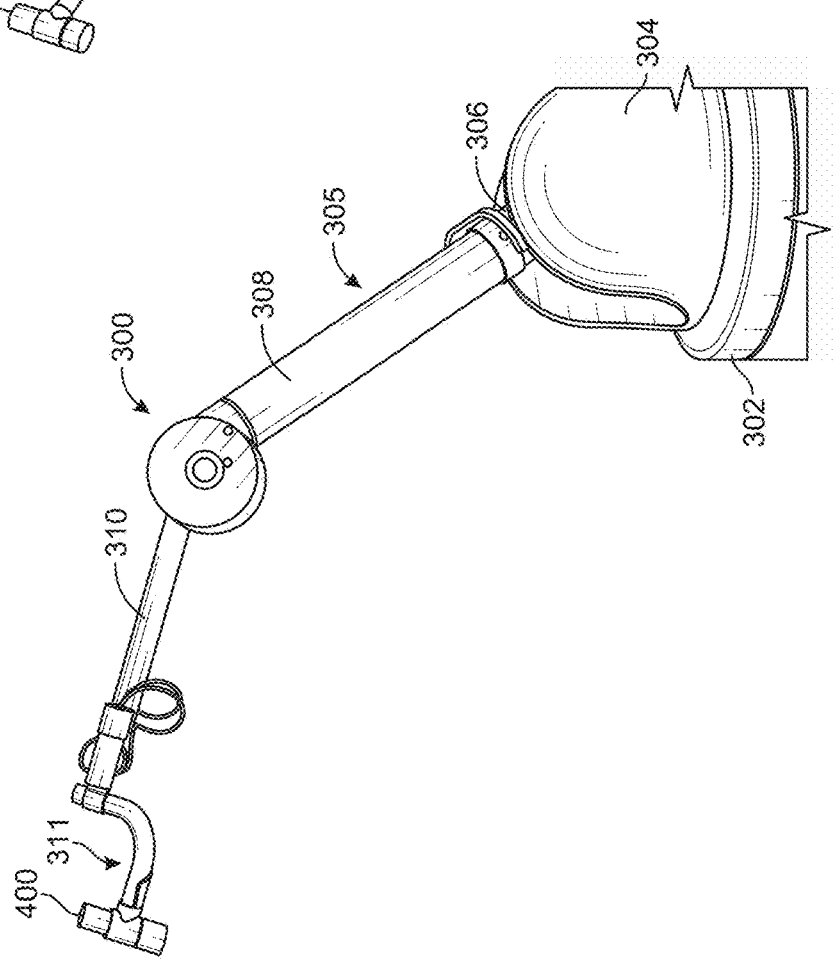
Figure 9B:
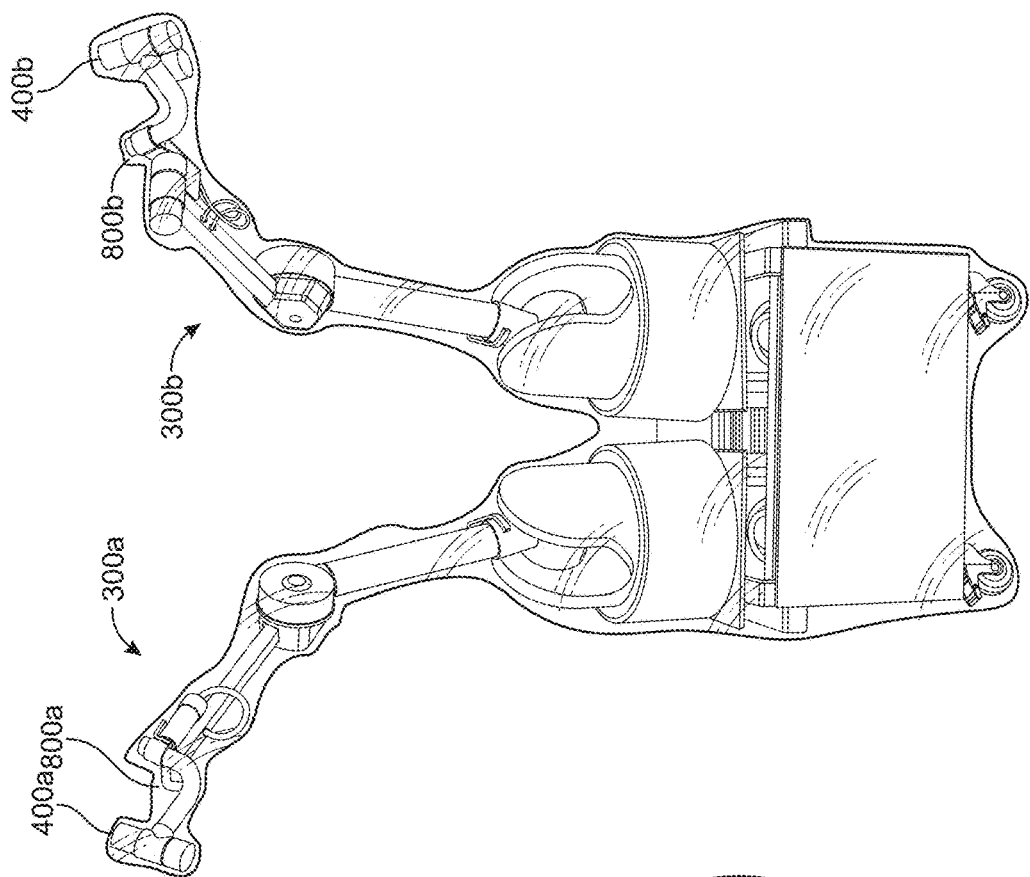
FIGS. 9A and 9B illustrate the robot arms covered in a sterile drape.
Figure 9A:
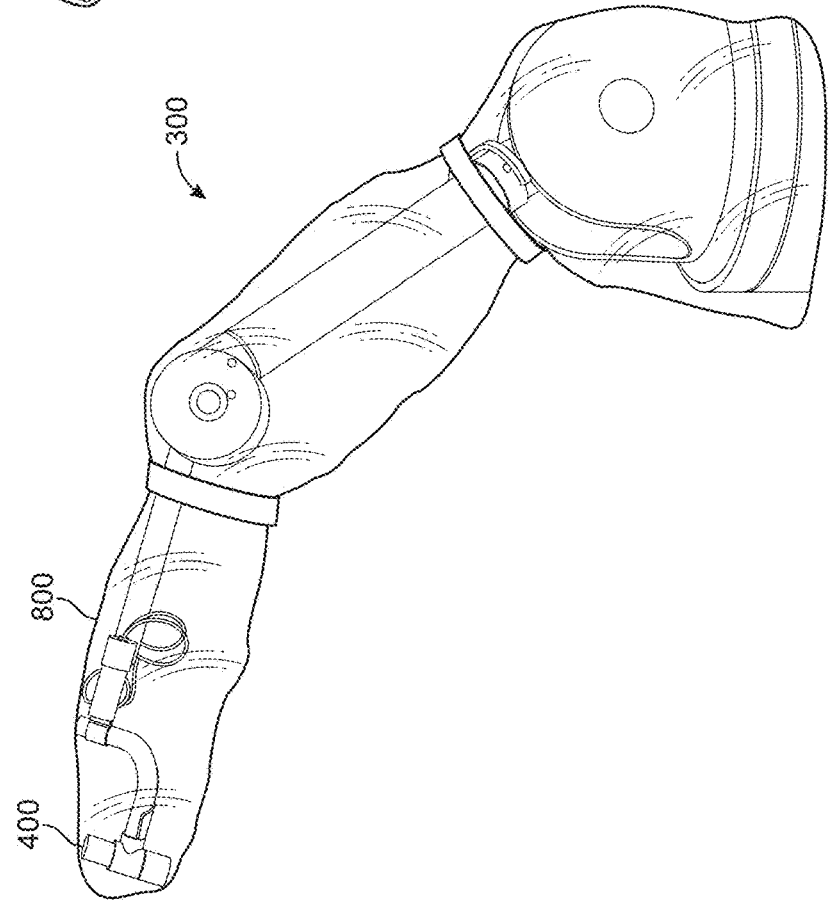

Referring now to FIGS. 8A and 8B, robot arm 300 may be positioned in a surgical drape-ready configuration. As shown in FIG. 8A, robot arm 300 may be extended such that wrist portion 311, elbow link 310, and shoulder link 305 extend away from shoulder portion 304 of the base to permit a surgical/sterile drape to be draped over each component of robot arm 300. Moreover, as shown in FIG. 8B, when there are two robot arms, e.g., robot arm 300*a* and robot arm 300*b*, robot arm 300*a* and robot arm 300*b* may be angled away from each other, e.g., by rotating shoulder portion 304*a* relative to base portion 302*a* of robot arm 300*a* and by rotating shoulder portion 304*b* relative to base portion 302*b* of robot arm 300*b*, such that wrist portion 311*a*, elbow link 310*a*, and shoulder link 305*a* extend away from wrist portion 311*b*, elbow link 310*b*, and shoulder link 305*b*. This configuration permits efficient and accessible draping of the respective robot arms with a surgical/sterile drape. Moreover, in the extended position, the robot arms may be outside the virtual haptic boundary, such that the robot arms are in the haptic mode and a high level of impedance is applied to the robot arms thereby making movement of the robot arms more viscous, which makes it easier for the operator to drape the robot arms, yet provide movement thereto if necessary. For example, FIG. 9A illustrates a single robot arm 300 draped with sterile drape 800, and FIG. 9B illustrates robot arms 300*a*, 300*b* draped with sterile drapes 800*a*, 800*b*, respectively.

Sterile drape 800 may be completely closed at an end portion thereof. In some embodiment, sterile drape 800 may have an opening (that can optionally have a sterile seal or interface) in a distal portion thereof that a portion of robot arm 300, coupler interface 400, coupler body 500, and/or the surgical instrument may pass through. Drapes having a sealed end portion without any openings, and being sealed along a length thereof may provide a better sterile barrier for system 200. Accordingly, all of robot arm 300 may be located inside sterile drape 800 and/or be fully enclosed within sterile drape 800, except at an opening at a proximal end of sterile drape 800, e.g., near the base of robot arm 300). In some embodiments, coupler body 500 and coupler interface 400 may have electrical connectors to produce an electronic connection between robot arm 300 and the surgical instrument. Accordingly, the electrical signals may be transmitted through sterile drape 800. Alternatively, sterile drape 800 may include an opening such that electrical wires or other components may pass through the opening to provide a wired communication channel to electrical components that may include, e.g., memory chips for calibration, radiofrequency probes for ablation, cameras, and other electronic components. The surgical instrument and the coupler body may instead be passive or non-electronic such that no electrical wires need pass through sterile drape 800.

Figure 10A:
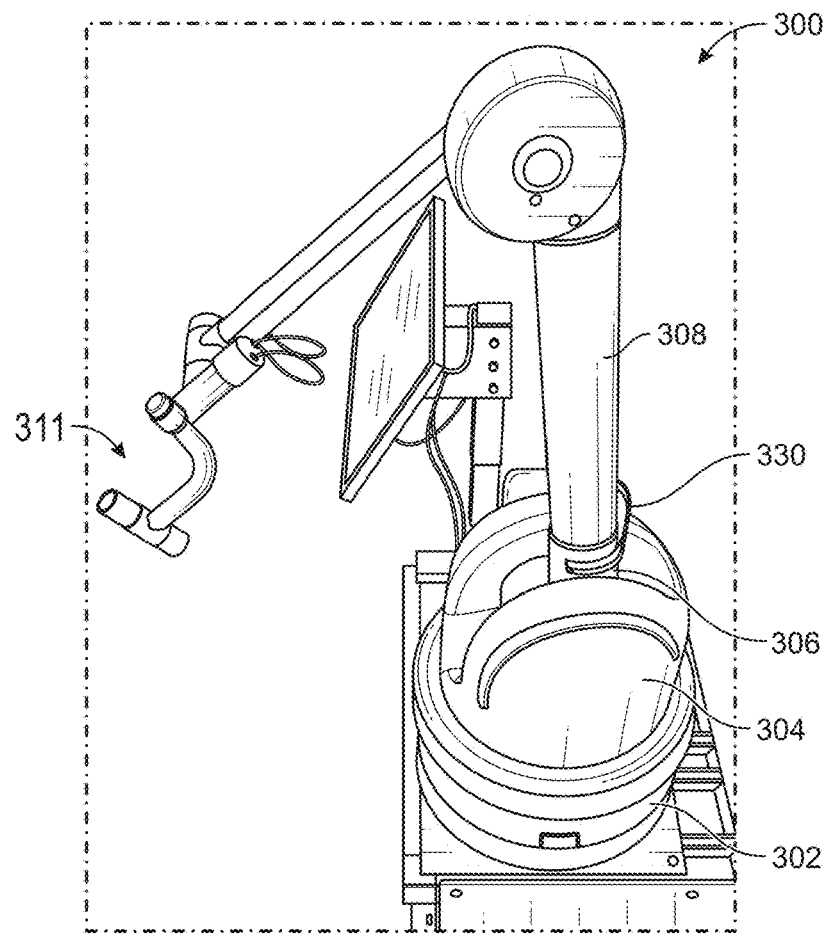
FIGS. 10A-10D illustrate rotation of the shoulder link of the robot arm in accordance with the principles of the present disclosure.
Figure 10B:
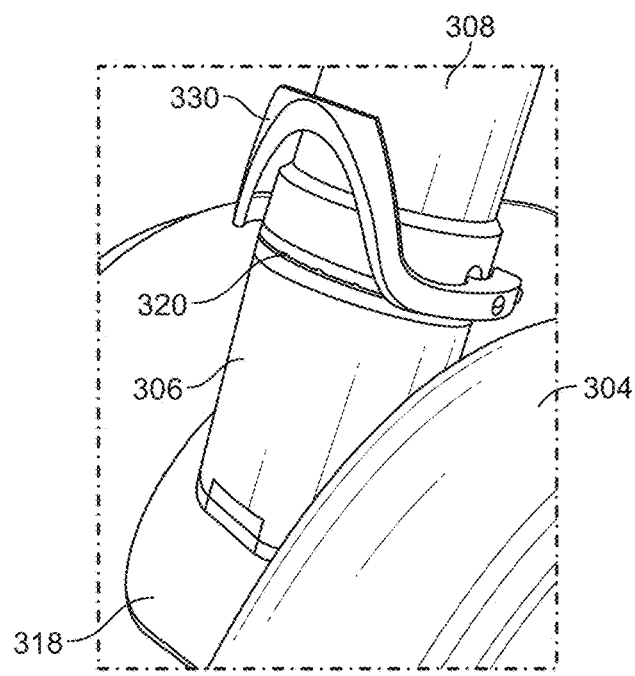
Figure 10C:
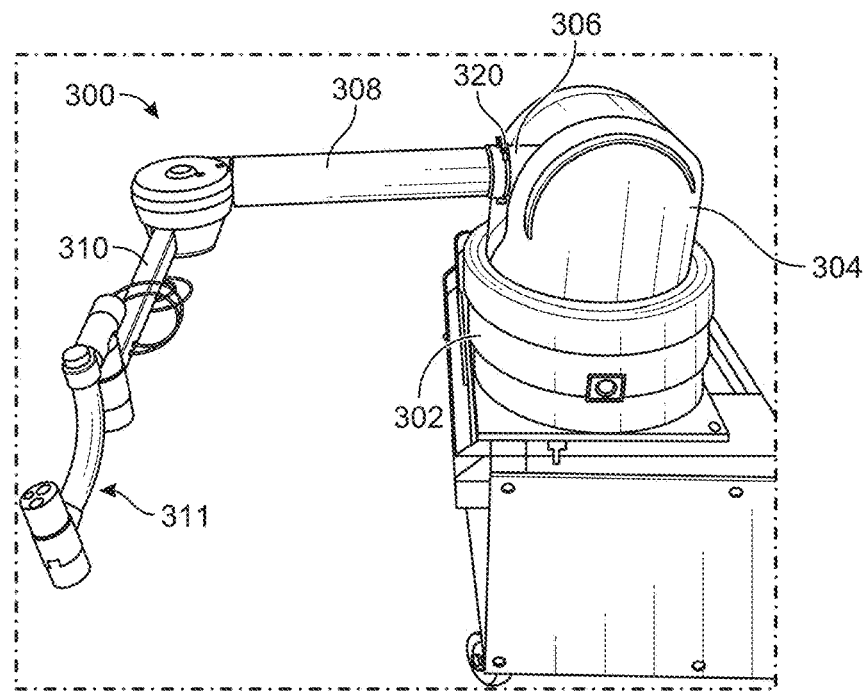
Figure 10D:
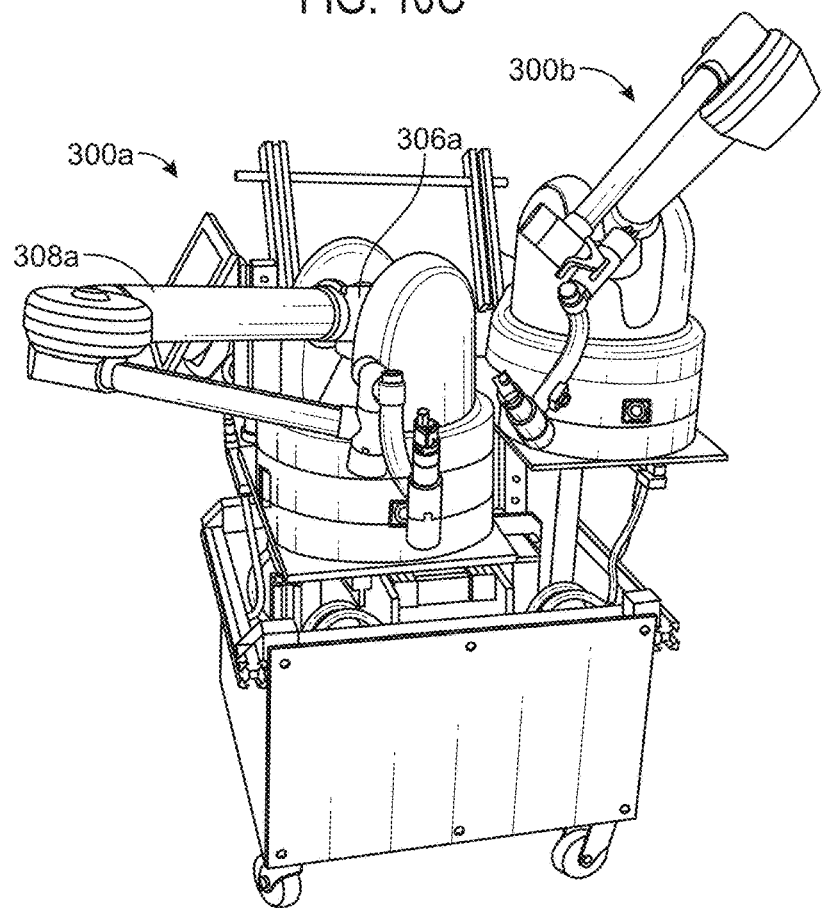

Referring now to FIGS. 10A to 10D, rotation of distal shoulder link 308 relative to proximal shoulder link 306 of shoulder link 305 is provided. As described above, axis Q3 may be a "setup" axis, such that distal shoulder link 308 may be rotated relative to proximal shoulder link 306 upon actuation of actuator 330 during a setup stage of robot arm 300, e.g., prior to operation of robot arm 300 in a surgical procedure. As shown in FIG. 10A, shoulder portion 304 optionally may be initially rotated relative to base portion 302 to a desired position, thereby causing rotation of all the link distal to proximal shoulder link 306, which is coupled to shoulder portion 304, to rotate relative to base portion 302 and provide ample space for rotation of robot arm 300 about joint 320. Moreover, as shown in FIG. 10, wrist portion 311 may be at least partially extended away from base portion 302 so as to not collide with any components of robot arm 300 upon rotation of robot arm 300 about joint 320. As shown in FIG. 10B, actuator 330 must be actuated to permit rotation of distal shoulder link 308 relative to proximal shoulder link 306 at joint 320. FIG. 10C illustrates robot arm 300 in a desirable location for a specific laparoscopic procedure upon rotation of distal shoulder link 308 relative to proximal shoulder link 306. FIG. 10D illustrates robot arm 300a in the desirable location upon rotation of distal shoulder link 308a relative to proximal shoulder link 306a, relative to robot arm 300b.

Figure 11B:
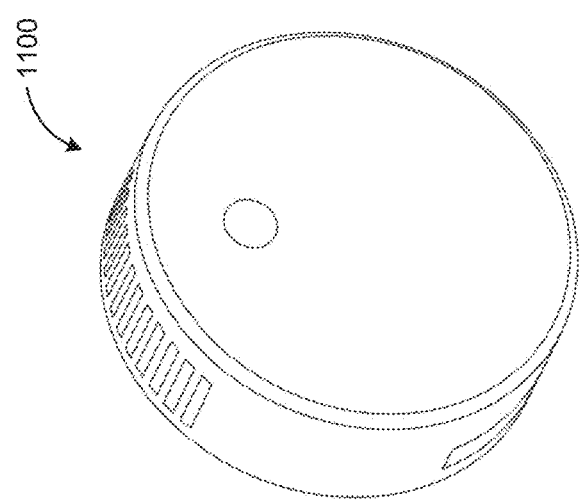
FIG. 11B illustrates the optical scanner of FIG. 11A.
Figure 11A:
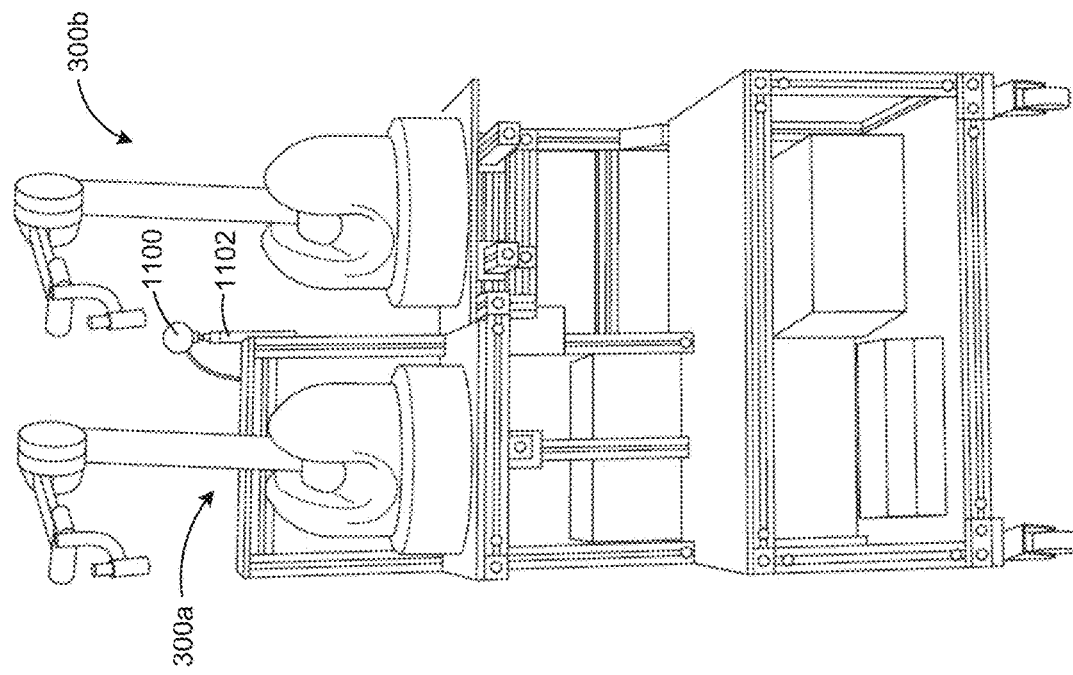
FIG. 11A illustrates an exemplary co-manipulation surgical system having an optical scanner in accordance with the principles of the present disclosure.

Referring now to FIGS. 11A and 11B, an exemplary co-manipulation robot surgical system having an optical scanner is provided. As shown in FIG. 11A, the system may be constructed similar to system 200 of FIG. 2, having a plurality of robot arms, e.g., robot arm 300a and robot arm 300b. As described above, although only two robot arms are shown in FIG. 11A, less or more robot arms may be used in conjunction with optical scanner 1100. In addition, the system may include optical scanner 1100, e.g., a LiDAR scanner or other suitable optical scanning device such as an RGBD camera or sensor, RGB camera with machine learning, a time-of-flight depth camera, structured light, multiple projection cameras, a stereo camera, ultrasound sensors, laser scanner, other type of coordinate measuring area scanner, or any combination of the foregoing. For example, the LiDAR camera/scanner may be capable of recording both color (RGB) and the Depth (D) of the surgical field, and may include, for example, an Intel RealSense LiDAR Camera L515 or an Intel RealSense Depth Camera D435i (made available by Intel, Santa Clara, California) or other LiDAR or depth cameras having similar or suitable specifications including, without limitation, any of the following specifications: (i) range: 25 cm to 500 cm; depth accuracy: 5 mm or approximately 5 mm; depth field of view: 70×55 or approximately 70×55 (degrees); depth output resolution: 1024×768 pixels or approximately 1024×768 pixels; depth/RGB frame rate: 30 frames per second; RGB frame resolution: 1920×1080; and/or RGB field of view: 70×43 degrees or approximately 70×43 degrees. The LiDAR scanner or optical scanner further may include both a ¼-20 UNC thread or 2×M3 thread mounting points. As will be understood by a person having ordinary skill in the art, optical scanner 1100 may be used in other co-manipulation robot surgical systems described herein, e.g., system 200, or any variations thereof.

As shown in FIG. 11A, the platform supporting robot arms 300a, 300b may support optical scanner 1100, and any other electronics, wiring, or other components of the system, such that optical scanner 1100 is mounted in a fixed location relative to the other objects in the surgical space, and the position and orientation of optical scanner 1100 is known or may be determined with respect to the global coordinate system of the system, and accordingly, the robot arms. This allows all data streams to be transformed into a single coordinate system for development purposes. For example, optical scanner 1100 may be supported on a rod or shaft, e.g., rod 1102, which may have an adjustable height or otherwise be adjustable in any direction, e.g., up/down, left/right, toward/away from the patient, to allow optical scanner 1100 to gain an optimum field-of-view or position relative to the other components of the system, for example, robot arms 300a, 300b, the surgical instruments attached thereto, the surgeon, and/or surgical assistant. Moreover, telemetry data captured by optical scanner 1100, e.g., indicative of the movements of the surgeon's hands, other body parts, and other components of the system, may be recorded to provide a rich and detailed dataset describing the precise movements and forces applied by the surgeon throughout the procedure.

For example, the data obtained may be used to optimize the procedures performed by the system including, e.g., automatic servoing (i.e., moving) of one or more portions of robot arm 300. By tracking the tendency of the surgeon to keep the tools in a particular region of interest and/or the tendency of the surgeon to avoid moving the tools into a particular region of interest, the system may optimize the automatic servoing algorithm to provide more stability in the particular region of interest. In addition, the data obtained may be used to optimize the procedures performed by the system including, e.g., automatic re-centering of the field of view of the optical scanning devices of the system. For example, if the system detects that the surgeon has moved or predicts that the surgeon might move out of the field of view, the system may cause the robot arm supporting the optical scanning device, e.g., a laparoscope, to automatically adjust the laparoscope to track the desired location of the image as the surgeon performs the desired procedure. This behavior may be surgeon-specific and may require an understanding of a particular surgeon's preference for an operating region of interest. Thus, the system may control the robot arms pursuant to specific operating requirements and/or preferences of a particular surgeon.

Figure 12:
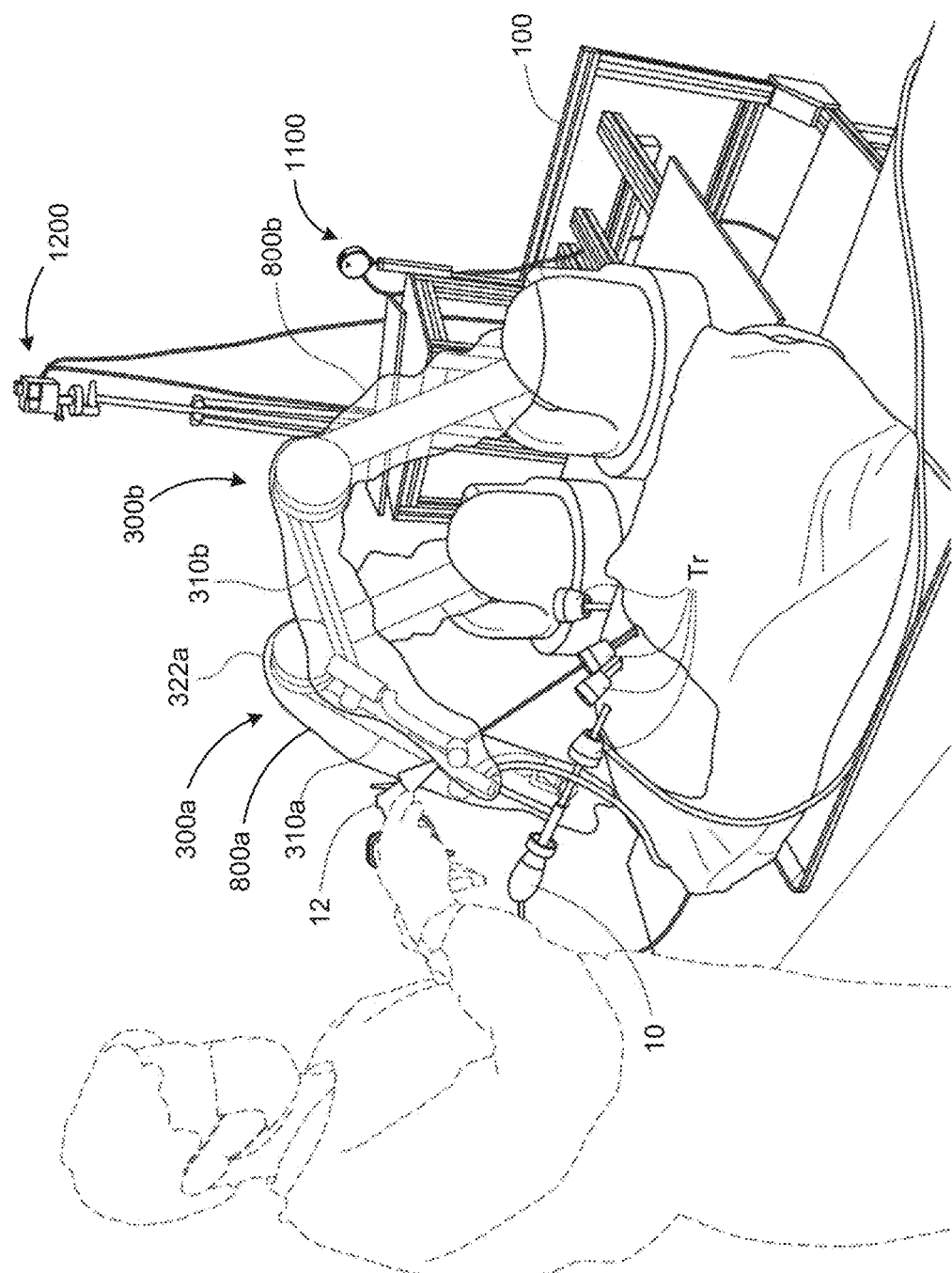
FIG. 12 illustrates a user operating the co-manipulation surgical system of FIG. 11A in accordance with the principles of the present disclosure.

FIG. 12 shows the system having optical scanner 1100 in operation during a laparoscopic procedure. As shown in FIG. 12, an optional additional optical scanner, e.g., camera 1200, may be utilized to provide an additional point of view, e.g., redundant measurement of the movements of the instruments held by the robot arms, and/or provide a video stream of the surgical scene, e.g., via streaming, for monitoring and analysis. As shown in FIG. 12, the system may include two robot arms, e.g., robot arms 300a, 300b, such that robot arm 300a holds laparoscope 10 in a fixed position relative to the patient, while the surgeon operates and manipulates retractor 12, which is coupled to the distal end of robot arm 300b. Moreover, during the surgical procedure, robot arms 300a, 300b may be draped with sterile drapes 800a, 800b, respectively. As described above, the surgeon may freely manipulate retractor 12 while retractor 12 is coupled to robot arm 300b, thereby causing movement of robot arm 300b due to movement of retractor 12 by the surgeon, and while robot arm 300b accounts for weight of retractor 12 and robot arm 300b. During the surgical procedure, optical scanner 1100 may be used to monitor an identity, position, orientation, and/or movement of the surgical instrument coupled to robot arm 300a, e.g., laparoscope 10, and an identity, position, orientation, and/or movement of the surgical instrument coupled to robot arm 300b, e.g., retractor 12, as well as if either surgical instrument is detached from the respective robot arm, either intentionally or unintentionally. Moreover, optical scanner 1100 may be used to monitor an identity, position, orientation, and/or movement/displacement of any of trocars Tr to ensure proper alignment of the robot arms and/or surgical instruments relative to the respective trocars. The system may be used in a surgical procedure having one, two, three, four, or more trocars, depending on the surgical procedure intended to be performed by the system.

Figure 13A:
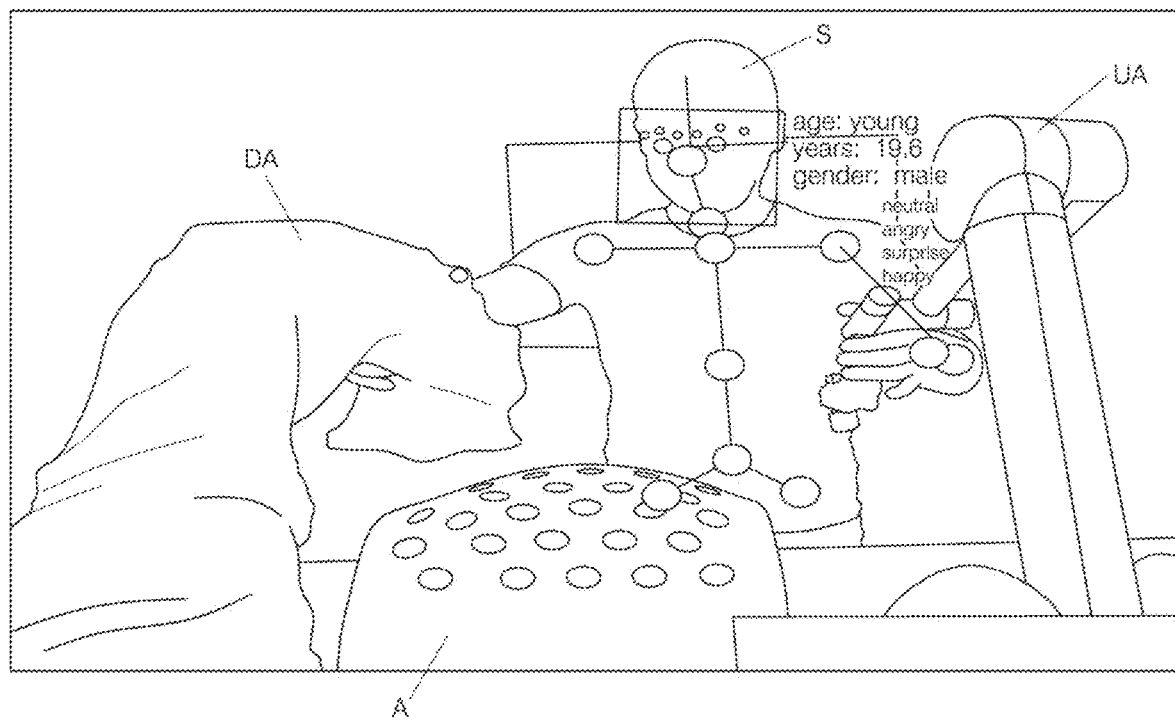
FIG. 13A illustrates a field of view of the optical scanner during a laparoscopic surgical procedure.
Figure 13B:
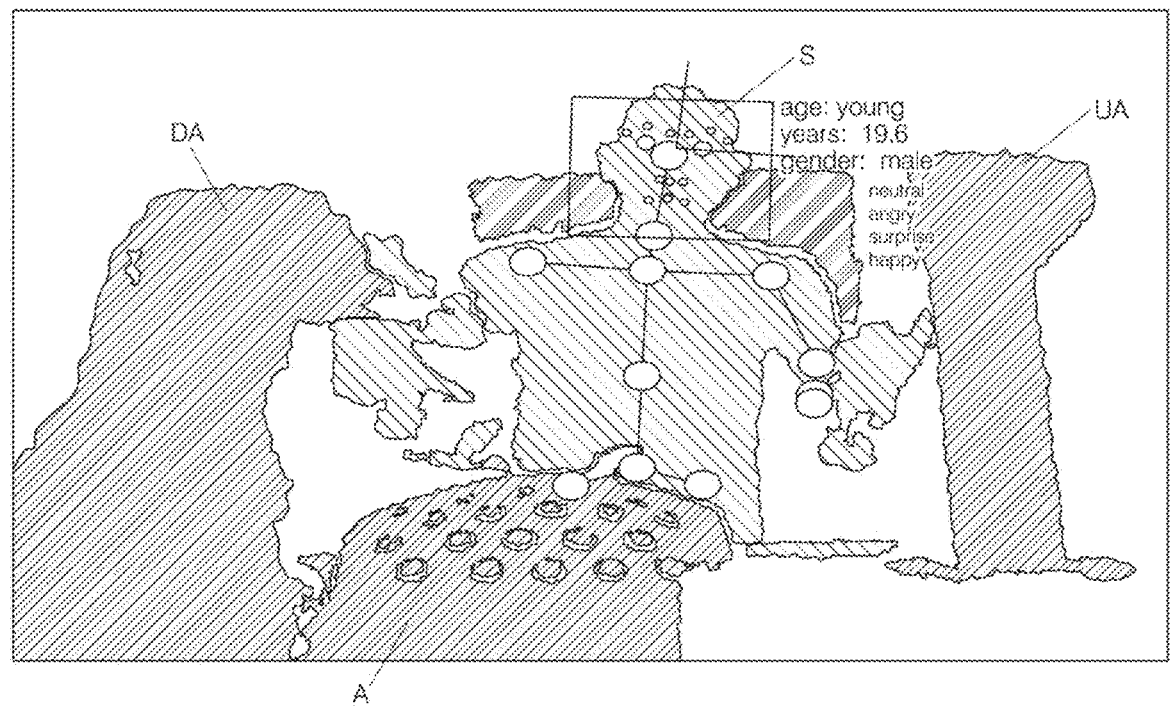
FIG. 13B illustrates a depth map of the field of view the optical scanner of FIG. 13A.

FIGS. 13A and 13B illustrate exemplary data produced by optical scanner 1100. For example, FIG. 13A illustrates image data captured by optical scanner 1100, and FIG. 13B illustrates a depth map of at least some objects within the surgical space generated from the data captured by optical scanner 1100. Specifically, optical scanner 1100 may create a depth map, e.g., point clouds, where each pixel's value is related to the distance from optical scanner 1100. For example, the difference between pixels for a first object (such as a first surgical instrument) and a second object (for example, a trocar) will enable the system to calculate the distance between the surgical instrument and the trocar. Moreover, the difference between pixels for a first object (such as a first surgical instrument) at a first point in time and the first object at a second point in time will enable the system to calculate whether the first object has moved, the trajectory of movement, the speed of movement, and/or other parameters associated with the changing position of the first object.

As shown in FIGS. 13A and 13B, surgeon S is manipulating surgical tools and/or the draped robot arm (DA) and the undraped robot arm (UA) that are positioned relative to insufflated abdomen (A). As described above, the data streams from the robot arms, the camera feed from the laparoscope, the data acquired from optical scanner 1100, as well as data optionally captured from one or more imaging devices disposed on a structure adjacent to the robot arms, the walls, ceiling, or other structures within the operating room, may be recorded, stored, and used individually or in combination to understand and control the surgical system and procedures of the surgical system. The foregoing components, devices, and combinations thereof are collectively referred to herein as optical scanners or optical scanning devices.

For example, the system may measure and record any of the following within the coordinate space of the system: motion of the handheld surgical instruments manipulated by the surgeon (attached to or apart from a robot arm); the presence/absence of other surgical staff (e.g., scrub nurse, circulating nurse, anesthesiologist, etc.); the height and angular orientation of the surgical table; patient position and volume on the surgical table; presence/absence of the drape on the patient; presence/absence of trocar ports, and if present, their position and orientation; gestures made by the surgical staff; tasks being performed by the surgical staff; interaction of the surgical staff with the system; surgical instrument identification; attachment or detachment "action" of surgical instruments to the system; position and orientation tracking of specific features of the surgical instruments relative to the system (e.g., camera head, coupler, fiducial marker(s), etc.); measurement of motion profiles or specific features in the scene that allow for the phase of the surgery to be identified; position, orientation, identity, and/or movement of any other instruments, features, and/or components of the system or being used by the surgical team.

The system may combine measurements and/or other data described above with any other telemetry data from the system and/or video data from the laparoscope to provide a comprehensive dataset with which to improve the overall usability, functionality, and safety of the co-manipulation robot-assisted surgical systems described herein. For example, as the system is being setup to start a procedure, optical scanner 1100 may detect the height and orientation of the surgical table. This information may allow the system to automatically configure the degrees of freedom of platform 200 supporting robot arms 300 to the desired or correct positions relative to the surgical table. Specifically, optical scanner 1100 may be used to ensure that the height of platform 100 is optimally positioned to ensure that robot arms 300 overlap with the intended surgical workspace. Moreover, based on the data obtained by optical scanner 1100, the system may alert the surgical staff of a potential collision (either during setup or intra-operatively) between the system and other pieces of capital equipment in the operating room, e.g., the surgical table, a laparoscopic tower, camera booms, etc., as well as with a member of the surgical staff, e.g., an inadvertent bump by the staff member. The system may use this information to recommend a repositioning of platform 100 and/or other components of the system, the surgical table, and/or patient, and/or prevent the robot arm from switching to the co-manipulation mode as a result of the force applied to the robot arm by the collision with the staff member, even if the force exceeds the predetermined force threshold of the robot arm.

In addition, the data obtained from optical scanner 1100 may be used to monitor the progress of setup for a surgical procedure and may be combined with the known state of the system to inform remote hospital staff (e.g., the surgeon) of the overall readiness to start the procedure. Such progress steps may include: (i) patient on table; (ii) patient draped; (iii) sterile instruments available; (iv) robot arm draped; (v) trocar ports inserted; and (vi) confirmation that instruments (e.g., a laparoscope and retractor) are attached to the robotic arms of system. For example, the data obtained from optical scanner 1100 may include detected gestures indicative of the system state (e.g., system is draped), readiness to start the procedure, etc., and further may be used to prepare the system for the attachment or detachment of a surgical instrument.

In addition, optical scanner 1100 may identify the specific surgeon carrying out the procedure, such that the system may use the surgeon's identity to load a system profile associated with the particular surgeon into the system. The system profile may include information related to a surgeon's operating parameter and/or preferences, a surgeon's patient list having parameters for each patient, the desired or required algorithm sensitivity for the surgeon, the degree of freedom positioning of the support platform, etc. Examples of algorithm sensitivities that may be surgeon-specific include: adapting/adjusting the force required to transition from passive mode to co-manipulation mode (e.g., from low force to high force), adapting/adjusting the viscosity felt by the surgeon when co-manipulating the robot arm (e.g., from low viscosity to high viscosity), etc. Moreover, the surgeon's preferences may include preferred arrangements of robot arm 300, e.g., the positioning of the links and joints of robot arm 300 relative to the patient, with regard to specific surgical instruments, e.g., the preferred arrangement may be different between a laparoscope and a retractor.

Figure 24:
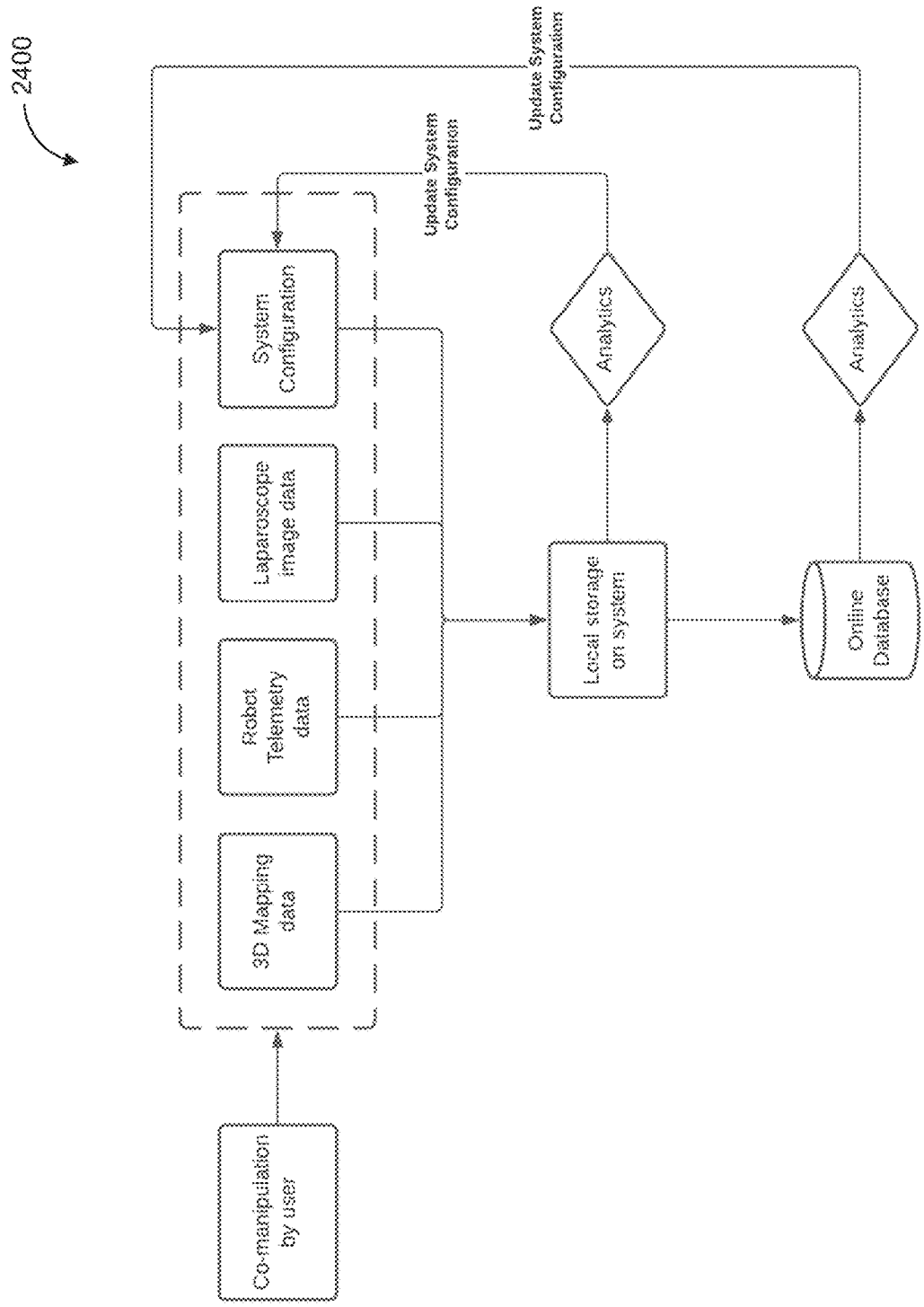
FIG. 24 is another schematic overview of data flow the co-manipulation surgical system in accordance with the principles of the present disclosure.

In some embodiments, the surgeon's preferences may be learned based on data from past procedures and/or sensors collecting information about current procedure including a surgeon's current pose, a surgeon's height, a surgeon's hand preference, and other similar factors. For example, the system may record when a user interacts with the system and also record what the user does with the system, such that the dataset may allow for surgeon preferences to be "learned"

and updated over time. This learning may be done either via traditional algorithmic methods (i.e., trends over time, averaging, optical flow, etc.) or via machine learning approaches (classification, discrimination, neural networks, reinforcement learning, etc.). FIG. 24 illustrates data flow 2400 for updating the system configurations based on learned behaviors of the user. As shown in FIG. 24, the system may be connected to an online database that may store a surgeon profile and each of a plurality of possible data sources, which may include optical sensors, encoders, and/or other sensors, and/or a database of manually entered user input. The data sources may be associated with a given surgeon, their preferred robot arm arrangement and operating parameters, and each procedure performed with the system, which may allow the recording and analysis of the system configuration and how it changes from procedure to procedure, and within the procedure. In the case of machine learning, the co-manipulation capability of the system may be leveraged such that the user's actions may be used to annotate the data to create a training dataset.

Regarding the degree of freedom positioning, a height of a surgical table is typically adjusted to accommodate the height of the surgeon in some operating rooms. Thus, by detecting the surgeon and loading the surgeon's specific profile, the system may position the platform at a height that is suitable for the respective surgeon to accommodate the preferred height of the surgical table. In addition, the horizontal translation of a robot arm may depend on the size of the patient. Thus, by accessing the patient list, the system may adjust the position of the arm based on the patient's body mass index ("BMI"). For example, for a patient with a high BMI, the system may move the robot arm away from the operating table and, for a patient with a low BMI, the system may move the robot arm closer to the operating table. Accordingly, the system permits the surgical team to fine-tune the position of the robot arm relative to the patient as necessary. The system further may be configured to access a hospital medical record database to access the procedure type and any other medical data available (e.g., CT scan images, x-ray images, MRI images, and/or other patient specific information), which may be used to inform positioning of the trocar ports, and the position and orientation of platform 100 relative to the patient.

Based on the data captured by optical scanner 1100, the system may generate a virtual model of the pieces of capital equipment and/or other objects in an operating room that are within a range of movement of the robot arms in the same co-ordinate space as the robot arms and surgical instruments coupled thereto, such that the virtual model may be stored and monitor, e.g., to detect potential collisions. Additionally, the system may track the position and orientation of each virtual model, and the objects within the virtual models as the objects move relative to each other, such that the system may alert the user if the proximity of (i.e., spacing between) any of the virtual models or objects falls below a predefined threshold, e.g., within 50 mm, 75 mm, from 30 mm or less to 100 mm, or more. In some embodiments, the distance threshold may be based off the Euclidean distance between the closest points on two virtual models, the normal distance between two surfaces of the virtual models, etc. Moreover, the system may stop or inhibit (e.g., prevent) further movement of a robot arm, e.g., freeze the robot arm, if the proximity of any of the virtual models or objects, e.g., a robot arm reaches or falls below the predefined threshold relative to a laparoscopic tower, or the surface of the surgical table, or other objects within the surgical space. In addition, the system may freeze the robot arm if the system detects that the proximity between an object, e.g., capital equipment or a member of the surgical staff other than the surgeon, moving toward a respective robot arm reaches or falls below the predefined threshold, to thereby prevent the inadvertent movement of the robot arm that may otherwise result from such a collision or inadvertent force, e.g., an inadvertent bump from a member of the staff or another piece of capital equipment, etc.

Moreover, based on the data captured by optical scanner 1100, the system may track the motion of the handheld surgical instruments that are directly and independently controlled by the surgeon, that are not coupled with the robot arm. For example, the optical scanner 1100 may track a clearly defined feature of the instrument, a fiducial marker attached to the instrument or to the gloves (e.g., the sterile gloves) of the surgeon, the coupler between the robot arm and the instrument, a distal tip of the instrument, and/or any other defined location on the instrument. For example, fiducial markers may include Manus virtual reality gloves (made available by Manus, The Netherlands) or other wearables, and/or the OptiTrack systems (made available by NaturalPoint, Corvallis, Oregon). The following are examples of uses and purposes of the motion data: (i) closing a control loop between a handheld instrument and the robot arm holding the camera, thus allowing the surgeon to servo (i.e., move) the camera by "pointing" with a handheld instrument; (ii) tracking information that may be used independently or in combination with other data streams to identify the phase of the surgical procedure; (iii) to identify the dominant hand of the surgeon; (iv) to monitor metrics associated with the experience of the surgeon; (v) to identify which tools the surgeon is using and when to change them for other tools; and/or (vi) tracking of the skin surface of the patient, as well as the number, position and orientation of the trocar ports. This data and information also may be used and computed by the system as part of the co-manipulation control paradigm. By measuring the true position and orientation of the trocar ports, the system may be provided an additional safety check to ensure that the system level computations are correct, e.g., to ensure that the actual motion of the robot arms or instrument matches a commanded motion of the robot arms or instrument in robotic assist mode.

Based on the data captured by optical scanner 1100, the system further may track the which instrument is being used in a respective port, how often instruments are swapped between ports, which ports have manually held instruments versus instruments coupled to the robot arm, to monitor and determine if additional trocar ports are added, if the system is holding the instruments in place while the patient or surgical table is moving (in which case, the system may change the operational mode of the robot arms to a passive mode and accommodate the movement by repositioning robot arm 300 and/or platform 100), and/or other conditions or parameters of the operating room or the system. The knowledge of the position and orientation of the skin surface and trocar ports relative to the robot arms may facilitate the implementation of "virtual boundaries" as described in further detail below.

Figure 14:
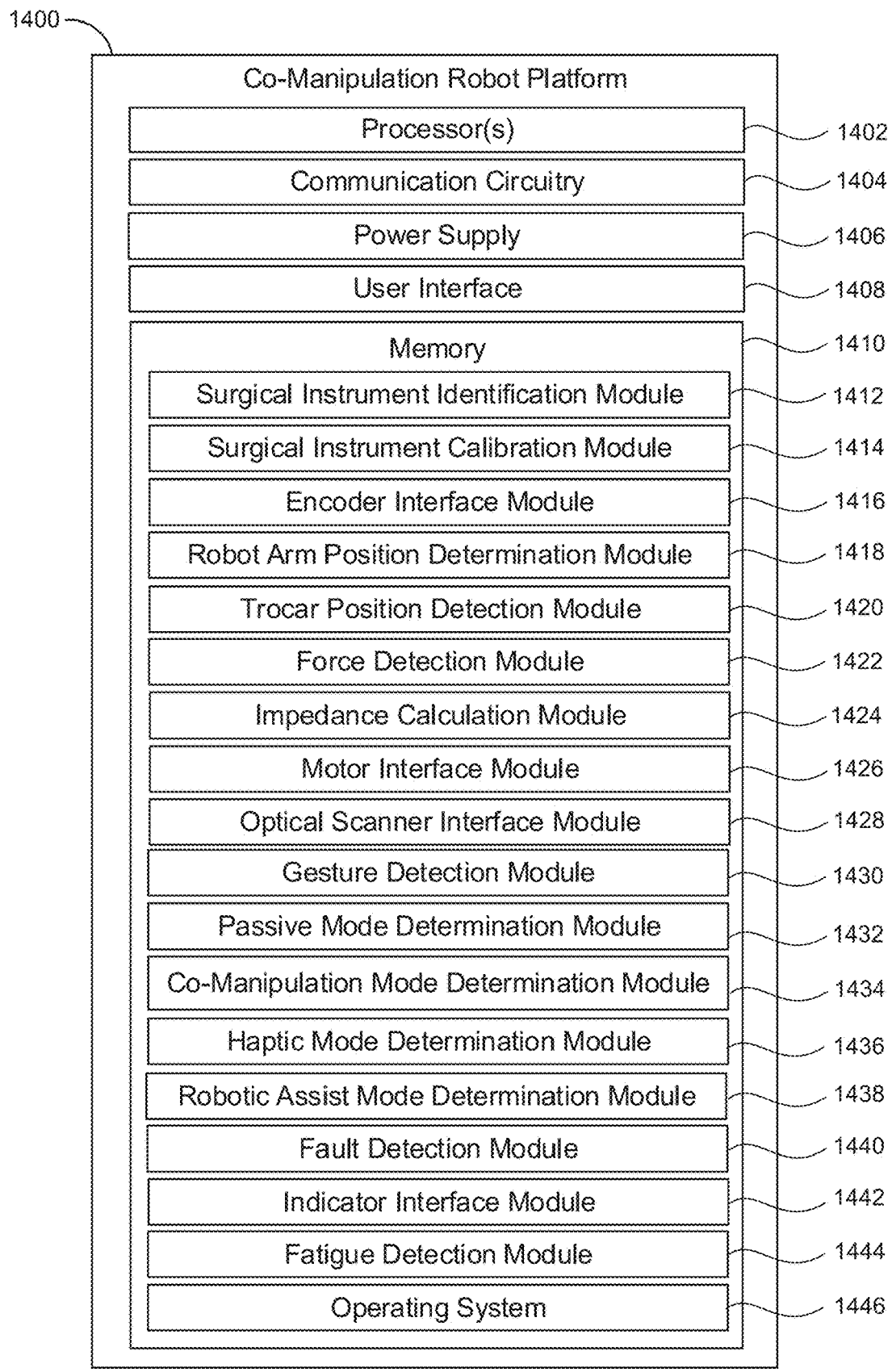
FIG. 14 shows some example components that may be included in a co-manipulation robot platform in accordance with the principles of the present disclosure.

Referring now to FIG. 14, components that may be included in co-manipulation robot platform 1400 are described. Platform 1400 may include one or more processors 1402, communication circuitry 1404, power supply 1406, user interface 1408, and/or memory 1410. One or more electrical components and/or circuits may perform some of or all the roles of the various components described herein. Although described separately, it is to be appreciated that electrical components need not be separate structural elements. For example, platform 1400 and communication circuitry 1404 may be embodied in a single chip. In addition, while platform 1400 is described as having memory 1410, a memory chip(s) may be separately provided.

Platform 1400 may contain memory and/or be coupled, via one or more buses, to read information from, or write information to, memory. Memory 1410 may include processor cache, including a multi-level hierarchical cache in which different levels have different capacities and access speeds. The memory also may include random access memory (RAM), other volatile storage devices, or non-volatile storage devices. Memory 1410 may be RAM, ROM, Flash, other volatile storage devices or non-volatile storage devices, or other known memory, or some combination thereof, and preferably includes storage in which data may be selectively saved. For example, the storage devices can include, for example, hard drives, optical discs, flash memory, and Zip drives. Programmable instructions may be stored on memory 1410 to execute algorithms for, e.g., calculating desired forces to be applied along robot arm 300 and/or the surgical instrument coupled thereto and applying impedances at respective joints of robot arm 300 to effect the desired forces.

Platform 1400 may incorporate processor 1402, which may consist of one or more processors and may be a general purpose processor, a digital signal processor (DSP), an application specific integrated circuit (ASIC), a field programmable gate array (FPGA) or other programmable logic device, discrete gate or transistor logic, discrete hardware components, or any suitable combination thereof designed to perform the functions described herein. Platform 1400 also may be implemented as a combination of computing devices, e.g., a combination of a DSP and a microprocessor, a plurality of microprocessors, one or more microprocessors in conjunction with a DSP core, or any other such configuration.

Platform 1400, in conjunction with firmware/software stored in the memory may execute an operating system (e.g., operating system 1446), such as, for example, Windows, Mac OS, QNX, Unix or Solaris 5.10. Platform 1400 also executes software applications stored in the memory. For example, the software may be programs in any suitable programming language known to those skilled in the art, including, for example, C++, PHP, or Java.

Communication circuitry 1404 may include circuitry that allows platform 1400 to communicate with an image capture devices such as optical scanner and/or endoscope. Communication circuitry 1404 may be configured for wired and/or wireless communication over a network such as the Internet, a telephone network, a Bluetooth network, and/or a WiFi network using techniques known in the art. Communication circuitry 1404 may be a communication chip known in the art such as a Bluetooth chip and/or a WiFi chip. Communication circuitry 1404 permits platform 1400 to transfer information, such as force measurements on the body wall at the trocar insertion point locally and/or to a remote location such as a server.

Power supply 1406 may supply alternating current or direct current. In direct current embodiments, power supply may include a suitable battery such as a replaceable battery or rechargeable battery and apparatus may include circuitry for charging the rechargeable battery, and a detachable power cord. Power supply 1406 may be a port to allow platform 1400 to be plugged into a conventional wall socket, e.g., via a cord with an AC to DC power converter and/or a USB port, for powering components within platform 1400.

Power supply 1406 may be operatively coupled to an emergency switch, such that upon actuation of the emergency switch, power stops being supplied to the components within platform 1400 including, for example, the braking mechanism disposed on at least some joints of the plurality of joints of robot arm 300. For example, the braking mechanisms may require power to disengage, such that without power supplied to the braking mechanisms, the braking mechanisms engage to prevent movement of robot arm 300 without power.

User interface 1408 may be used to receive inputs from, and/or provide outputs to, a user. For example, user interface 1408 may include a touchscreen, display, switches, dials, lights, etc. Accordingly, user interface 1408 may display information such as selected surgical instrument identity and force measurements observed during operation of robot arm 300. Moreover, user interface 1408 may receive user input including adjustments to the predetermined amount of movement at the handle of the surgical instrument or the predetermined dwell time period to cause the robot arm to automatically switch to the passive mode, the predetermined threshold of force applied at the handle of the surgical instrument to cause the robot arm to automatically switch to the co-manipulation mode, a position of the predefined haptic barrier, an identity of the surgical instrument coupled to the distal end of the robot arm, a vertical height of the robot arm, a horizontal position of the robot arm, etc., such that platform 1400 may adjust the information/parameters accordingly. In some embodiments, user interface 1408 is not present on platform 1400, but is instead provided on a remote, external computing device communicatively connected to platform 1400 via communication circuitry 1404.

Memory 1410, which is one example of a non-transitory computer-readable medium, may be used to store operating system (OS) 1446, surgical instrument identification module 1412, surgical instrument calibration module 1414, encoder interface module 1416, robot arm position determination module 1418, trocar position detection module 1420, force detection module 1422, impedance calculation module 1424, motor interface module 1426, optical scanner interface module 1428, gesture detection module 1430, passive mode determination module 1432, co-manipulation mode determination module 1434, haptic mode determination module 1436, robotic assist mode determination module 1438, fault detection module 1440, indicator interface module 1442, and fatigue detection module 1444. The modules are provided in the form of computer-executable instructions/algorithms that may be executed by processor 1402 for performing various operations in accordance with the disclosure.

For example, during a procedure, the system may continuously run the algorithms described herein based on the data collected by the system. That data may be collected and/or recorded using any of the components and methods disclosed herein, including, e.g., from sensors/encoders within the robots, from optical scanning devices in communication with the other components of the robotic system, and/or from manual inputs by an operator of the system. Accordingly, the algorithms, the data, and the configuration of the system may enable the user to co-manipulate the robot arms with minimal impact and influence from the weight of the robot arms and/or surgical instruments coupled thereto, force of gravity, and other forces that traditional robot arms fail to compensate for. Some of the parameters of the algorithms described herein may control an aspect of the behavior of the system including, e.g., robustness of detected features, sensitivity to false positives, robot control gains, number of features to track, dead zone radius, etc.

Surgical instrument identification module 1412 may be executed by processor 1402 for identifying the surgical instrument coupled to each of the robot arms, and loading the appropriate calibration file into the controller system. For example, the calibration file for each surgical instrument may be stored in a database accessible by surgical instrument identification module 1412, and may include information associated with the surgical instrument such as, e.g., instrument type, weight, center of mass, length, instrument shaft diameter, etc. Accordingly, when the appropriate calibration file is loaded, and the associated surgical instrument is coupled to robot arm 300, the system will automatically account for the mass of the surgical instrument, e.g., compensate for gravity on the surgical instrument, when the surgical instrument is attached to robot arm 300 based on the data in the calibration file, such that robot arm 300 may hold the surgical instrument in position after the surgical instrument is coupled to the robot arm and the operator lets go of the surgical instrument. For example, surgical instrument identification module 1412 may identify the surgical instrument based on user input via user interface 1408, e.g., the operator may select the surgical instrument from a database of surgical instruments stored in memory 1410.

In some embodiments, surgical instrument identification module 1412 may automatically identify the surgical instrument coupled with the robotic arm via the coupler body and the coupler interface using, e.g., an RFID transmitter chip and reader or receiver (e.g., placing an RFID sticker or transmitter on the surgical instrument that may transmit information about the surgical instrument to a receiver of the system), an near field communication ("NFC") device such as a near field magnetic induction communication device, a barcode and scanner or other optical device, a magnet based communication system, reed switches, a Bluetooth transmitter, the weight of the instrument and/or data gathered from the optical scanner and a lookup table, and/or any other features or mechanisms described herein or suitable for identification of the surgical instrument. As described above, the coupler body may be selected based on the size and shape of the lumen extending therethrough to accommodate and engage with a surgical instrument having a known elongated shaft diameter. Accordingly, surgical instrument identification module 1412 may automatically identify the surgical instrument based on the coupler body that is coupled to the surgical instrument via the magnetic connection between the coupler body and the coupler interface.

In some embodiments, surgical instrument identification module 1412 may identify the surgical instrument based on data obtained by optical scanner 1100 via optical scanner interface module 1428 described in further detail below. For example, the data may include measurement data associated with the specific instrument, such that surgical instrument identification module 1412 may compare such data with information contained within the database to identify the instrument and load the appropriate calibration file into the controller system. Similarly, surgical instrument identification module 1412 may detect if the instrument is removed and return the calibration parameters to a default configuration.

Surgical instrument calibration module 1414 may be executed by processor 1402 for calibration a surgical instrument, e.g., a surgical instrument that does not currently have an associated calibration file in the database stored in memory 1410. Accordingly, surgical instrument calibration module 1414 may calculate measurements and specifications of a surgical instrument when it is coupled to robot arm 300 and the system is in calibration mode, as described in further detail below with regard to FIG. 16, based on force measurements of robot arm 300 applied by the surgical instrument via force detection module 1422. For example, surgical instrument calibration module 1414 may generate a calibration file for the surgical instrument including information such as instrument type, weight, center of mass, length, instrument shaft diameter, a viscosity parameter of the surgical instrument, etc. At least some of the surgical instrument information in the calibration file may be provided by user input via user interface 1408, e.g., the instrument type.

If surgical instrument calibration module 1414 determines that re-calibration results are consistently different from the configurations already loaded into the system, surgical instrument calibration module 1414 may replace existing information or add to its list of known tools without any user inputs and load them automatically. Surgical instrument calibration module 1414 may determine that the calibration factors are not adequate to compensate for the force of gravity if, e.g., when a surgical instrument is coupled with the robot arm, the robot arm moves due only to forces of gravity acting on the robot arm and/or the surgical instrument, which may be done when the surgical instrument is positioned completely outside of the patient's body. Moreover, surgical instrument calibration module 1414 may automatically update or adjust the calibration factors (e.g., the forces applied to the joints of the robot arm) if it determines that the calibration factors are not adequate to compensate for the force of gravity. Thus, surgical instrument calibration module 1414 may update the calibration factors for the particular surgical instrument and store the updated calibration factors for the particular surgical instrument in the associated calibration file for future use.

Encoder interface module 1416 may be executed by processor 1402 for receiving and processing angulation measurement data from the plurality of encoders of robot arm 300, e.g., encoders E1-E7, in real time. For example, encoder interface module 1416 may calculate the change in angulation over time of the links of robot arm 300 rotatably coupled to a given joint associated with the encoder. As described above, the system may include redundant encoders at each joint of robot arm 300, to thereby ensure safe operation of robot arm 300. Moreover, additional encoders may be disposed on platform 100 to measure angulation/position of each robot arm relative to platform 100, e.g., the vertical and horizontal position of the robot arms relative to platform 100. Accordingly, an encoder may be disposed on platform 100 to measure movement of the robot arms along the vertical axis of platform 100 and another encoder may be disposed on platform 100 to measure movement of the robot arms along the horizontal axis of platform 100.

Robot arm position determination module 1418 may be executed by processor 1402 for determining the position of robot arm 300 and the surgical instrument attached thereto, if any, in 3D space in real time based on the angulation measurement data generated by encoder interface module 1416. For example, robot arm position determination module 1418 may determine the position of various links and joints of robot arm 300 as well as positions along the surgical instrument coupled to robot arm 300. Based on the position data of robot arm 300 and/or the surgical instrument, robot arm position determination module 1418 may calculate the velocity and/or acceleration of movement of robot arm 300 and the surgical instrument attached thereto in real time.

Trocar position detection module 1420 may be executed by processor 1402 for determining the position and/or orientation of one or more trocar port inserted within the patient. The position and/or orientation of a trocar port may be derived based on data obtained from, e.g., inertial measurement units and/or accelerometers, optical scanners, electromechanical tracking instruments, linear encoders, the sensors and data as described above. For example, the position of the trocar ports on the patient may be determined using a laser pointing system that may be mounted on one or more of the components of the system, e.g., wrist portion 311 of the robot arm, and may be controlled by the system to point to the optimal or determined position on the patient's body to insert the trocar. Moreover, upon insertion of the surgical instrument that is attached to robot arm 300 through a trocar, virtual lines may continuously be established along the longitudinal axis of the surgical instrument, the alignment/orientation of which may be automatically determined upon attachment of the surgical instrument to coupler interface 400 via the coupler body via the magnetic connection as described above, in real time as the surgical instrument moves about the trocar point. Moreover, when the surgical instrument is inserted within the trocar port, it will be pointing toward the trocar point, and accordingly, distal wrist link 316 will also point toward the trocar point, the angle of which may be measured by an encoder associated therewith. Accordingly, the trocar point may be calculated as the intersection of the plurality of virtual lines continuously established along the longitudinal axis of the surgical instrument. In this manner, the calculated trocar point will remained fixed relative to the patient as the surgical instrument is maneuvered about the trocar port, e.g., rotated or moved in or out of the patient.

Based on the known position and/or orientation of a trocar port in addition to the known position of the distal end of robot arm 300 from robot arm position determination module 1418, the system may maintain the position of the distal end of robot arm 300 relative to the trocar point as robot arm 300 moves, e.g., via vertical or horizontal adjustment thereof by platform 100, or as the patient table height is adjusted, thereby causing the height of the patient's abdomen to move, thereby keeping the surgical instrument within the patient's body and coupled to robot arm 300 steady during these external movements. To achieve this, the known position of the distal end of robot arm 300 from robot arm position determination module 1418 is calculated in the global frame of the system by adding position of platform 100 to the kinematics calculations (e.g., the "forward kinematics" of robot arm 300 in the context of serial chain robotic manipulators). With the position of the distal end of robot arm 300 known globally, the system may hold that position steady by applying appropriate forces to robot arm 300 during the external movements that minimize the error between its current and desired positions.

Force detection module 1422 may be executed by processor 1402 for detecting forces applied on robot arm 300, e.g., at the joints or links of robot arm 300 or along the surgical instrument, as well as applied on the trocar, e.g., body wall forces. For example, force detection module 1422 may receive motor current measurements in real time at each motor, e.g., M1, M2, M3, disposed within the base of robot arm 300, which are each operatively coupled to a joint of robot arm 300, e.g., base joint 303, shoulder joint 318, elbow joint 322, wrist joint 332. The motor current measurements are indicative of the amount of force applied to the associated joint. Accordingly, the force applied to each joint of robot arm 300 as well as to the surgical instrument attached thereto may be calculated based on the motor current measurements and the position data generated by robot arm position determination module 1418 and/or trocar position detection module 1420.

Due to the passive axes at the distal end of robot arm 300, the force applied by the instrument coupled with the robot arm on the trocar may remain generally consistent throughout the workspace of the robot arm. The force on the trocar may be affected by the interaction of the distal tip of the instrument with tissue within the body. For example, if a tissue retractor advanced through the trocar is engaged with (e.g., grasping) bodily tissue or another object inside the body, the force exerted on the end of the instrument from the bodily tissue or other object may cause a change in the force applied to the trocar. In some aspects, the force on the trocar may be a function of how much weight is being lifted by the instrument being used.

Impedance calculation module 1424 may be executed by processor 1402 for determining the amount of impedance/torque needed to be applied to respective joints of robot arm 300 to achieve the desired effect, e.g., holding robot arm 300 in a static position in the passive mode, permitting robot arm 300 to move freely while compensating for gravity of robot arm and the surgical instrument attached thereto in the co-manipulation mode, applying increased impedance to robot arm 300 when robot arm 300 and/or the surgical instrument attached thereto is within a predefined virtual haptic barrier in the haptic mode, etc. For example, by determining the forces applied on robot arm 300 via force detection module 1422, as well as the position/velocity/acceleration of the distal end of robot arm 300 in 3D space via robot arm position determination module 1418, the desired force/impedance to be applied to robot arm 300 to compensate for the applied forces may be calculated, e.g., for gravity compensation or to hold robot arm 300 in a static position in the passive mode. Accordingly, the desired force may be converted to torque to be applied at the joints of robot arm 300, e.g., by the motors operatively coupled to the joints of robot arm 300. For example, the robot Jacobian may be used for this purpose. Jacobian is a matrix that is computer at each given post of the robot arm, and relates the velocities at the joints to the velocity at the distal end of robot arm 300:

$$V = J * q_{dot}$$

Here, V is the velocity vector at the distal end of robot arm 300, J is its Jacobian matrix, and $q_{dot}$ is its joint velocities expressed in vector form. Using the energy principle, and assuming negligible masses for the links of robot arm 300 and negligible friction/dampening, the power of the system may be determined by multiplying its force and velocity:

$$F \cdot V = \tau \cdot q_{dot}$$
$$\Rightarrow$$
$$F \cdot (J * q_{dot}) = \tau \cdot q_{dot}$$

Here, F is the generalized force vector at the distal end of robot 300. Further, vector manipulation results in:

$$(J^t * F) \cdot q_{dot} = \tau \cdot q_{dot}$$
$$\Rightarrow$$
$$\tau = J^t * F$$

Here, t denotes the transpose of the matrix, such that the forces at the distal end of robot arm 300 may be converted to torques to be applied at the joints using the Jacobian matrix.

Motor interface module 1426 may be executed by processor 1402 for receiving motor current readings at each motor, e.g., M1, M2. M3, disposed within the base of robot arm 300, and for actuating the respective motors, e.g., by applying a predetermined impedance to achieved the desired outcome as described herein and/or to cause the joints operatively coupled to the respective motors to move, such as in the robotic assist mode.

Optical scanner interface module 1428 may be executed by processor 1402 for receiving depth data obtained by optical scanner 1100 and processing the depth data to detect, e.g., predefined conditions therein. Moreover, optical scanner interface module 1428 may generate depth maps indicative of the received depth data, which may be displayed to the operator, e.g., via a monitor. For example, optical scanner interface module 1428 may map the location of the trocar ports in 3D space, such that the mapping of trocar ports may be communicated to the operator, e.g., via display or user interface 1408. Optical scanner interface module 1428 further may receive image data from additional optical scanning devices as defined herein, including for example, an endoscope operatively coupled to the system.

Gesture detection module 1430 may be executed by processor 1402 for detecting predefined gestural patterns as user input, and executing an action associated with the user input. The predefined gestural patterns may include, for example, movement of a surgical instrument (whether or not attached to robot arm 300), movement of robot arm 300 or other components of the system, e.g., foot pedal, buttons, etc., and/or movement of the operator in a predefined pattern. For example, movement of the surgical instrument back and forth in a first direction (e.g., left/right, up/down, forward/backward, in a circle) may be associated with a first user input requiring a first action by the system and/or back and forth in a second direction (e.g., left/right, up/down, forward/backward, in a circle) that is different than the first direction may be associated with a second user input requiring a second action by the system. Similarly, pressing the foot pedal or a button operatively coupled with the system in a predefined manner may be associated with a third user input requiring a third action by the system, and movement of the operator's head back and forth or up and down repeatedly may be associated with a fourth user input requiring a fourth action by the system. Various predefined gestural patterns associated with different components or operators of the system may be redundant such that the associated user input may be the same for different gestural patterns. The predefined gestural patterns may be detected by, e.g., an optical scanning device such as a laparoscope or optical scanner 1100 via optical scanner interface module 1428 or directly by force applied to robot arm 300 via force detection module 1422 or other components of the system.

Actions responsive to user input associated with predefined gestural patterns may include, for example, enabling tool tracking to servo (i.e., move) the laparoscope based on the motion of a handheld tool; engaging the brakes on (e.g., preventing further movement of) the robot arm; engaging a software lock on the robot arm; dynamically changing the length of time that the robot arm takes to transition between states from a default setting; and/or identifying which member of the surgical staff is touching the robot arm, if any. This information may be used to ensure that the system does not move if the surgeon is not touching the robot arm, e.g., to avoid the scenario where an external force is acting on the robot arm (e.g., a light cable or other wire being pulled across the robot arm) and the system perceives the force to be intentional from the surgeon. The same information may be used to detect the gaze direction of the surgeon, e.g., whether the surgeon is looking at the video feed or somewhere else in the room, such that the system may freeze the robot arm if the surgeon's gaze is not in the direction it should be. Additionally, the system may reposition a field of view of a camera based on, for example, the direction a surgeon is facing or based on the objects that the surgeon appears to be looking at, based on the data from the optical scanner 1100.

In some embodiments, the operator may actively switch the system to a command mode, e.g., via user interface 1408, where particular movements or gestures of the robot arm, surgical instrument, operator, or otherwise as described herein are monitored by gesture detection module 1430 to determine if they are consistent with a predefined gestural pattern associated with a predefined user input.

Passive mode determination module 1432 may be executed by processor 1402 for analyzing the operating characteristics of robot arm 300 to determine whether to switch the operational mode of robot arm 300 to the passive mode where the system applies impedance to the joints of robot arm 300 via motor interface module 1426 in an amount sufficient to maintain robot arm 300, and accordingly a surgical instrument attached thereto, if any, in a static position, thereby compensating for mass of robot arm 300 and the surgical instrument, and any other external forces acting of robot arm 300 and/or the surgical instrument. If robot arm 300 is moved slightly while in the passive mode, but not with enough force to switch out of the passive mode, the system may adjust the amount of impedance applied the robot arm 300 to maintain the static position, and continuous this process until robot arm 300 is held in a static position. For example, passive mode determination module 1432 may determine to switch the operational mode of robot arm 300 to the passive mode if movement of the robot arm due to movement at the handle of the surgical instrument as determined by force detection module 1422 is less than a predetermined amount, e.g., no more than 1 to 5 mm, for at least a predetermined dwell time period associated with robot arm 300. The predetermined dwell time period refers to the length of time that robot arm 300 and/or the surgical instrument attached thereto, if any, are held in a static position. For example, the predetermined dwell time may range between, e.g., 0.1 to 3 seconds or more, and may be adjusted by the operator. FIG. 19 illustrates a table or exemplary values of the threshold dwell times for a range of sample instrument types.

In some embodiments, passive mode determination module 1432 may determine to switch the operational mode of robot arm 300 to the passive mode if movement of the robot arm due to movement at the handle of the surgical instrument as determined by force detection module 1422 has a velocity that is less than a predetermined dwell velocity/speed. For example, if passive mode determination module 1432 determines that robot arm 300 and/or the surgical instrument attached thereto, if any, moves at a speed that is lower than the predetermined dwell speed during an entire predetermined dwell period, then passive mode determination module 1432 may switch the operational mode of robot arm 300 to the passive mode. FIG. 19 illustrates a table or exemplary values of the threshold dwell speeds for a range of sample instrument types. For example, for surgical instruments such as scopes and tissue manipulation devices, the threshold dwell speeds may be, e.g., 3-5 mm/second, and for surgical instruments such as suturing instruments, needle drivers, high force instruments, staplers, and clip appliers, the threshold dwell speeds may be, e.g., 1-2 mm/second. In some embodiments, passive mode determination module 1432 may determine to switch the operational mode of robot arm 300 to the passive mode based on the identity of the surgical instrument upon attachment of the surgical instrument to robot arm 300 and/or responsive detachment of the surgical instrument from robot arm 300.

Co-manipulation mode determination module 1434 may be executed by processor 1402 for analyzing the operating characteristics of robot arm 300 to determine whether to switch the operational mode of robot arm 300 to the co-manipulation mode where robot arm 300 is permitted to be freely moveable responsive to movement at the handle of the surgical instrument for performing laparoscopic surgery using the surgical instrument, while the system applies an impedance to robot arm 300 via motor interface module 1426 in an amount sufficient to account for mass of the surgical instrument and robot arm 300. Moreover, the impedance applied to robot arm 300 may provide a predetermined level of viscosity perceivable by the operator. FIG. 19 illustrates a table or exemplary values of viscosity levels for a range of sample instrument types. In some embodiments, the viscosity level may be a function of the speed that the surgical instrument is being moved and the distance of the tip of the instrument from the trocar point. For example, co-manipulation mode determination module 1434 may determine to switch the operational mode of robot arm 300 to the co-manipulation mode if force applied at robot arm 300 due to force applied at the handle of the surgical instrument exceeds a predetermined threshold associated with robot arm 300 (e.g., a "breakaway force"). The predefined force threshold may be, e.g., at least 7 Newtons, approximately 7 Newtons, at least 7 Newtons, 4-15 Newtons, 4-10 Newtons. The predefined force threshold may be dependent on the type of surgical instrument that is being used and/or whether there is an external force being applied to the surgical instrument.

FIG. 19 illustrates a table or exemplary values of the predefined force thresholds for a range of sample instrument types. As shown in FIG. 19, the predefined force thresholds may reflect the typical external tissue forces that may be exerted on the surgical instrument. In some embodiments, predefined force threshold may be increased if a force is exerted on the surgical instrument by tissue or an organ or otherwise, depending on the direction of the breakaway force. For example, if the breakaway force is in the same direction as the force exerted on the surgical instrument from the tissue or organ, the predefined force threshold may be increased by an amount equal to or commensurate with the force exerted on the surgical instrument from the tissue or organ. In some embodiments, the predefined force threshold for a respective robot arm be adjusted based on a patient's body mass index ("BMI"). For example, a patient with a higher BMI may have a heavier liver that would likely exert a greater force on the instrument. Accordingly, the predefined force threshold may selected to be higher for the patients with a higher BMI. Accordingly, the operation may actuate a "high force mode," e.g., via user interface 1408, where predefined force threshold is increased to accommodate for engaging with heavier tissue or organs. For example, the predefined force threshold may be selectively increased by 20-100% or more.

Moreover, the force exerted by the user on the surgical instrument and any external tissue forces applied to the surgical instrument may be directionally dependent. For example, if the force exerted by the user on the surgical instrument is in the same direction as an external tissue force applied to the surgical instrument, the two forces may be additive such that the amount of force exerted by the user on the surgical instrument needed to overcome the predefined force threshold may be reduced by the magnitude of the external tissue force such that a lower force than the predefined force threshold would be required to exit the passive mode and enter the co-manipulation mode. On the other hand, if the force exerted by the user on the surgical instrument is in a direction opposite to an external tissue force applied to the surgical instrument, than the necessary amount of force exerted by the user on the surgical instrument needed to overcome the predefined force threshold may be increased by the magnitude of the external tissue force such that a higher force than the predefined force threshold would be required to exit the passive mode and enter the co-manipulation mode.

In addition, if the force exerted by the user on the surgical instrument is in a direction that is perpendicular to an external tissue force applied to the surgical instrument, than the necessary amount of force exerted by the user on the surgical instrument needed to overcome the predefined force threshold may not be affected by the magnitude of the external tissue force such that the necessary force exerted by the user on the surgical instrument needed to exit the passive mode and enter the co-manipulation mode will equal the predefined force threshold. For other directions, the force vectors of the applied forces may be added to or offset by the force vectors of the external tissue forces to overcome predefined force threshold values for the system or the particular surgical instrument that is coupled with the robot arm, depending on the direction of the external tissue force, if any, and the force applied by the user. In some embodiments, co-manipulation mode determination module 1434 may determine to switch the operational mode of robot arm 300 to the co-manipulation mode based on the identity of the surgical instrument.

Haptic mode determination module 1436 may be executed by processor 1402 for analyzing the operating characteristics of robot arm 300 to determine whether to switch the operational mode of robot arm 300 to the haptic mode where the system applies an impedance to robot arm 300 via motor interface module 1426 in an amount higher than applied in the co-manipulation mode, thereby making movement of robot arm 300 responsive to movement at the handle of the surgical instrument more viscous in the co-manipulation mode. For example, haptic mode determination module 1436 may determine to switch the operational mode of robot arm 300 to the haptic mode if at least a portion of robot arm 300 and/or the surgical instrument attached thereto is within a predefined virtual haptic boundary. Specifically, a virtual haptic boundary may be established by the system, such that the robot arm or the surgical instrument coupled thereto should not breach the boundary. For example, a virtual boundary may be established at the surface of the patient to prevent any portion of the robot arms or the instruments supported by the robot arms from contacting the patient, except through the one or more trocars. Similarly, the virtual haptic boundary may include a haptic funnel to help guide the instrument into the patient as the operator inserts the instrument into a trocar port. Accordingly, based on position data of robot arm 300 and/or the surgical instrument coupled thereto, e.g., received by robot arm position determination module 1418 and/or trocar position detection module 1420, haptic mode determination module 1436 may determine if robot arm 300 and/or the surgical instrument is within the predefined virtual haptic boundary, and accordingly transition robot arm 300 to the haptic mode where processor 1402 may instruct associated motors to apply an effective amount of impedance to the joints of robot arm 300 perceivable by the operator to communicate to the operator the virtual haptic boundary. Accordingly, the viscosity of robot arm 300 observed by the operator will be much higher than in co-manipulation mode. In some embodiments, haptic mode determination module 1436 may determine to switch the operational mode of robot arm 300 to the haptic mode based on the identity of the surgical instrument.

Robotic assist mode determination module 1438 may be executed by processor 1402 for analyzing the operating characteristics of robot arm 300 to determine whether to switch the operational mode of robot arm 300 to the robotic assist mode where processor 1402 may instruct associated motors via motor interface module 1426 to cause movement of corresponding link and joints of robot arm 300 to achieve a desired outcome. For example, robotic assist mode determination module 1438 may determine to switch the operational mode of robot arm 300 to the robotic assist mode if a predefined condition exists based on data obtained from, e.g., optical scanner interface module 1428.

For example, robotic assist mode determination module 1438 may determine that a condition exists, e.g., the field of view of a laparoscope coupled to robot arm 300 or optical scanner 1100 is not optimal for a given surgical procedure, e.g., due to blocking by the surgeon or assistant or another component of the system, based on image data obtained from the laparoscope or optical scanner 1100 via optical scanner interface module 1428, such that the robot arm coupled to the laparoscope or optical scanner 1100 should be repositioned or zoom in/out to optimize the field of view of the surgical site for the operator. Thus, in robotic assist mode, processor 1402 may instruct robot arm 300, either automatically/quasi-automatically or responsive to user input by the operator, to move to reposition the laparoscope and/or cause the laparoscope to zoom in or zoom out, or to increase a resolution of an image, or otherwise. For example, the user input by the operator may be determined by gesture detection module 1430, as described above, such that movement of the robot arm or a surgical instrument in a predefined gestural pattern in a first direction causes the endoscope to increase resolution or magnification and in a second direction causes the endoscope to decrease resolution or magnification, and movement in another predefined gestural pattern causes the robot arm holding the laparoscope to retract away from the patient's body.

In addition, robotic assist mode determination module 1438 may determine that a condition exists, e.g., that one or more trocars are not in an optimal position, for example, due to movement of the patient, such that robot arm 300 should be repositioned to maintain the trocar in the optimal position, e.g., in an approximate center of the movement range of robot arm 300, thereby minimizing the risk of reaching a joint limit of the robot arm during a procedure. Thus, in robotic assist mode, processor 1402 may instruct system to reposition robot arm 300, e.g., via vertical/horizontal adjustment by platform 100 or via the joints and links of robot arm 300, to better align the surgical instrument workspace.

Robotic assist mode determination module 1438 may determine that a condition exists, e.g., the distance between an object and robot arm 300 is within a predetermined threshold, based on image data obtained from the laparoscope or optical scanner 1100 via optical scanner interface module 1428, such that the robot arm should be frozen to avoid collision with the object. Thus, in robotic assist mode, processor 1402 may instruct robot arm 300 apply the brakes to slow down the robot arm or inhibit or prevent movement within a predetermined distance from the other object.

Fault detection module 1440 may be executed by processor 1402 for analyzing the data indicative of the operating characteristics of the system, e.g. position data generated by robot arm position determination module 1418 and/or trocar position detection module 1420 and/or force measurement calculated by force detection module 1422, to detect whether a fault condition is present. For example, fault detection module 1440 may a fault condition of the system and determine whether the fault condition is a "minor fault," a "major fault," or a "critical fault," wherein each category of fault condition may be cleared in a different predefined manner.

For example, fault detection module 1440 may detect a minor fault condition such as robot arm 300 being moved with a velocity exceeding a predetermined velocity threshold, which may be cleared, e.g., by slowing down the movement of robot arm 300. In some embodiments, the system may automatically apply additional impedance to robot arm 300 when robot arm 300 is moving too fast to thereby force the operator to slow down movement of robot arm 300. Moreover, fault detection module 1440 may detect a major fault condition such as an inadvertent bump of robot arm 300 as indicated by a large force applied to robot arm 300 by a person other than the operator. In response to detection of a major fault condition, fault detection module 1440 may actuate the braking mechanism associate with each motorized joint of robot arm 300 (or at least the joints associated with the major fault condition), to thereby freeze robot arm 300 and inhibit further movement of robot arm 300. Such a major fault condition may be cleared by the operator actuating a "clear" option displayed on user interface 1408. Fault detection module 1440 may detect a critical fault condition such as redundant encoders associated with a given joint of robot arm 300 generating different angulation measurements with a delta exceeding a predetermined threshold. In response to detection of a critical fault condition, fault detection module 1440 may actuate the braking mechanism associate with each motorized joint of robot arm 300 to thereby freeze robot arm 300 and inhibit further movement of robot arm 300. Such a critical fault condition may be cleared by the operator restarting the system. Upon restart of the system, if the critical fault condition is still detected by fault detection module 1440, robot arm 300 will remain frozen until the critical fault condition is cleared.

Indicator interface module 1442 may be executed by processor 1402 for causing indicators 334 to communicate the state of the system, e.g., the operational mode of robot arm 300, to the operator or other users, based on, for example, determinations made by passive mode determination module 1432, co-manipulation mode determination module 1434, haptic mode determination module 1436, and/or robotic assist mode determination module 1438. For example, indicator interface module 1442 may cause indicators 334 to illuminate in specific color light associated with a specific state of the system. For example, indicator interface module 1442 may cause indicators 334 to illuminate in a first color (e.g., yellow) to indicate that no surgical instrument is attached to the robot arm, and that the robot arm may be moved freely such that the system compensates for the mass of the robot arm; in a second color (e.g., purple) to indicate that a surgical tool is attached to the robot arm, and that the robot arm may be moved freely such that the system compensates for the mass of the robot arm and the mass of the surgical instrument coupled to the robot arm; in a third color (e.g., blue) to indicate that a surgical instrument is attached to the robot arm, and that the robot arm is in the passive mode as determined by passive mode determination module 1432; in a fourth color (e.g., pulsing orange) to indicate that at least a portion of the robot arm and/or the surgical instrument attached thereto is within the virtual haptic boundary, e.g., 1.4 m or more above the ground; in a fifth color (e.g., pulsing red) to indicate that a fault has been detected by the system by fault detection module 1440. As will be understood by a person having ordinary skill in the art, different colors and patterns may be communicated by indicators 334 to indicate the states of the system described above.

Additionally, indicators 334 may be illuminated in other distinct colors and/or patterns to communicate additional maneuvers by robot arm 300, e.g., when robot arm 300 retracts the surgical arm in the robotic assist mode, or performs another robotically-assisted maneuver in the robotic assist mode. As described above, indicators 334 further may include devices for emitting other alerts such as an audible alert or text alert. Accordingly, indicator interface module 1442 may cause indicators 334 to communicate the state of the system to the operator using audio or text, as well as or instead of light.

Fatigue detection module 1444 may be executed by processor 1402 for detecting user fatigue that may occur during operation of robot arm 300 in a surgical procedure, as described in further detail below with regard to FIG. 25. For example, based on data from, e.g., robot arm position determination module 1418, force detection module 1422, impedance calculation module 1424, fatigue detection module 1444 may determine the level of fatigue of the operator using the surgical instrument coupled to robot arm 300, and compare the level of fatigue with a predetermined fatigue threshold. For example, fatigue detection module 1444 may assess an overall score for a given procedure to determine the level of fatigue based on, e.g., operator hand tremor, distance/minimum path travelled by the instrument tip, time to achieve procedure steps, and/or time to complete the procedure. Based on the data generated by fatigue detection module 1444, impedance calculation module 1422 may determine an amount of impedance necessary to apply to robot arm 300 to, e.g., reduce tremor of the operator, such that motor interface module 1426 may cause the associated motors to apply the requisite impedance to robot arm 300. Moreover, based on the data generated by fatigue detection module 1444, motor interface module 1426 may cause the associated motors to move the links of robot arm 300 to guide the operator's manipulation of the surgical instrument attached thereto.

The co-manipulation surgical robot systems described herein may include additional modules within memory 1410 of platform 200 for executing additional tasks based on the data obtained. For example, the system may determine that a surgical instrument has been attached to robot arm 300 by detecting a rapid or sudden change in force (a "snapping motion") applied to robot, e.g., due to the attraction force of the magnetic connection between the coupler body and coupler interface 400, via force detection module 1422. For example, the attractive forces of the magnets on the coupler body and coupler interface 400 may cause a sudden movement on at least an end portion of the robot arm, and/or a sudden rotation of the last joint of the robot arm when the magnets are aligning. Accordingly, this sudden movement may be detected and may trigger surgical instrument identification module 1412 to determine that an instrument has been attached or detached from the robot arm. Similarly, surgical instrument identification module 1412 may determine that the surgical instrument has been detached from robot arm 300, e.g., when subsequent motions of the distal end of robot arm 300 are accompanied by little to no rotation in the distal-most joint of robot arm 300.

Additionally, the system may determine if the surgical instrument has been detached from robot arm 300 based on data indicative of the position of the distal end of robot arm 300 relative to the trocar point generated by trocar position detection module 1420, as well as the direction of an instrument shaft and/or an orientation of the distal-most link of robot arm 300, e.g., distal wrist link 316. For example, if the instrument is pointing directly at the trocar, then there is a higher probability that a tool is attached to the robot arm. Moreover, axis Q7 of robot arm 300 may indicate the pointing direction of the instrument and, if the instrument is passing through the trocar port, the distal wrist link 316 will point in a direction of the trocar port. Therefore, if distal wrist link 316 is not pointing toward the trocar port, then the system may determine that the robot arm is not supporting an instrument or the instrument is not advanced through the trocar port. For example, when an instrument is detached from robot arm 300 and robot arm 300 is moved, the computed direction of the instrument shaft (e.g., the direction that the instrument would point if attached to robot arm 300) may no longer point to the trocar entry point and likely will not point to the trocar entry point. Accordingly, the may alert a user if the system determines that no tool is coupled with robot arm 300, e.g., via indicators 334.

In addition, the system may identify when a user may be attempting to remove or decouple a surgical instrument from robot arm 300 and adjust the removal force required to decouple the surgical instrument, and accordingly the coupler body, from coupler interface 400. For example, where one or more magnets are used to provide a biasing force to bias the surgical coupler body to the coupler interface, a force greater than the attraction force provided by the one or more magnets in a direction opposing the force provided by the one or more magnets must be exerted on the surgical instrument and/or the coupler body that is coupled with the surgical instrument to overcome the attracting force and decouple the coupler body and surgical instrument from the coupler interface. For example, the removal force may be 30-60 Newtons.

Moreover, the system may gather and analyze telemetry data regarding forces being applied to the robot arm to assess or estimate whether a user is attempting to remove a tool from the robot arm and, if so, reduce the coupling force between the coupler body and the coupler interface to make it easier for the user to disengage the surgical instrument from the robot arm. For example, the coupling/removal force may be reduced by 50-80%. Based on historical data and user feedback, as well as on data such as whether a user replaces the instrument without adjusting a location of the instrument, which could indicate inadvertent removal of the instrument, the system may estimate the optimal times to reduce a coupling force between the coupler body and the coupler interface. Moreover, the coupling force may be increased during operation to prevent inadvertent removal of surgical instrument from the robot arm.

Additionally, the system may determine an optimum positioning of robot arms 300 and its joints, the surgical instruments coupled with the robot arms, or other components of the robot arms and/or the system based on data obtained from the optical scanning devices used with the system, and provide guidance to the operator of the system to achieve the optimum positioning. Data indicative of the optimum positioning further may be used by processor 1402 to instruct the motors to cause corresponding links and joints of robot arm 300 to move, e.g., in robotic assist mode, to automatically reposition robot arm 300 and/or the optical scanning devices in the optimum position, e.g., during the setup stage or thereafter.

In addition, the system may collect data from sensors, e.g., position data of robot arm 300 or the surgical instrument attached thereto via the encoders or optical scanning devices and/or position data of the operator via body sensors or optical scanning devices, during a procedure, e.g., during setup or operation of robot arm 300, such that processor 1402 may detect deviations of movements or processes of the current user as compared to a model or optimal movement pattern, and communicate the deviations to the current user in real-time. For example, processor 1402 may cause a monitor to display the deviations to the current user in real-time, as well as the optimal and/or actual movement pattern. Additionally, or alternatively, indicator interface module 1440 may cause indicators 334 to indicate deviations from the model or optimal movement pattern, e.g., by illuminating a specific color and/or in a specific pattern. Additionally, or alternatively, motor interface module 1426 may apply impedance to robot arm 30 perceivable by the operator as haptic feedback including vibrations, restrictions on movement, or sensations to indicate deviations from the model or optimal movement pattern. Accordingly, the system may be used as a training tool for new users as such data may be used to optimize the position of a surgical device in real-time.

The system further may analyze the depth map generated by the optical scanning devices and cluster different groups of (depth) pixels into unique objects, a process which is referred to as object segmentation. Examples of such algorithms for segmentation may include: matching acquired depth map data to a known template of an object to segment; using a combination of depth and RGB color image to identify and isolate relevant pixels for the object; and/or machine learning algorithms trained on a real or synthetic dataset to objects to identify and segment. Examples of such segmentation on a depth map may include: locating the robot arms or determining the position of the robot arms; identifying patient ports (e.g., trocar ports) and determining a distance from the instruments to the trocar ports; identifying the surgeon and distinguishing the surgeon from other operators in the room; and/or identifying the surgeon in the sensor's field of view. Moreover, the system may use object segmentation algorithms to uniquely identify the surgeon and track the surgeon with respect to, for example, a surgical table, a patient, one or more robot arms, etc. In addition, the system may use object segmentation algorithms to determine if a surgeon is touching or handling either of the robot arms and, if so, identify which robot arm is being touched or handled by the surgeon.

Figure 15:
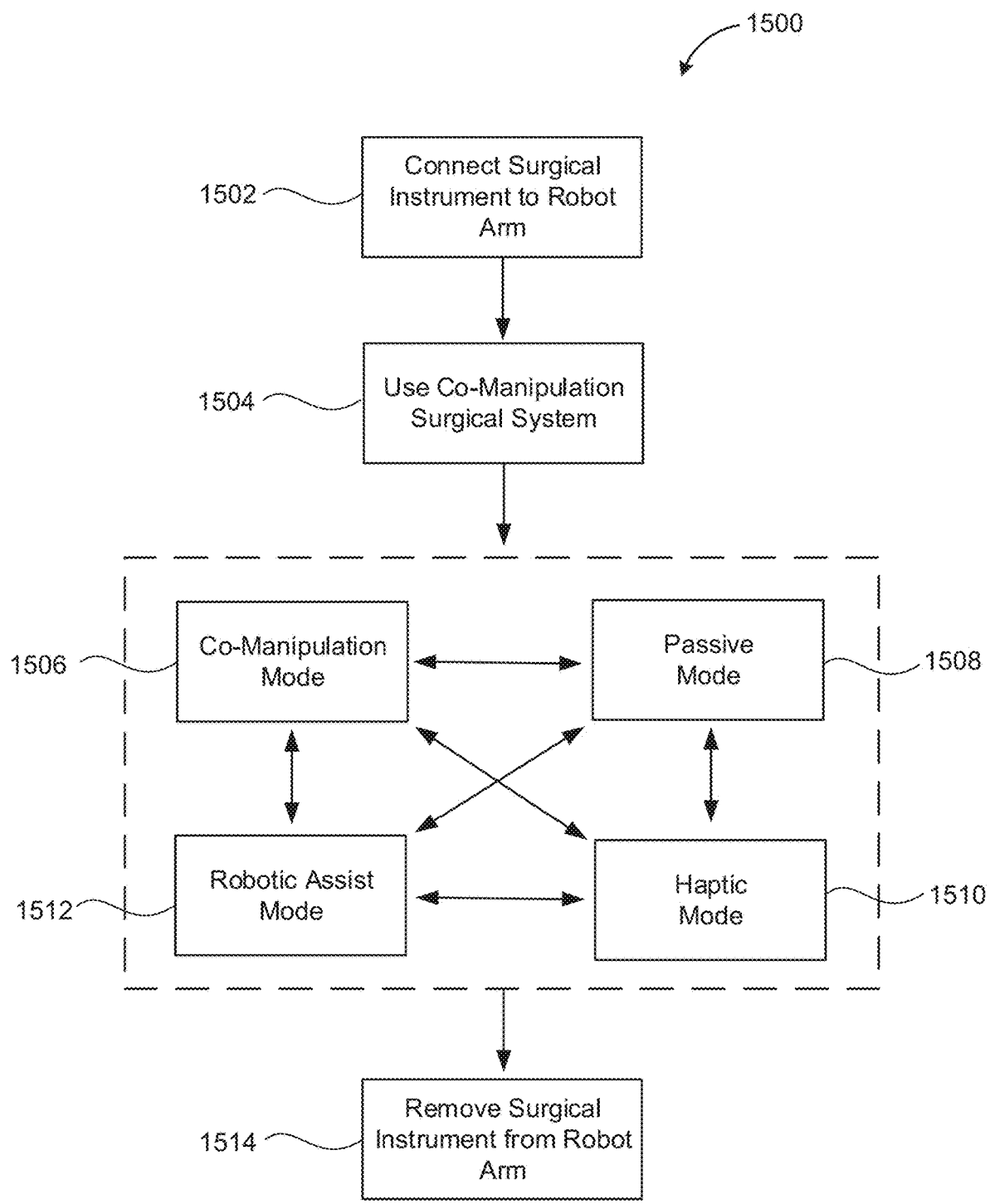
FIG. 15 is a flow chart illustrating operation of the co-manipulation surgical system in accordance with the principles of the present disclosure.

Referring now to FIG. 15, operation 1500 of the co-manipulation surgical robot systems described herein is provided. As shown in FIG. 15, at step 1502, the operator may couple a selected surgical instrument to coupler interface 400 of robot arm 300 via a coupler body, e.g., coupler body 500, 600, 700. As described above, the operator may select a coupler body sized and shaped to couple with the selected surgical instrument, e.g., based on the elongated shaft diameter of the surgical instrument. When the surgical instrument and coupler body are ready to be coupled to robot arm 300, the operator may load the calibration file of the selected surgical instrument, e.g., via user interface 1408, such that information associated with the selected surgical instrument, e.g., a laparoscope or retractor, is loaded into the system. For example, the operator may select the calibration file from a database of calibration files for a variety of surgical instruments. The calibration files may be stored from previous procedures, and may be pre-loaded to include calibration files of commonly used laparoscopic instruments.

Figure 16:
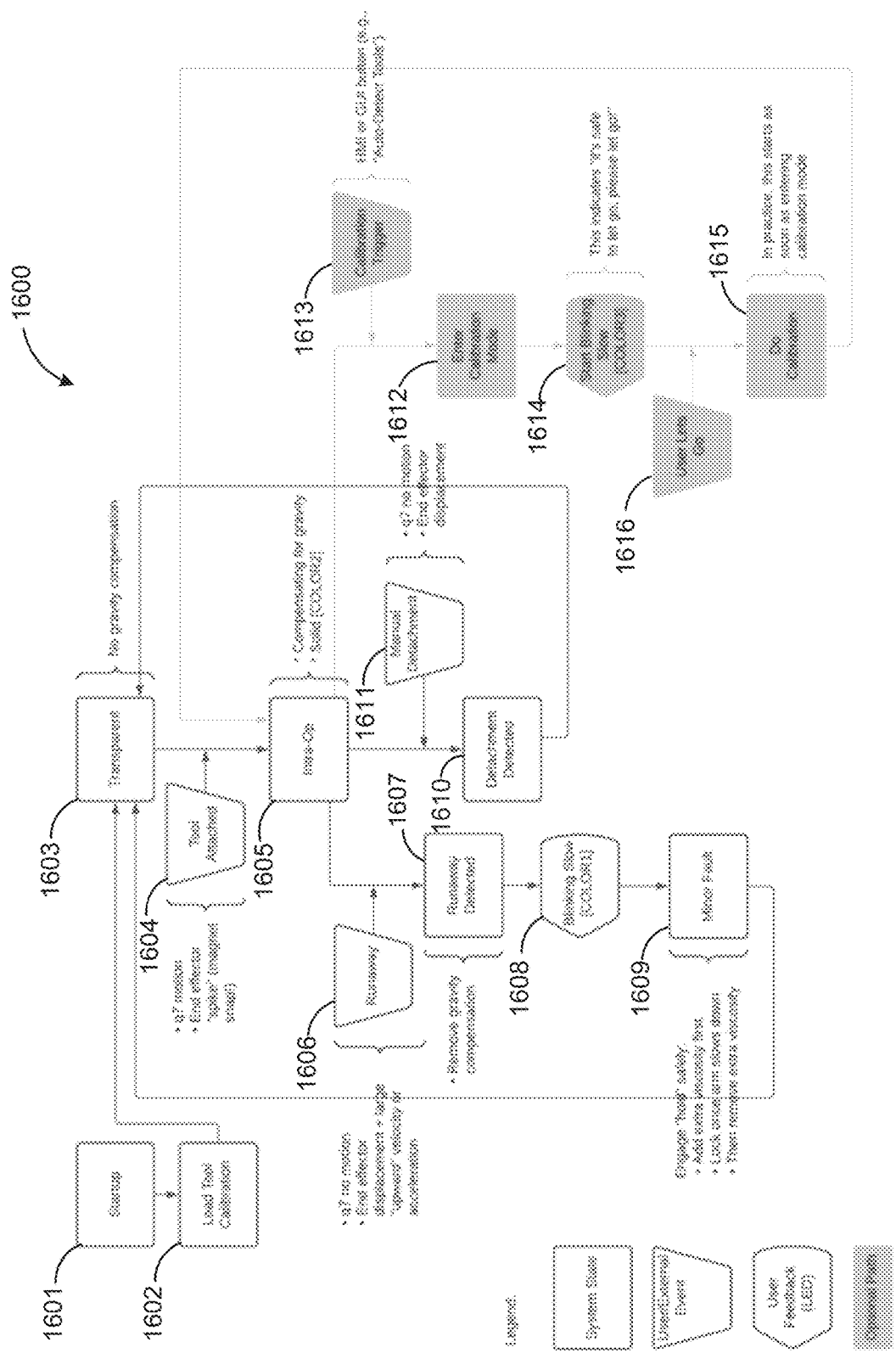
FIG. 16 is a flow chart illustrating surgical instrument calibration of the co-manipulation surgical system in accordance with the principles of the present disclosure.

If the calibration file for the selected surgical instrument is not available in the database, the operator may self-calibrate the surgical instrument using the system. For example, FIG. 16 illustrates surgical instrument calibration process 1600 for calibrating a surgical instrument, e.g., to determine the center of mass of the surgical instrument, which may be used in calculating accurate force measurements on the surgical instrument and robot arm 300 during operation. At step 1601, the operator may actuate the "startup" option on user interface 1408. At step, 1602, the operator may select the "load tool calibration" to begin the calibration process. At step 1603, the system does not apply any impedance to robot arm 300 for gravity compensation of a surgical instrument. The system may apply impedance to robot arm 300 to account for the weight of robot arm 300, e.g., to prevent robot arm 300 from dropping to the ground. At step 1604, the surgical instrument is coupled to coupler interface 400 of robot arm 300 via the appropriate sized coupler body, which may cause wrist portion 411 of robot arm 300 to rotate about axis Q7 to engage with the coupler body.

At step 1605, the system compensates for the gravity of the surgical instrument and the force applied by the hand of the operator, e.g., by measuring the force applied to the distal end of robot arm 300 due to the mass of the surgical instrument. As described above, the force applied to the distal end of robot arm 300 may be measured by measuring the motor current across the motors disposed in the base of robot arm 300. If the system overcompensates for the gravity of the surgical instrument, at step 1606, robot arm 300 may "runaway", e.g., drift upward. The runaway effect may be detected at step 1607, and at step 1608, indicators 334 may blink to indicate to the operator of the runaway. At step 1609, the system may identify the runaway as a minor fault, and accordingly apply additional impedance to robot arm 300 and freeze robot arm 300 when robot arm 300 slows down before removing the additional impedance. Once the minor fault is addressed, calibration process 1600 may return to step 1603.

After step 1605, when the system compensates for the gravity of the surgical instrument, if the surgical instrument is detached, either accidentally or manually by the operator at step 1611, at step 1610, the system detected the detachment of the surgical instrument from robot arm 300. As a result, the system will stop compensating for the gravity of the surgical instrument, and calibration process 1600 may return to step 1603. After step 1605, when the system compensates for the gravity of the surgical instrument, calibration process 1600 is ready to enter calibration mode at step 1612. For example, the operator may initiate calibration mode via user interface 1408 at step 1613. At step 1614, the system may indicate to the operator, e.g., via user interface 1408 and/or blinking of indicators 334, that it is safe to let go of surgical instrument, such that the operator may let go of the surgical instrument at step 1616. At step 1615, the system calibrations the surgical instrument.

Referring again to FIG. 15, when the surgical instrument and coupler body are ready to be coupled to robot arm 300, and the appropriate calibration file is loaded, the operator may easily place the coupler body near coupler interface 400, such that the magnetic connection between the coupler body and coupler interface 400 automatically aligns and coupled the surgical instrument to robot arm 300. The system will now accurately compensate for the gravity of the selected surgical instrument. At step 1504, the user may use the co-manipulation surgical system by freely manipulating the surgical instrument coupled to robot arm 300 in the ordinary manner that the operator would without robot arm 300 coupled thereto. As shown in FIG. 15, as the operator manipulates the surgical instrument, and accordingly robot arm 300 coupled thereto, the system may automatically switch between, e.g., co-manipulation mode 1506, passive mode 1508, haptic mode 1510, and robotic assist mode 1512 (collectively referred to as "operational modes"), upon detection of predefined conditions, as described below with regard to FIG. 17. In some embodiments, the system may automatically switch between only co-manipulation mode 1506, passive mode 1508, and haptic mode 1510. In some embodiments, the operator may select which operational mode to set the system in prior to using the co-manipulation surgical system at step 1504.

For example, an operator may exert a particular force on the distal end of robot arm 300, e.g. by manipulating the surgical instrument coupled to robot arm 300, to indicate that the operator wishes to change the operational mode of the particular robot arm. Sensors and/or motor current readings may be used to detect the force applied to the distal end of robot arm 300 and to determine if the force matches a predefined force signature associated with an operational change, e.g., by comparing the force with one or more predefined force signatures stored in the system. If there is a match, then the system may change the operational mode of the robot arm to the particular operational mode that matches the force signature.

Figure 17:
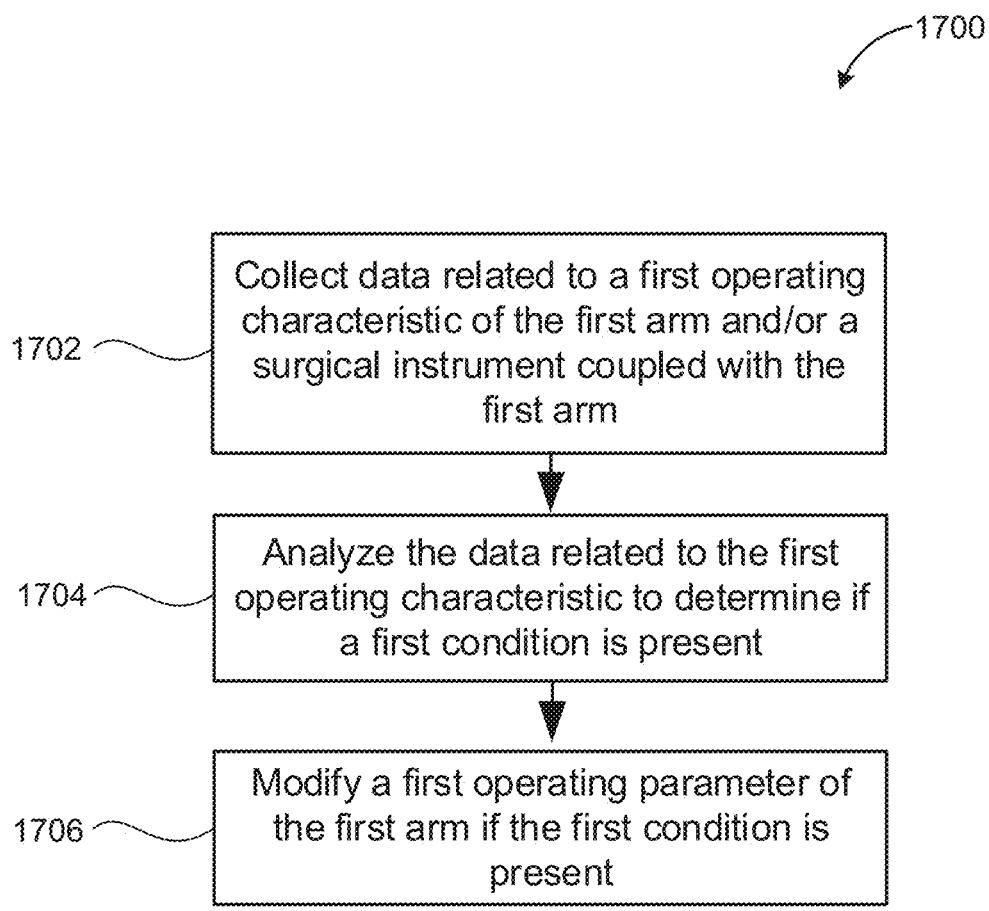
FIG. 17 is a flow chart illustrating operation of the robot arm in accordance with the principles of the present disclosure.

As described above, during operation of the co-manipulation surgical system, the system may continuously monitor the robot arm and forces applied thereto to detect predefined conditions that require switching the operational modes of the system, as described in method 1700 of FIG. 17. As shown in FIG. 17, at step 1702, the system continuously collects data related to a first operating characteristic of the robot arm and/or of the surgical instrument coupled with the robot arm. For example, as described above, the system may measure motor current of the motors operatively coupled to the joints of the robot arm as well as angulations of the links of the robot arm based on measurements by the encoders of the robot arm to calculate the positon of the robot arm and the surgical instrument as well as the forces acting on any portion of the robot arm as well as on the surgical instrument, if any, in real time. At step 1704, the system may analyze the data related to the first operating characteristic to determine if a first condition is present. For example, based on the position and force data of the robot arm and/or surgical instrument, the system may determine if the movement of the robot arm due to movement of the surgical instrument coupled thereto is within a predetermined movement threshold of the robot arm for a period of time longer than the predetermined dwell time of the robot arm. Upon detection of this first condition, at step 1706, the system may modify a first operating parameter of the robot arm. For example, the system may switch the operational mode of the robot arm to the passive mode, where the robot arm maintains the surgical instrument in a static position.

For example, a first robot arm may be coupled to a laparoscope, and the operator may manipulate the laparoscope within the patient until a desirable field of view is provided by the laparoscope, e.g., via a monitor displaying the image feed from the laparoscope. In order to freely move the laparoscope coupled to the first robot arm in the co-manipulation mode, the operator must apply a sufficient force to the laparoscope that exceeds a predetermined force threshold. The predetermined force threshold should be low enough such that it does not require much force by the operator to freely move the laparoscope. Moreover, the predetermined force threshold may be selected so as to resist inadvertent movement away from the passive mode. As the operator freely moves the laparoscope in the co-manipulation mode, as described above, the system will apply enough impedance to the first robot arm to compensate for the effects of mass (i.e., inertia) and/or gravity of the first robot arm and the laparoscope during the movement, such that a mass or weight of the first robot arm is not detectable by the operator or is otherwise significantly attenuated. In some embodiments, if when the operator couples the laparoscope to the first robot arm, the laparoscope is not already positioned within the body of the patient, the system may determine that there are no external forces acting on the surgical instrument and may automatically switch the first robot arm to the haptic mode in order to guide the operator to move the laparoscope to the appropriate location through the trocar port, e.g., via a virtual haptic funnel established about the trocar port.

When the laparoscope is in the desired position relative to the patient and the surgical site within the patient, the system will automatically switch from co-manipulation mode to passive mode upon detection that movement of the first robot arm due to movement of the surgical instrument is within a predetermined movement threshold for a period of time exceeding a predetermined dwell time. For example, upon reaching the desired position, the operator will hold the laparoscope in the desired position, e.g., for at least a quarter of the second. Thus, if the predetermined dwell time is a quarter of a second, holding the laparoscope in the desired position for any longer than the predetermined dwell period will cause the system to automatically switch to passive mode. Moreover, as the operator may not be able to hold the laparoscope perfectly still, at least some movement of the laparoscope is permitted for the duration of the predetermined dwell time to enter into the passive mode. As described above, in passive mode, the first robot arm will hold the laparoscope in a static position, e.g., by the system applying enough impedance to the first robot arm to compensate for all external forces acting on the laparoscope.

Similarly, a second robot arm may be coupled to a retractor, and the operator may freely manipulate the retractor within the patient in the co-manipulation mode, e.g., to grasp tissue within the patient and retract the tissue to provide a clear field of view of the surgical site by the laparoscope coupled to the first robot arm, by applying a sufficient force to the second robot arm due to force applied at the retractor exceeding the predetermined force threshold of the second robot arm. As the operator grasps/lifts/retracts the tissue with retractor, the system may only compensate for the gravity of the second robot arm and/or the instrument and not of the tissue being grasped, such that the operator may feel any other forces acting on the retractor, including without limitation the forces acting on the instrument from the tissue. In this optional configuration. Accordingly, the haptics associated with the tissue being grasped may be preserved.

When the retractor sufficiently grasps and retracts the tissue, the system may automatically transition to the passive mode upon the operator holding the retractor in position, e.g., with movement not exceeding a predetermined movement threshold of the second robot arm, for a period of time exceeding the predetermined dwell period of the second robot arm. Accordingly, when the retractor is retracting the tissue within the patient in the passive mode, the second robot arm will account for the mass of the tissue in addition to the mass of the retractor and the second robot arm. Thus, the predetermined force threshold to cause the second robot arm to switch out of the passive mode must be greater than the force applied to second robot arm due to force applied to the tip of the retractor by the tissue, such that if the force applied by the tissue to the surgical instrument exceeds the predetermined first threshold of the second robot arm, the system will automatically cause the second robot arm to switch out of the passive mode and into, e.g., the co-manipulation mode. However, the predetermined force threshold should not be so high that it is very difficult for the operator to move the retractor. As described above, the operator may adjust the predetermined force threshold via, e.g., user interface 1408.

Upon retraction of the tissue via the retractor coupled to the second robot arm, the operator may need to readjust the field of view of the laparoscope coupled to the first robot arm. Accordingly, the operator may apply a force to the laparoscope that exceeds the predetermined force threshold of the first robot arm, such that the system automatically switches the first robot arm from the passive mode to the co-manipulation mode. When the new desired position of the laparoscope is achieved, the first robot arm may automatically switch back to the passive mode if the predefined conditions described above are met. Alternatively, to readjust the laparoscope or to reposition the links of the first robot arm to avoid potential collisions during the laparoscopic procedure or to switch the laparoscope to a different robot arm altogether, the operator may elect to decouple the laparoscope, readjust the robot arm and/or laparoscope, and reattach the laparoscope to the first robot arm (or to the other robot arm). Upon reattachment of the laparoscope to the first robot arm, the first robot arm may automatically switch to the passive mode if the predefined conditions described above are met.

Moreover, as the operator freely moves the retractor in the co-manipulation mode, e.g., prior to inserting the tip of the retractor through the trocar within the patient, if the operator moves the tip of the retractor too close to the patient's skin away from the trocar port, and a virtual haptic boundary has been established by the system on the skin of the patient outside the trocar ports, the system may automatically switch to the haptic mode. Accordingly, the system may apply an impedance to the second robot arm that is much higher than the impedance applied to the second robot arm in co-manipulation mode to indicate to the operator that they are approaching or within the virtual haptic boundary. For example, movement of the retractor by the operator may feel much more viscous in the haptic mode. The system may remain in the haptic mode until the operator moves the retractor out of the virtual haptic boundary. In some embodiments, in the haptic mode, the second robot arm may reduce the effects of gravity, eliminate tremor of the instrument tip, and apply force feedback to avoid critical structures as defined by the virtual haptic boundary. Accordingly, the system does not replace the operator, but rather augments the operator's capabilities through features such as gravity compensation, tremor removal, haptic barriers, force feedback, etc.

In some embodiments, the system may switch the second robot arm to the robotic assist mode. For example, as the operator attempts to retract the tissue, if more force is required to retract the tissue than the operator is able or willing to apply to the retractor, the operator may provide user input to the system indicating that the operator wants the second robot arm to assist in the retraction of the tissue. For example, as described above, the operator may perform a predefined gestural pattern that may be detected by, e.g., optical scanner 1100, such that the system switches the second robot arm to the robotic assist mode and causes the motors of the second robot arm to move the second robot arm, and accordingly the retractor, to provide the additional force required to retract the tissue.

In addition, instead of manually manipulating the laparoscope coupled to the first robot arm as described, the operator may provide another user input to the system indicating that the operator wants the system to reposition the laparoscope. For example, if the operator is actively manipulating a surgical scissor, which may or may not be coupled to a robot arm of the system, such that the tip of the surgical scissor is within the field of view of the laparoscope coupled to the first robot arm, the operator may perform a predefined gestural pattern with the tip of the surgical scissor, e.g., moving the surgical scissor quickly back in forth in a particular direction. The predefined gestural pattern of the surgical scissor may be captured as image data by the laparoscope, and based on the data, the system may detect and associated the predefined gestural pattern with a predefined user input requiring that the system switch the first robot arm from the passive mode to the robotic assist mode, and cause the first robot arm to reposition itself, and accordingly the laparoscope, to adjust the field of view in the direction of the pattern motion of the surgical scissor. As described above, additional gestural patterns may be performed via the surgical scissor within the field of view of the laparoscope to cause the first robot arm to retract the laparoscope and/or to cause the laparoscope itself to zoom in or zoom out or improve resolution. In some embodiments, based on the image data captured by the laparoscope, using object tracking of the additional tools in the field of view of the laparoscope, e.g., the surgical scissors actively operated by the operator, the system may cause the first robot arm coupled to the laparoscope to automatically switch to the robotic assist mode and cause the first robot arm to reposition itself to adjust the field of view to ensure that the tip of the surgical scissors remain within an optimum position within the field of view of the laparoscope during the procedure.

The operational mode of any one of the robot arms may be changed independent of the operational mode of the other robot arms of the system. In addition, the operational parameters of each robot arm may be tailored to the specific surgical instrument coupled thereto. For example, the predetermined force threshold for the robot arm coupled to the retractor device may be higher than the predetermined force threshold for the robot arm coupled to the laparoscope, as the retractor will endure higher forces during the procedure. The sensors, motors, etc. of the system may be active in all modes, but may act very differently in each mode, e.g., including acting as if inactive. As will be understood by a person having ordinary skill in the art, the system may include more than two robot arms, such that the operator may couple a third surgical instrument, e.g., a grasper device, to a third robot arm and a fourth surgical instrument, e.g., a surgical scissor device, to a fourth robot arm for operation during the laparoscopic procedure.

In some embodiments, the operational mode of a robot arm may be changed responsive to user input provided by the operated. For example, the operator may selectively change the operational mode of the robot arm by actuating a button, dial, or switch located on the robot arm, a foot pedal or foot switch, voice command, an input on a touch-screen, or using gestures or force signatures as described above. In some embodiments, the operational mode of a robot arm may be changed based only on the coupling of the surgical instrument to the coupler interface via the coupler body. As described above, the system may automatically identify the surgical instrument based on the coupling of the coupler body to the coupler interface. Accordingly, based on the identity of the surgical instrument coupled to the robot arm, the system may automatically switch the operational mode of the robot arm to a predetermined operational mode, e.g., passive mode if the surgical instrument is an endoscope, or if the robot arm is already in the passive mode, the system will remain in the passive mode upon coupling of the endoscope with the robot arm.

Similarly, based on the identity of the surgical instrument upon attachment of the surgical instrument to the robot arm, the system may automatically switch the operational mode of the robot arm to the co-manipulation mode, e.g., is the surgical instrument identity indicates that it is a tool that will be actively operated by the operator during the laparoscopic procedure. Additionally, based on the identity of the surgical instrument upon attachment of the surgical instrument to the robot arm, the system may automatically switch the operational mode of the robot arm to the robotic assist mode, e.g., if the surgical instrument identity indicates that it is a tool that the operate desires to be completely robotically controlled such as an irrigation device. Accordingly, upon attachment of the irrigation device to the robot arm, the system will switch to the robotic assist mode and cause the robot arm to position the irrigation device in the desired position within the body.

Moreover, the system may be instructed by the operator, e.g., via user interface 1408, to operate the robot arm in less than the four operational modes discussed above. For example, the operator may deactivate any one of the operational modes for a give procedure. In some embodiments, the system may cause the robot arm to operate in an additional operational mode, such as a locking mode, which may be similar to the passive mode, except that the predetermined force threshold of the robot arm to switch out of passive/locking mode may be so high that the robot arm is effectively frozen so as to protect the robot arm from inadvertently switching out of the passive/locking mode, e.g., to avoid movement due to inadvertent bumps of the robot arm. In this locking mode, if the force from the inadvertent bump is sufficiently high to cause even a slight movement of the robot arm, the system may cause the robot arm to reposition itself to the position it was in prior to the inadvertent bump.

In addition, when no surgical instrument is coupled to the distal end of a robot arm of the system, the system is still capable of automatically switching the operational modes of the robot arm responsive to movement of the robot arm by an operator upon detection of the predefined conditions described above. Accordingly, the system will apply an impedance to the joints of the robot arm to compensate for the mass of the robot arm such that the robot arm may remain in a static position when in the passive mode, and will permit the robot arm to be freely moveably by the operator in the co-manipulation mode if the system detects that the force applied to the robot arm by the operator exceeds the predetermined force threshold of the robot arm. Additionally, the system will switch the robot arm to the haptic mode if the operator attempts to move any portion of the robot arm within a predefined virtual haptic barrier.

At step 1514, when the laparoscopic procedure is complete, the operator may remove the surgical instruments from the respective robot arms.

Figure 18A:
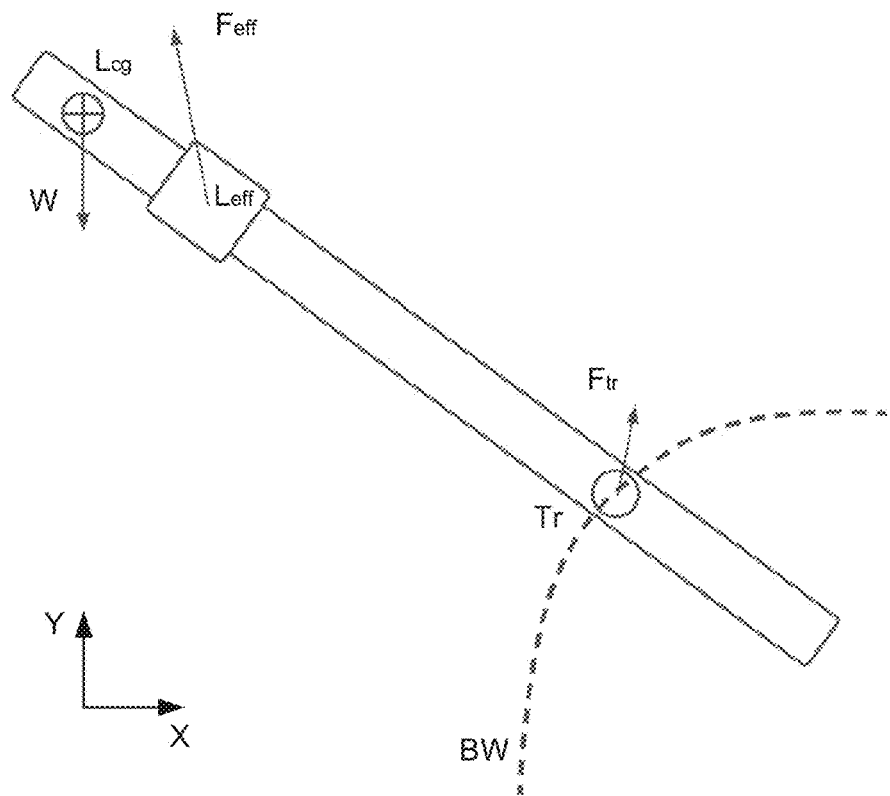
FIGS. 18A and 18B are free-body diagrams illustrating forces applied to the surgical instrument coupled to the robot arm during a laparoscopic surgical procedure.
Figure 18B:
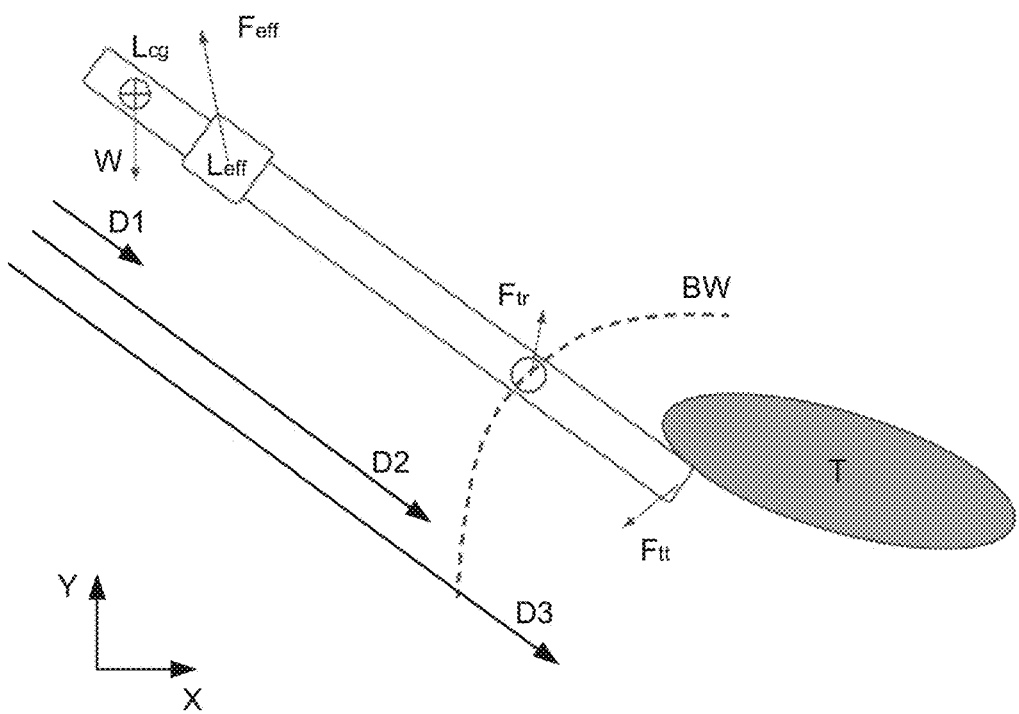

Referring now to FIGS. 18A to 18C, force measurements during operation of robot arm 300 are provided. As described above, upon attachment of the surgical instrument to coupler interface 400 via the coupler body coupled to the surgical instrument, the orientation of the surgical instrument may be automatically determined based on the magnetic connection between the coupler interface and the coupler body. Moreover, as described above, the calibration file of the surgical instrument coupled to robot arm 300 loaded on the system may include information of the surgical instrument including, e.g., the mass of the surgical instrument, the center of mass of the surgical instrument, and the length of the surgical instrument, such that distance D3 between the center of mass and the instrument tip may be derived. In addition, as described above, the position of the surgical instrument at the trocar, e.g., where the surgical instrument enters the patient's body, may be calculated in real-time, such that distance D2 between the center of mass of the surgical instrument and the trocar may be derived in real time. Additionally, as described above, the coupler body is preferably coupled to the surgical instrument at a fixed, known position along the elongated shaft of the surgical instrument (which may be included in the calibration file), e.g., adjacent to the proximal portion of the surgical instrument, and thus distance D1 between the center of mass of the surgical instrument and the coupler body, e.g., the point of attachment to the distal end of robot arm 300, may be derived. Alternatively or additionally, as described above, optical scanning devices may be used determine any one of D1, D2, or D3.

As shown in FIG. 18A, when the surgical instrument is positioned through trocar Tr, without any additional external forces acting on the surgical instrument other than at trocar Tr, e.g., the surgical instrument is not lifting or retracting tissue within the patient, the force applied to the surgical instrument at trocar Tr by the body wall (e.g., the "body wall force" or the "trocar force") may be calculated with the following equation:

$$F_{eff} + W + F_{tr} = 0 => F_{tr} = -W - F_{eff}$$

Where $F_{eff}$ is the force at the distal end of robot arm 300 (e.g., the "end-effector force" of robot arm 300), W is the weight vector of the surgical instrument (=−mgz), and $F_{tr}$ is the trocar force. Accordingly, $F_{eff}$ is the desired force sent to the system, which is the sum of all the forces generated in the algorithm pipeline including, e.g., gravity compensation, hold, etc.

As shown in FIG. 18B, when the surgical instrument is positioned through trocar Tr and holding/retracting tissue, such that an external force is applied to the tip of the surgical instrument, there are two forces to resolve: $F_{tr}$ and $F_{tt}$. Accordingly, two equations are needed to solve for the two unknown vectors, which may be the balances of forces and also the balance of moments around the center of mass of the surgical instrument, e.g., $L_{cg}$.

$$W + F_{eff} + F_{tr} + F_{tt} = 0$$

$$F_{eff} \times D1 + F_{tr} \times D2 + F_{tt} \times D3 = 0$$

Here, distances D1 and D3 are known as described above, and D2 may be derived based on the known position of the distal end of robot arm 300 and the calculated position of trocar Tr. As shown in FIG. 18B, the center of mass $L_{cg}$ of the surgical instrument is behind the point of attachment of the coupler body to the distal end of robot arm 300.

As described above, the system may alert the operator if the forces, e.g., force $F_{tt}$ applied to the tip of the instrument and/or force $F_{tr}$ applied by the instrument at the trocar using, are greater than the respective threshold forces, and accordingly freeze the system if the calculated force is greater than the threshold force, and/or reduce the force exerted at the trocar point at the body wall or at the tip of the instrument by automatically applying brakes or stopping forces to robot arm 300, by slowing or impeding further movement of the instrument in the direction that would increase forces applied at the tip of the instrument or the trocar, and/or automatically moving the robotic arm in a direction that reduces the force being exerted at the instrument tip and/or at the trocar point at the body wall.

Figure 20:
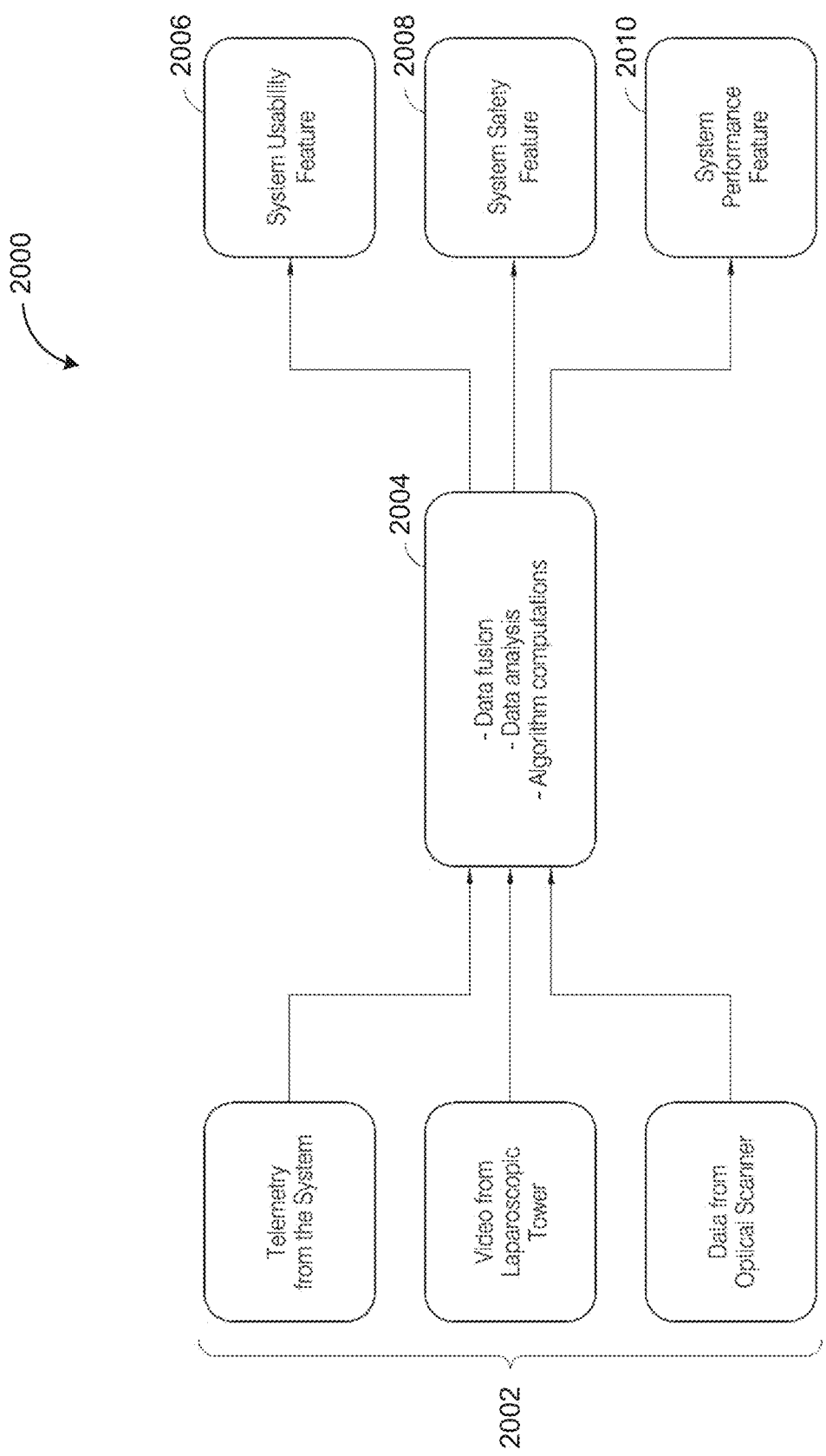
FIG. 20 illustrates an example overview of some features and capabilities of the co-manipulation surgical system in accordance with the principles of the present disclosure.

Referring now to FIG. 20, a high level example 2000 of the different combinations of data inputs for the various sensors and devices of the systems disclosed herein, e.g., system 200, and the multiple features and capabilities that any implementations of the systems disclosed herein may have and can produce based at least in part on the multiple possible data inputs is provided. As shown in FIG. 20, some implementations of the system may be configured to gather data from at least three monitoring sources 2002, including telemetry from the system (which may include force data from the robot arms, position data from the robot arms, etc.), video from the laparoscopic tower, and/or data from optical scanner 1100. The data gathered from the monitoring sources 2002 may undergo data processing steps 2004 using one or more processors in the system. The data processing steps may include, e.g., data fusion (e.g., fusion of the data gathered from the monitoring sources 2002) and data analysis, which may include algorithm computations. In addition, the data from the monitoring sources 2002 may undergo processing 2004 for the development of system usability features 2006, system safety features 2008, and system performance features 2010. The system may provide the features in real-time. For example, the system usability features may include identifying the surgeon and adjusting the platform height based on the surgeon's profile, detecting the skin surface of the patient and creating a virtual boundary around the skin surface to prevent inadvertent contact with the skin surface of the patient, detecting an instrument type and automatically loading the calibration file appropriate for the particular instrument, etc.

Figure 21:
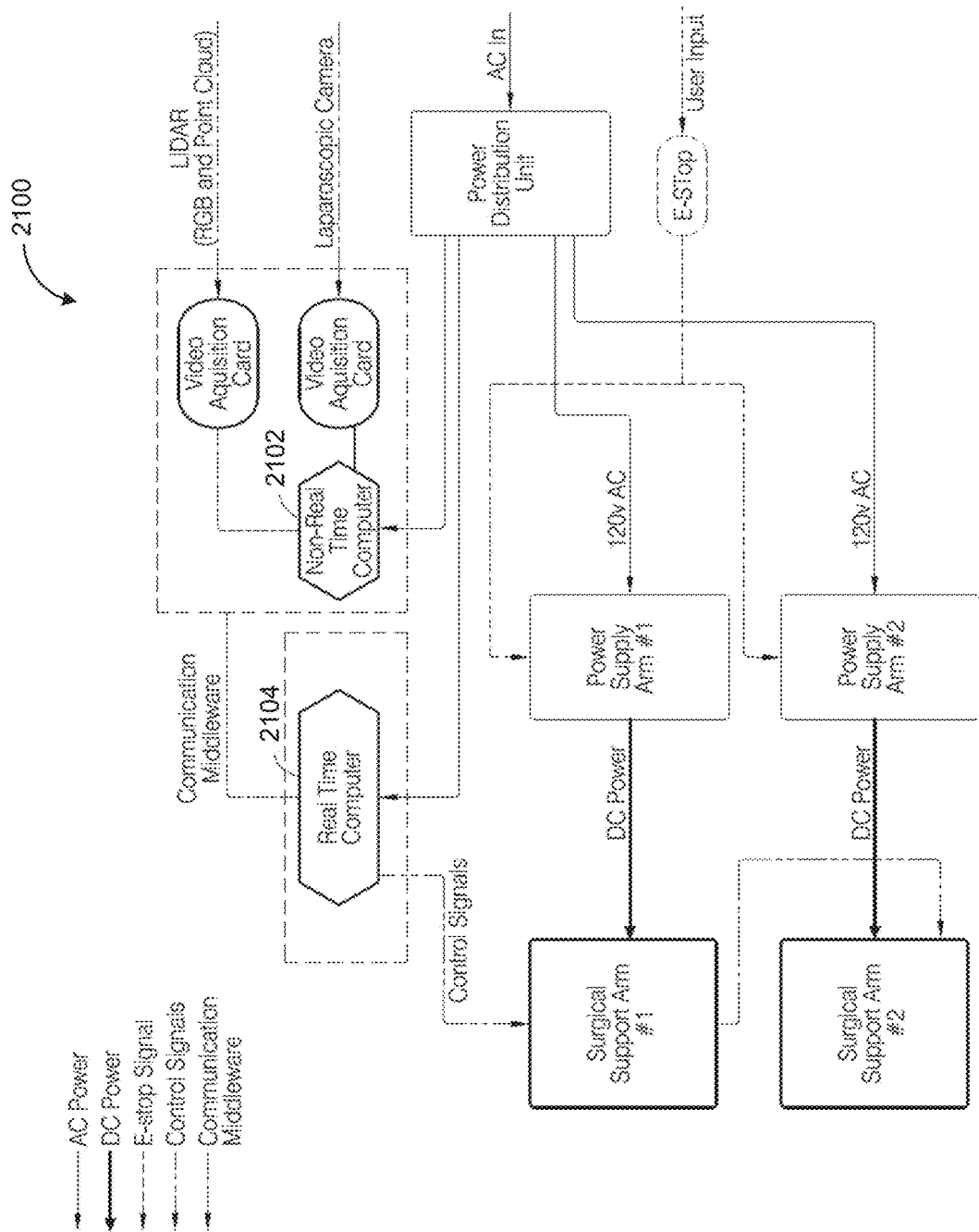
FIG. 21 is a schematic overview of some electrical components and connectivity of the co-manipulation surgical system in accordance with the principles of the present disclosure.

Referring to FIG. 21, a schematic overview of the electrical components of the electrical system and connectivity 2100 of the system is provided. This includes the flow of energy throughout the illustrated portion of the system, the ports that may be used for connectivity, and other details related to the various electronic components. For example the system may include non-real time computer 2102 that may be used to acquire data from the optical scanning devices and perform other functions. Non-real time computer 2102 also may control the graphical user interface of the system for the surgeon to interact with. As described above, the graphical user interface may include a touch screen. Non-real time computer 2102 may include, e.g., a 10th Gen Intel® Core™ i7-10700 processor, 32 GB of RAM (which can optionally be 2×16 GB, DDR4, 2933 Mhz), a standard keyboard and a 512 GB PCIe M.2 SSD +1 TB SATA 7200 RPM hard drive, a wireless and Bluetooth card such as the Killer™ Wi-Fi 6 AX1650i (2×2) 802.11ax Wireless and Bluetooth 5.1, and/or a NVIDIA® GeForce RTX™ 2060 6 GB GDDR6 graphics card. The system further may include real-time computer 2104 that may be used to operate and control the robot arms and the related robot controllers and/or other functions, such as acquiring data and information from the optical scanning devices. Real-time computer 2104 may include, e.g., an Intel Core i7 (8th Gen) processor, 32 GB of RAM for memory, a 500 GB SDD hard drive, and/or two or more RJ45 connectors for Ethernet connectivity.

Figure 22:
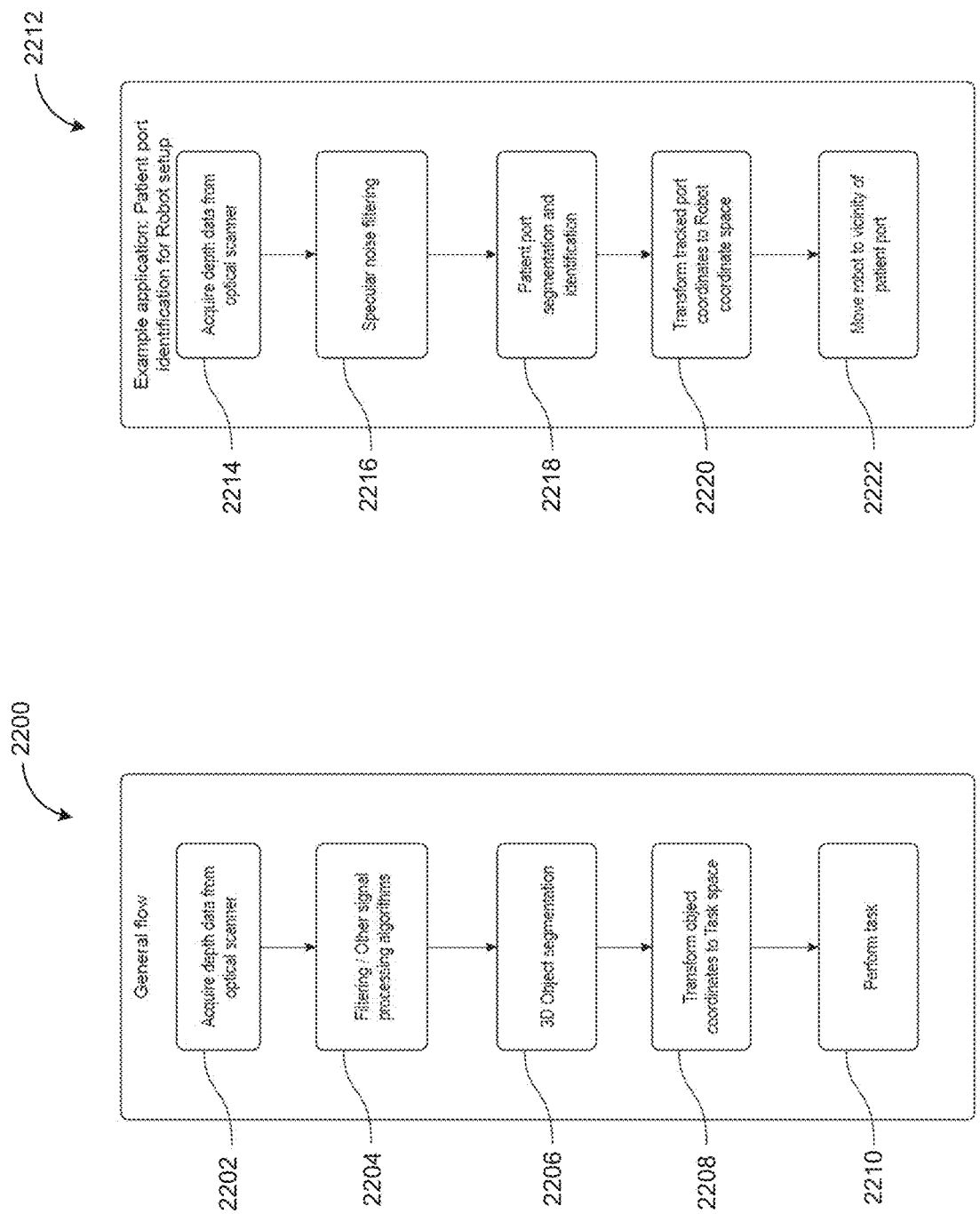
FIG. 22 is a flow chart illustrating an example process of acquisition and processing of data from an optical scanner and an example application of the data in accordance with the principles of the present disclosure.

Referring now to FIG. 22, a flow chart of process 2200 for the acquisition and processing of data from an optical scanning device is provided. As shown in FIG. 22, at step 2202, depth data may be acquired from one or more optical scanning devices, e.g., optical scanner 1100. At step 2204, filtering/other signal processing algorithms may be performed, e.g., median filter, Gaussian noise removal, anti-aliasing algorithms, morphological operations, ambient light adjustments, etc. At step 2206, 3D object segmentation may be performed using, e.g., template matching, machine learning, Brute force matching, color plus depth segmentation, 2D-3D registration, pixel value thresholding, etc. At step 2208, object coordinates may be transformed to task space. For example, transforming object coordinates to task space may include converting a position and an orientation of an object from the optical scanning device's coordinate frame to the coordinate frame of the task needed (e.g., a robot frame for robot control, a cart frame for system setup, etc.). Additionally or alternatively, transforming object coordinates to task space may include using known optical scanning device to the support platform (e.g., a cart) transformations, the surgical robot transformations, and/or the user interface screen transformations, and generating new transformations for specific tasks such as tracking the surgeon's body (e.g., face, hands, etc.) with respect to different elements of the system (e.g., support platform, robot arms, screen, etc.), tracking the surgical table with respect to the cart platform, tracking patient orientation for system setup, tracking trocar port location and orientation for setup, and tracking the position of operating room staff for safety. At step 2210, the desired task may be performed, e.g., moving the robot arms into the vicinity of the patient/trocar port for easy setup, tracking operating room staff to ensure the system only responds to surgeon commands, recording the surgeon's hand movements during different phases of surgery, etc.

In addition, FIG. 22 illustrates a flow chart of process 2212 for the acquisition and processing of data from an optical scanning device. At step 2214, depth data may be acquired from one or more optical scanning devices, e.g., optical scanner 1100. At step 2216, specular noise filtering may be performed. At step 2218, patient/trocar port segmentation and identification may be performed. At step 2218, tracked port coordinates may be transformed to robot coordinate space. At step 2222, the robot arms may be moved to a desired vicinity of the patient/trocar port.

Figure 23:
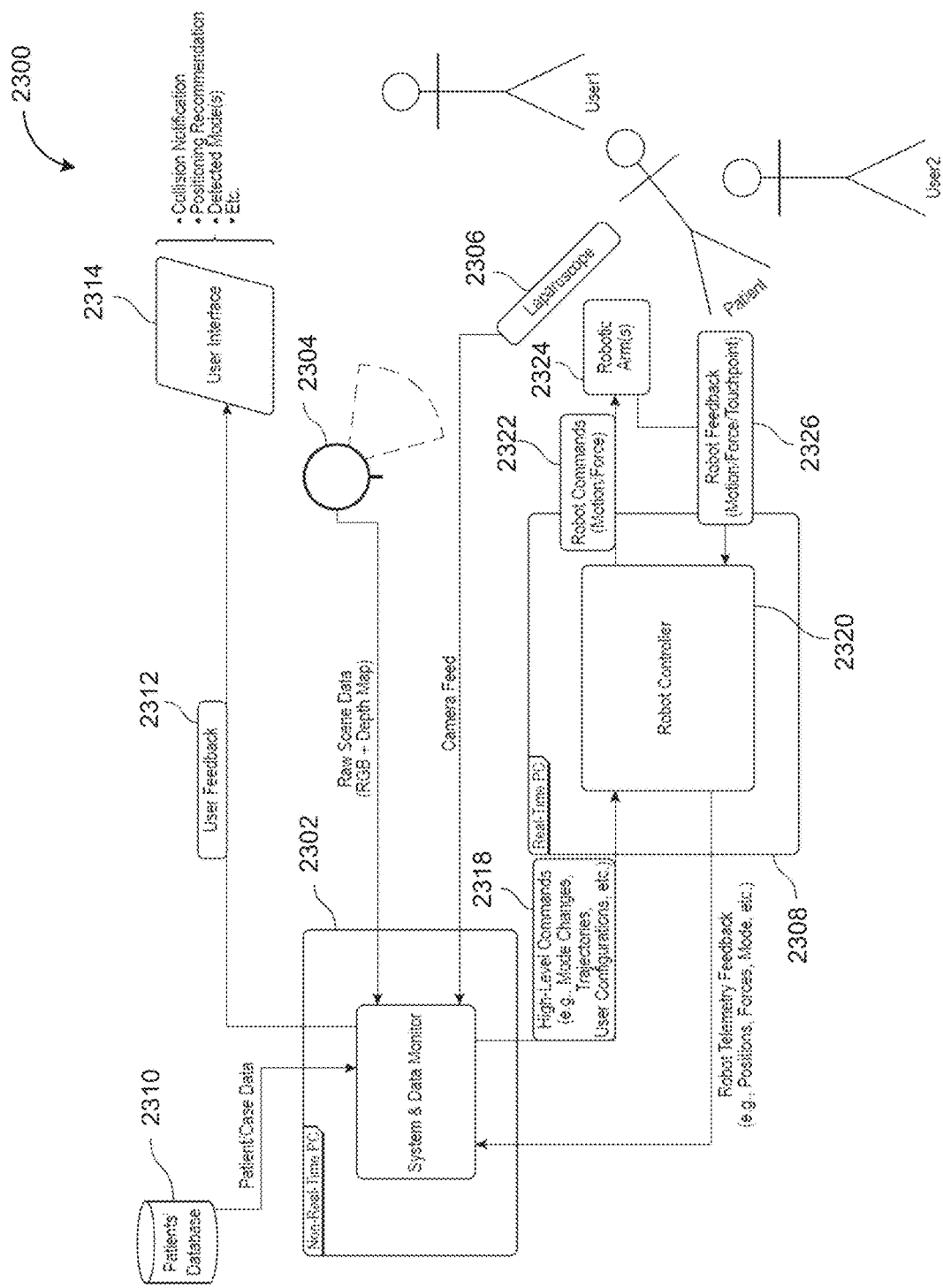
FIG. 23 is a schematic overview of data flow of the co-manipulation surgical system in accordance with the principles of the present disclosure.

Referring now to FIG. 23, an example data flow 2300 of the system is provided. As shown in FIG. 23, non-real-time computer 2302 may gather data from an optical scanning device, e.g., optical scanner 1100 and/or from a camera feed from a laparoscope. Non-real-time computer 2302 also may receive data from real-time computer 2308 having a robot controller, including telemetry information such as positions of the robot arms, forces applied to the various motors/sensors of the robot arms, operational mode information, etc. Non-real-time computer 2302 also may receive data from patient database 2310 having information specific to the patient in the procedure including, e.g., CT scan data, relevant health conditions, and other information that may be desired by the surgeon.

Non-real-time computer 2302 further may provide user feedback 2312 to the user via user interface 2314. User feedback may include, e.g., collision notifications, positioning information and/or recommendations regarding the various components of the system, the operational mode that has been detected by the system, etc. Non-real-time computer 2302 further may provide commands 2318, e.g., high level commands, to real-time computer 2308. High-level commands may include, e.g., mode changes, trajectories, haptic barriers, user configurations, etc. Real-time computer 2308 may include robot controller 2320 programmed to provide robot commands 2322, e.g., motion or force commands, to the one or more robot arms 2324, e.g., robot arms 300. Robot controller 2320 may receive robot feedback data 2326, e.g., motion, force, and/or touchpoint data, etc., from the one or more robotic arms 2324.

Figure 25:
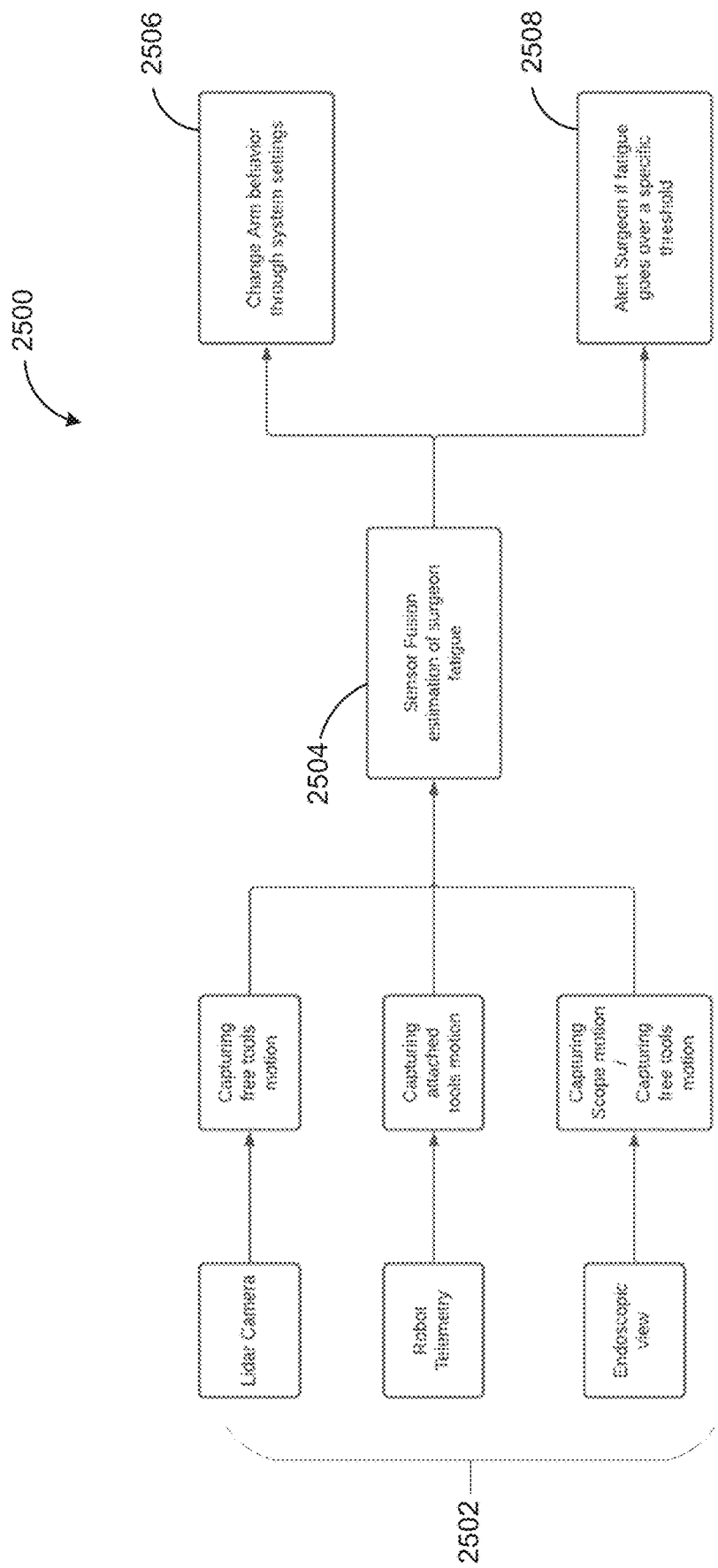
FIG. 25 is a schematic overview of data flow and output control of the co-manipulation surgical system in accordance with the principles of the present disclosure.

Referring now to FIG. 25, method 2500 for estimating user fatigue during a surgical procedure using robot arm 300 is provided. As described above, the algorithms for gravity compensation, viscosity, and/or effects of mass may be used to account for user fatigue. Specifically, during a laparoscopic procedure, a surgeon may be subject to fatigue and may experience hand tremor or erroneous tool motion for surgical tools such as, e.g., scissors, needle drivers, cautery tools, graspers, as the procedure progresses. As shown in FIG. 25, at step 2502, the system may receive and monitor data indicative of the operator's performance, e.g. from optical scanner 1100 such as a LiDAR camera, robot telemetry, and/or an endoscope, during the surgical procedure while the operator maneuvers the surgical instruments coupled to robot arm 300. Learning from a large dataset of clinical procedures and/or gathering and analyzing data during a procedure or a portion of a procedure may allow the system to infer a level of competency of the surgeon as the procedure progresses, at step 2504, and further may allow the system to adapt algorithm parameters in order to help the surgeon to move more effectively while co-manipulating the surgical instruments attached to the robot arm. For example, at step 2506, the system may adjust one or more operating parameters of robot arm 300 to change its behavior. If the fatigue level goes above a specific threshold, at step 2608, the system may warn the surgeon. In addition, ranking procedures may be used to allow the system to provide the surgeon a summary of their performance for a given procedure and show their overall progress, procedure after procedure.

In some embodiments, the system may collect data during a procedure indicative of at least one of operator hand tremor, distance/minimum path travelled by the instrument tip, time to achieve procedure steps, and/or time to complete the procedure, and compare such data with threshold or predefined values for each of the factors to determine whether a magnitude of any one of the factors has reached a level sufficient to cause the system to warn the operator and/or sufficient to cause the system to adjust one or more operating parameters to mitigate the user's fatigue. For example, the system may eliminate or reduce tremor of the instrument tip by exerting forces on the instrument to increase the impedance or viscosity of the instrument, to avoid critical structures, and/or to apply force feedback. User fatigue may be identified when, for example, a procedure time increases beyond a threshold value for a particular procedure, the number of movements of the surgical instrument increases beyond a threshold value for a particular procedure or otherwise indicates errant or uncontrolled movements, if an operator moves an instrument into a haptic barrier a predefined number of times, if an operator exerts an excessive force on the trocar one or a predetermined number of times, etc. As described above, such data may be collected using the sensors on the robot arms and/or one or more optical scanning devices. When a particular level of user fatigue is identified by the system, the system may increase a viscosity or impedance of the instrument and/or the robot arm associated with the instrument to reduce a magnitude of movements and/or a number of movements of the surgical instrument and/or the robot arm.

Additionally, the system may collect data regarding the speed and frequency with which the operator moves the various instruments/laparoscopes along with estimates of how much tremor is involved in the movements, estimate the required added viscosity to reduce tremors while not hindering their motions or adding unnecessary fatigue to the operator. In some embodiments, a controller of robot arm 300 may iteratively adjust a viscosity value for a particular instrument, collect data related to the movement of the instrument, and to assess whether an additional adjustment is needed to the viscosity applied to the instrument. Moreover, the system may use additional algorithms to adopt an iterative approach to optimizing a particular operational characteristic or parameter of robot arm 300, including collecting data related to a particular operational characteristic or parameter, changing operational characteristic or parameter, collecting additional data related to the operational characteristic or parameter, and analyzing the data to determine if additional changes to the operational characteristic or parameter should be made, which may be based on, e.g., deviations between the actual data values and preferred or optimal values of an operational characteristic or parameter.

Figure 26:
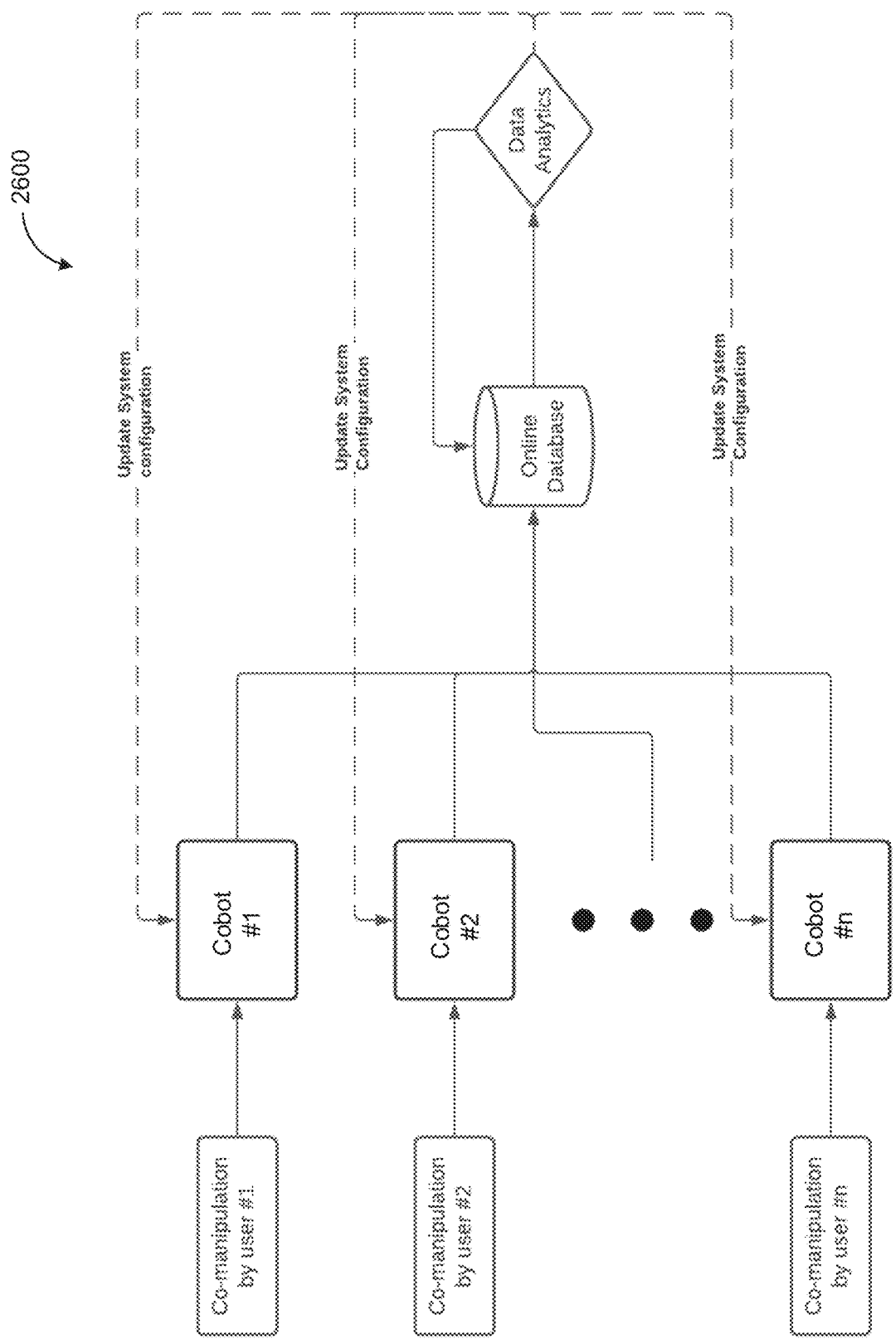
FIG. 26 is a schematic overview of data flow in a network of co-manipulation surgical systems in accordance with the principles of the present disclosure.

Referring now to FIG. 26, dataflow 2600 of a distributed network of co-manipulation surgical robot systems is provided. For example, a distributed network of co-manipulation robotic ("cobot") surgical systems may be used in multiple hospitals, each of which may be connected to an online database. This arrangement may provide considerably more data and user information that may be used by any of the cobot systems in operation. The systems may aggregate the data from the distributed network of systems to identify the optimum configuration based on factors such as procedure type, surgeon experience, patient attributes etc. Through analytics or clinician input, the cobot systems may identify a routine procedure versus a procedure that may be more complicated. This information may be used to provide advice or guidance to novice surgeons.

Moreover, centralizing procedure data may enable the running of large data analytics on a wide range of clinical procedures coming from different users. Analysis of data may result in optimized settings for a specific procedure, including, e.g., optimized system positioning, optimal ports placement, optimal algorithms settings for each robot arm and/or detection of procedure abnormalities (e.g., excessive force, time, bleeding, etc.). These optimal settings or parameters may depend on patient and tool characteristics. As described above, a surgeon may load and use optimal settings from another surgeon or group of surgeons. This way, an optimal setup may be achieved depending on, e.g., the surgeon's level of expertise. To keep track of the various users in the distributed network of cobot systems, it may be beneficial to identify each user. As such, the user may log into the cobot system and access their profile online as necessary. This way the user may have access to their profile anywhere and will be able to perform a clinical procedure with their settings at a different hospital location.

An example user profile may contain the user's specific settings and information, including, e.g., username; level of expertise; different procedures performed, and/or region of clinical practice. In addition, the clinical procedure may require a user to store specific settings such as clinical procedure (e.g., cholecystectomy, hernia, etc.), table orientation and height, preferred port placement, settings per assistant arm for each algorithm, patient characteristics (e.g., BMI, age, sex), and/or surgical tools characteristics and specifications (e.g., weights, length, center of gravity, etc.). The user may be able to enable his own profile, and optionally may enable another user's profile, such as the profile of a peer, the most representative profile of a surgeon of the user's area of practice, the most representative profile of a surgeon with a specific level of expertise, and/or the recommended profile according to patient characteristics.

The identification of a user may be performed via password, RFID key, facial recognition, etc. Learning from a large number of procedures may result in a greater level of optimization of the cobot system setup for a given procedure. This may include, e.g., cart position, individual robot arm position, surgical table height and orientation, port placement, and/or setup joints position. These settings may be based on patient height, weight, and sex, and further may be interdependent. For example, the optimal port placement may depend on patient table orientation.

Additionally, a clinical procedure may be described as a sequence of clinical procedures steps. Learning these different steps may allow the cobot system to infer in real time the actual step for a given procedure. For example learning clinical steps from procedures may allow or enable: adjustment of algorithm settings, the system to give the practical custom reminders, the system to notify staff of an estimate procedure end time, the system to alert staff if necessary equipment is not available in the room, and/or the system to alert staff of the occurrence of an emergency situation.

During a clinical procedure, the surgeon will often realize simple and routine surgical tasks such as grasping, retracting, cutting etc. Learning these different tasks may allow the cobot system to infer in real time preferences and habits of the surgeon regarding a sequence of a procedure in real time. Some algorithms of the cobot system may be tuned (i.e., adjusted and optimized) during the procedure based on this sequence recognition and help the user to be better at this simple surgical task. An example of such a task is the automated retraction of a liver during a gall bladder procedure. By aggregating the information over many cases, the optimized force vectors may be developed.

Further, some complications may occur during a clinical procedure that may result in unexpected steps or surgical acts. Learning how to discriminate these unexpected events would help the cobot system to enable some specific safety features. In case of emergency, the robot arms may be stopped or motion restricted depending on the level of emergency detected by the system.

Figure 27A:
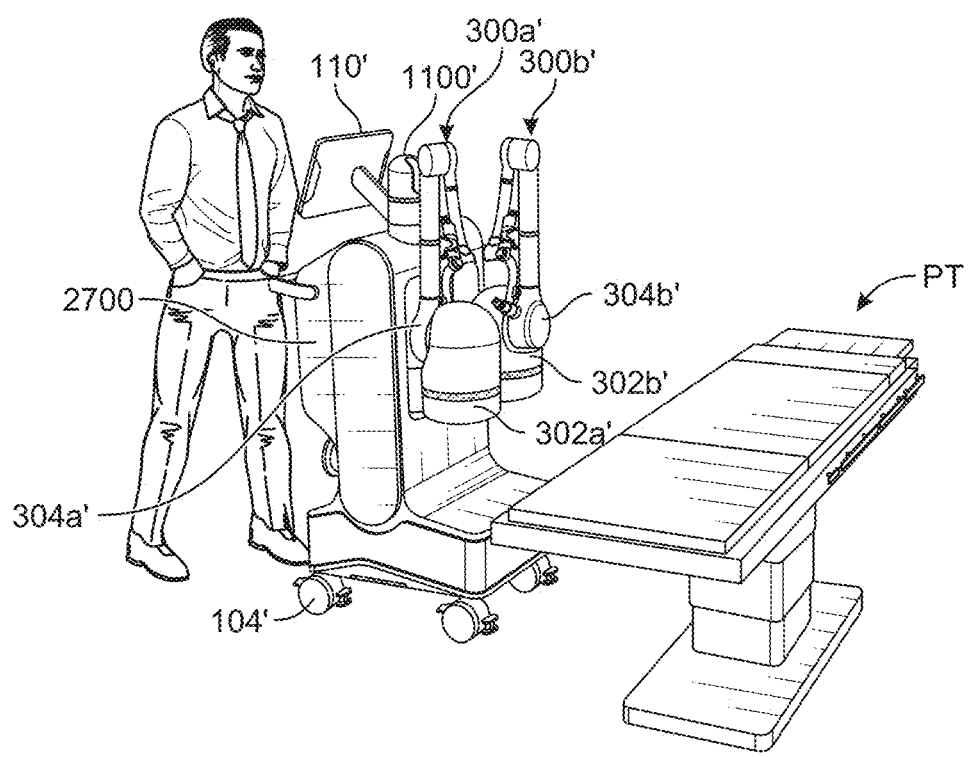
FIGS. 27A-27D illustrate vertical and horizontal movement of the robot arms in accordance with the principles of the present disclosure.

Referring now to FIGS. 27A to 27D, setup of the co-manipulation surgical system is provided. Platform 2700 may be constructed similar to platform 100, such that platform 2700 supports one or more robot arms, e.g., robot arm 300a' and robot arm 300b', and may cause the robot arms to move relative to platform 2700. As shown in FIG. 27A, platform 2700 may be moved to a desirable position relative to patient table PT by a user, e.g., via wheels 104', while robot arms 300a', 300b' are in their respective stowed configurations.

As platform 2700 is being moved toward the patient, the scene may be directly observed by a depth mapping sensor, e.g., optical scanner 1100', which may be mounted on platform 2700. From the depth maps observed and generated by optical scanner 1100', key features may be identified such as, for example, the height and/or location of patient table PT, the surface of the patient's abdomen, position and other characteristics of the surgeon, including the surgeon's height, and the trocar port(s), the base of robot arms 300a', 300b', e.g., base portions 302a', 302b' and shoulder portions 304a', 304b', robot arms 300a', 300b', and/or one or more surgical instruments coupled with the robot arms. Identification of such key features may be carried out using standard computer vision techniques such as template matching, feature tracking, edge detection, etc. As each feature is registered, its position and orientation may be assigned a local co-ordinate system and transformed into the global co-ordinate system the system using standard transformation matrices. Once all features are transformed into a single global co-ordinate system, an optimization algorithm, e.g., least squares and gradient descent, may be used to identify the most appropriate vertical and horizontal positions of robot arms 300a', 300b', which may be adjusted via platform 2700, to maximize the workspace of the robot arms with respect to the insertion point on the patient. The optimal workspace may be dependent on the surgical operation to be performed and/or the surgeon's preferred position.

Figure 27B:
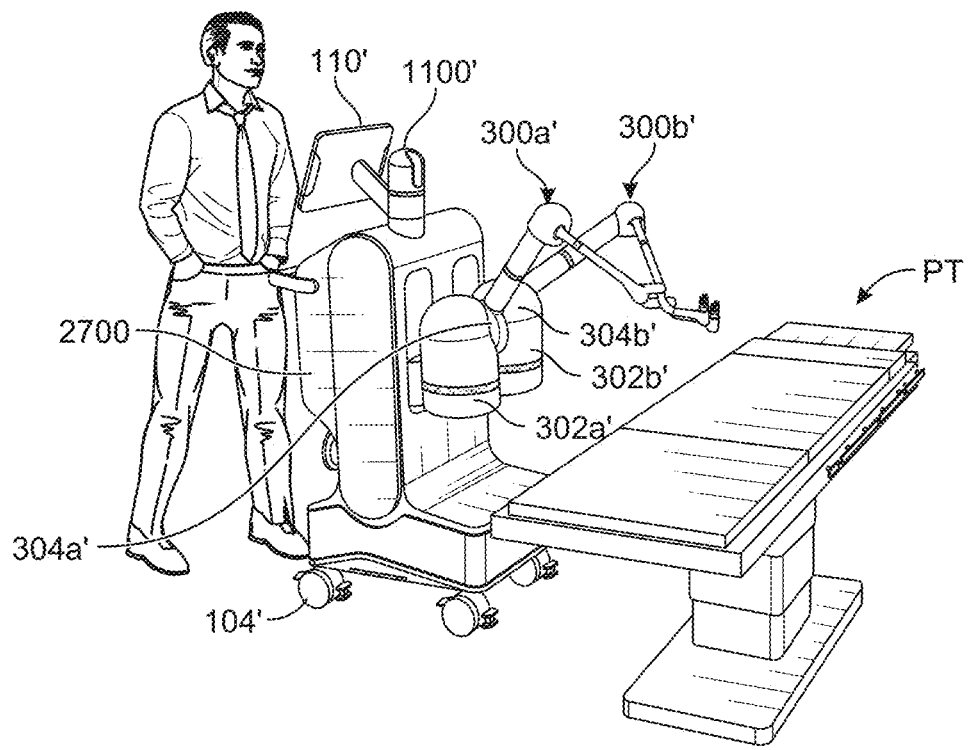
Figure 27C:
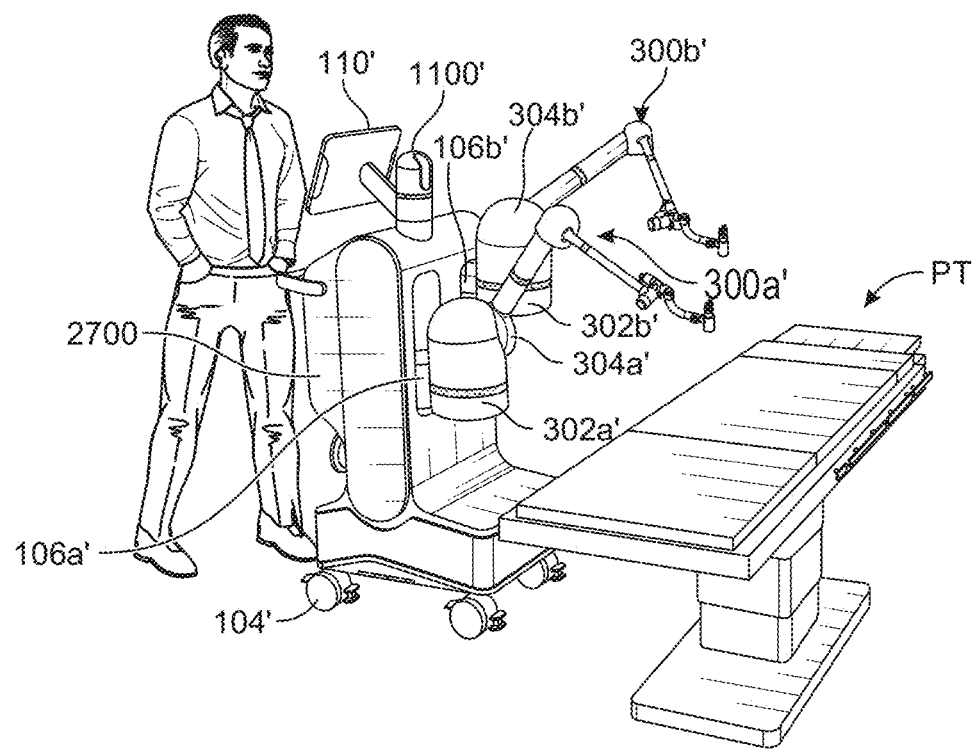

As shown in FIG. 27B, when platform 2700 is in its desired position relative to patient table PT, such that wheels 104' are locked, robot arms 300a', 300b' may be extended away from their respective stowed configurations. As shown in FIG. 27C, the vertical position of the robot arms relative to platform 2700 may be adjusted to the desired position, and as shown in FIG. 27D, the horizontal position of the robot arms relative to platform 2700 may be adjusted to the desired position.

Figure 28A:
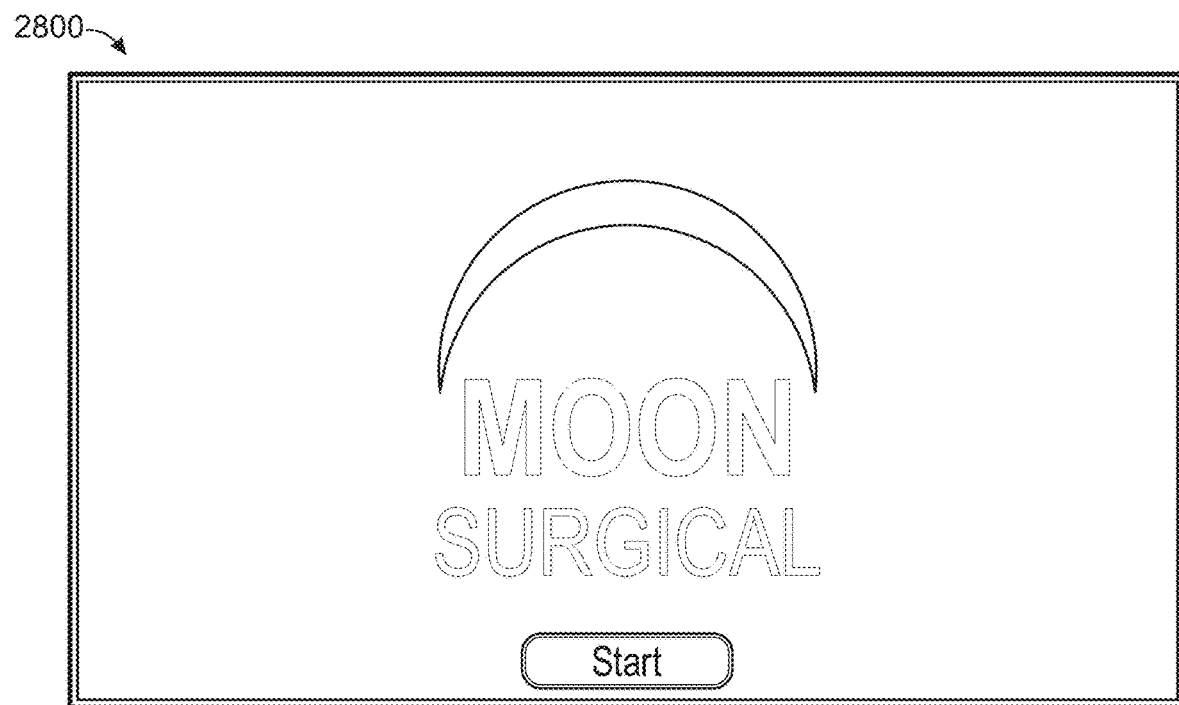
FIGS. 28A-28D illustrate an exemplary graphical user interface of the co-manipulation surgical system.
Figure 28B:
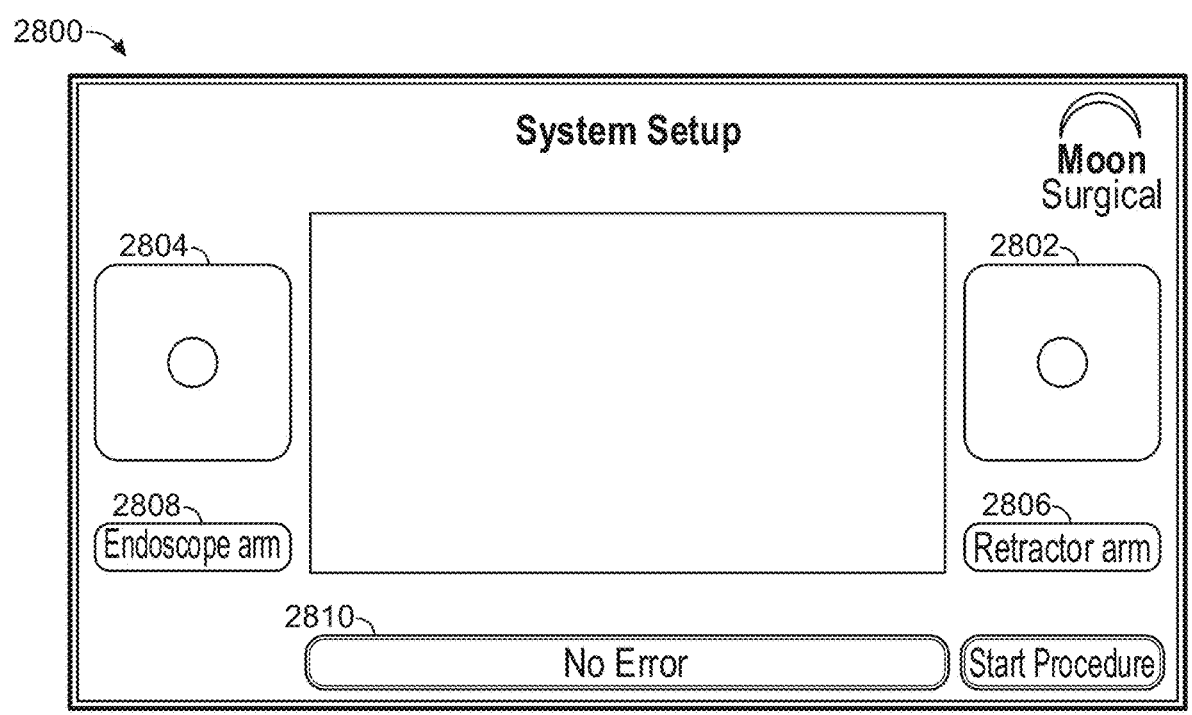

Referring now to FIGS. 28A to 28D, screenshots of exemplary graphical user interface 2800 are provided. Exemplary graphical user interface 2800 may be configurable by a user and may be integrated with display 110. FIG. 28A illustrates an exemplary start menu. The operator may initiate operation of the co-manipulation system by actuating the "start" option. FIG. 28B illustrates an exemplary system setup screen. As shown in FIG. 28B, when the system includes two robot arms, graphical user interface 2800 may identify which robot arm is to be used with which instrument, e.g., retractor arm 2806 and endoscope arm 2808, as well as the procedure to be completed. Graphical user interface 2800 may permit the user to pre-load specific calibration files or setup joint positions based on the procedure being performed and/or the surgeon performing the procedure. For example, if the user inputs that a procedure is a laparoscopic cholecystectomy, the system may pre-load tool types known to be associated with that procedure. Populating these pre-loaded settings may be achieved by monitoring which tools a user manually selects for a given procedure. If a given tool is consistently selected for a predetermined number of procedures, the system may automatically pre-populate that tool the next time the procedure is selected by the user.

Figure 27D:
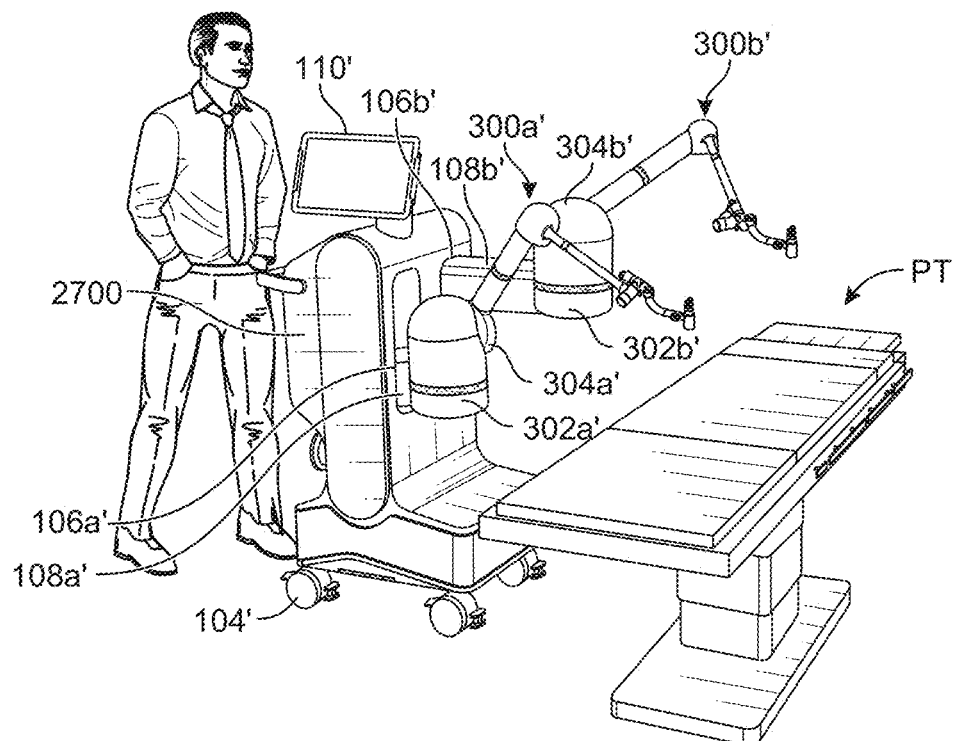

In addition, the operator may adjust the vertical and horizontal position of each robot arm, as shown in FIGS. 27C and 27D above. As shown in FIG. 28B, to adjust the vertical and/or horizontal position of the robot arm that will be or is currently coupled to the retractor device, the operator may toggle adjustment actuator 2802, and to adjust the vertical and/or horizontal position of the robot arm that will be or is currently coupled to the endoscope device, the operator may toggle adjustment actuator 2804. In some embodiments, the user may adjust the horizontal and vertical position of the robot arms by using the robot arm as a force sensitive input device. For example, the robot arm may be configured to sense the user's intention by measuring the force applied by the user onto the robot arm. If the user applies a force in the positive horizontal direction, platform may move the robot arm in that direction until the user no longer applies a force. A similar approach be taken for the other directions, e.g., negative horizontal, positive vertical, and negative vertical. As shown in FIG. 28B, graphical user interface 2800 may indicate whether an error, e.g., fault condition, is detected by the system during setup or operation of the system, via error notification 2810.

Figure 28C:
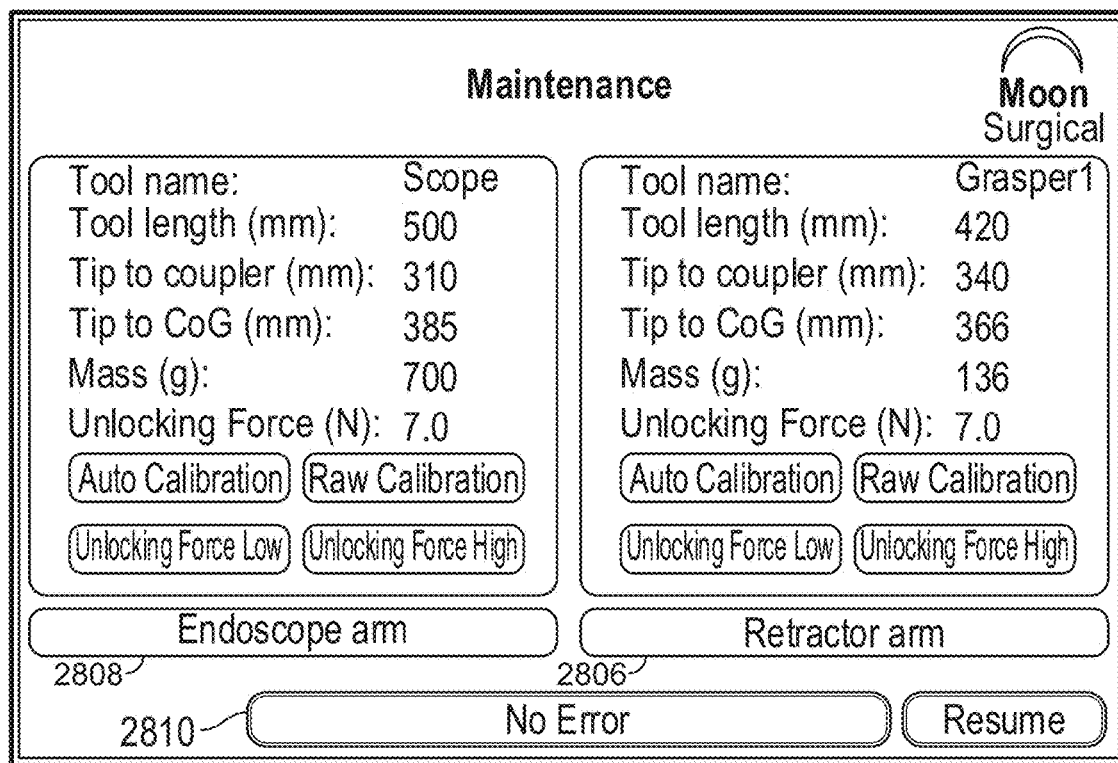
Figure 28D:
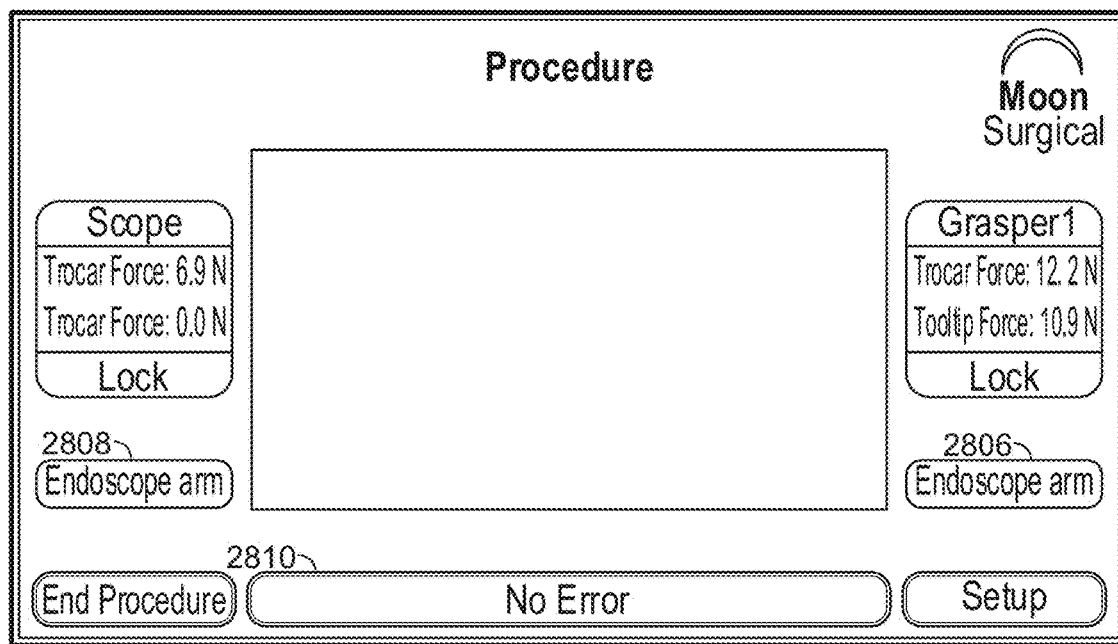

As shown in FIG. 28C, graphical user interface 2800 may display information associated with the selected surgical instruments, as described above. For example, graphical user interface 2800 may display, for each instrument to be coupled to each robot arm, the instrument type, overall length, distance between the coupler body and the instrument tip, distance between the center of mass to the instrument tip, mass, and the preset unlocking force required to unlock the instrument. As shown in FIG. 28C, graphical user interface 2800 may permit the operator to select between a high or low unlocking force of the surgical instrument. In addition, graphical user interface 2800 may permit the operator to initiate a surgical instrument calibration, e.g., for a new surgical instrument that does not already have an associated calibration file stored in the system. FIG. 28D illustrates an exemplary screen during operation of the system, e.g. during a surgical procedure. As shown in FIG. 28D, graphical user interface 2800 may display the trocar force and the force being applied to the tip of the surgical instrument, e.g., by tissue within the patient's body.

Figure 29:
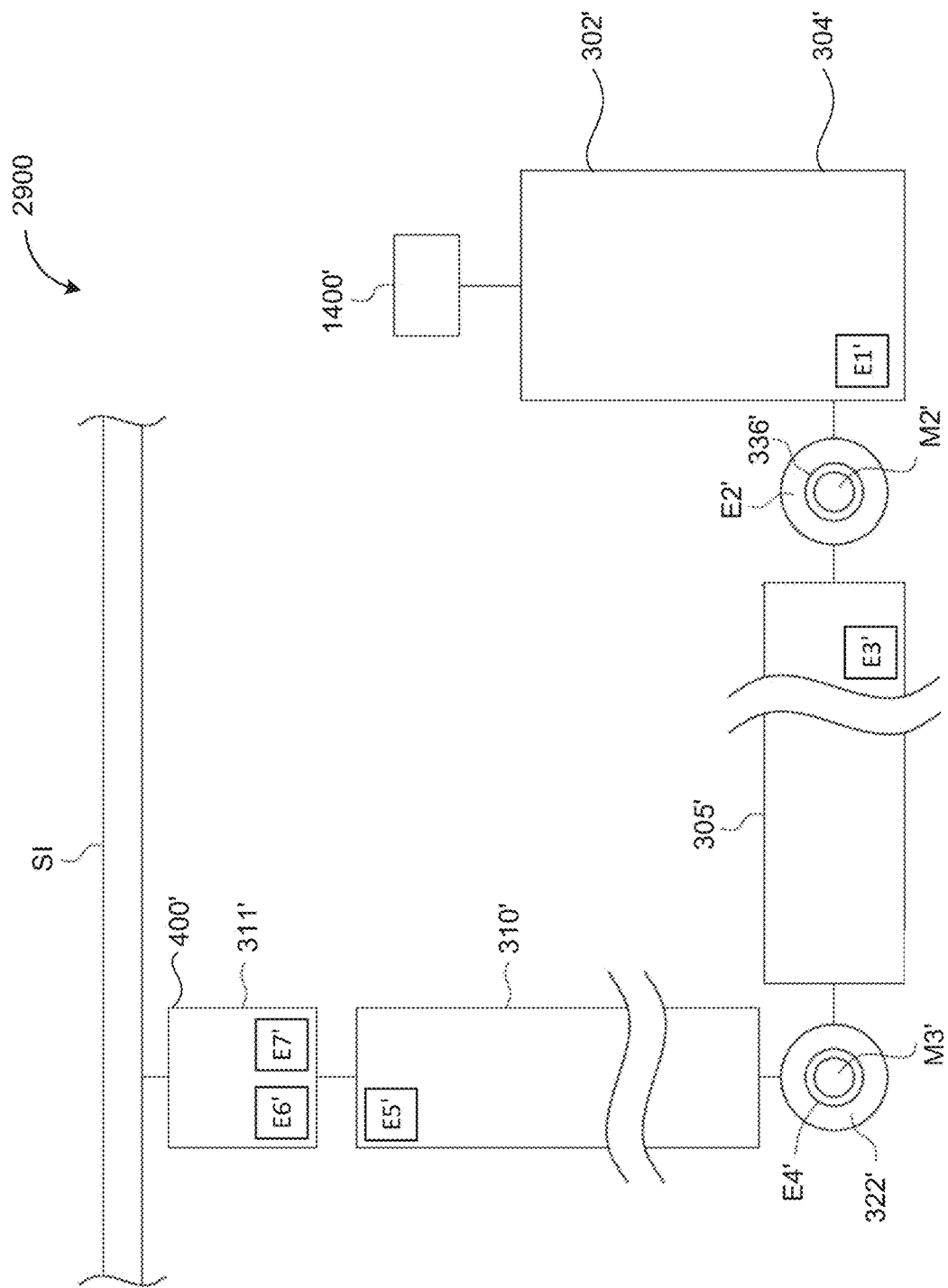
FIG. 29 is a schematic of an alternative co-manipulation surgical system constructed in accordance with the principles of the present disclosure.

Referring now to FIG. 29, an alternative co-manipulation surgical robot system is provided. System 2900 may be constructed similar to system 200 of FIG. 2. For example, platform 1400', base portion 302', shoulder portion 304', encoders E1', E2', E3', E5', E6', E7', motor M1', shoulder joint 318', shoulder link 305', elbow joint 322', elbow link 310', wrist portion 311', and coupler interface 400' for coupling surgical instrument SI to the robot arm, may be constructed similar to platform 1400, base portion 302, shoulder portion 304, encoders E1, E2, E3, E5, E6, E7, motor M1, shoulder joint 318, shoulder link 305, elbow joint 322, elbow link 310, wrist portion 311, and coupler interface 400, respectively. System 2900 differs from system 200 in that system 2900 includes motors disposed at the joints of the robot arm. For example, system 2900 may include motor M2' disposed at elbow joint 318' and motor M3' disposed at elbow joint 322', configured to rotate the associated links to manipulate the robot arm. In addition, encoder E4' may be positioned on or adjacent to elbow join 322'.

Some implementations of the systems described herein may be configured to be controlled or manipulated remotely, e.g., via joystick or other suitable remote control device, computer vision algorithm, force measuring algorithm, and/or by other means. However, in a preferred embodiment, the systems described herein operate without any telemetry, e.g., the robot arm is not teleoperated via a remote surgeon console separate from the robot arm, but instead the robot arm moves in response to movement applied to the surgical instrument coupled thereto. Any robot-assisted movements applied to the surgical instrument by the system, e.g., in the robotic assist mode, are not responsive to user input received at a remote surgeon console.

Figure 30A:
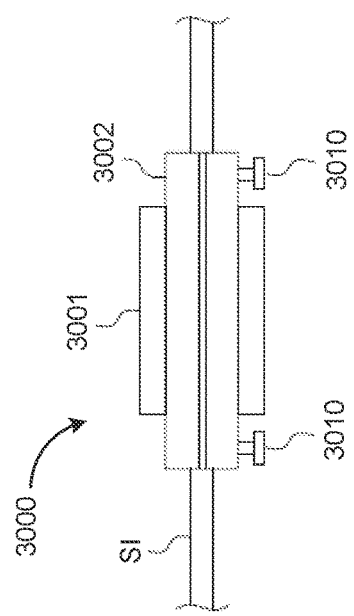
Figure 30B:
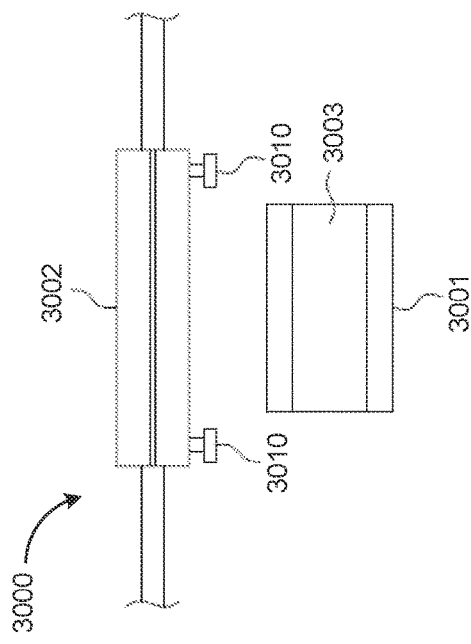

FIG. 30A illustrates a top view of coupler 3000 for coupling surgical instrument SI to the robot arm, showing coupler body 3002 (also referred to herein as a body) coupled with coupler interface 3001 (also referred to herein as an interface). FIG. 2B illustrates a top view of coupler 3000 of FIG. 30A, showing coupler body 3002 decoupled from coupler interface 3001. As shown in FIGS. 30A and 30B, coupler 3000 may have coupler body 3002 and coupler interface 3001. Coupler interface 3001 may be coupled with robotic arm 300 and may be configured such that coupler body 3002 may be removably coupled with coupler interface 3001. Coupler body 150 may be coupled with surgical instrument SI at any desired axial position on surgical instrument SI. Once coupler body 3002 is coupled with surgical instrument SI, coupler body 3002 and surgical instrument SI that is coupled with coupler body 3002 may be coupled with coupler interface 3001. Coupler body 3002 may be configured such that, once coupler body 3002 is coupled with surgical instrument SI, surgical instrument SI may be at least inhibited (e.g., prevented) from moving axially or, in some embodiments, moving axially and rotationally relative to coupler body 3002. Coupler 3000 may be configured such that coupler body 3002 may be at least inhibited (e.g., prevented) from moving in any axial direction relative to coupler interface 3001. In some embodiments, coupler 3000 may be configured such that coupler body 3002 is free to rotate relative to coupler interface 3001. In this configuration, surgical instrument SI coupled with coupler body 3002 may be free to rotate relative to coupler interface 3001 that coupler body 3002 is coupled with, and may be at least inhibited from (e.g., prevented from) any axial movement relative to coupler interface 3001 that coupler body 3002 is coupled with.

In other embodiments, coupler 300 may be configured such that surgical instrument SI may be moved in an axial direction relative to coupler body 3002 upon the application of at least a threshold force on surgical instrument SI relative to coupler body 3002 or upon actuation of a release or a state change of coupler body 3002. Such actuation may be achieved in some embodiments by, e.g., pressing a button, loosening a locking screw or other connector, moving a dial, or otherwise changing coupler 3000, coupler body 3002, and/or coupler interface 3001 from a second, secured state to a first, unsecured state. For example, in some embodiments, surgical instrument SI may be axially repositioned relative to coupler 3000 by loosening one or more thumbscrews 3010 or other hand-operated fastener or fastening mechanism such as a clamp in coupler body 3002, repositioning surgical instrument SI in the desired axial position, and re-tightening thumbscrew 3010 or other hand-operated fastener or fastening mechanism.

As shown in FIG. 30B, coupler interface 3001 may have recess 3003 sized and shaped to receive coupler body 3002. Recess 3003 may inhibit (e.g., prevent) an axial movement or, in some embodiments, an axial and a rotational movement of coupler body 3002 relative to coupler interface 3001 while permitting free rotational movement of coupler body 3002 relative to coupler interface 3001. Coupler 3000 may be configured such that surgical instrument SI may be at least inhibited (e.g., prevented) from rotational movement relative to coupler 3000. This may be achieved by at least inhibiting (e.g., preventing) the rotational movement between surgical instrument SI and coupler 3000, or between coupler body 3002 and coupler interface 3001. In some embodiments, a surgical drape may be pinched or clamped between coupler body 3002 and coupler interface 3001.

Figure 30C:
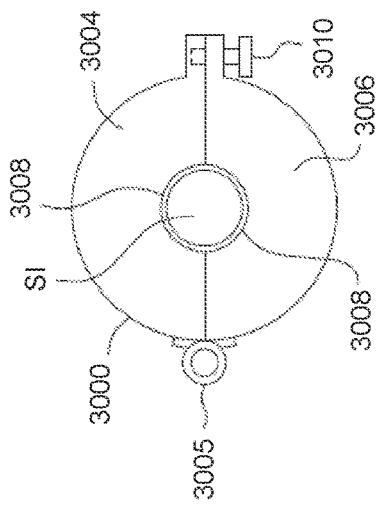
Figure 30D:
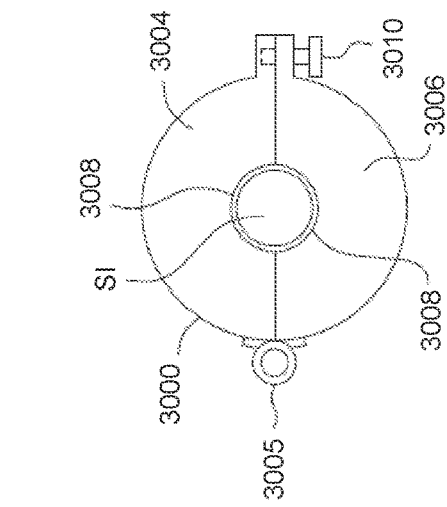

FIG. 30C illustrates an end view of coupler body 3002 and surgical instrument SI, showing coupler body 3002 in the first, unsecured or open state in which surgical instrument SI may be removed and replaced or repositioned relative to coupler body 3002. FIG. 30D illustrates an end view of coupler body 3002 of FIG. 30C, showing coupler body 3002 in the second, secured or closed state in which surgical instrument SI may be at least inhibited (e.g., prevented) from axial movement or, in some embodiments, axial and rotational movement relative to coupler body 3002. In some embodiments, coupler body 3002 may have first portion 3004 and second portion 3006. In some embodiments, first portion 3004 may be rigidly coupled with second portion 3006 via hinge 3005 or shaft or otherwise. In some embodiments, first and second portions 3004, 3006 may have a semicircular cut out or recess 3008 therein sized and shaped to receive surgical instrument SI therein. Fastener 3010 may be used to couple first portion 3004 with second portion 3006, such as when surgical instrument SI is positioned in recesses 3008, as shown in FIG. 30D. As described above, coupler body 3002 may be configured to at least substantially inhibit (e.g., prevent) an axial movement or, in some embodiments, an axial and a rotational movement of surgical instrument SI relative to coupler body 3002. Rubber pads, sheets, bumps, O-rings, projections, or other components or features configured to grip an outside of surgical instrument SI may be used with any of the coupler embodiments disclosed herein. For example, the rubber interface may be positioned within the recess or recesses of the coupler body, such as recesses 3008 of first portion 3004 and/or second portion 3006 of coupler body 3002 and may be coupled to coupler body 3002. The rubber may be a silicone rubber or any other suitable type of rubber.

FIGS. 31A to 31D illustrate another embodiment of coupler 3100 that may be used with any robotic system embodiments disclosed herein to couple an instrument to an end portion of a robot arm. Coupler 3100 may include coupler body 3101 and coupler interface 3120 that may have a recess or depression 3190 configured to receive coupler body 3101 therein. Coupler interface 3120 may be coupled with an end portion of robot arm 300. Coupler 3100 may have coupler body 3101 that removably or nonremovably couples directly with an end portion of robot arm 300.

As shown in FIG. 31A, coupler body 3101 may have cylindrical body portion 3102 having annular flange 3104 projecting away from the surface of cylindrical body portion 3102. Body portion 3102 may have opening 3106 extending axially through body portion 3102. Opening 3106 may be sized and shaped to receive surgical instrument SI therein. Opening 3106 may be slightly larger than a diameter or outside size of surgical instrument SI. Coupler body 3101 may have one or more deflectable tabs 3108 (two being shown), or four or more deflectable tabs 3108 that may be configured to deflect radially inwardly so that, when tabs 3108 are deflected radially inwardly, tabs 3108 exert a force on an outside surface of surgical instrument SI. Coupler 3100 may be configured such that, when coupler body 3101 is positioned within recess 3109 of coupler interface 3120 and coupler interface 3120 is in a second, closed or secured state, coupler interface 3120 may exert a force or otherwise deflect tabs 3108 radially inward so as to grip surgical instrument SI and at least inhibit (e.g., prevent) an axial movement or axial and rotational movement of surgical instrument SI relative to coupler body 3101. For example, tabs 3108 may have a greater thickness near distal end 3110 of tabs 3108 such that, in a relaxed state or in the first, open state, distal end 3110 of tabs 3108 may project or protrude away from an outside surface of body portion 3102 of coupler body 3101. In this configuration, when coupler body 3101 is positioned within recess 3109 of coupler interface 3120, moving coupler interface 3120 to the second, closed state may cause a force to be applied to distal end portions 3110 of the tabs 3108 to thereby deflect tabs 3108 inwardly against an outside surface of surgical instrument SI.

In some embodiments, recess 3109 may have enlarged portion 3111 sized and shaped to receive annular flange 3104 therein and to permit a rotational movement of flange 3104, while also restricting or at least inhibiting (e.g., preventing) an axial movement of coupler body 3101 by providing an axial limit to the movement of annular flange 3104. In this arrangement, surgical instrument SI may be axially advanced through opening 3106 of coupler body 3101 to any desired location. Thereafter, surgical instrument SI with coupler body 3101 coupled thereto may be positioned within recess 3109 of coupler interface 3120. Coupler interface 3120 may be removably or non-removably coupled with an end portion of robot arm 300 of any of the co-manipulation surgical systems disclosed herein.

Figure 31D:
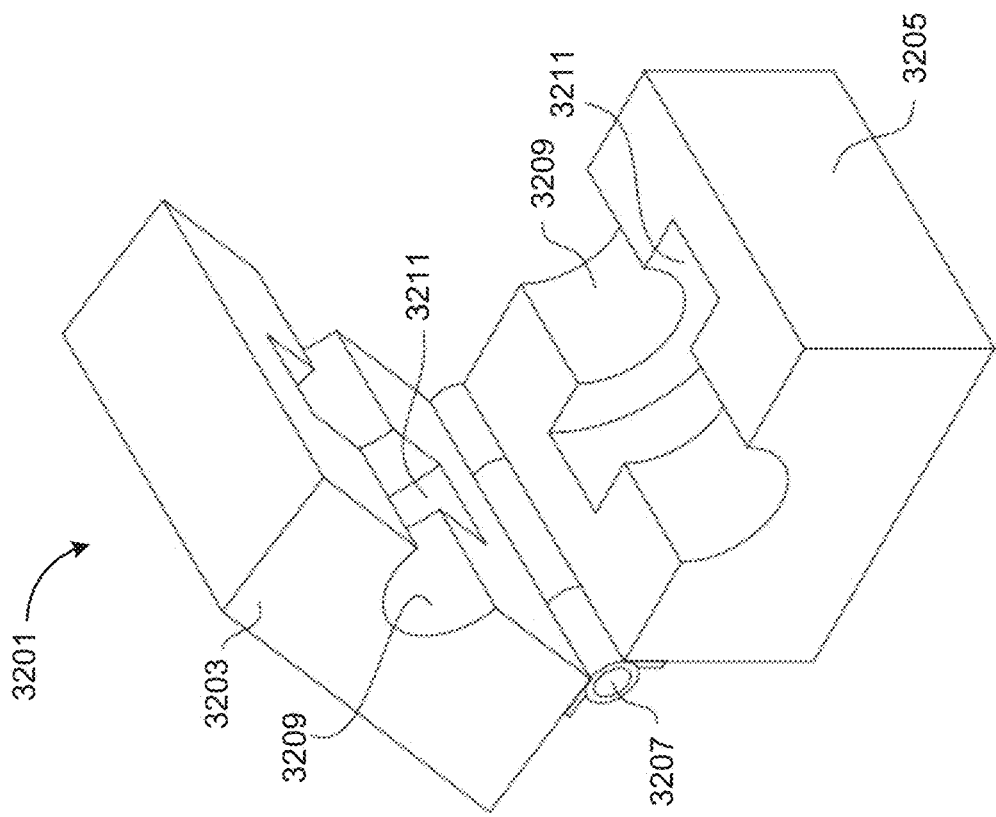
Figure 31C:
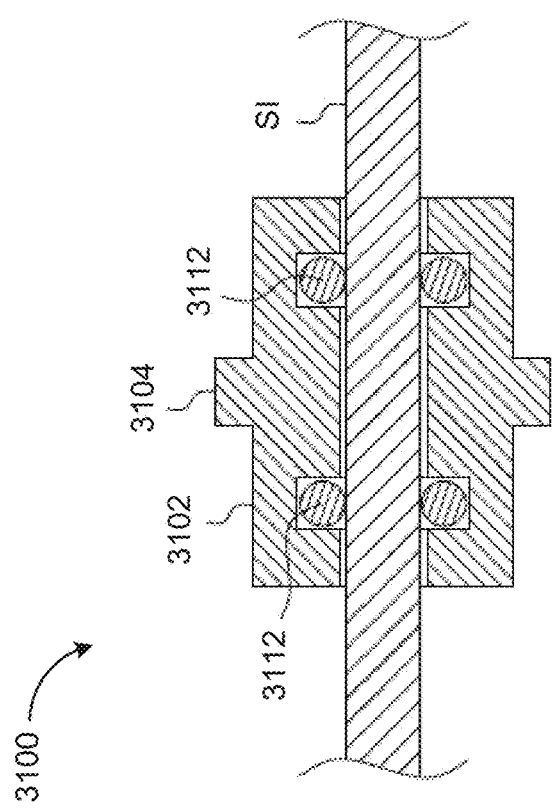

As shown in FIG. 31C, rubber pads, sheets, bumps, O-rings, projections, or other gripping features 3112 (O-rings being shown) configured to grip an outside of surgical instrument SI may be positioned within coupler body 3101 to increase a frictional force between surgical instrument SI and coupler body 3101. In some embodiments, one or more tabs 3108 may be configured to exert a force on gripping features 3112 when one or more tabs 3108 are deflected inwardly.

As shown in FIG. 31D, coupler interface 3120 may have first portion 3105 that may be coupled with second portion 3103. In some embodiments, first and second portions 3105, 3103 may be rigid and may be coupled to one another via mechanical hinge 3107. Alternatively, a living hinge, a shaft, one or more fasteners, or other components or features may be used to couple first and second portions 3105, 3103 together. In some embodiments, second portion 3103 may be flexible and may be configured to extend over surgical instrument SI and/or a coupler body 3101 supported within recess 3109, such as an elastically elongatable or an elastically rigid strap. Additional fasteners, clamps, clasps, or other components or features may be used in conjunction with or in place of hinge 3107 to securely couple first and second portions 3105, 3103 together once coupler body 3101 is received within recess 3109 of coupler interface 3120 to securely couple surgical instrument SI with coupler 3100.

In some embodiments, the coupler may include a coupler body and a coupler interface having a recess configured to receive the coupler body. The coupler body may have an opening extending axially therethrough configured to receive an instrument and an annular flange extending around an outside surface thereof. The recess in the coupler interface may have an enlarged portion configured to receive the annular flange and to permit a rotational movement of the flange while at least inhibiting (e.g., preventing) an axial movement of the coupler body by providing an axial limit to the movement of the annular flange. The coupler interface may be configured to couple with an end portion of a robotic arm.

Figure 32A:
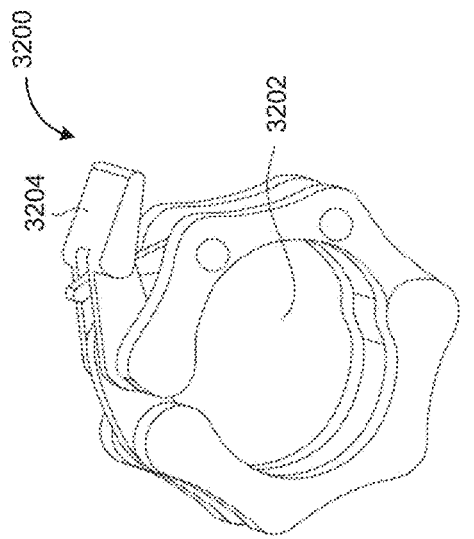
Figure 32B:
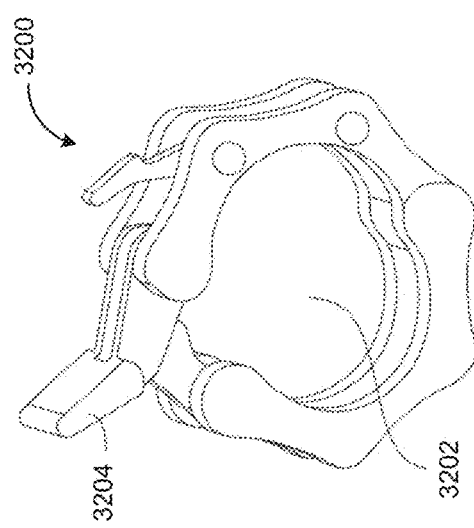

FIGS. 32A and 32B illustrate coupler body 3200 that may be used with any robotic system embodiments disclosed herein to couple an instrument to an end portion of a robot arm. Coupler body 3200 may have any of the components, features, and/or other details of any of the other embodiments of the coupler body disclosed herein, in any combination with any of the components, features, and/or other details of the embodiment of coupler body 3200 shown in FIGS. 32A and 32B. Any of the other embodiments of the coupler body disclosed herein may have any of the components, features, and/or other details of coupler body 3200, in any combination with any of the components, features, and/or other details of the other coupler body embodiments disclosed herein.

Coupler body 3200 may have opening 3202 axially therethrough sized and shaped to receive a surgical instrument therein and clamping mechanism 3204 configured to reduce an inside diameter of opening 3202 as clamping mechanism 3204 is actuated so as to cause coupler body 3200 to move from the first, unsecured or open state as shown in FIG. 32A to the second, secured or closed state as shown in FIG. 32B. In this arrangement, coupler body 3200 may be positioned around an outside surface of the surgical instrument while coupler body 3200 is in the first, open or unsecured state. Thereafter, clamping mechanism 3204 may be actuated so as to cause coupler body 3200 to secure itself to an outside surface of a surgical instrument. Then, coupler body 3200 may be coupled with a coupler interface sized and configured to receive and support coupler body 3200.

Figure 33A:
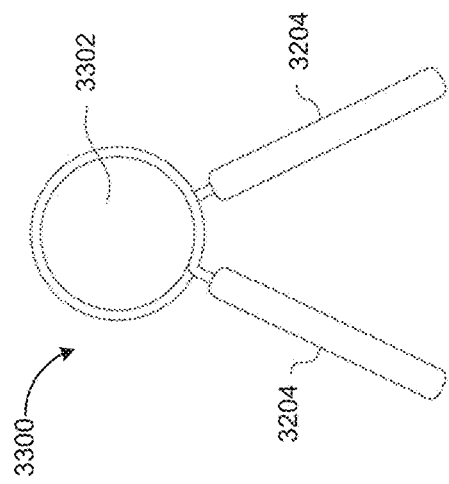
Figure 33B:
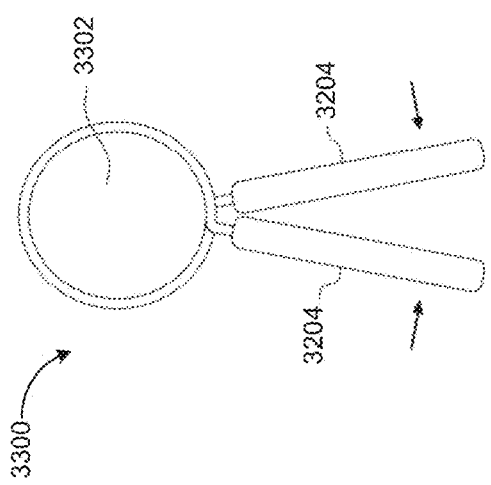

FIGS. 33A and 33B illustrate coupler body 3300 that may be used with any robotic system embodiments disclosed herein to couple an instrument to an end portion of a robot arm. Coupler body 3300 may have any of the components, features, and/or other details of any of the other embodiments of the coupler body disclosed herein, in any combination with any of the components, features, and/or other details of the embodiment of coupler body 3300. Any of the other embodiments of the coupler body disclosed herein may have any of the components, features, and/or other details of coupler body 3300, in any combination with any of the components, features, and/or other details of the other coupler body embodiments disclosed herein.

Coupler body 3300 may have an opening 3302 axially therethrough sized and shaped to receive a surgical instrument therethrough and clamping mechanism 3304 having a first and second handle member or tab configured to reduce an inside diameter of opening 3302 as clamping mechanism 3304 is actuated so as to cause coupler body 3300 to move from the first, unsecured or open state as shown in FIG. 33A to the second, secured or closed state as shown in FIG. 33B. In this arrangement, coupler body 3300 may be positioned around an outside surface of the surgical instrument while coupler body 3300 is in the first, open or unsecured state. Coupler body 3300 may be moved to the first, open or unsecured state by squeezing or moving the handles of clamping mechanism 3204 together, as shown in FIG. 33A. Thereafter, clamping mechanism 3204 may be released so as to cause coupler body 3300 to secure itself to an outside surface of a surgical instrument. Coupler body 3300 may then be coupled with a coupler interface sized and configured to receive and support coupler body 3300.

Figure 34B:
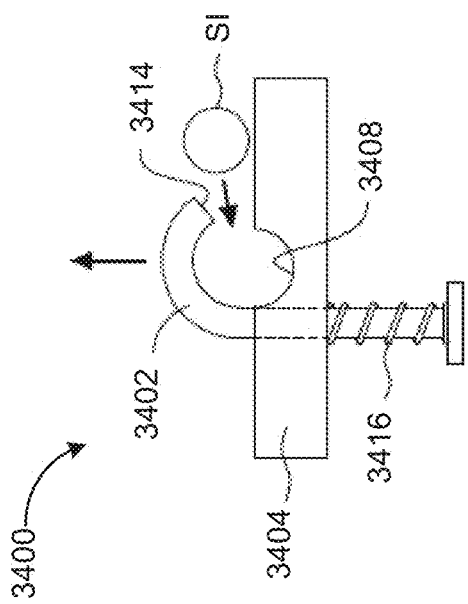
Figure 34C:
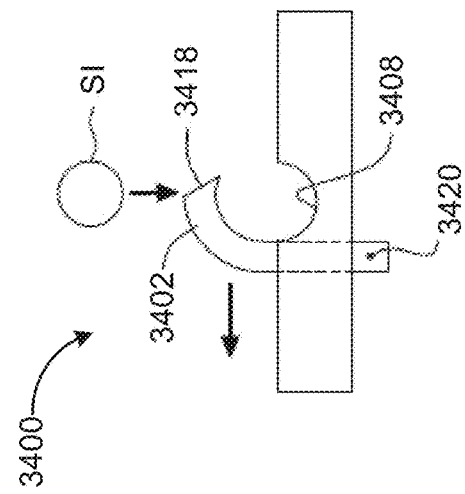
Figure 34A:
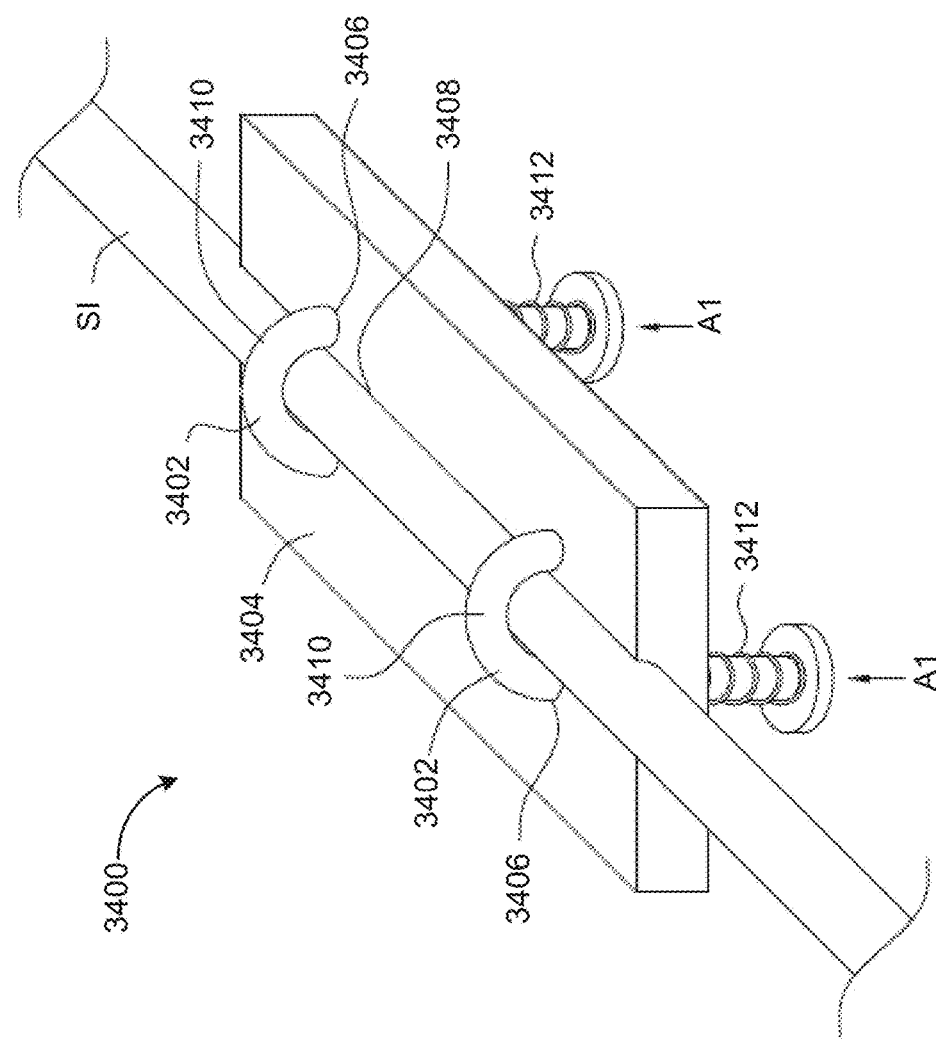

FIGS. 34A to 34C illustrate coupler 3400 that may be used with any robotic system embodiments disclosed herein to couple an instrument to an end portion of a robot arm. Coupler 3400 may have any of the components, features, and/or other details of any of the other coupler embodiments disclosed herein, in any combination with any of the components, features, and/or other details of the embodiment of coupler 3400. Any of the other coupler embodiments disclosed herein may have any of the components, features, and/or other details of coupler 3400, in any combination with any of the components, features, and/or other details of the other coupler embodiments disclosed herein.

Coupler 3400 may have one or more coupler bodies 3402 (two being shown) coupled with coupler interface 3404. Coupler bodies 3402 may be slidably received within openings 3406 in coupler interface 3404. Coupler interface 3404 may have recess 3408 which may have a semicircular cross-sectional shape or other cross-sectional shape that matches a shape of an outside surface of the surgical instrument extending along a length thereof that may be configured to receive an outside surface of surgical instrument SI therein. Coupler bodies 3402 may have a curved end portion 3410 sized and shaped to route or curve at least partially around an outside surface of surgical instrument SI. In this configuration, coupler bodies 3402 when in a second, secured or closed position as shown in FIG. 34A, may be used to selectively secure surgical instrument SI in recess 3408 or otherwise secure surgical instrument SI to coupler interface 3404. Springs or other biasing mechanisms 3412 may be used to bias coupler bodies 3402 in the second, closed or secured position, as shown in FIG. 34A. The user may push coupler bodies 3402 in the axial direction indicated by arrow A1 so as to move coupler bodies 3402 from the second, closed or secured position to the first, open or unsecured position. The force exerted on coupler bodies 3402 should be greater than the spring or biasing force from the spring or biasing mechanisms 3412 coupled with each of coupler bodies 3402.

As shown in FIG. 34B, coupler bodies 3402 may have sloped end surface 3414. Sloped end surface 3414 may be configured such that a space between coupler end surface 3414 and an adjacent surface of coupler interface 3404 is greater at a position of coupler end surface 3414 that is further away from the recess such that, as surgical instrument SI is advanced laterally toward recess 3408 in coupler interface 3404, an outside surface of surgical instrument SI may contact end surface 3414 of the coupler body and the slope of end surface 3414 of coupler body 3400 will cause coupler body 3400 to move from the second, closed or secured state toward a first, open or unsecured state to permit surgical instrument SI to be received within recess 3408. Coupler body 3400 may have a spring or other biasing mechanism 3416 configured to bias coupler body 3400 to the second, closed or secured state or position.

As shown in FIG. 34C, sloped end surface 3414 of any embodiments of coupler bodies 3402 may be sloped such that, as surgical instrument SI is advanced in a downward direction relative to end surface 3418 of coupler body 3400, such interaction between an outside surface of surgical instrument SI and sloping surface 3418 of coupler body 3402 may cause coupler body 3400 to rotate about pivot point 3420 away from recess 3408 and permit surgical instrument SI to be received within recess 3408.

FIGS. 35A to 35D illustrate coupler 3500 that may be used with any robotic system embodiments disclosed herein to couple an instrument to an end portion of a robot arm. Coupler 3500 may have any of the components, features, and/or other details of any of the other coupler embodiments disclosed herein, in any combination with any of the components, features, and/or other details of the embodiment of coupler 3500. Any of the other coupler embodiments disclosed herein may have any of the components, features, and/or other details of the coupler 3500, in any combination with any of the components, features, and/or other details of the other coupler embodiments disclosed herein.

Figure 35B:
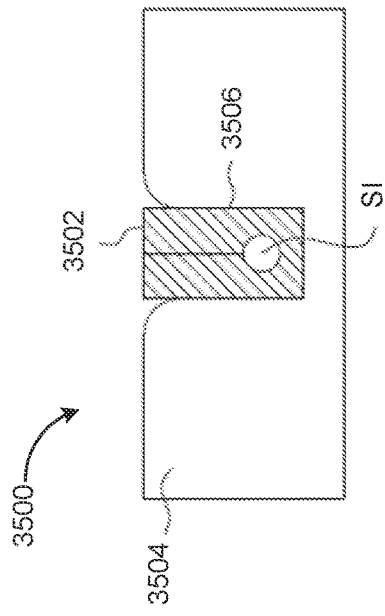

Coupler 3500 may have coupler body 3502 that may be coupled with or engaged with coupler interface 3504. For example, coupler body 3502 may be slidably received within recess 3506 formed in coupler interface 3504. Coupler body 3502 also may have recess 3505 that may have a semicircular cross-sectional shape or other cross-sectional shape that matches a shape of an outside surface of the surgical instrument extending along a length of coupler body 3502 that may be configured to receive and at least partially surround, or in some embodiments fully surround, an outside surface of surgical instrument SI at least when coupler 3500 is in the second state, as shown in FIG. 35B.

Figure 35D:
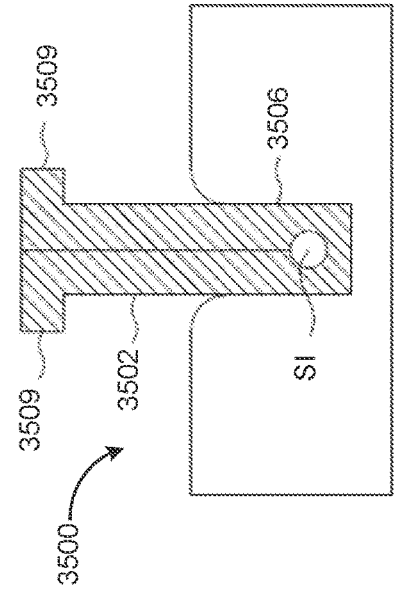
Figure 35A:
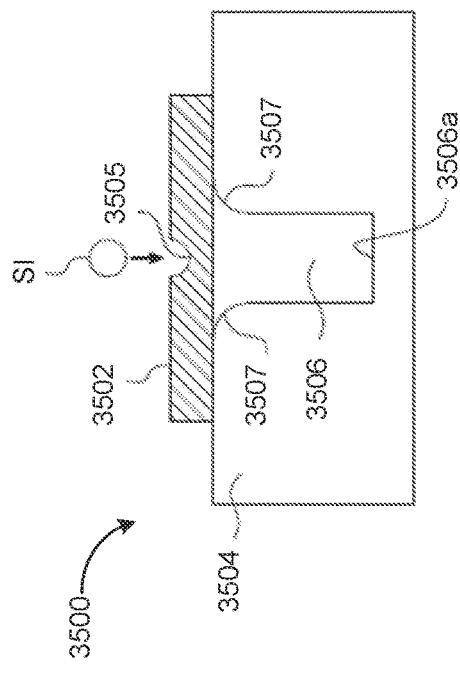

Coupler body 3502 may be made from a flexible material, such as rubber including neoprene. Coupler body 3502 may have a width that is greater than a width of the recess and may be biased toward a planar or generally planar shape, as shown in FIG. 35A. Coupler body 3502 may be flexible enough such that, when coupler body 3502 is forced toward a distal surface 3506a of recess 3506, coupler body 3502 will bend or fold about a middle portion or other portion adjacent to recess 3505. Once coupler body 3502 is fully advanced into recess 3506 of coupler interface 3504, coupler 3500 may be configured to bias coupler body 3502 to remain within the second, secured position within recess 3506. In this configuration, to secure surgical instrument SI in coupler 3500, an operator can advance surgical instrument SI into recess 3505 of coupler body 3502, and continue to advance surgical instrument SI and/or coupler body 3502 toward distal surface 3506a. Some embodiments of coupler 3500 may be configured such that, once coupler body 3502 and surgical instrument SI have been advanced into recess 3506 of coupler interface 3504, surgical instrument SI will be axially and/or rotationally secured to coupler 3500. Thereafter, coupler 3500 may be coupled with an end portion of robot arm 300 such that robot arm 300 may be coupled with surgical instrument SI. In any embodiments, the recess may have sloped, curved, or otherwise tapered leading edge surfaces 3507 leading into the recess to facilitate the advancement of coupler body 3502 into recess 3506 of coupler interface 3504.

Figure 35C:
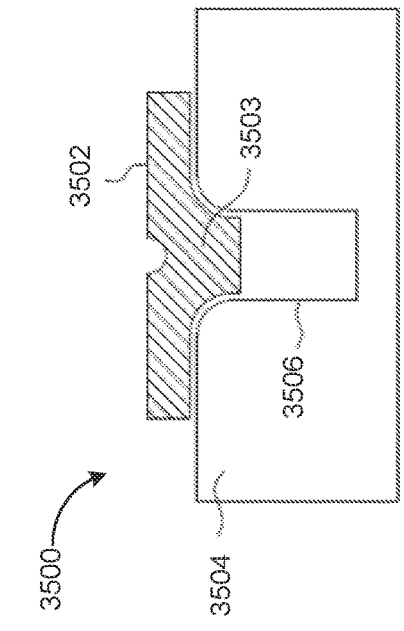
Figure 35F:
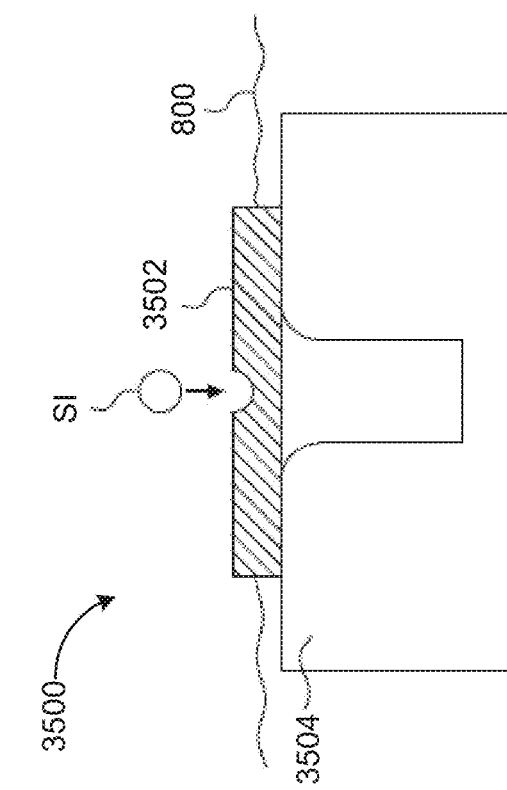
Figure 35E:
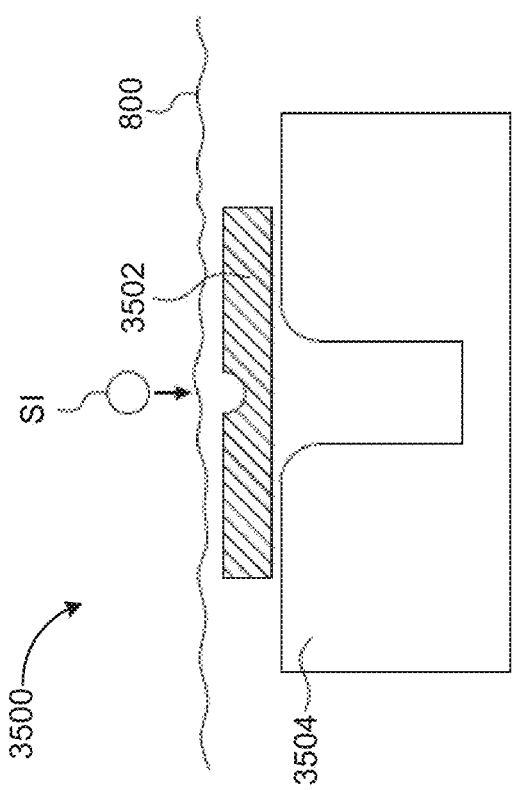

As shown in FIG. 35E, surgical drape 800 may be positioned between surgical instrument SI and coupler body 3302. In other embodiments, surgical drape 800 may be integrated into coupler body 3052 so that coupler body 3502 may form a portion of the surgical drape, as shown in FIG. 35F. Coupler body 3502 may be flexible enough to return to the original shape of coupler body 3502 once coupler body 3502 is removed from recess 3506. In any embodiments disclosed herein, the coupler body or other components or features of the coupler can be configured to radially restrain the instrument.

As shown in FIG. 35C, coupler 3500 may be configured such that coupler body 3502 has a projection 3503 configured to extend into recess 3506 of coupler interface 3504 even when coupler body 3502 is in the first, open or unsecured state as shown in FIG. 35C. Projection 3503 may help bias coupler body 3502 to remain engaged with recess 3506 of coupler interface 3504 even when coupler body 3502 is in the first, open or unsecured state. As shown in FIG. 35D, coupler body 3502 also may have protrusions, flanges, handles, tabs, or other projections 3509 at a proximal end portion thereof configured to facilitate gripping and removal of coupler body 3502 from recess 3506.

In some embodiments, the coupler may include a coupler body made from a flexible material and a coupler interface having a recess configured to receive the coupler body. The coupler body may have a recess having a curved profile along a length of a first main surface thereof that is configured to receive an instrument therein. The coupler body may be flexible enough such that, when the coupler body is forced toward a distal surface of the recess, the coupler body will fold about a portion thereof adjacent to the recess, thereby at least axially and radially restraining the instrument. The coupler body may be flexible enough to return to the original shape of coupler body 3502 once the coupler body is removed from the recess.

FIG. 36 illustrates coupler 3600 that may be used with any robotic system embodiments disclosed herein to couple an instrument to an end portion of a robot arm. Coupler 3600 may have any of the components, features, and/or other details of any of the other coupler embodiments disclosed herein, in any combination with any of the components, features, and/or other details of the embodiment of coupler 3600. Any of the other coupler embodiments disclosed herein may have any of the components, features, and/or other details of coupler 3600, in any combination with any of the components, features, and/or other details of the other coupler embodiments disclosed herein.

Coupler 3600 may have a coupler body 3602 that may be coupled with or engaged with coupler interface 3604. For example, coupler body 3602 may be received within recess 3606 formed in coupler interface 3604. Coupler body 3602 also may have recess 3615 that may have a semicircular cross-sectional shape or other cross-sectional shape that matches a shape of an outside surface of the surgical instrument extending along a length of coupler body 3602 that may be configured to receive and at least partially surround, or in some embodiments fully surround, an outside surface of surgical instrument SI at least when coupler 3600 is in the second state.

Coupler body 3202 may be made from a flexible material, such as rubber including neoprene. Other embodiments of coupler body 3202 may be made from multiple materials, including first layer 3608 made from a flexible material that may have increased gripping such as a rubber and second layer 3610 that may be a backing layer or support layer for first layer 3608 may be made from a more rigid material, such as plastic, metal, or otherwise. Recess 3615 may be formed in first layer 3608. Recess 3615 may be formed in a middle portion of first layer 3608. Some embodiments of second layer 3610 may have hinge 3612 in or attached to a middle portion thereof. In some embodiments, hinge 3612 may run generally parallel to recess 3615 formed in first layer 3608 and recess 3606 formed in coupler interface 3604. In some embodiments, coupler body 3602 may fold or hinge between the first, open state and the second, closed or secured state about surgical instrument SI by folding or hinging about hinge 3612.

Coupler body 3600 may have a width that is greater than a width of recess 3606. Coupler body 3602 may be configured such that, when coupler body 3602 is forced toward distal surface 3606a of recess 3606, coupler body 3602 will bend or fold about hinge 3612 so as to collapse or close about surgical instrument SI positioned within recess 3615 of coupler body 3602 so as to secure surgical instrument SI within coupler body 3602 and coupler interface 3604.

Some embodiments of coupler interface 3604 may have one or more rollers 3614 (two being shown) at proximal end 3606b of the recess 3606 formed in coupler interface 3604. The one or more rollers 3614 may facilitate the movement of coupler body 3602 into recess 3606 by permitting coupler body 3602 to roll on the rollers as coupler body 3602 is advanced into recess 3606. Some embodiments of coupler interface 3604 may have additional rollers 3616 along the side wall surfaces 3606c of recess 3606 to continue to facilitate the advancement of coupler body 3602 into recess 3606. In some embodiments, recess 3606 may have a generally rectangular shape. In other embodiments, recess 3606 may have a tapered or narrowing profile.

Once coupler body 3602 is fully advanced into recess 3606 of coupler interface 3604, some embodiments of coupler 3600 may be configured to bias coupler body 3602 to remain within the second, secured position within recess 3606. In this configuration, to secure surgical instrument SI in coupler 3600, an operator may advance surgical instrument SI into recess 3615 of coupler body 3602, and continue to advance surgical instrument SI and/or coupler body 3602 toward distal surface 3606a of recess 3606. Some embodiments of coupler 3600 may be configured such that, once coupler body 3602 and surgical instrument SI have been advanced into recess 3606 of coupler interface 3604, surgical instrument SI will be axially and/or rotationally secured to coupler 3600. Thereafter, coupler 3600 may be coupled with an end portion of robot arm 300 such that robot arm 300 may be coupled with surgical instrument SI.

FIG. 37 illustrates coupler 3700 that may be used with any robotic system embodiments disclosed herein to couple an instrument to an end portion of a robot arm. Coupler 3700 may have any of the components, features, and/or other details of any of the other coupler embodiments disclosed herein, in any combination with any of the components, features, and/or other details of the embodiment of coupler 3700. Any of the other coupler embodiments disclosed herein may have any of the components, features, and/or other details of coupler 3700, in any combination with any of the components, features, and/or other details of the other coupler embodiments disclosed herein.

Coupler 3700 may have coupler body 3702 that may be coupled with or engaged with coupler interface 3704. Coupler body 3702 may be received within recess 3796 formed in coupler interface 3704. Coupler body 3702 also may have recess 3705 that may have a semicircular cross-sectional shape or other cross-sectional shape that matches a shape of an outside surface of the surgical instrument extending along a length of coupler body 3702 that may be configured to receive and at least partially surround, or in some embodiments fully surround, an outside surface of surgical instrument SI at least when coupler 3704 is in the second state, as shown in FIG. 37.

Coupler body 3702 may be made from multiple materials, including first layer 3710 made from a flexible material that may have increased gripping such as a rubber and second layer 3712 that may be a backing layer or support layer for first layer 3710 may be made from a more rigid material, such as plastic, metal, or otherwise. Recess 3705 may be formed in first layer 3710. In some embodiments, recess 3705 may be formed in a middle portion of first layer 3710. Some embodiments of second layer 3712 may have hinge 3714 in or attached to a middle portion thereof. In some embodiments, hinge 3714 may run generally parallel to recess 3705 formed in first layer 3710 and recess 3706 formed in coupler interface 3704. In some embodiments, coupler body 3702 may fold or hinge between the first, open state and the second, closed or secured state about surgical instrument SI by folding or hinging about hinge 3714.

Coupler body 3702 may have a width that is greater than a width of recess 3706. Coupler body 3702 may be configured such that, when coupler body 3702 is forced toward a distal surface 3706a of the recess 3706, coupler body 3702 will bend or fold about hinge 3714 so as to collapse or close about surgical instrument SI positioned within recess 3705 of coupler body 3702 so as to secure surgical instrument SI within coupler body 3702 and coupler interface 3704. In some embodiments, second layer 3712 may have wings or tabs 3716 that may be used to facilitate removal of coupler body 3702 from recess 3706. Tabs 3716 may be formed such that, when coupler body 3702 is in the second position, as shown in FIG. 37, tabs 3716 may be spaced apart from first surface 3704a (which can be an upper surface when coupler interface 3704 is positioned as shown in FIG. 37) such that a gap or space 3720 exists between tabs 3716 and upper surface 3704a of coupler interface 3704. Space 3720 may be large enough to permit tabs 3716 to move toward first surface 3704a when a force is applied to tabs 3716 in the direction of first surface 3704a. As tabs 3716 are deflected toward first surface 3704a, such movement of tabs 3716 may force a remainder of coupler body 3702 to move away from a distal surface 3706a of recess 3706, thereby allowing coupler body 3704 to be removed from recess 3706.

Some embodiments of coupler interface 3704 may have one or more rollers 3717 (two being shown) at proximal end 3706b of recess 3706 formed in coupler interface 3704. The one or more rollers 3717 may facilitate the movement of coupler body 3702 into recess 3706 by permitting coupler body 3702 to roll on the rollers as coupler body 3702 is advanced into recess 3706. Some embodiments of coupler interface 3704 may have additional rollers 3718 along the side wall surfaces 3706c of recess 4706 to continue to facilitate the advancement of coupler body 3702 into recess 3706.

Once coupler body 3702 is fully advanced into recess 3706 of coupler interface 3704, some embodiments of coupler 3700 may be configured to bias coupler body 3702 to remain within the second, secured position within recess 3706. In this configuration, to secure surgical instrument SI in coupler 3700, an operator may advance surgical instrument SI into recess 3705 of coupler body 3703, and continue to advance surgical instrument SI and/or coupler body 3702 toward distal surface 3706a of recess 3706. Some embodiments of coupler 3700 may be configured such that, once coupler body 3702 and surgical instrument SI have been advanced into recess 3706 of coupler interface 3704, surgical instrument SI will be axially and/or rotationally secured to coupler 3700. Thereafter, coupler 3700 may be coupled with an end portion of robot arm 300 such that robot arm 300 may be coupled with surgical instrument SI.

FIGS. 38A and 38B illustrate coupler 3800 that may be used with any robotic system embodiments disclosed herein to couple an instrument to an end portion of a robot arm. Coupler 3800 may have any of the components, features, and/or other details of any of the other coupler embodiments disclosed herein, in any combination with any of the components, features, and/or other details of the embodiment of coupler 3800. Any of the other coupler embodiments disclosed herein may have any of the components, features, and/or other details of coupler 3800, in any combination with any of the components, features, and/or other details of the other coupler embodiments disclosed herein.

Coupler 3800 may have coupler body 3802 that may be coupled with or engaged with a coupler interface (not shown) or may be coupled with or engaged with a robot arm without the presence of a coupler interface (e.g., the coupler body of any embodiments disclosed herein can directly engage or interface with an end portion of robot arm 300). Coupler body 3802 may have first portion 3804 and second portion 3806 coupled with first portion 3804. In some embodiments, first portion 3804 may be hingedly or rotatably coupled with second portion 3806. For example, coupler body 3802 may have a hinge or joint 3810 that may couple first and second portions 3804, 3806 together.

In some embodiments, first portion 3804 of coupler body 3802 may have proximal portion 3804a and distal portion 3804b that is integrally formed with or coupled with proximal portion 3804a. First portion 3804 of coupler body 3802 may have recess 3812 and second portion 3806 of coupler body 3820 may have recess 3814, each of which can have a semicircular cross-sectional shape or other cross-sectional shape that matches a shape of an outside surface of the surgical instrument extending along a length of coupler body 3802 that may be configured to receive and at least partially surround, or in some embodiments fully surround, an outside surface of surgical instrument SI at least when coupler 3800 is in the second state. The second state of coupler body 3802 is shown FIG. 38B. In some embodiments, second portion 3806 may be similarly situated and may be a mirror copy of first portion 3804, with proximal portion 3806a and distal portion 3806b that is integrally formed with or coupled with the proximal portion 3806a.

Some embodiments of coupler 3800 may be configured to be bistable in that the coupler 3800 will be biased toward either the first, open or unsecured state or the second, closed or secured state and is unstable in any position or state except the first and second states. In the first state, distal portion 3804b of first portion 3804 of coupler 3800 is in contact with the distal portion 3806b of second portion 3806 of coupler 3800 and proximal portion 3804a of first portion 3804 of coupler 3800 is rotated away and spaced apart from proximal portion 3806a of second portion 3806 of coupler 3800. In the first, open or unsecured state, surgical instrument SI may be loaded into or removed from coupler 3800. In the second state, proximal portion 3804a of first portion 3804 of coupler 3800 is in contact with proximal portion 3806a of second portion 3806 of coupler 3800 and distal portion 3804b of first portion 3804 of coupler 3800 is rotated away and spaced apart from distal portion 3806b of second portion 3806 of coupler 3800. In the second, closed or secured state, surgical instrument SI loaded into coupler 3800 may be secured or supported by coupler 3800 such that surgical instrument SI may be at least inhibited (e.g., prevented) from an axial movement or, in some embodiments, an axial and a rotational movement relative to the coupler 3800.

In this configuration, when coupler 3800 is in the first, open state as shown in 38A, after positioning surgical instrument SI in either recess 3812 with recess 3814, the operator may change coupler 3800 to the second, closed state by pinching or moving the proximal portion 3804a of first portion 3804 toward proximal portion 3806a of second portion 3806, such as by exerting a force on proximal portions 3804a, 3806a of first and second portions 3804, 3806 along the directions A3 and A4, as shown in FIG. 38A (e.g., by squeezing the proximal portions 3804a, 3806a of first and second portions 3804, 3806 together). When coupler 3800 is in the second, closed state as shown in FIG. 38B, the operator may change coupler 3800 to the first, open state by pinching or moving distal portion 3804b of first portion 3804 toward distal portion 3806b of second portion 3806, such as by exerting a force on distal portions 3804b, 3806b of first and second portions 3804, 3806 along the directions A5 and A6, as shown in FIG. 38B (e.g., by squeezing distal portions 3804b, 3806b of first and second portions 3804, 3806 together).

FIGS. 39A and 39B illustrate coupler 3900 that may be used with any robotic system embodiments disclosed herein to couple an instrument to an end portion of a robot arm.

Coupler 3900 may have any of the components, features, and/or other details of any of the other coupler embodiments disclosed herein, in any combination with any of the components, features, and/or other details of the embodiment of coupler 3900. Any of the other coupler embodiments disclosed herein may have any of the components, features, and/or other details of the coupler 3900, in any combination with any of the components, features, and/or other details of the other coupler embodiments disclosed herein.

Coupler 3900 may have a coupler body 3902 that may be coupled with or engaged with a coupler interface (not shown) or may be coupled with or engaged with a robotic arm without the presence of a coupler interface. Coupler body 3902 may have one or more projections 3903 (two being shown) that may be used to center or position coupler body 3902 relative to the coupler interface. For example, projections 3903 may be conical projections configured to engage with depressions or openings in the coupler interface to align coupler body 3902 with the coupler interface. In some embodiments, the coupler interface may have an equal number or a different number of depressions or openings as compared to the number of projections 3903. In other embodiments, projections 3903 may be cylindrically shaped. In some embodiments, coupler body 3902 may have three or more projections 3903.

Coupler body 3902 may have first tab 3904 hingedly or rotatably coupled with coupler body 3902 and second tab 3906 hingedly or rotatably coupled with coupler body 3902. For example, coupler body 3902 may have a first hinge or joint 3910 that may couple first tab 3904 with coupler body 3902 and a second hinge or joint 3911 that may couple second tab 3906 with coupler body 3902. First tab 3904 may have proximal end portion 3904a and distal end portion 3904b, as shown in FIG. 39B. Second tab 3906 may have proximal end portion 4906a and distal end portion 4906b.

Coupler body 3902 may have recess 3914 formed therein, first tab 3904 may have recess 3916 formed in a distal end portion thereof and second tab 3906 may have recess 3918 formed in a distal end portion thereof, each of which may have a semicircular cross-sectional shape or other cross-sectional shape that, all together, may match a shape of an outside surface of surgical instrument SI extending along a length of coupler body 3902, first tab 3904, and second tab 3906 and that may be configured to receive and at least partially surround, or in some embodiments fully surround, an outside surface of surgical instrument SI at least when coupler 3900 is in the second state. The second state of coupler body 3902 is shown in FIG. 39B. In some embodiments, second tab 3906 may be similarly situated and may be a mirror copy of first tab 3904.

Some embodiments of coupler 3900 may be biased toward the second state, using springs or other torsional biasing elements. An operator may overcome the bias or otherwise move coupler body 3902 from the second state as shown in FIG. 39B to the first state as shown in FIG. 39A by squeezing together or toward one another proximal end portions 3904a, 3906a of first and second tabs 3904, 3906. In the first state, the operator may remove surgical instrument SI from coupler 3900. To support a surgical instrument SI in coupler 3900, while coupler 3900 is in the first, open state, the operator may position surgical instrument SI in contact with or near recess 3914 and release the force that was applied to first and second tab 3904, 3906 or otherwise relax first and second tab 3904, 3906 and allow first and second tabs 3904, 3906 to return to the relaxed position of first and second tabs 3904, 3906.

FIGS. 40 to 43 illustrate additional couplers 4000, 4100, 4200, 4300. Couplers 4000, 4100, 4200, 4300 may have any of the components, features, and/or other details of any of the other coupler embodiments disclosed herein, in any combination with any of the components, features, and/or other details of the embodiment of couplers 4000, 4100, 4200, 4300. Any of the other coupler embodiments disclosed herein may have any of the components, features, and/or other details of couplers 4000, 4100, 4200, 4300 in any combination with any of the components, features, and/or other details of the other coupler embodiments disclosed herein.

As shown in FIG. 40, coupler 4000 may have first body portion 4002 and second body portion 4004 that may be slidably coupled with or engaged with first body portion 4002. Coupler 4000 may have a recess or opening 4006 that may be enlarged and may be configured to receive surgical instrument SI therein when second body portion 4004 is moved toward first body portion 4002. A spring or other biasing mechanism 4008 may be used to bias coupler 4000 toward the second, closed or secured state so that, when an operator releases first and second body portions 4002, 4004, coupler 4000 may exert a force on a surgical instrument to secure the surgical instrument therein. Some embodiments of coupler 400 may be figured to axially restrain a surgical instrument therein, but to permit a rotation of the surgical instrument. Coupler 4000 may be coupled with a coupler interface or directly to an end portion of robot arm 300.

As shown in FIG. 41, coupler 4100 may have first body portion 4102 and second body portion 4104 that may be slidably coupled with or engaged with first body portion 4102. Coupler 4100 may have a recess or opening 4106 that may be enlarged and may be configured to receive surgical instrument SI therein when second body portion 4104 is moved toward first body portion 4102. Spring 4108 or other biasing mechanism may be used to bias coupler 4100 toward the second, closed or secured state so that, when an operator releases first and second body portions 4102, 4104, coupler 4100 may exert a force on a surgical instrument to secure the surgical instrument therein. Some embodiments of coupler 4100 may be figured to axially restrain a surgical instrument therein, but to permit a rotation of the surgical instrument. Coupler 4100 may be coupled with a coupler interface or directly to an end portion of robot arm 300.

As shown in FIG. 42, coupler 4200 may have first body portion 4202 having proximal end portion 4202*a* and distal end portion 4202*b* and second body portion 4204 having proximal end portion 4204*a* and distal end portion 4204*b* that may be rotatably coupled with or engaged with first body portion 4202 about an axis or shaft 4207. Coupler 4200 may have a recess or opening 4206 formed in distal end portions 4202*b*, 4204*b* that may be enlarged and may be configured to receive surgical instrument SI therein when distal end portion 4204*b* of second body portion 4204 is rotated away from distal end portion 4202*b* of first body portion 4202. Spring 4208 or other biasing mechanism may be used to bias coupler 4200 toward the second, closed or secured state so that, when an operator releases first and second body portions 4202, 4204, coupler 4200 may exert a force on a surgical instrument to secure the surgical instrument therein. Some embodiments of coupler 4200 may be figured to axially restrain a surgical instrument therein, but to permit a rotation of the surgical instrument. Coupler 4200 may be coupled with a coupler interface or directly to an end portion of robot arm 300.

As shown in FIG. 43, coupler 4300 may be configured to engage with a coupler interface or the distal end portion 4301 of a robot arm. Coupler 4300 may be constructed similar to coupler 4200, with similar components having like-prime reference numerals. Coupler 4300 differs from coupler 4200 in that coupler 4300 may have projections 4302 extending inwardly from an inner surface of proximal end portion 4202*a*' of first body portion 4202' and an inner surface of proximal end portion 4204*a*' of second body portion 4204' that may be received within recesses 4304 formed in distal end portion 4301 of the robot arm when coupler 4300 is in the second, closed state.

While various illustrative embodiments of the invention are described above, it will be apparent to one skilled in the art that various changes and modifications may be made therein without departing from the invention. The appended claims are intended to cover all such changes and modifications that fall within the true scope of the invention.

What is claimed:

1. A co-manipulation surgical system to assist with laparoscopic surgery performed using a surgical instrument having a handle, an operating end, and an elongated shaft therebetween, the co-manipulation surgical system comprising:
   a robot arm comprising a proximal end, a distal end configured to be removably coupled to the surgical instrument, a plurality of links, and a plurality of joints; and
   a controller operatively coupled to the robot arm and comprising instructions that, when executed by one or more processors of the controller, cause the controller to:
      cause the robot arm to maintain a static position in a calibration mode when the surgical instrument is coupled to the distal end of the robot arm;
      determine one or more instrument parameters of the surgical instrument when the robot arm is in the static position in the calibration mode based on force applied by the surgical instrument to the distal end of the robot arm while the surgical instrument and the robot arm remain static in the static position;
      generate and store a calibration file associated with the surgical instrument, the calibration file comprising information indicative of the one or more instrument parameters;
      execute the calibration file for performing laparoscopic surgery using the surgical instrument in a co-manipulation mode; and
      cause, in the co-manipulation mode, the robot arm to be freely moveable responsive to movement at the handle of the surgical instrument for performing the laparoscopic surgery using the surgical instrument.

2. The co-manipulation surgical system of claim 1, wherein the controller is programmed to access the calibration file associated with the surgical instrument responsive to user input provided via a graphical user interface operatively coupled to the controller.

3. The co-manipulation surgical system of claim 1, wherein the one or more instrument parameters comprise an instrument type, and wherein the controller is programmed to determine the instrument type based on the coupling between the surgical instrument and the distal end of the robot arm.

4. The co-manipulation surgical system of claim 3, wherein the controller is programmed to access the calibration file associated with the surgical instrument responsive to identification of the surgical instrument.

5. The co-manipulation surgical system of claim 1, wherein the distal end of the robot arm comprises a coupler interface, the system further comprising a coupler body configured to be removeably coupled to the coupler interface and to the elongated shaft of the surgical instrument, such that the distal end of the robot arm is configured to be removeably coupled to the surgical instrument via the coupler interface and the coupler body.

6. The co-manipulation surgical system of claim 5, wherein the coupler body is non-electronic.

7. The co-manipulation surgical system of claim 5, wherein the coupler body comprises a lumen sized and shaped to slidably receive the elongated shaft of the surgical instrument therethrough.

8. The co-manipulation surgical system of claim 5, wherein, when the surgical instrument is coupled to the coupler body, rotational movement of the elongated shaft relative to the coupler body is permitted, while longitudinal movement of the elongated shaft relative to the coupler body is inhibited.

9. The co-manipulation surgical system of claim 1, further comprising a sensor operatively coupled to the controller, the sensor configured to collect sensor data comprising at least one of 3D depth data or pixel image data.

10. The co-manipulation surgical system of claim 9, wherein the controller is programmed to determine an instrument type of the surgical instrument based on the sensor data.

11. The co-manipulation surgical system of claim 9, wherein the controller is programmed to determine a center of mass of the surgical instrument based on the sensor data.

12. The co-manipulation surgical system of claim 9, wherein the controller is programmed to determine a length of the surgical instrument based on the sensor data.

13. The co-manipulation surgical system of claim 9, wherein the controller is programmed to determine an instrument shaft diameter of the surgical instrument based on the sensor data.

14. The co-manipulation surgical system of claim 9, wherein the sensor comprises a LIDAR device.

15. The co-manipulation surgical system of claim 9, wherein the sensor comprises a stereo camera.

16. The co-manipulation surgical system of claim 1, wherein the one or more instrument parameters comprise an instrument type, and wherein the controller is programmed to determine a center of mass of the surgical instrument based on the instrument type.

17. The co-manipulation surgical system of claim 1, wherein the robot arm comprises a base operatively coupled to the proximal end of the robot arm, the system further comprising:
a plurality of motors disposed within the base, the plurality of motors operatively coupled to at least some joints of the plurality of joints,
wherein the controller is programmed to:
measure current of the plurality of motors; and
determine the mass of the surgical instrument based on the current.

18. The co-manipulation surgical system of claim 1, wherein the controller is programmed to:
measure a position of the distal end of the robot arm;
determine a point of entry of the surgical instrument into the patient by determining a point of intersection of a plurality of virtual lines parallel to the longitudinal axis of the surgical instrument as the position of the distal end of the robot arm moves relative to the point of entry;
calculate a compensation force required to compensate for gravity of the surgical instrument based on the position of the distal end of the robot arm, the point of entry, and at least one of the one or more instrument parameters; and apply torque to the at least some joints of the plurality of joints of the robot arm via a plurality of motors operatively coupled to at least some joints of the plurality of joints based on the compensation force to compensate for gravity of the surgical instrument during operation of the co-manipulation surgical system.

19. The co-manipulation surgical system of claim 18, wherein the controller is programmed to:
measure a change of position of the distal end of the robot arm responsive to an external force;
calculate a hold force required to maintain a static position of the robot arm based on the position of the distal end of the robot arm, the point of entry, and at least one of the one or more instrument parameters; and
apply torque to the at least some joints of the plurality of joints of the robot arm via the plurality of motors based on the compensation force and the hold force to maintain the static position of the robot arm in the passive mode.

20. The co-manipulation surgical system of claim 19, wherein the controller is programmed to calculate a force applied by the surgical instrument to the patient at the point of entry based on the compensation force, the hold force, at least one of the one or more instrument parameters, and the point of entry.

21. The co-manipulation surgical system of claim 20, wherein the controller is programmed to calculate a force applied to the operating end of the surgical instrument based on the compensation force, the hold force, at least one of the one or more instrument parameters, and the point of entry.

22. The co-manipulation surgical system of claim 1, further comprising a graphical user interface operatively coupled to the controller, the graphical user interface is configured to display at least one of the one or more instrument parameters.

23. The co-manipulation surgical system of claim 22, wherein the graphical user interface is configured to receive user input indicative of a procedure type associated with the laparoscopic surgery, and wherein the controller is configured to pre-load one or more surgical instrument types associated with the procedure type for selection by a user via the graphical user interface.

24. The co-manipulation surgical system of claim 1, wherein, during the laparoscopic surgery, the controller is configured to permit the robot arm to be freely moveable only responsive to movement at the handle of the surgical instrument, and wherein the movement at the handle of the surgical instrument applies a force to a plurality of links and a plurality of joints of the robot arm via the distal end of the robot arm.

25. The co-manipulation surgical system of claim 1, wherein the robot arm is not teleoperated via user input received at a remote surgeon console.

26. A method for calibrating a co-manipulation surgical system to assist with laparoscopic surgery performed using a surgical instrument, the method comprising:
coupling a distal end of a robot arm to the surgical instrument;
after the coupling, entering a calibration mode where the robot arm maintains a static position;
determining one or more instrument parameters of the surgical instrument when the robot arm is in the static position in the calibration mode based on force applied by the surgical instrument to the distal end of the robot arm while the surgical instrument and the robot arm remain static in the static position;

generating a calibration file associated with the surgical instrument, the calibration file comprising information indicative of the one or more instrument parameters;

executing instructions stored in the calibration file for performing laparoscopic surgery using the surgical instrument in a co-manipulation mode; and after executing the instructions, permitting the robot arm to be freely moveable responsive to movement at the handle of the surgical instrument in the co-manipulation mode for performing laparoscopic surgery using the surgical instrument.

27. The method of claim 26, wherein coupling the distal end of the robot arm to the surgical instrument comprises removably coupling a coupler body to a coupler interface disposed at the distal end of the robot arm, and removably coupling the surgical instrument to the coupler body.

28. The method of claim 27, wherein removably coupling the surgical instrument to the coupler body comprises slidably inserting an elongated shaft of the surgical instrument within a lumen of the coupler body, and wherein, when the surgical instrument is coupled to the coupler body, rotational movement of the elongated shaft relative to the coupler body is permitted, while longitudinal movement of the elongated shaft relative to the coupler body is inhibited.

29. The method of claim 28, wherein slidably inserting the elongated shaft of the surgical instrument within the lumen of the coupler body comprises positioning the coupler body at a fixed point along the elongated shaft to provide a consistent point of reference for force calculations of the surgical instrument.

30. The method of claim 26, wherein, during the laparoscopic surgery, permitting the robot arm to be freely moveable responsive to movement at the handle of the surgical instrument comprises permitting the robot arm to be freely moveable only responsive to movement at the handle of the surgical instrument coupled to the distal end of the robot arm, and wherein the movement at the handle of the surgical instrument applies a force to a plurality of links and a plurality of joints of the robot arm via the distal end of the robot arm.

* * * * *